United States Patent
Donnelly et al.

(10) Patent No.: US 10,722,473 B2
(45) Date of Patent: Jul. 28, 2020

(54) METHODS AND COMPOSITIONS PARTICULARLY FOR TREATMENT OF ATTENTION DEFICIT DISORDER

(71) Applicant: Purdue Pharma L.P., Stamford, CT (US)

(72) Inventors: Graeme Donnelly, Toronto (CA); Sailaja Bhaskar, Pickering (CA)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 16/195,418

(22) Filed: Nov. 19, 2018

(65) Prior Publication Data
US 2020/0155471 A1    May 21, 2020

(51) Int. Cl.
| A61P 25/26 | (2006.01) |
| A61K 9/50 | (2006.01) |
| A61K 31/4458 | (2006.01) |
| A61P 25/00 | (2006.01) |

(52) U.S. Cl.
CPC .......... *A61K 9/5078* (2013.01); *A61K 9/5026* (2013.01); *A61K 9/5036* (2013.01); *A61K 9/5073* (2013.01); *A61K 31/4458* (2013.01); *A61P 25/00* (2018.01)

(58) Field of Classification Search
CPC .......................... A61K 9/50; A61P 25/00–26
See application file for complete search history.

(56) References Cited

U.S. PATENT DOCUMENTS

| 2,377,237 A | 5/1945 | James |
| 2,507,631 A | 5/1950 | Hartmann |
| 2,676,169 A | 4/1954 | Baldoni |
| 2,772,488 A | 12/1956 | Meltzer |
| 2,791,509 A | 5/1957 | Cosler |
| 3,365,365 A | 1/1968 | Butler et al. |
| 3,370,054 A | 2/1968 | Loew |
| 3,371,015 A | 2/1968 | Sjogren et al. |
| 3,424,842 A | 1/1969 | Eberhard |
| 3,623,997 A | 11/1971 | Thomas |
| 3,629,393 A | 12/1971 | Atsushi et al. |
| 3,845,770 A | 11/1974 | Theeuwes et al. |
| 3,870,790 A | 3/1975 | Lowey et al. |
| 3,883,647 A | 5/1975 | Geller |
| 3,901,968 A | 8/1975 | Cohen et al. |
| 3,916,899 A | 11/1975 | Theeuwes et al. |
| 3,927,205 A | 12/1975 | Ohno et al. |
| 3,935,326 A | 1/1976 | Groppenbacher et al. |
| 3,983,233 A | 9/1976 | Brattsand et al. |
| 3,996,356 A | 12/1976 | Grunberg |
| 4,000,254 A | 12/1976 | Gordon et al. |
| 4,060,598 A | 11/1977 | Groppenbacher et al. |
| 4,083,949 A | 4/1978 | Benedikt |
| 4,088,798 A | 5/1978 | Michaelis |
| 4,093,709 A | 6/1978 | Choi et al. |
| 4,140,755 A | 2/1979 | Sheth et al. |
| 4,167,558 A | 9/1979 | Sheth et al. |
| 4,173,626 A | 11/1979 | Dempski et al. |
| 4,182,756 A | 1/1980 | Guzek et al. |
| 4,226,849 A | 10/1980 | Schor |
| 4,234,565 A | 11/1980 | Flodin et al. |
| 4,252,786 A | 2/1981 | Weiss et al. |
| 4,256,108 A | 3/1981 | Theeuwes |
| 4,259,314 A | 3/1981 | Lowey |
| 4,318,400 A | 3/1982 | Peery et al. |
| 4,341,759 A | 7/1982 | Bogentoft et al. |
| 4,357,469 A | 11/1982 | Schor |
| 4,369,172 A | 1/1983 | Schor et al. |
| 4,389,393 A | 6/1983 | Schor et al. |
| 4,439,453 A | 3/1984 | Vogel |
| 4,443,497 A | 4/1984 | Samejima et al. |

(Continued)

FOREIGN PATENT DOCUMENTS

| AU | 1632692 A | 11/1992 |
| AU | 653223 B2 | 9/1994 |

(Continued)

OTHER PUBLICATIONS

Andersson, P., et al., "In Vitro Biotransformation of Glucocorticoids in Liver and Skin Homogenate Fraction from Man, Rat and Hairless Mouse," Steroid Biochemistry 16(6):787-795, Pergamon Press, England (Jun. 1982).

Aoyama, T., et al., "Pharmacokinetics and Pharmacodynamics of (+)-Threo-Methylphenidate Enantiomer In Patients With Hypersomnia," Clinical Pharmacology and Therapeutics 55(3):270-276, Hoboken, NJ : Wiley, United States (Mar. 1994).

Aqua coat (Ethylcellulose ), pp. 17-36, 1985, Manufacturer's Info.
Aquacoat, Ethylcellulose, 1987, Manufacturer's Info.

Ariens, E.J, "Racemic Therapeutics-Ethical and Regulatory Aspects," European Journal of Clinical Pharmacology 41(2):89-93, New York, Springer, Germany (1991).

(Continued)

*Primary Examiner* — Micah Paul Young
(74) *Attorney, Agent, or Firm* — Sterne, Kessler, Goldstein & Fox P.L.L.C.; Matthew Bodenstein

(57) ABSTRACT

There is described, inter alia, a coated bead comprising: (a) a granule; (b) a first layer coated over the granule, the first layer comprising a first amount of an active pharmaceutical ingredient comprising a central nervous system stimulant; and (c) a second layer coated over the first layer, the second layer being present in an amount sufficient to substantially delay release of the active pharmaceutical ingredient in the first layer until after the coated bead reaches a distal intestine portion of a subject to whom the coated bead is administered; and (d) the third layer coated over the second layer, the third layer comprising a second amount of the active pharmaceutical ingredient, the third layer being configured to permit substantially immediate release of the active pharmaceutical ingredient comprised therein. Embodiments related to a solid oral pharmaceutical composition are also described.

4 Claims, 72 Drawing Sheets

(56) References Cited

U.S. PATENT DOCUMENTS

| | | |
|---|---|---|
| 4,454,108 A | 6/1984 | Iida et al. |
| 4,464,170 A | 8/1984 | Clemens et al. |
| 4,503,031 A | 3/1985 | Glassman |
| 4,520,172 A | 5/1985 | Lehmann et al. |
| 4,526,777 A | 7/1985 | Blume et al. |
| 4,540,566 A | 9/1985 | Davis et al. |
| 4,548,990 A | 10/1985 | Mueller et al. |
| 4,574,080 A | 3/1986 | Roswall et al. |
| 4,592,753 A | 6/1986 | Panoz |
| 4,600,645 A | 7/1986 | Ghebre-Sellassie et al. |
| 4,606,909 A | 8/1986 | Bechgaard et al. |
| 4,606,940 A | 8/1986 | Frank et al. |
| 4,609,542 A | 9/1986 | Panoz et al. |
| 4,610,870 A | 9/1986 | Jain et al. |
| 4,611,008 A | 9/1986 | Heinzelmann |
| 4,634,587 A | 1/1987 | Hsiao |
| 4,666,703 A | 5/1987 | Kopf |
| 4,693,895 A | 9/1987 | Wong et al. |
| 4,695,467 A | 9/1987 | Uemura et al. |
| 4,705,695 A | 11/1987 | Lehmann et al. |
| 4,708,867 A | 11/1987 | Hsiao |
| 4,708,874 A | 11/1987 | De Haan et al. |
| 4,710,519 A | 12/1987 | Finnan et al. |
| 4,716,040 A | 12/1987 | Panoz |
| 4,716,041 A | 12/1987 | Kjornaes et al. |
| 4,721,619 A | 1/1988 | Panoz et al. |
| 4,724,148 A | 2/1988 | Sonobe et al. |
| 4,728,513 A | 3/1988 | Ventouras |
| 4,729,190 A | 3/1988 | Lee |
| 4,740,365 A | 4/1988 | Yukimatsu et al. |
| 4,748,023 A | 5/1988 | Tamas et al. |
| 4,765,988 A | 8/1988 | Sonobe et al. |
| 4,766,012 A | 8/1988 | Valenti |
| 4,770,809 A | 9/1988 | Heidenreich et al. |
| 4,772,475 A | 9/1988 | Fukui et al. |
| 4,783,337 A | 11/1988 | Wong et al. |
| 4,786,503 A | 11/1988 | Edgren et al. |
| 4,786,505 A | 11/1988 | Lovgren et al. |
| 4,786,506 A | 11/1988 | Fontanelli |
| 4,794,001 A | 12/1988 | Mehta et al. |
| 4,798,724 A | 1/1989 | Khanna |
| 4,800,084 A | 1/1989 | Zerbe |
| 4,811,845 A | 3/1989 | Baggett |
| 4,814,178 A | 3/1989 | Bolton et al. |
| 4,816,264 A | 3/1989 | Phillips et al. |
| 4,820,522 A | 4/1989 | Radebaugh et al. |
| 4,826,688 A | 5/1989 | Panoz et al. |
| 4,828,840 A | 5/1989 | Sakamoto et al. |
| 4,837,004 A | 6/1989 | Wu et al. |
| 4,839,177 A | 6/1989 | Colombo et al. |
| 4,842,867 A | 6/1989 | Ayer et al. |
| 4,853,230 A | 8/1989 | Lovgren et al. |
| 4,861,599 A | 8/1989 | Springolo et al. |
| 4,863,744 A | 9/1989 | Urquhart et al. |
| 4,867,984 A | 9/1989 | Patel |
| 4,867,987 A | 9/1989 | Seth |
| 4,880,830 A | 11/1989 | Rhodes |
| 4,889,238 A | 12/1989 | Batchelor |
| 4,891,230 A | 1/1990 | Geoghegan et al. |
| 4,892,739 A | 1/1990 | Shah et al. |
| 4,892,742 A | 1/1990 | Shah |
| 4,894,240 A | 1/1990 | Geoghegan et al. |
| 4,900,557 A | 2/1990 | Dell et al. |
| 4,917,899 A | 4/1990 | Geoghegan et al. |
| 4,931,295 A | 6/1990 | Courtright et al. |
| 4,940,586 A | 7/1990 | Cheng et al. |
| 4,946,685 A | 8/1990 | Edgren et al. |
| 4,950,486 A | 8/1990 | Ayer et al. |
| 4,952,402 A | 8/1990 | Sparks et al. |
| 4,954,350 A | 9/1990 | Jones et al. |
| 4,966,769 A | 10/1990 | Guittard et al. |
| 4,966,770 A | 10/1990 | Giannini et al. |
| 4,968,509 A | 11/1990 | Radebaugh et al. |
| 4,971,805 A | 11/1990 | Kitanishi et al. |
| 4,981,468 A | 1/1991 | Benefiel et al. |
| 4,981,693 A | 1/1991 | Higashi et al. |
| 4,983,401 A | 1/1991 | Eichel et al. |
| 4,983,403 A | 1/1991 | Ardaillon et al. |
| 4,984,592 A | 1/1991 | Hellein |
| 4,994,279 A | 2/1991 | Aoki et al. |
| 5,004,613 A | 4/1991 | Radebaugh et al. |
| 5,008,118 A | 4/1991 | Iwanami et al. |
| 5,011,694 A | 4/1991 | Nuernberg et al. |
| 5,015,479 A | 5/1991 | Mulligan et al. |
| 5,019,397 A | 5/1991 | Wong et al. |
| 5,024,842 A | 6/1991 | Edgren et al. |
| 5,026,560 A | 6/1991 | Makino et al. |
| 5,026,709 A | 6/1991 | Harwood et al. |
| 5,032,406 A | 7/1991 | Dansereau et al. |
| 5,047,007 A | 9/1991 | McNichols et al. |
| 5,047,258 A | 9/1991 | Belanger et al. |
| 5,051,262 A | 9/1991 | Panoz et al. |
| 5,055,306 A | 10/1991 | Barry et al. |
| 5,068,110 A | 11/1991 | Fawzi et al. |
| 5,073,380 A | 12/1991 | Babu et al. |
| 5,084,278 A | 1/1992 | Mehta |
| 5,085,865 A | 2/1992 | Nayak |
| 5,085,866 A | 2/1992 | Cowsar et al. |
| 5,091,175 A | 2/1992 | Imondi et al. |
| 5,093,200 A | 3/1992 | Watanabe et al. |
| 5,095,054 A | 3/1992 | Lay et al. |
| 5,096,717 A | 3/1992 | Wirth et al. |
| 5,112,384 A | 5/1992 | Miura et al. |
| 5,112,621 A | 5/1992 | Stevens et al. |
| 5,128,142 A | 7/1992 | Mulligan et al. |
| 5,130,140 A | 7/1992 | Urban et al. |
| 5,130,171 A | 7/1992 | Prud'homme et al. |
| 5,133,974 A | 7/1992 | Paradissis et al. |
| 5,158,777 A | 10/1992 | Abramowitz et al. |
| 5,160,737 A | 11/1992 | Friedman et al. |
| 5,160,742 A | 11/1992 | Mazer et al. |
| 5,167,964 A | 12/1992 | Muhammad et al. |
| 5,171,580 A | 12/1992 | Iamartino et al. |
| 5,178,866 A | 1/1993 | Wright et al. |
| 5,186,943 A | 2/1993 | Okada et al. |
| 5,198,228 A | 3/1993 | Urban et al. |
| 5,200,193 A | 4/1993 | Radebaugh et al. |
| 5,202,128 A | 4/1993 | Morella et al. |
| 5,202,159 A | 4/1993 | Chen et al. |
| 5,219,621 A | 6/1993 | Geoghegan et al. |
| 5,229,131 A | 7/1993 | Amidon et al. |
| 5,229,134 A | 7/1993 | Mention et al. |
| 5,233,987 A | 8/1993 | Fabian et al. |
| 5,252,341 A | 10/1993 | Sauerbier et al. |
| 5,262,169 A | 11/1993 | Sauerbier et al. |
| 5,266,331 A | 11/1993 | Oshlack et al. |
| 5,273,760 A | 12/1993 | Oshlack et al. |
| 5,275,824 A | 1/1994 | Carli et al. |
| 5,275,825 A | 1/1994 | Okada et al. |
| 5,286,493 A | 2/1994 | Oshlack et al. |
| 5,288,505 A | 2/1994 | Deboeck et al. |
| 5,310,558 A | 5/1994 | Pozzi et al. |
| 5,316,774 A | 5/1994 | Eury et al. |
| 5,320,853 A | 6/1994 | Noda et al. |
| 5,324,717 A | 6/1994 | Berglindh et al. |
| 5,324,718 A | 6/1994 | Loftsson |
| 5,326,570 A | 7/1994 | Rudnic et al. |
| 5,330,766 A | 7/1994 | Morella et al. |
| 5,334,372 A | 8/1994 | Kawamata et al. |
| 5,342,627 A | 8/1994 | Chopra et al. |
| 5,356,467 A | 10/1994 | Oshlack et al. |
| 5,358,718 A | 10/1994 | Sauerbier et al. |
| 5,368,861 A | 11/1994 | Ushimaru et al. |
| 5,370,878 A | 12/1994 | Shah |
| 5,374,430 A | 12/1994 | Newton et al. |
| 5,374,759 A | 12/1994 | Imperante et al. |
| 5,378,474 A | 1/1995 | Morella et al. |
| 5,384,130 A | 1/1995 | Kamada |
| 5,395,626 A | 3/1995 | Kotwal et al. |
| 5,407,687 A | 4/1995 | Coffin et al. |
| 5,439,689 A | 8/1995 | Hendrickson et al. |
| 5,445,829 A | 8/1995 | Paradissis et al. |
| 5,451,409 A | 9/1995 | Rencher et al. |
| 5,472,708 A | 12/1995 | Chen |

(56) References Cited

U.S. PATENT DOCUMENTS

| | | |
|---|---|---|
| 5,472,711 A | 12/1995 | Baichwal |
| 5,474,786 A | 12/1995 | Kotwal et al. |
| 5,478,573 A | 12/1995 | Eichel et al. |
| 5,489,436 A | 2/1996 | Hoy et al. |
| 5,494,678 A | 2/1996 | Paradissis et al. |
| 5,500,227 A | 3/1996 | Oshlack et al. |
| 5,521,208 A | 5/1996 | York |
| 5,547,878 A | 8/1996 | Kell |
| 5,576,022 A | 11/1996 | Yang et al. |
| 5,580,578 A | 12/1996 | Oshlack et al. |
| 5,597,072 A | 1/1997 | Lieberman et al. |
| 5,639,476 A | 6/1997 | Oshlack et al. |
| 5,643,602 A | 7/1997 | Ulmius |
| 5,652,146 A | 7/1997 | Kell |
| 5,658,590 A | 8/1997 | Heiligenstein et al. |
| 5,661,123 A | 8/1997 | Stalker et al. |
| 5,672,360 A | 9/1997 | Sackler et al. |
| 5,711,967 A | 1/1998 | Juch |
| 5,763,396 A | 6/1998 | Weiner et al. |
| 5,773,031 A | 6/1998 | Shah et al. |
| 5,773,478 A | 6/1998 | Richards et al. |
| 5,785,994 A | 7/1998 | Wong et al. |
| 5,837,284 A | 11/1998 | Mehta et al. |
| 5,840,329 A | 11/1998 | Bai |
| 5,874,090 A | 2/1999 | Baker et al. |
| 5,885,616 A | 3/1999 | Hsiao et al. |
| 5,945,123 A | 8/1999 | Hermelin |
| 6,093,420 A | 7/2000 | Baichwal |
| 6,143,322 A | 11/2000 | Sackler et al. |
| 6,214,379 B1 | 4/2001 | Hermelin |
| 6,228,398 B1 | 5/2001 | Devane et al. |
| 6,255,325 B1 | 7/2001 | Dariani et al. |
| 6,322,819 B1 | 11/2001 | Burnside et al. |
| 6,372,254 B1 | 4/2002 | Ting et al. |
| 6,419,960 B1 | 7/2002 | Krishnamurthy et al. |
| 6,602,887 B2 | 8/2003 | Dariani et al. |
| 6,605,300 B1 | 8/2003 | Burnside et al. |
| 6,627,223 B2 | 9/2003 | Percel et al. |
| 6,632,454 B2 | 10/2003 | Beckert et al. |
| 6,673,367 B1 | 1/2004 | Goldenheim et al. |
| 6,730,325 B2 | 5/2004 | Devane et al. |
| 6,761,904 B2 | 7/2004 | Bertelsen et al. |
| 6,793,936 B2 | 9/2004 | Devane et al. |
| 6,878,387 B1 | 4/2005 | Petereit et al. |
| 6,897,205 B2 | 5/2005 | Beckert et al. |
| 6,902,742 B2 | 6/2005 | Devane et al. |
| 7,048,945 B2 | 5/2006 | Percel et al. |
| 7,070,803 B2 | 7/2006 | Skinhoj et al. |
| 7,083,808 B2 | 8/2006 | Goldenheim et al. |
| 7,195,778 B2 | 3/2007 | Fleshner-Barak et al. |
| 7,247,318 B2 | 7/2007 | Krishnamurthy et al. |
| 7,438,929 B2 | 10/2008 | Beckert et al. |
| 7,438,930 B2 | 10/2008 | Krishnamurthy et al. |
| RE41,148 E | 2/2010 | Burnside et al. |
| RE42,096 E | 2/2011 | Burnside et al. |
| 8,124,653 B2 | 2/2012 | Matalon et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,168,217 B2 | 5/2012 | Yum et al. |
| 8,354,124 B2 | 1/2013 | Yum et al. |
| 8,420,120 B2 | 4/2013 | Yum et al. |
| 8,580,310 B2 | 11/2013 | Krishnamurthy et al. |
| 8,846,100 B2 | 9/2014 | Shojaei et al. |
| 8,911,777 B2 | 12/2014 | Coulter |
| 8,945,614 B2 | 2/2015 | Yum et al. |
| 8,951,556 B2 | 2/2015 | Yum et al. |
| 8,974,821 B2 | 3/2015 | Yum et al. |
| 9,066,869 B2 | 6/2015 | Krishnamurthy et al. |
| 9,107,804 B2 | 8/2015 | Rubino et al. |
| 9,161,918 B2 | 10/2015 | Venkatesh |
| 9,161,919 B2 | 10/2015 | Venkatesh |
| 9,233,160 B2 | 1/2016 | Yum et al. |
| 9,364,430 B2 | 6/2016 | Babul |
| 9,517,271 B2 | 12/2016 | Yum et al. |
| 9,522,119 B2 | 12/2016 | Odidi |
| 9,566,249 B2 | 2/2017 | Venkatesh |
| 9,579,293 B2 | 2/2017 | Venkatesh |
| 9,700,515 B2 | 7/2017 | Odidi |
| 9,700,516 B2 | 7/2017 | Odidi |
| 9,801,823 B2 | 10/2017 | Krishnamurthy et al. |
| 9,801,939 B2 | 10/2017 | Odidi |
| 9,884,022 B2 | 2/2018 | Deshmukh et al. |
| 9,974,752 B2 | 5/2018 | Vargas Rincon et al. |
| 10,111,839 B2* | 10/2018 | Vargas Rincon .... A61K 9/5026 |
| 10,292,939 B2* | 5/2019 | Vargas Rincon .... A61K 9/5036 |
| 10,449,159 B2* | 10/2019 | Vargas Rincon .... A61K 9/5084 |
| 2001/0012847 A1 | 8/2001 | Lam et al. |
| 2001/0055613 A1* | 12/2001 | Burnside ............. A61K 9/5026 |
| | | 424/468 |
| 2002/0034544 A1 | 3/2002 | Skinhoj et al. |
| 2002/0054907 A1 | 5/2002 | Devane et al. |
| 2002/0147232 A1 | 10/2002 | Sundgreen et al. |
| 2002/0192282 A1 | 12/2002 | Beckert et al. |
| 2002/0193445 A1 | 12/2002 | Bertelsen et al. |
| 2003/0054033 A1 | 3/2003 | Krishnamurthy et al. |
| 2003/0124188 A1 | 7/2003 | Burnside et al. |
| 2003/0129237 A1 | 7/2003 | Devane et al. |
| 2003/0153607 A1 | 8/2003 | Glinecke et al. |
| 2003/0170304 A1 | 9/2003 | Devane et al. |
| 2004/0091531 A1 | 5/2004 | Glinecke et al. |
| 2004/0091532 A1 | 5/2004 | Mehta et al. |
| 2004/0131680 A1 | 7/2004 | Goldenheim et al. |
| 2004/0161382 A1 | 8/2004 | Yum et al. |
| 2004/0197405 A1 | 10/2004 | Devane et al. |
| 2004/0219213 A1 | 11/2004 | Burnside et al. |
| 2004/0228802 A1 | 11/2004 | Chang et al. |
| 2005/0089571 A1 | 4/2005 | Beckert et al. |
| 2005/0136111 A1 | 6/2005 | Glinecke et al. |
| 2006/0046008 A1 | 3/2006 | Wildfang |
| 2006/0204576 A1 | 9/2006 | Petereit et al. |
| 2006/0240105 A1 | 10/2006 | Devane et al. |
| 2007/0104789 A1 | 5/2007 | Spector |
| 2007/0264323 A1 | 11/2007 | Shojaei et al. |
| 2007/0264325 A1 | 11/2007 | Krishnamurthy et al. |
| 2007/0281023 A1 | 12/2007 | Glinecke et al. |
| 2008/0069872 A1 | 3/2008 | Rubio Badia et al. |
| 2008/0118556 A1 | 5/2008 | Devane et al. |
| 2008/0193522 A1 | 8/2008 | Meier et al. |
| 2008/0206321 A1 | 8/2008 | Yum et al. |
| 2008/0206324 A1 | 8/2008 | Gryczke et al. |
| 2009/0023689 A1 | 1/2009 | Yum et al. |
| 2009/0023690 A1 | 1/2009 | Yum et al. |
| 2009/0123554 A1 | 5/2009 | Krishnamurthy et al. |
| 2009/0280176 A1 | 11/2009 | Vieira et al. |
| 2009/0297597 A1 | 12/2009 | Liversidge et al. |
| 2009/0297602 A1 | 12/2009 | Devane et al. |
| 2009/0324716 A1 | 12/2009 | Shen et al. |
| 2010/0136106 A1 | 6/2010 | Liversidge et al. |
| 2010/0151010 A1 | 6/2010 | Petereit et al. |
| 2010/0151020 A1 | 6/2010 | Rosenberger et al. |
| 2010/0226978 A1 | 9/2010 | Petereit et al. |
| 2010/0260844 A1* | 10/2010 | Scicinski ............. A61K 9/1617 |
| | | 424/484 |
| 2010/0297221 A1 | 11/2010 | Coulter |
| 2010/0316712 A1 | 12/2010 | Nangia et al. |
| 2011/0064803 A1 | 3/2011 | Devane et al. |
| 2011/0212175 A1 | 9/2011 | Kim et al. |
| 2011/0268799 A1 | 11/2011 | Dixit et al. |
| 2012/0015007 A1 | 1/2012 | Bredenberg et al. |
| 2012/0065221 A1 | 3/2012 | Babul |
| 2012/0128771 A1 | 5/2012 | Venkatesh |
| 2012/0135072 A1 | 5/2012 | Yum et al. |
| 2012/0135073 A1 | 5/2012 | Yum et al. |
| 2012/0178771 A1 | 7/2012 | Babul et al. |
| 2013/0022654 A1 | 1/2013 | Deshmukh et al. |
| 2013/0236554 A1 | 9/2013 | Tengler et al. |
| 2013/0287845 A1 | 10/2013 | Yum et al. |
| 2013/0295168 A1 | 11/2013 | Yum et al. |
| 2014/0099361 A1 | 4/2014 | Krishnamurthy et al. |
| 2014/0120185 A1 | 5/2014 | Hirose et al. |
| 2014/0200237 A1 | 7/2014 | Babul |
| 2014/0212483 A1 | 7/2014 | Lickrish et al. |
| 2014/0255594 A1 | 9/2014 | Rubino et al. |

(56) References Cited

U.S. PATENT DOCUMENTS

| | | |
|---|---|---|
| 2015/0196644 A1 | 7/2015 | Yum et al. |
| 2015/0313850 A1 | 11/2015 | Krishnamurthy et al. |
| 2016/0193345 A1 | 7/2016 | Yum et al. |
| 2016/0215069 A1 | 7/2016 | Stern et al. |
| 2016/0220491 A1 | 8/2016 | Rubino et al. |
| 2017/0000783 A1 | 1/2017 | Devane et al. |
| 2017/0071926 A1 | 3/2017 | Krishnamurthy et al. |
| 2017/0079921 A1 | 3/2017 | Krishnamurthy et al. |
| 2017/0112774 A1 | 4/2017 | Venkatesh |
| 2017/0135999 A1 | 5/2017 | Krishnamurthy et al. |
| 2017/0165255 A1 | 6/2017 | Yum et al. |
| 2017/0258912 A1 | 9/2017 | Odidi |
| 2018/0235895 A1 | 8/2018 | Vargas Rincon et al. |
| 2019/0183808 A1 | 6/2019 | Vargas Rincon et al. |
| 2019/0183809 A1 | 6/2019 | Vargas Rincon et al. |
| 2019/0254981 A1 | 8/2019 | Vargas Rincon et al. |
| 2019/0254982 A1* | 8/2019 | Vargas Rincon .. A61K 31/4458 |
| 2019/0262273 A1 | 8/2019 | Vargas Rincon et al. |
| 2019/0314290 A1* | 10/2019 | Vargas Rincon .... A61K 9/5078 |

FOREIGN PATENT DOCUMENTS

| | | |
|---|---|---|
| CA | 1183665 A | 3/1985 |
| CA | 1297368 C | 3/1992 |
| CA | 2 348 090 A1 | 4/2000 |
| CA | 2 355 644 A1 | 6/2000 |
| CA | 2 368 367 A1 | 10/2000 |
| CA | 2 373 909 A1 | 9/2001 |
| CA | 2 426 883 A1 | 5/2002 |
| CA | 2 502 371 A1 | 5/2004 |
| CA | 2507631 A1 | 6/2004 |
| CA | 2 537 103 A1 | 5/2005 |
| CA | 2 566 497 A1 | 12/2005 |
| CA | 2 683 409 A1 | 10/2008 |
| CA | 2 754 604 A1 | 9/2010 |
| CA | 2 830 788 A1 | 9/2012 |
| CA | 2 877 190 A1 | 1/2014 |
| CA | 2 926 082 A1 | 4/2015 |
| CA | 2 933 587 A1 | 6/2015 |
| EP | 0054010 A1 | 6/1982 |
| EP | 0040590 A3 | 1/1983 |
| EP | 0074584 A2 | 3/1983 |
| EP | 0122077 A2 | 10/1984 |
| EP | 0232690 A1 | 8/1987 |
| EP | 0239361 A1 | 9/1987 |
| EP | 0248548 A2 | 12/1987 |
| EP | 0278174 A2 | 8/1988 |
| EP | 0325086 A2 | 7/1989 |
| EP | 0325843 A2 | 8/1989 |
| EP | 0327295 A2 | 8/1989 |
| EP | 0377517 A3 | 10/1990 |
| EP | 0250374 B1 | 5/1991 |
| EP | 0463877 A1 | 1/1992 |
| EP | 0514814 A1 | 11/1992 |
| EP | 0631781 A1 | 1/1995 |
| GB | 377518 A | 7/1932 |
| GB | 1182124 A | 2/1970 |
| GB | 1245467 A | 9/1971 |
| GB | 2098867 A | 12/1982 |
| GB | 2141342 A | 12/1984 |
| GB | 2159715 A | 12/1985 |
| GB | 2178313 A | 2/1987 |
| GB | 2209280 A | 5/1989 |
| GB | 2253348 A | 9/1992 |
| JP | S55149211 A | 11/1980 |
| JP | H01165518 A | 6/1989 |
| JP | H0291028 A | 3/1990 |
| JP | 2000516610 A | 12/2000 |
| JP | 2016006608 A | 1/2016 |
| WO | WO-8300435 A1 | 2/1983 |
| WO | WO-8500481 A1 | 1/1985 |
| WO | WO-8603676 A1 | 7/1986 |
| WO | WO-8908448 A1 | 9/1989 |
| WO | WO-9221333 A3 | 1/1993 |
| WO | WO-9317673 A1 | 9/1993 |
| WO | WO-9703671 A1 | 2/1997 |
| WO | WO-9703672 A1 | 2/1997 |
| WO | WO-9703673 A1 | 2/1997 |
| WO | WO-9806380 A2 | 2/1998 |
| WO | WO-9814168 A2 | 4/1998 |
| WO | WO-9818454 A1 | 5/1998 |
| WO | WO-9823263 A1 | 6/1998 |
| WO | WO-9848782 A1 | 11/1998 |
| WO | WO-9908662 | 2/1999 |
| WO | WO-9908662 A1 | 2/1999 |
| WO | WO-9962496 A1 | 12/1999 |
| WO | WO-0023055 A1 | 4/2000 |
| WO | WO-0025752 A1 | 5/2000 |
| WO | WO-0028990 A1 | 5/2000 |
| WO | WO-0035426 A2 | 6/2000 |
| WO | WO-0035450 A1 | 6/2000 |
| WO | WO-0168058 A1 | 9/2001 |
| WO | WO-0174334 A1 | 10/2001 |
| WO | WO-0174335 A1 | 10/2001 |
| WO | WO-0188092 A2 | 11/2001 |
| WO | WO-0189473 A1 | 11/2001 |
| WO | WO-0235426 A1 | 5/2002 |
| WO | WO-03000032 A1 | 1/2003 |
| WO | WO-2003080032 | 10/2003 |
| WO | WO-2004054542 A2 | 7/2004 |
| WO | WO-2006078811 A2 | 7/2006 |
| WO | WO-2006132752 A1 | 12/2006 |
| WO | WO-2007011473 A1 | 1/2007 |
| WO | WO-2007037790 A2 | 4/2007 |
| WO | WO-2007070082 A1 | 6/2007 |
| WO | WO-2007093642 A2 | 8/2007 |
| WO | WO-2008079102 A1 | 7/2008 |
| WO | WO-2008083442 A1 | 7/2008 |
| WO | WO-2012080834 A1 | 6/2012 |
| WO | WO-2014174387 A1 | 10/2014 |
| WO | WO 2015/188092 A1 | 12/2015 |

OTHER PUBLICATIONS

Ariens, E.J, "Stereoselectivity in Pharmacodynamics and Pharmacokinetics," Swiss Medical Weekly 120(5):131-134, EMH Swiss Medical Publishers, Switzerland (Feb. 1990).
Biederman, J., et al., "A Double-Blind Placebo Controlled Study of Desipramine in the Treatment of ADD: I. Efficacy," American Academy of Child and Adolescent Psychiatry 28(5):777-784, New York : Elsevier, United States (Sep. 1989).
Biederman, J., et al., "Comorbidity of Attention Deficit Hyperactivity Disorder with Conduct, Depressive, Anxiety, and Other Disorders," American Journal of Psychiatry 148(5):564-577, American Psychiatric Association, United States (May 1991).
Biederman, J., et al., "Patterns of Psychiatric Comorbidity, Cognition, and Psychosocial Functioning in Adults with Attention Deficit Hyperactivity Disorder," American Journal of Psychiatry 150(12):1792-1798, American Psychiatric Association, United States (Dec. 1993).
Birmaher, B., et al., "Sustained Release Methylphenidate: Pharmacokinetic Studies in ADDH Males," American Academy of Child and Adolescent Psychiatry 28(5):768- 772, New York : Elsevier, United States (Sep. 1989).
Castle, W.E., et al., "Linkage Studies of the Rat (*Rattus norvegicus*)," Proceedings of the National Academy of Sciences 27(8):394-398, National Academy of Sciences, United States (Aug. 1941).
Catapres (Cionidine). Physicians' Desk Reference, 48th Edition. ed. Montvale, NJ: Thomson Healthcare, 1994, pp. 612-614.
Child, A.H., et al., "Joint Hypermobility Syndrome: Inherited Disorder of Collagen Synthesis," Rheumatology 13(2):239-243, Journal Of Rheumatology Publishing Co, Canada (1986).
Chouinard, G., et al., "An Early Phase II Clinical Trial of Tomoxetine (LY139603) in the Treatment of Newly Admitted Depressed Patients," Psychopharmacology (Berl) 83(1):126-128, New York, Springer-Verlag, Germany (1984).
Chouinard, G., et al., "An Early Phase II Clinical Trial with Followup of Tomoxetine (LY139603) in the Treatment of Newly Admitted Depressed Patients," Psychopharmacology Bulletin 21(1):73-76, Redondo Beach, CA : MedWorks Media, United States (1985).
Chumpradit, S., et al., "Iodinated Tomoxetine Derivatives as Selective Ligands for Serotonin and Norepinephrine Uptake Sites,"

(56) References Cited

OTHER PUBLICATIONS

Medicinal Chemistry 35(23):4492-4497, Washington Dc : American Chemical Society, United States (Nov. 1992).
Corrigan, O.I., et al., "The Biopharmaceutic Drug Classification and Drugs Administered in Extended Release (ER) Formulations," Advances in Experimental Medicine and Biology 423:111-128, Kluwer Academic/Plenum Publishers, United States (1997).
Covera-HS, Physicians' Desk Reference. 51st Edition, Montvale, NJ: Thomson Healthcare, 1997, pp. 2573-2576.
Cusack, B., et al., "Binding of Antidepressants to Human Brain Receptors: Focus on Newer Generation Compounds," Psychopharmacology 114(4):559-565, Springer-Verlag, Germany (May 1994).
Danielsson, A., et al., "A Controlled Randomized Trial of Budesonide Versus Prednisolone Retention Enemas in Active Distal Ulcerative Colitis," Scandinavian Journal of Gastroenterology 22(8):987-992, Informa Healthcare, England (Oct. 1987).
De Haan, P., et al., "Oral Controlled Release Dosage Forms. A Review," Pharmaceutisch Weekblad 6(2):57-67, Bohn, Scheltema En Holkema, Netherlands (Apr. 1984).
De Scalzi, M., et al., "Circadian Rhythms of Arterial Blood Pressure," Chronobiologia 13(3):239-244, Associated Chronobiologia Researchers, Italy (Jul.-Sep. 1986).
Depakote Tablets, Physicians' Desk Reference. 51st Edition, Montvale, NJ: Thomson Healthcare, 1997, pp. 418-422.
Drimmer, E.J., et al., "Desipramine and Methylphenidate Combination Treatment for Depression: Case Report," American Journal of Psychiatry 140(2):241-242, American Psychiatric Association, United States (Feb. 1983).
Eckerman, D.A., et al., "Enantioselective Behavioral Effects of Threo-Methylphenidate In Rats," Pharmacology Biochemistry and Behavio 40(4):875-880, NY : Elsevier, United States (Dec. 1991).
Elavil (Amitriptyline), Physicians' Desk Reference, 47th Edition, Montvale, NJ: Thomson Healthcare, 1993, pp. 2372-2374.
Erramouspe, J., et al., "Effect on Dissolution from Halving Methylphenidate Extended-Release Tablets," Annals of Pharmacotherapy 31(10):1123-1126, Thousand Oaks, CA : Sage, United States (Oct. 1997).
Farid, N.A., et al., "Single-Dose and Steady-State Pharmacokinetics of Tomoxetine in Normal Subjects," Clinical Pharmacology 25(4):296-301, Oxford : Wiley, England (May-Jun. 1985).
Fuller, R.W., et al., "Antagonism By Tomoxetine of the Depletion of Norepinephrine and Epinephrine In Rat Brain By Alpha-Methyl-M-Tyrosine," Research Communications in Chemical Pathology and Pharmacology 41(1):169-172, P. J. D. Publications, United States (Jul. 1983) ).
Fuller, R.W., et al., "Effects of Duloxetine, an Antidepressant Drug Candidate, On Concentrations of Monoamines and Their Metabolites in Rats and Mice," Journal of Pharmacology and Experimental Therapeutics 269(1):132-136, American Society for Pharmacology and Experimental Therapeutics, United States (Apr. 1994).
Fuller, R.W., et al., "Serotonin Reuptake Blockers in Vitro and In Vivo," Clinical Psychopharmacology 7(6 Suppl):36S-43S, Williams And Wilkins, United States (Dec. 1987).
Gamstedt, A., et al., "Effect of Betamethasone Treatment on Iodothyronines and Thyroid Hormone-Binding Proteins During controlled nutrition. A study on patients with chronic inflammatory bowel disease," Acta Endocrinol (Copenh) 103(2):188-191, Periodica, Denmark (Jun. 1983).
Gehlert, D.R., et al., "Localization of Rat Brain Binding Sites for [3H]Tomoxetine, An Enantiomerically Pure Ligand for Norepinephrine Reuptake Sites," Neuroscience Letters 157(2):203-206, Elsevier Scientific Publishers Ireland, Ireland (Jul. 1993) ).
Gilman, V., et al., "The Top Pharmaceuticals that Changed the World: Ritalin," Chemical & Engineering News 83:25, (2005).
Green, W.H., et al., "Nonstimulant Drugs in the Treatment of Attention Deficit Hyperactivity Disorder," Child and adolescent psychiatric clinics of North America 1:449-465, (1992).
Grob, C.S., et al., "Suspected Adverse Methylphenidate-Imipramine Interactions in Children," Developmental & Behavioral Pediatrics 7(4):265-267, Lippincott Williams.& Wilkins, United States (Aug. 1986).
Helle Bechgaard, "Critical Factors Influencing Gastrointestinal Absorption—What is the Role of Pellets?," Acta Pharmaceutica Technologica 28 (2):149-157, (1982).
International Search Report and Written Opinion for Application No. PCT/US2015/34466 dated Aug. 26, 2015.
Jewell D.P, "Corticosteroids for the Management of Ulcerative Colitis and Crohn's Disease," Gastroenterology Clinics of North America 18(1):21-34, Elsevier Health Science Division, United States (Mar. 1989).
Johanson, C.E., et al., "The Discriminative Stimulus Effects of Cocaine in Pigeons," Pharmacology and Experimental Therapeutics 267(1):1-8, American Society for Pharmacology and Experimental Therapeutics, United States (Oct. 1993).
Johansson, S.A., et al., "Topical and Systemic Glucocorticoid Potencies of Budesonide, Beclomethasone Dipropionate and Prednisolone in Man," European journal of respiratory diseases. Supplement 122:74-82, Munksgaard International Publishers, Denmark (1982).
Kapseals Dilantin, Physicians' Desk Reference. 51st Edition, Montvale, NJ: Thomson Healthcare, 1997, pp. 1965-1970.
Keshavarzian, A., et al., "MPTP-Induced Duodenal Ulcers in Rat. Prevention by Reuptake Blockers for Serotonin and Norepinephrine, but Not Dopamine," Gastroenterology 98(3):554-560, W.B. Saunders, United States (1990).
Khutoryanskiy, V.V., "Supramolecular Materials: Longer and Safer Gastric Residence," Nature Materials 14(10): 963-964, London, Nature Pub. Group, United Kingdom (2015).
Krasznai, A., et al., "Decreased Number of Steroid Receptors of Circulating Lymphocytes in Crohn's Disease and Ulcerative Colitis," Haematologia (Budapest) 19(4):299-301, Utrecht : Vsp, Netherlands (1986).
Kumana, C.R., et al., "Beclomethasone Dipropionate Enemas for Treating Inflammatory Bowel Disease without Producing Cushing's Syndrome Or Hypothalamic Pituitary Adrenal Suppression," Lancet 1(8272):579-583, London : Elsevier, England (Mar. 1982).
Lehmann., et al., Practical Course in Lacquer Coating. N.p.:K. Lehmann, 1989.
Levine, D.S., et al., "Coating of Oral Beclomethasone Dipropionate Capsules with Cellulose Acetate Phthalate Enhances Delivery of Topically Active Antiinflammatory Drug to the Terminal Ileum," Gastroenterology 92(4):1037-1044, W.B. Saunders, United States (Apr. 1987).
Licamele, W.L., et al., "The Concurrent Use of Lithium and Methylphenidate in a Child," American Academy of Child and Adolescent Psychiatry 28(5):785-787, New York : Elsevier, United States (Sep. 1989).
Ismo, Physicians' Desk Reference, 51st Edition, Montvale, NJ: Thomson Healthcare, 1997, pp. 2844-2845.
Malchow, H., et al., "Therapy of Crohn's disease," Deutsche Medizinische Wochenschrift 109(47):1811-1816, Thieme, Germany (Nov. 1984).
Manley, R.H., et al., "Binary Solvents for Zein," Industrial & Engineering Chemistry 35(6):661-665, (1943).
McGinity, Aqueous Polymeric Coatings for Pharmaceutical Dosage Forms, Second Edition, pp. 124-125, 272-273, 280-285.
Medical Economics Company. "Anafranil (Clomipramine)" Physicians' Desk Reference. 47th Edition, Montvale, NJ: Thomson Healthcare, 1993, pp. 671-675.
Munday, D.L., et al., "Changes in Drug Release Rate: Effect of Stress Storage Conditions on Film Coated Mini-Tablets," Drug Development and Industrial Pharmacy 17(15):2135-2143, (1991).
Norpramin (Desipramine), Physicians' Desk Reference. 47th Edition, Montvale, NJ:.Thomson Healthcare, 1993, pp. 1389-1390.
Oberlender, R., et al., "Tomoxetine and the Stereo selectivity of Drug Action," Pharmacy and Pharmacology 39(12):1055-1066, Pharmaceutical Society of Great Britain, England (Dec. 1987).
Pamelor (Nortriptyline), Physicians' Desk Reference. 47th Edition, Montvale, NJ: Thomson Healthcare, 1993, pp. 2115-2116.

(56) References Cited

OTHER PUBLICATIONS

Patrick, K.S., et al., "Pharmacology of the Enantiomers of Threo-Methylphenidate," Journal of Pharmacology and Experimental Therapeutics 241(1):152-158, American Society for Pharmacology and Experimental Therapeutics, United States (Apr. 1987).
Patrick, K.S., et al., "The Absorption of Sustained-Release Methylphenidate Formulations Compared To an Immediate-Release Formulation," Biopharmaceutics & Drug Disposition 10(2):165-171, Wiley, England (Mar.-Apr. 1989).
Pelham, W.E., et al., "Relative Efficacy of Long-Acting Stimulants on Children with Attention Deficit-Hyperactivity Disorder: A Comparison of Standard Methylphenidate, Sustained-Release Methylphenidate, Sustained-Release Dextroamphetamine, and Pemoline," Pediatrics 86(2):226-237, American Academy of Pediatrics, United States (Aug. 1990).
Product Monograph Biphentin, prepared on Mar. 8, 2006, and revised on Jul. 27, 2007.
Prozac (Fluoxetine), Physicians' Desk Reference, 48th Edition, Montvale, NJ: Thomson Healthcare, 1994, pp. 877-880.
Purdue Pharma. "Biphentin" ,package insert, Pickering, ON, 2012.
Quinn, D., et al., "Single-Dose Pharmacokinetics of Multilayer-Release Methylphenidate and Immediate-Release Methylphenidate in Children with Attention-Deficit/Hyperactivity Disorder," Clinical Pharmacology 47(6):760-766, Wiley, England, (Jun. 2007).
Rapport, M.D., et al., "Methylphenidate and Desipramine In Hospitalized Children: i. Separate and Combined Effects On Cognitive Function," American Academy of Child and Adolescent Psychiatry 32(2):333-342, New York : Elsevier, United States (Mar. 1993).
Remington: The Science and Practice of Pharmacy, pp. 1585-1593, 1980.
Ritalin S.R. Physicians' Desk Reference. 46th Edition, Montvale, NJ: Thomson Healthcare, 1992, pp. 880-881.
Ryan, N.D, "Heterocyclic Antidepressants in Children and Adolescents," Child and Adolescent Psychopharmacology 1(1):21-31, (1990).
Sinemet, Physicians' Desk Reference, 51st Edition, 1997, pp. 959-963.
Spencer, T., et al., "Nortriptyline Treatment of Children with Attention-Deficit Hyperactivity Disorder and Tic Disorder or Tourette's Syndrome," American Academy of Child and Adolescent Psychiatry 32(1):205-210, New York : Elsevier, United States (Jan. 1993).
Springer, J.P., et al., "Facilitatory and Inhibitory Effects of Selective Norepinephrine Reuptake Inhibitors on Hypogastric Nerve-Evoked Urethral Contractions in the Cat: A Prominent Role of Urethral Beta-Adrenergic Receptors," Journal of Urology 152(2 Pt 1):515-519, New York : Elsevier, United States (Aug. 1994).
Steele, M., et al., "A Randomized, Controlled Effectiveness Trial of OROS-Methylphenidate Compared to Usual Care with Immediate-Release Methylphenidate in Attention Deficit-Hyperactivity Disorder," Clinical Pharmacology 13(1): e50-e62, Pulsus Group [for the] Canadian Society for Clinical Pharmacology, (Winter 2006).
Steinberg, S., et al., "A Case of Mania Associated with Tomoxetine," American.Journal of Psychiatry 142(12):1517-1518, (Dec. 1985).
Swallen, L.C., et al., "Zein. A new industrial protein," Industrial and Engineering Chemistry 33(3):394-397, (1941).
Swanson, J.M., et al., "The Use of a Laboratory School Protocol to Evaluate Concepts about Efficacy and Side Effects of New Formulations of Stimulant Medications," Attention Disorders 6 Suppl 1:S73-S88, Thousand Oaks : SAGE Publications, United States (2002).
Terry, P., et al., "Pharmacological Characterization of the Novel Discriminative Stimulus Effects of a Low Dose of Cocaine," Pharmacology and Experimental Therapeutics 270(3):1041-1048, American Society for Pharmacology and Experimental Therapeutics, United States (Sep. 1994).
Thomas, P., et al., "Absorption of Delayed-Release Prednisolone in Ulcerative Colitis and Crohn's Disease," Pharmacy and Pharmacology 37(10):757-758, Wiley, England (Oct. 1985).
Thorazine (Chlorpromazine), Physicians' Desk Reference. 47th Edition, Montvale, NJ: Thomson Healthcare, 1993. pp. 2327-2330.

Tofranil (Imipramine), Physicians' Desk Reference. 47th Edition, Montvale, NJ: Thomson Healthcare, 1993, pp. 1070-1074.
Tyndale, R.F., et al., "Neuronal Cytochrome P45011D1 (debrisoquinelsparteine-Type): Potent Inhibition of Activity by (−)-Cocaine and Nucleotide Sequence Identity to Human Hepatic P450 Gene CYP2D6," Molecular pharmacology 40(1):63-68, American Society for Pharmacology and Experimental Therapeutics, United States (Jul. 1991).
United States Pharmacopeia Convention. "<2040> Disintegration and Dissolution of Nutritional Supplements." United States Pharmacopeia & National Formulary. USP23INF18 vol. Rockville, MD: United States Pharmacopeial Convention, Inc., 1995. 2184-5, 2577-8, 2833-4, 3794-5.
United States Pharmacopeia Convention. "<711> Dissolution." United States Pharmacopeia & National Formulary. USP23INF18 vol. Rockville, MD: United States Pharmacopeial Convention, Inc., 1995. 1791-4, 2185, 2577-8, 2833-4, 3208-9, 3794-5.
United States Pharmacopeia Convention. "<724> Drug Release." United States Pharmacopeia & National Formulary. USP23INF18 vol. Rockville, MD: United States Pharmacopeial Convention, Inc., 1995. 1793-9, 2534-6, 2709-15, 3012-7, 3209-15, 3468-74.
Vitiello, B., et al., "Methylphenidate Dosage for Children with ADHD Over Time Under Controlled Conditions: Lessons From the MTA," American Academy of Child and Adolescent Psychiatry 40(2):188-196, New York : Elsevier, United States (Feb. 2001).
Wellbutrin (Bupropion), Physicians' Desk Reference, 47th Edition, Montvale, NJ: Thomson Healthcare, 1993, pp. 842-844.
Wilens, T.E., et al., "Nortriptyline in the Treatment of Adhd: A Chart Review of 58 Cases," American Academy of Child & Adolescent Psychiatry 32(2):343-349, New York : Elsevier, United States (Mar. 1993).
Wolman, S.L., et al., "Use of Oral Budesonide in a Patient with Small Bowel Crohn's Disease and Previous Pseudotumor Cerebri Secondary to Steroids," Scandinavian Journal of Gastroenterology 24 Suppl 158:146-147, (1989).
Wong, D.T., et al., "A New Inhibitor of Norepinephrine Uptake Devoid of Affinity for Receptors in Rat Brain," Pharmacology and Experimental Therapeutics 222(1):61-65, Williams & Wilkins, United States (Jul. 1982).
Wong, D.T., et al., "LY248686, a New Inhibitor of Serotonin and Norepinephrine Uptake," Neuropsychopharmacology 8(1):23-33, London : Nature Publishing Group, England (Jan. 1993).
Wong, D.T., et al., "The Comparison of Fluoxetine and Nisoxetine with Tricyclic Antidepressants in Blocking the Neurotoxicity of P-Chloroamphetamine and 6-Hydroxydopamine in the Rat Brain," Research Communications in Chemical Pathology and Pharmacology 15(2):221-231, P. J. D. Publications, United States (Oct. 1976).
Zerbe, R.L., et al., "Clinical Pharmacology of Tomoxetine, a Potential Antidepressant," Pharmacology and Experimental Therapeutics 232(1):139-143, American Society for Pharmacology and Experimental Therapeutics, United States (Jan. 1985).
Zhang, L., et al., "Imipramine as a Discriminative Stimulus," Pharmacology and Experimental Therapeutics 259(3):1088-1093, American Society for Pharmacology and Experimental Therapeutics, United States (Dec. 1991).
*Rhodes Pharmaceuticals L.P.* vs. *Actavis, Inc., Actavis Elizabeth LLC, Actavis LLC, and Allergan PLC*, Defendants' Preliminary Invalidity Contentions for U.S. Pat. Nos. 6,419,960, 7,083,808, 7,438,930, 7,247,318, 8,580,310, and 9,066,869, Civil Action No. 16-1668 (WHW)(CLW), Oct. 7, 2016. 229 pages.
Co-pending U.S. Appl. No. 16/120,900, inventors Rincon, V., et al., filed Sep. 4, 2018 (Not Published).
Co-pending U.S. Appl. No. 16/120,999, inventors Rincon, V., et al., filed Sep. 4, 2018 (Not Published).
Co-pending U.S. Appl. No. 16/185,730, inventors Rincon, V., et al., filed Nov. 9, 2018 (Not Published).
Coghill, D., et al., "Long-acting methylphenidate formulations in the treatment of attention-deficit/hyperactivity disorder: a systematic review of head-to-head studies," BMC Psychiatry 13: 1-24, Springer Nature, United Kingdom (2013).
Office Action dated Feb. 1, 2019, in U.S. Appl. No. 16/185,730, Vargas Rincon et al., filed Nov. 9, 2018, 13 pages.

(56) References Cited

OTHER PUBLICATIONS

Office Action dated Apr. 4, 2019, in U.S. Appl. No. 16/282,858, Vargas Rincon et al., filed Feb. 22, 2019, 10 pages.
Office Action dated Apr. 4, 2019, in U.S. Appl. No. 16/282,876, Vargas Rincon et al., filed Feb. 22, 2019, 8 pages.
Office Action dated May 31, 2019, in U.S. Appl. No. 16/399,580, inventor Vargas Rincon, R.A., et al., filed Apr. 30, 2019, 9 pages.
Office Action dated Jun. 13, 2019, in U.S. Appl. No. 16/195,418, Donnelly, G., et al., filed Nov. 19, 2008, 7 pages.
Office Action dated Jun. 14, 2019, in U.S. Appl. No. 16/399,574, inventor Vargas Rincon, R.A., et al., filed Apr. 30, 2019, 12 pages.
Office Action dated Jul. 22, 2019, in U.S. Appl. No. 16/422,177, inventor Vargas Rincon, R.A., et al., filed May 24, 2019, 14 pages.
Office Action dated Aug. 19, 2019, in U.S. Appl. No. 16/399,571, inventor Vargas Rincon, R.A., et al., filed Apr. 30, 2019, 18 pages.
Office Action dated Oct. 11, 2018, in U.S. Appl. No. 16/120,999, inventor Vargas Rincon, R.A., et al., filed Sep. 4, 2018, 18 pages.
Office Action dated Dec. 4, 2018, in U.S. Appl. No. 16/120,900, inventor Vargas Rincon, R.A., et al., filed Sep. 4, 2018, 7 pages.
U.S. Appl. No. 16/422,177, inventor Rincon, V., et al., filed May 24, 2019 (Not Published).

\* cited by examiner

Figure 1: Results of PK Study 063-001
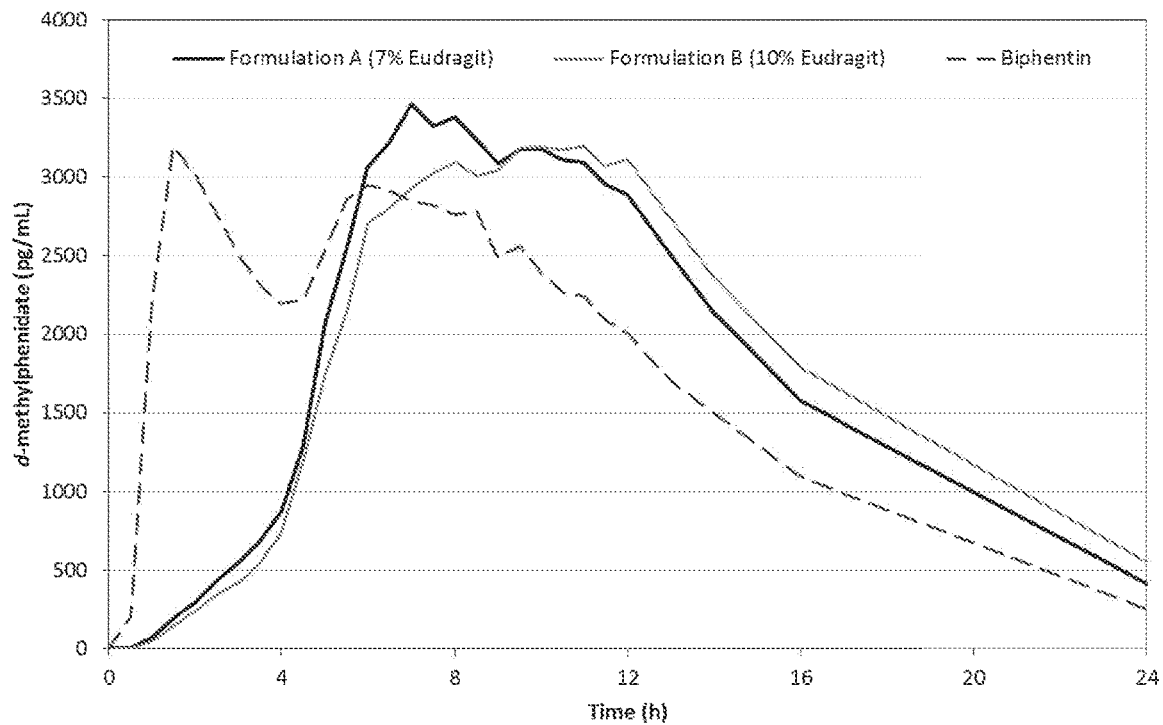
Figure 2: Results of PK Study 063-002
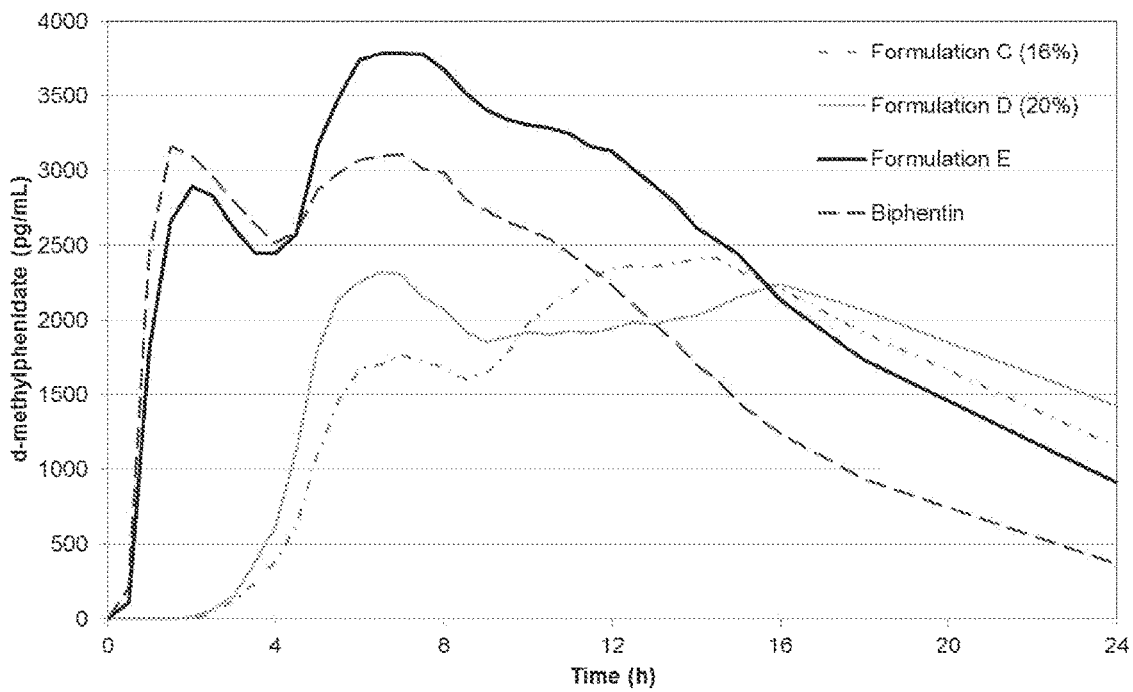

Figure 3: Results of PK Study 063-003
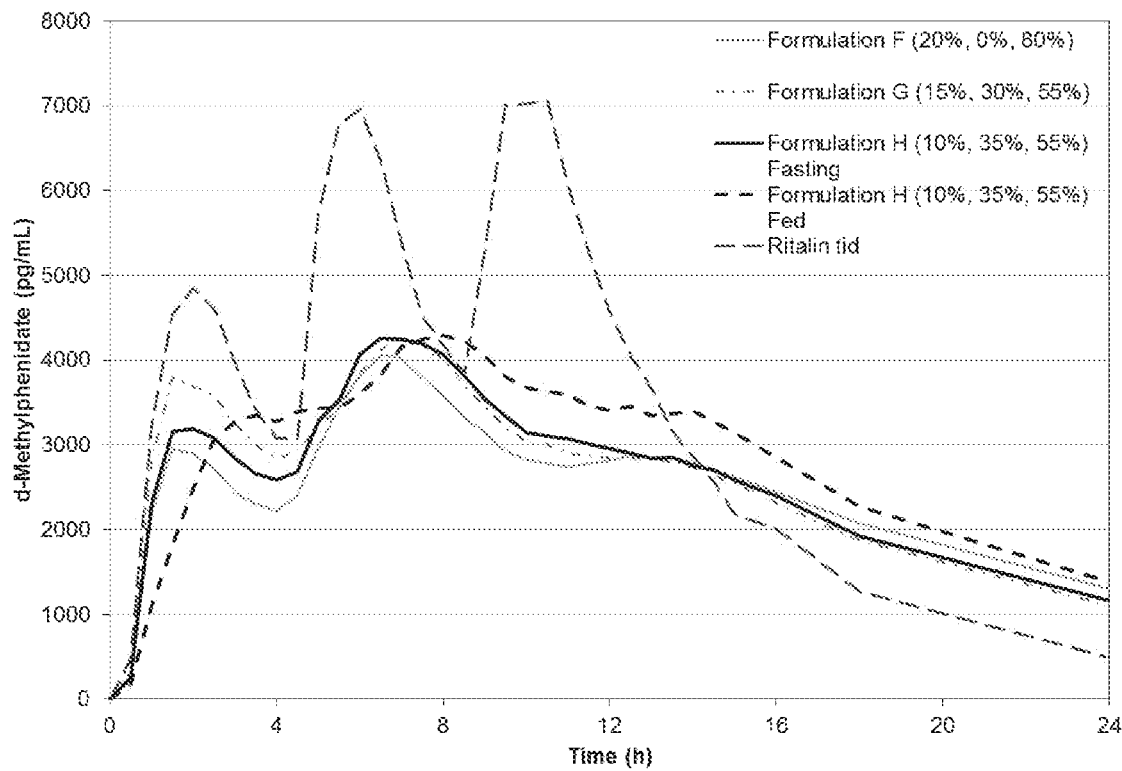
Figure 4: Results of PK Study 063-005 Formulation I (100 mg)
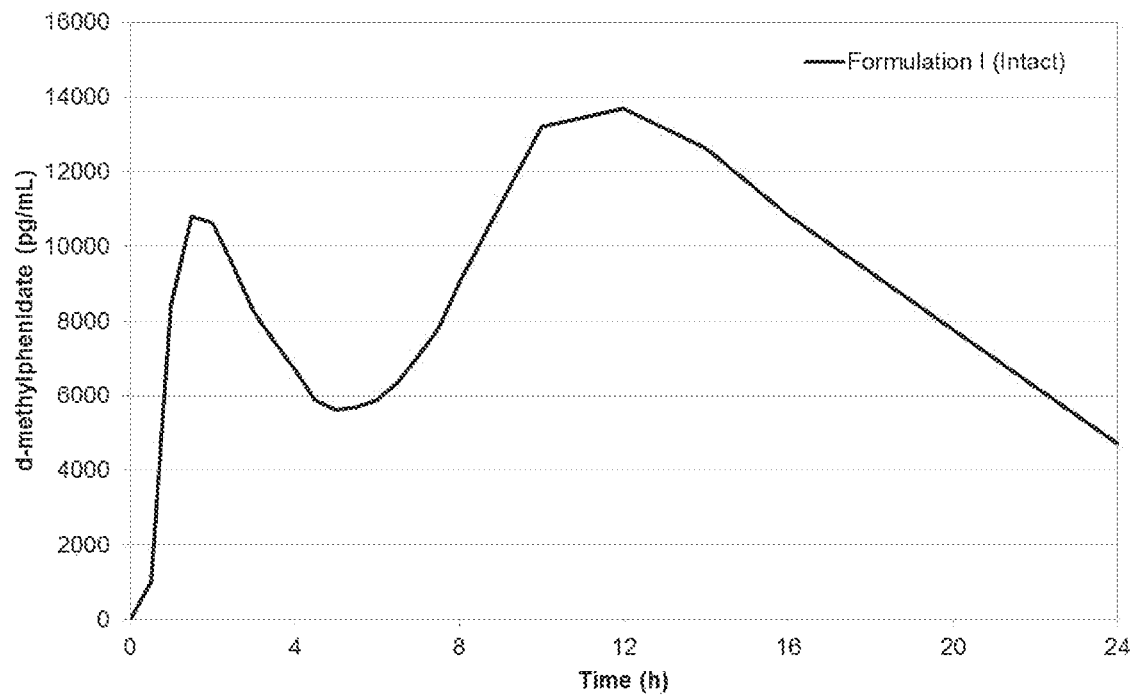

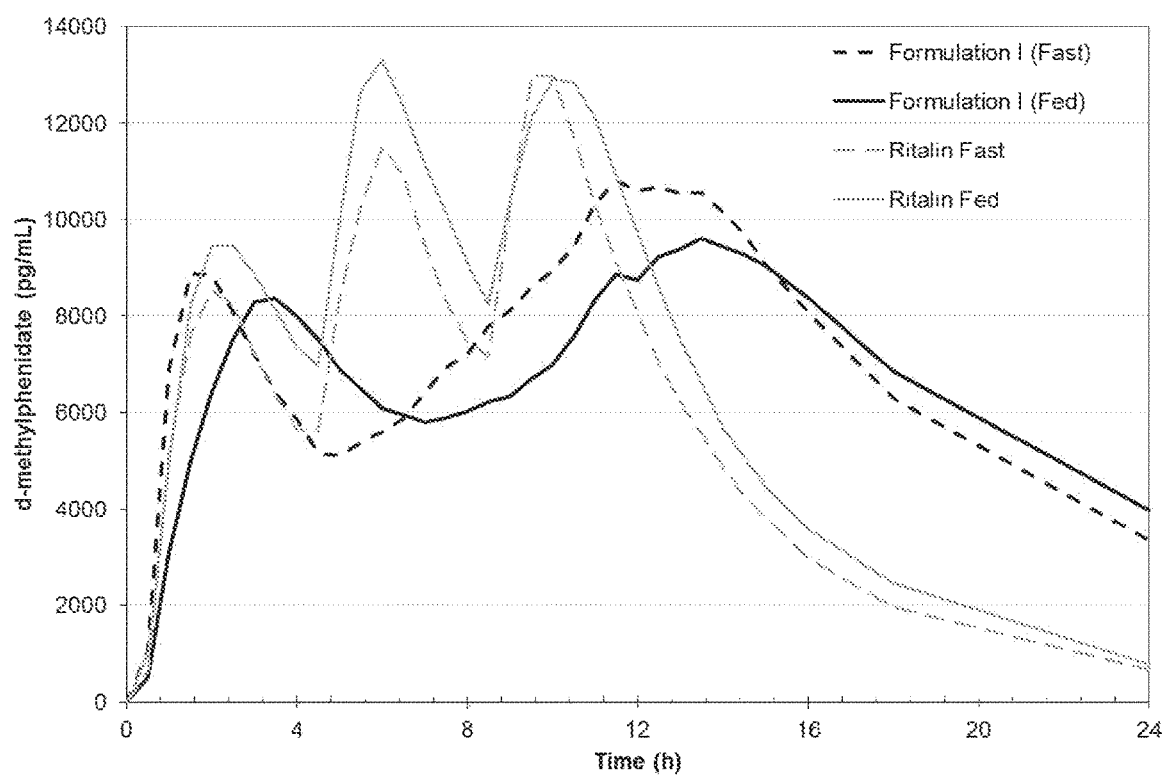
Figure 5: Results of PK Study 063-004 (Formulation I 100 mg vs Ritalin 60 mg)

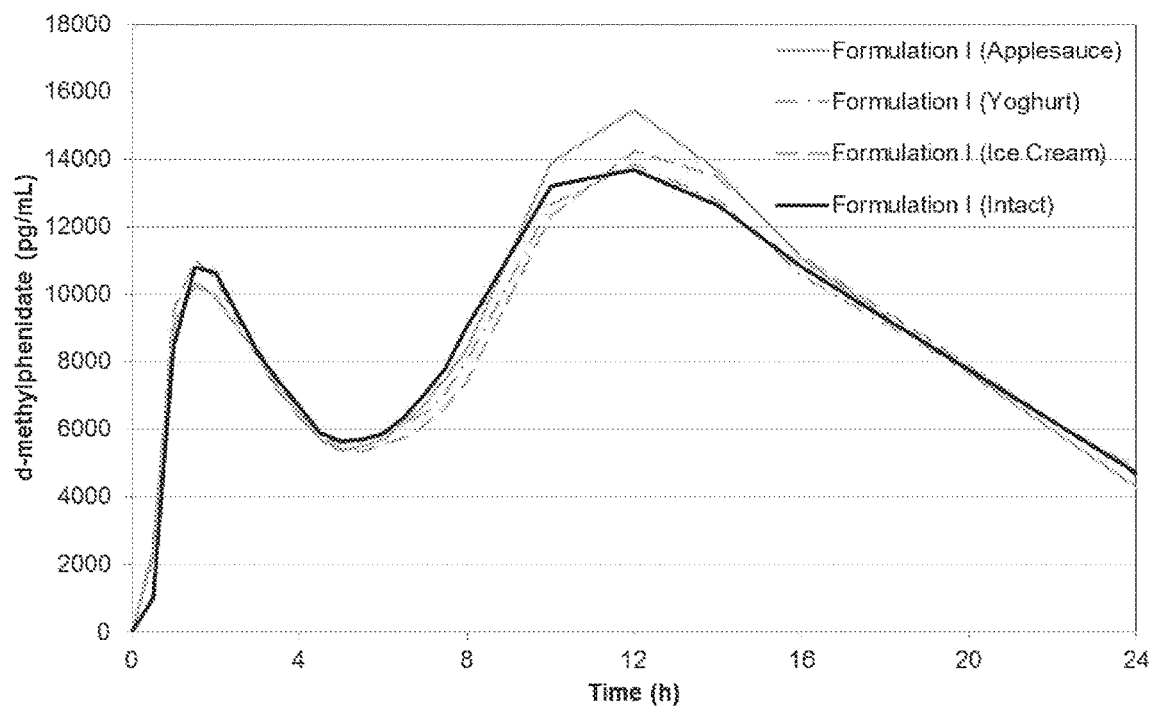
Figure 6: Results of PK Study 063-005 Sprinkle Comparison of Formulation I 100 mg

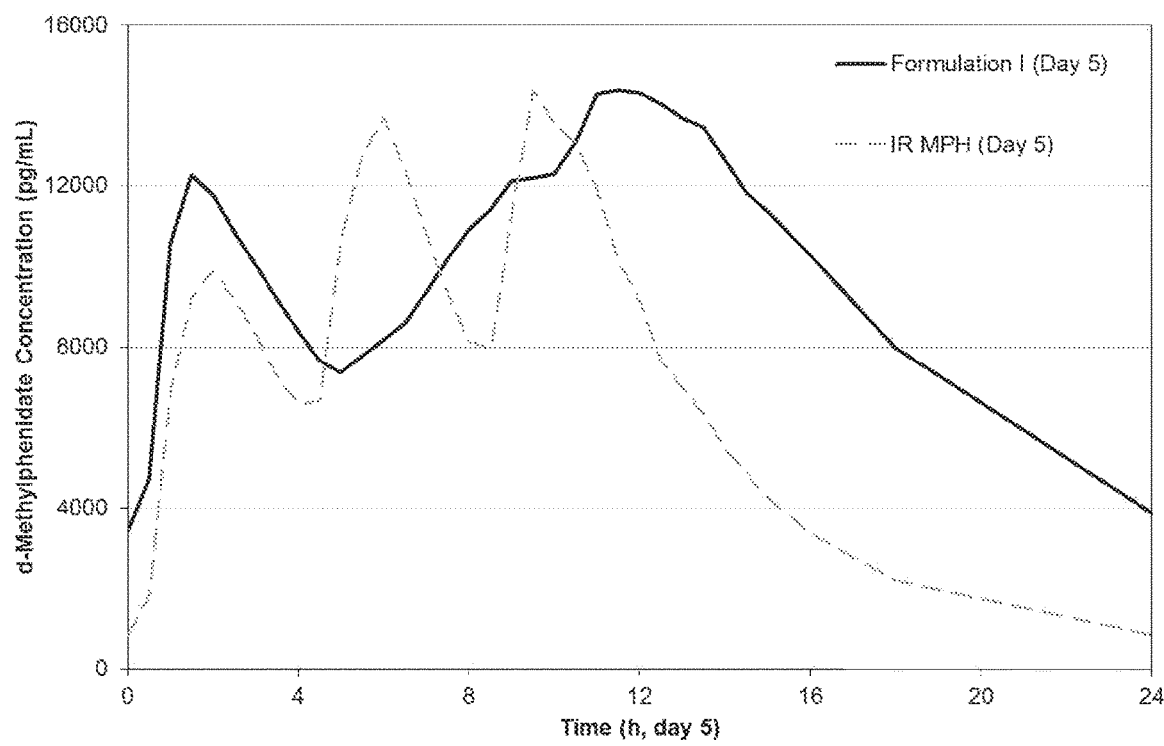
Figure 7: Results of PK Study 063-007 (Formulation I 100 mg vs Ritalin 60 mg)

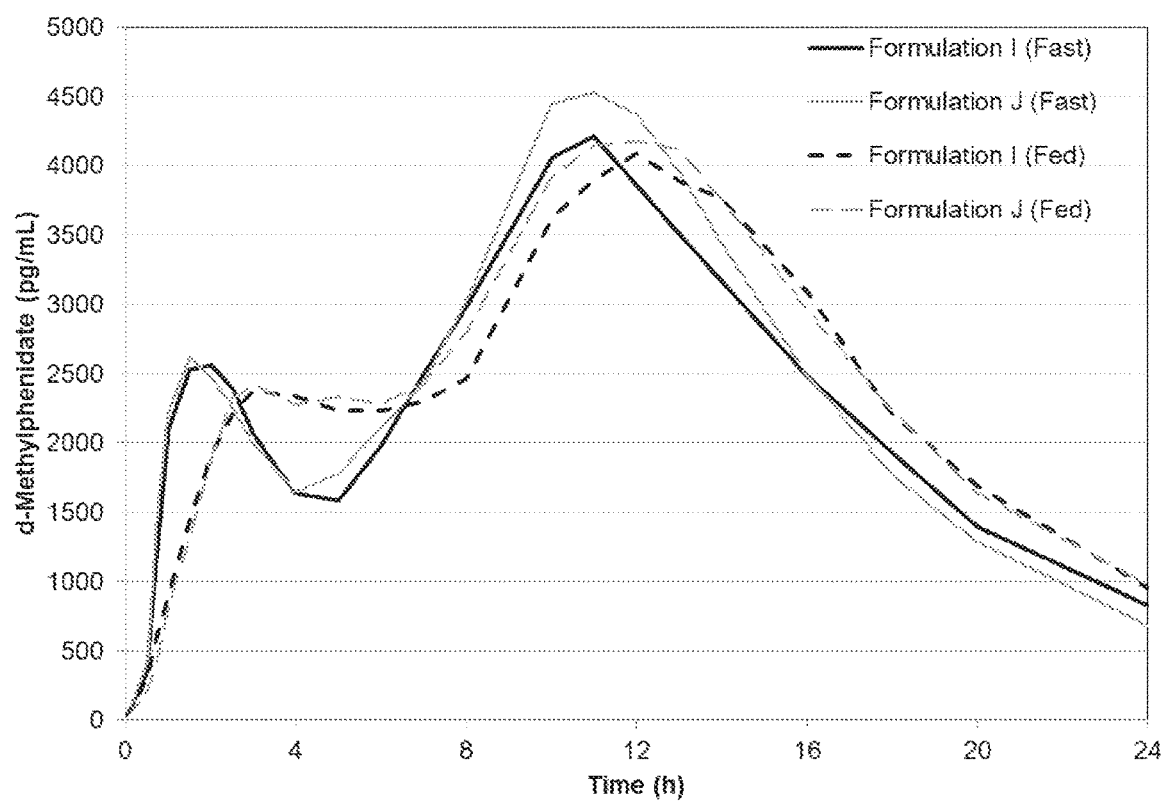
Figure 8: Results of PK Study 063-011 (Smaller Bead Formulation J)

Figure 11

| Ingredient | Strength (label claim) 20 mg | | | | Strength (label claim) 20 mg | | | |
|---|---|---|---|---|---|---|---|---|
| | Formulation A – 7% 063-001 DRCRIR bead | | Formulation B – 10% 063-001 DRCRIR bead | | Formulation C – 16% 063-002 DRCRIR bead | | Formulation D – 20% 063-002 DRCRIR bead | |
| | Quantity per unit | % | Quantity per unit | % | Quantity per unit | % | Quantity per unit | % |
| Methylphendate HCl, USP | 20.0 | 11.25 | 20.0 | 10.88 | 20.0 | 10.19 | 20.0 | 9.79 |
| Sugar spheres 14/18 mesh, USP/NF | 107.0 | 60.2 | 107.0 | 58.2 | 107.0 | 54.5 | 106.8 | 52.3 |
| Opadry Clear YS-1-7006, USP | 6.4 | 3.6 | 6.4 | 3.5 | 6.5 | 3.3 | 6.4 | 3.1 |
| Ammonio methacrylate copolymer dispersion, Type B, 30% dispersion (Eudragit RS30D Solids), NF | 9.4 | 5.26 | 13.3 | 7.24 | 21.3 | 10.86 | 26.7 | 13.05 |
| Triethyl Citrate, USP/NF | 1.4 | 0.80 | 2.0 | 1.10 | 3.3 | 1.67 | 4.1 | 2.00 |
| Glyceryl monostearate emulsion (Plasacryl T20), HS | 3.8 | 2.18 | 4.3 | 2.37 | 5.3 | 2.74 | 6.0 | 2.94 |
| Silicon dioxide, (Syloid 244FP), NF | 0.7 | 0.4 | 0.7 | 0.4 | 0.8 | 0.4 | 0.8 | 0.4 |
| Eudragit FS30D Liquid, HS | 29.0 | 16.32 | 30.0 | 16.32 | 32.0 | 16.32 | 33.3 | 16.32 |
| Total weigh in capsule (mg) | ~178 | ~100 | ~184 | ~100 | ~196 | ~100 | ~204 | ~100 |

Figure 12

| Ingredient | Strength (label claim) 30 mg | Strength (label claim) 30 mg |
|---|---|---|
| | Formulation E – 70:30 063-002 ECCRIR bead (70%) + DRCRIR bead (30%) | Formulation F – 80:20 063-003 DRCRIR bead (80%) + IR bead (20%) |
| | Quantity per unit (%) | Quantity per unit (%) |
| 1. IR bead | IR bead (0%) | IR bead (20%) |
| Methylphenidate HCl, USP | - | 15.0 |
| Sugar spheres 14/18 mesh, USP/NF | - | 80.2 |
| Opadry Clear YS-1-7006, USP | - | 4.8 |
| Total IR bead | - | ~100% |
| 7. CR/EC/IR bead | ECCRIR bead (70%) | ECCRIR bead (0%) |
| Methylphenidate HCl, USP | 12.78 | - |
| Sugar spheres 14/18 mesh, USP/NF | 62.02 | - |
| Opadry Clear YS-1-7006, USP | 4.04 | - |
| Ammonio methacrylate copolymer dispersion, Type B, 30% dispersion (Eudragit RS30D Solids), NF | 5.44 | - |
| Methacrylic Acid copolymer dispersion, 30% dispersion (Eudragit L30 D-55 solids), USP NF | 8.15 | - |
| Triethyl Citrate, USP/NF | 2.70 | - |
| Talc Ph.Eur/USP | 4.87 | - |
| Total CR/EC/IR bead | ~100% | ~100% |
| 6. CR/DR bead | DRCRIR bead (30%) | DRCRIR bead (80%) |
| Methylphenidate HCl, USP | 10.19 | 10.19 |
| Sugar spheres 14/18 mesh, USP/NF | 54.5 | 54.5 |
| Opadry Clear YS-1-7006, USP | 3.3 | 3.3 |
| Ammonio methacrylate copolymer dispersion, Type B, 30% dispersion (Eudragit RS30D Solids), NF | 10.86 | 10.86 |
| Triethyl Citrate, USP/NF | 1.67 | 1.67 |
| Glyceryl monostearate emulsion (Plasacryl T20), HS | 2.74 | 2.74 |
| Silicon dioxide, (Syloid 244FP), NF | 0.4 | 0.4 |
| Eudragit FS30D Liquid, HS | 16.32 | 16.32 |
| Total CR/DR bead (30%) | ~100% | ~100% |
| Total weight in capsule | ~211 mg | ~275 mg |

Figure 13

| Ingredient | Strength (label claim) 30 mg | Strength (label claim) 30 mg |
|---|---|---|
| | Formulation G – 30:55:15 063-003<br>ECCRIR bead (30%) + DRCRIR bead (55%) + IR bead (15%) | Formulation H – 35:55:10 063-003<br>ECCRIR bead (35%) + DRCRIR bead (55%) + IR bead (10%) |
| | Quantity per unit (%) | Quantity per unit (%) |
| 1. IR bead | IR bead (15%) | IR bead (10%) |
| Methylphenidate HCl, USP | 15.0 | 15.0 |
| Sugar spheres 14/18 mesh, USP/NF | 80.2 | 80.2 |
| Opadry Clear YS-1-7006, USP | 4.8 | 4.8 |
| Total IR bead | ~100% | ~100% |
| 7. CR/EC/IR bead | ECCRIR bead (30%) | ECCRIR bead (35%) |
| Methylphenidate HCl, USP | 12.78 | 12.78 |
| Sugar spheres 14/18 mesh, USP/NF | 62.02 | 62.02 |
| Opadry Clear YS-1-7006, USP | 4.04 | 4.04 |
| Ammonio methacrylate copolymer dispersion, Type B, 30% dispersion (Eudragit RS30D Solids), NF | 5.44 | 5.44 |
| Methacrylic Acid copolymer dispersion, 30% dispersion (Eudragit L30 D-55 solids), USP NF | 8.15 | 8.15 |
| Triethyl Citrate, USP/NF | 2.70 | 2.70 |
| Talc Ph.Eur/USP | 4.87 | 4.87 |
| Total CR/EC/IR bead | ~100% | ~100% |
| 6. CR/DR bead | DRCRIR bead (55%) | DRCRIR bead (55%) |
| Methylphenidate HCl, USP | 10.19 | 10.19 |
| Sugar spheres 14/18 mesh, USP/NF | 54.5 | 54.5 |
| Opadry Clear YS-1-7006, USP | 3.3 | 3.3 |
| Ammonio methacrylate copolymer dispersion, Type B, 30% dispersion (Eudragit RS30D Solids), NF | 10.86 | 10.86 |
| Triethyl Citrate, USP/NF | 1.67 | 1.67 |
| Glyceryl monostearate emulsion (Plasacryl T20), HS | 2.74 | 2.74 |
| Silicon dioxide, (Syloid 244FP), NF | 0.4 | 0.4 |
| Eudragit FS30D Liquid, HS | 16.32 | 16.32 |
| Total CR/DR bead (30%) | ~100% | ~100% |
| Total weight in capsule | ~262 mg | ~264 mg |

Figure 14

| Ingredient | Strength (label claim) 100 mg | | Strength (label claim) 100 mg | | Strength (label claim) 100 mg | |
|---|---|---|---|---|---|---|
| | Formulation F 80:20 063-003 DRCRIR bead + IR bead | | Formulation I 80:20 063-004, 063-005, 063-007 063-008 MPH IR distal bead | | Formulation J 80:20 063-011 MPH IR distal bead | |
| | Quantity per unit (%) | | Quantity per unit (%) | | Quantity per unit (%) | |
| 1. IR bead | IR bead (20%) | | IR bead (0%) | | IR bead (0%) | |
| Methylphenidate HCl, USP | 15.0 | | - | | - | |
| Sugar spheres 14/18 mesh, USP/NF | 80.2 | | - | | - | |
| Opadry Clear YS-1-7006, USP | 4.8 | | - | | - | |
| Total IR bead | ~100% | | - | | - | |
| 6. CR/DR bead | DRCRIR bead (80%) | | DRCRIR bead (0%) | | DRCRIR bead (0%) | |
| Methylphenidate HCl, USP | 10.19 | | - | | - | |
| Sugar spheres 14/18 mesh, USP/NF | 54.5 | | - | | - | |
| Opadry Clear YS-1-7006, USP | 3.3 | | - | | - | |
| Ammonio methacrylate copolymer dispersion, Type B, 30% dispersion (Eudragit RS30D Solids), NF | 10.86 | | - | | - | |
| Triethyl Citrate, USP/NF | 1.67 | | - | | - | |
| Glyceryl monostearate emulsion (Plasacryl T20), HS | 2.74 | | - | | - | |
| Silicon dioxide, (Syloid 244FP), NF | 0.4 | | - | | - | |
| Eudragit FS30D Liquid, HS | 16.32 | | - | | - | |
| Total CR/DR bead | ~100% | | - | | - | |
| 8. CR/DR/IR bead | MPH IR distal bead | | MPH IR distal bead | | MPH IR distal bead | |
| | | | Quantity per unit (mg) | % | Quantity per unit (mg) | % |
| Methylphenidate HCl, USP | - | | 100 | 12.3 | 100 | 18.4 |
| Sugar spheres 14/18 mesh or 18/20 mesh, USP/NF | - | | 428.5 | 52.7 | 243.1 | 44.7 |
| Opadry Clear YS-1-7006, USP | - | | 31.7 | 3.9 | 32.2 | 5.9 |
| Ammonio methacrylate copolymer dispersion, Type B, 30% dispersion (Eudragit RS30D Solids), NF | - | | 85.4 | 10.5 | 55.55 | 10.3 |
| Triethyl Citrate, USP/NF | - | | 13.0 | 1.6 | 8.61 | 1.6 |
| Glyceryl monostearate emulsion (Plasacryl T20), HS | - | | 22.0 | 2.7 | 14.1 | 2.6 |
| Silicon dioxide, (Syloid 244FP), NF | - | | 4.1 | 0.5 | 4.52 | 0.8 |
| Eudragit FS30D Liquid, HS | - | | 128.5 | 15.8 | 84.61 | 15.6 |
| Total weight in capsule | ~1100 mg | | ~813 mg | ~100 % | ~543 mg | ~100% |

Figure 15

Dissolution results

| Dissolution | Time (hours) | Formulation A | Formulation B | Formulation C | Formulation D | Formulation E | Formulation F | Formulation G | Formulation H | Formulation I | Formulation J |
|---|---|---|---|---|---|---|---|---|---|---|---|
| USP paddle method, 100 rpm, at 37°C, 900 ml simulated gastric fluid for 2 hours, 900 ml phosphate buffer pH 6.0 for 4 hours and 7h hour onwards, 900mL of phosphate buffer pH 7.4 USP<711>Acceptance Table 2 | 1 | 4 | 4 | 1 | 1 | 25 | 18 | 25 | 24 | 20 | 20 |
| | 4 | 11 | 10 | 3 | 4 | 31 | 22 | 29 | 28 | 21 | 21 |
| | 8 | 41 | 49 | 28 | 38 | 54 | 46 | 61 | 61 | 44 | 41 |
| | 12 | 68 | 76 | 44 | 40 | 64 | 58 | 71 | 71 | 83 | 73 |
| | 16[1] | 79 | 78 | 54 | 41 | 68 | 67 | 74 | 73 | 78 | 79 |

% Methylphenidate HCl dissolved

[1] The total amount of Methylphenidate HCl decreases as it degrades at pH 7.4.

Figure 16

Ratios, 90% Geometric CI for non-dose-normalized Parameters Study 063-004

| Parameter | Treatment Comparisons | Ratio | 90% Geometric C.I. | |
|---|---|---|---|---|
| | | | Lower | Upper |
| $AUC_{0-t}$ | Formulation I (fed) vs IR-MPH (fed) | 102.73% | 97.69% | 108.03% |
| | Formulation I (fast) vs IR-MPH (fast) | 123.92% | 117.87% | 130.29% |
| | Formulation I (fed) vs (fast) | 98.02% | 93.21% | 103.07% |
| $AUC_{0-inf}$ | Formulation I (fed) vs IR-MPH (fed) | 128.07% | 122.18% | 134.24% |
| | Formulation I (fast) vs IR-MPH (fast) | 147.91% | 141.31% | 154.83% |
| | Formulation I (fed) vs (fast) | 102.09% | 97.41% | 107.01% |
| $C_{max}$ | Formulation I (fed) vs IR-MPH (fed) | 71.17% | 65.92% | 76.83% |
| | Formulation I (fast) vs IR-MPH (fast) | 87.06% | 80.66% | 93.96% |
| | Formulation I (fed) vs (fast) | 89.31% | 82.73% | 96.41% |

Figure 17

Summary of non-dose-normalized Pharmacokinetic Results Study 063-004

|  | Formulation I (100 mg Fast) | Formulation I (100 mg Fed) | Ritalin (20 mg x 3 Fast) | Ritalin (20 mg x 3 Fed) |
|---|---|---|---|---|
| $AUC_{0-t}$ (pg·hr/mL) | 167783.86 ± 46487.66 | 161271.48 ± 40500.38 | 132957.12 ± 43955.82 | 155290.78 ± 37540.22 |
| $AUC_{0-inf}$ (pg·hr/mL) | 205610.43 ± 61472.88 | 202964.28 ± 57449.88 | 136436.27 ± 45902.96 | 159381.72 ± 39469.43 |
| Residual Area (%) | 17.62 ± 11.06 | 18.63 ± 8.51 | 2.42 ± 0.96 | 2.45 ± 0.92 |
| $C_{max}$ (pg/mL) | 12875.81 ± 4590.85 | 11088.11 ± 2699.06 | 14105.39 ± 3770.36 | 15247.79 ± 3288.76 |
| $T_{max}$ (hr) | 11.5 | 12.5 | 9.50 | 6.04 |
| $K_{el}$ (1/hr) | 0.1173 ± 0.0430 | 0.1074 ± 0.0296 | 0.1968 ± 0.0218 | 0.1976 ± 0.0247 |
| $T\frac{1}{2}$ el (hr) | 6.95 ± 3.25 | 7.03 ± 2.28 | 3.57 ± 0.40 | 3.56 ± 0.45 |
| $AUC_{0-4}$ (pg·hr/mL) | 24818.34 ± 7976.76 | 21160.21 ± 6420.56 | 22955.21 ± 8292.78 | 26886.10 ± 7606.67 |
| $AUC_{8-12}$ (pg·hr/mL) | 36457.19 ± 18489.84 | 29392.15 ± 8453.72 | 41094.69 ± 12181.51 | 44914.86 ± 8753.20 |
| $AUC_{12-16}$ (pg·hr/mL) | 39322.95 ± 10236.29 | 36653.88 ± 11521.14 | 20364.91 ± 9558.52 | 24467.89 ± 8948.65 |
| $AUC_{0-8}$ (pg·hr/mL) | 48626.93 ± 16709.44 | 47422.42 ± 9947.71 | 58725.69 ± 17067.12 | 70056.85 ± 16031.58 |
| $AUC_{0-12}$ (pg·hr/mL) | 85084.12 ± 33395.48 | 76814.57 ± 16722.84 | 99820.38 ± 28132.26 | 114971.70 ± 23607.37 |
| $AUC_{0-16}$ (pg·hr/mL) | 124407.07 ± 40902.66 | 113468.45 ± 26835.93 | 120185.29 ± 37077.85 | 139439.59 ± 30402.02 |
| $AUC_{0-24}$ (pg·hr/mL) | 167740.82 ± 46495.35 | 161217.02 ± 40475.17 | 132949.12 ± 43953.43 | 155281.82 ± 37538.47 |
| $AUC_{4-8}$ (pg·hr/mL) | 23500.00 ± 10293.79 | 25814.81 ± 6376.73 | 35446.96 ± 9454.91 | 42739.42 ± 10194.06 |
| $AUC_{12-t}$ (pg·hr/mL) | 82699.74 ± 21862.39 | 84456.90 ± 26718.88 | 33136.74 ± 16892.19 | 40319.08 ± 17657.25 |
| $C_{max0-4}$ (pg/mL) | 9365.42 ± 3213.96 | 9248.95 ± 1886.65 | 9206.46 ± 3371.78 | 10951.60 ± 3222.66 |
| $C_{max4-8}$ (pg/mL) | 7927.79 ± 4347.57 | 8162.71 ± 1932.67 | 12684.06 ± 3583.22 | 14454.13 ± 3450.37 |
| $C_{max8-16}$ (pg/mL) | 12413.97 ± 4546.66 | 10667.64 ± 3017.29 | 13650.77 ± 3689.34 | 14174.43 ± 3158.31 |
| $T_{max0-4}$ (hr) | 1.63 | 3.00 | 2.00 | 2.07 |
| $T_{max4-8}$ (hr) | 4.00 | 3.95 | 6.00 | 6.00 |
| $T_{max8-16}$ (hr) | 12.5 | 13.5 | 9.52 | 10.0 |

Figure 18

Ratios, 90% Geometric CI for non-dose-normalized Parameters Study 063-005

| Parameter | Treatment Comparisons | Ratio | 90% Geometric C.I. | |
|---|---|---|---|---|
| | | | Lower | Upper |
| AUC0-t | Test(A) - Reference(D) | 98.78% | 95.30% | 102.40% |
| | Test(B) - Reference(D) | 98.60% | 95.11% | 102.22% |
| | Test(C) - Reference(D) | 101.08% | 97.52% | 104.78% |
| AUC0-inf | Test(A) - Reference(D) | 97.87% | 94.45% | 101.41% |
| | Test(B) - Reference(D) | 98.45% | 95.01% | 102.02% |
| | Test(C) - Reference(D) | 101.35% | 97.82% | 105.01% |
| Cmax | Test(A) - Reference(D) | 108.31% | 100.05% | 117.26% |
| | Test(B) - Reference(D) | 100.08% | 92.43% | 108.37% |
| | Test(C) - Reference(D) | 105.84% | 97.77% | 114.57% |

Figure 19A

Ratios, 90% Geometric CI for non-dose-normalized Parameters Study 063-007

| Parameter | Treatment Comparisons | Ratio | 90% Geometric C.I. | |
|---|---|---|---|---|
| | | | Lower | Upper |
| $AUC_{0-24}$ | Formulation I vs IR-MPH | 147.61% | 143.02% | 152.34% |
| $C_{max}$ | Formulation I vs IR-MPH | 98.92% | 92.48% | 105.81% |
| $C_{min}$ | Formulation I vs IR-MPH | 456.91% | 404.67% | 515.90% |

Figure 19B

Ratios, 90% Geometric CI Parameters for Study 063-011

| Parameter | Treatment Comparisons | Ratio | 90% Geometric C.I. | |
|---|---|---|---|---|
| | | | Lower | Upper |
| $AUC_{0-t}$ | Formulation I vs Formulation J (fed) | 99.15% | 91.82% | 107.08% |
| | Formulation I vs Formulation J (fast) | 99.64% | 92.27% | 107.61% |
| $AUC_{0-inf}$ | Formulation I vs Formulation J (fed) | 98.66% | 91.67% | 106.20% |
| | Formulation I vs Formulation J (fast) | 98.76% | 91.75% | 106.29% |
| $C_{max}$ | Formulation I vs Formulation J (fed) | 98.34% | 83.67% | 115.60% |
| | Formulation I vs Formulation J (fast) | 90.87% | 77.31% | 106.81% |

Figure 20

| Time (hours) | % Methylphenidate HCl dissolved |
|---|---|
| 1 | NLT 15% |
| 4 | 18 – 38 % |
| 8 | 35 – 55% |
| 12 | 68 – 98 |
| 16 | NLT 68 |

Figure 21

| Production of Methylphenidate Immediate Release (IR) Beads | | | |
|---|---|---|---|
| Process Parameters | Recommended Parameters | | |
| Coating sugar spheres with methylphenidate solution | Preheating | Fluid bed coating | |
| Inlet air volume, cmh (to be adjusted as necessary) | 800 ± 300 | 1100 ± 200 | |
| Inlet air temperature, °C | 56 ± 5 | 65 ± 10 | |
| Atomization air pressure, bar | 1 ± 0.2 | 3 ± 1 | |
| Inlet dew point, °C | 8 ± 4 | 8 ± 4 | |
| Product temperature, °C | 35 ± 2 | 37.5 ± 3.5 | |
| Spraying rate, g/min (to be adjusted as necessary) | N/A | 150 - 400 | |
| Rinsing with purified water | Rinsing | Drying | Cooling |
| Amount of water used (kg) | 1 | N/A | N/A |
| Fluidized air volume, cmh (to be adjusted as necessary) | 1100 ± 200 | 1000 ± 200 | 1000 ± 300 |
| Inlet air temperature, °C (to be adjusted as necessary) | 65 ± 10 | 60 ± 6 | Minimum |
| Atomization air pressure, bar | 3 ± 1 | 1 ± 0.2 | 1 ± 0.2 |
| Inlet dew point, °C | 8 ± 4 | 8 ± 4 | 8 ± 4 |
| Product temperature, °C | 36 ± 3 | 41 ± 4 | 30 ± 1 |
| Spraying rate, g/min (to be adjusted as necessary) | 150 - 350 | N/A | N/A |
| Time, min | N/A | ~3 | N/A |

Figure 22

| Production of Methylphenidate Controlled Release (CRIR) Beads | | | |
|---|---|---|---|
| Process Parameters | Recommended Parameters | | |
| Coating IR beads with Controlled Release coating dispersion | Preheating | CR Coating | Rinsing |
| Amount of purified water used (Kg) | N/A | N/A | 1 |
| Inlet air volume, cmh (to be adjusted as necessary) | 1000 ± 250 | 1250 ± 350 | 1250 ± 250 |
| Inlet air temperature, °C | 45 ± 5 | 45 ± 15 | 45 ± 15 |
| Atomization air pressure, bar | 1 ± 0.2 | 2.8 ± 0.5 | 2.8 ± 0.5 |
| Inlet dew point, °C | 8 ± 4 | 8 ± 4 | 8 ± 4 |
| Product temperature, °C | 25 ± 3 | 25 ± 5 | 25 ± 5 |
| Spraying rate, g/ min (to be adjusted as necessary) | N/A | 100 - 400 | 100-350 |

Figure 23

| Production of Methylphenidate Distal (DRCRIR) Beads, cured | | | | |
|---|---|---|---|---|
| Process Parameters | Recommended Parameters | | | |
| Coating CRIR beads with Distal Release coating dispersion | DR Coating | Rinsing | Curing | Cooling |
| Amount of purified water used (Kg) | N/A | 1 | N/A | N/A |
| Inlet air volume, cmh (to be adjusted as necessary) | 1400 ± 400 | 1400 ± 400 | 800± 400 | 800± 100 |
| Inlet air temperature, °C | 45 ± 15 | 45 ± 15 | To be adjusted | 15 ± 10 |
| Atomization air pressure, bar | 2.8 ± 0.5 | 2.8 ± 0.5 | 1 ± 0.2 | 1 ± 0.2 |
| Inlet dew point, °C | 8 ± 4 | 8 ± 4 | 8 ± 4 | 8 ± 4 |
| Product temperature, °C | 25 ± 3 | 25 ± 3 | 40 ± 2 | 25 ± 3 |
| Spraying rate, g/ min (to be adjusted as necessary) | 150 - 400 | 150 - 350 | N/A | N/A |
| Time , min. | N/A | N/A | 60 | N/A |

Figure 24

| Production of Methylphenidate IR Distal (MPH IR distal) Beads | | | | | |
|---|---|---|---|---|---|
| Process Parameters | Recommended Parameters | | | | |
| Coating DRCRIR beads with Immediate Release layer | Preheating | IR coating | Rinsing | Drying | Cooling |
| Amount of purified water used (Kg) | N/A | N/A | 1 | N/A | N/A |
| Inlet air volume, cmh (to be adjusted as necessary) | 1100 ± 400 | 1400 ± 400 | 1400 ± 400 | 1100± 400 | 1100± 400 |
| Inlet air temperature, °C | 56 ± 15 | 56 ± 15 | 56 ± 15 | To be adjusted | 20 ± 10 |
| Atomization air pressure, bar | 3 ± 0.5 | 3 ± 0.5 | 3 ± 0.5 | 1 ± 0.2 | 1 ± 0.2 |
| Inlet dew point, °C | 8 ± 4 | 8 ± 4 | 8 ± 4 | 8 ± 4 | 8 ± 4 |
| Product temperature, °C | 36 ± 3 | 37.5 ± 3.5 | 37.5 ± 3.5 | 41 ± 4 | 30 ± 1 |
| Spraying rate, g/ min (to be adjusted as necessary) | N/A | 150-400 | 150 - 350 | N/A | N/A |
| Time , min. | 5 - 10 | N/A | N/A | 5 | N/A |

Figure 25

| Production of Methylphenidate IR (MPH IR distal) Beads coated with Sodium Alginate | | | | |
|---|---|---|---|---|
| Process Parameters | Recommended Parameters | | | |
| Coating MPH IR distal beads with sodium alginate layer | Preheating | Sodium Alginate coating | Drying | Cooling |
| Amount of purified water used (Kg) | N/A | N/A | N/A | N/A |
| Inlet air volume, cmh (to be adjusted as necessary) | 1100 ± 400 | 1400 ± 400 | 1100± 400 | 1100± 400 |
| Inlet air temperature, °C | 70 ± 15 | 70 ± 15 | To be adjusted | 20 ± 10 |
| Atomization air pressure, bar | 3 ± 0.5 | 3 ± 0.5 | 1 ± 0.2 | 1 ± 0.2 |
| Inlet dew point, °C | 8 ± 4 | 8 ± 4 | 8 ± 4 | 8 ± 4 |
| Product temperature, °C | 52 ± 5 | 52 ± 5 | 41 ± 4 | 30 ± 1 |
| Spraying rate, g/ min (to be adjusted as necessary) | N/A | 50-300 | N/A | N/A |
| Time, min. | 5 - 10 | N/A | 5 | N/A |

Figure 26

Dissolution Parameters (Example 10)

| Equipment | Conditions |
|---|---|
| Apparatus Basket, USP | apparatus 1 |
| Speed | 100 rpm |
| Bath | temperature: 37°C |
| Dissolution media 900 ml | 0%, 5%, 20%, 35% or 40% ethanol v/v in 0.1 N HCl |
| Sampling time points | 15, 30, 45, 60, 75, 90, 105, 120 minutes |

Figure 27

Composition of the dosage form (Formulation I 80:20) MPH IR distal:

| Ingredient | Quantity per capsule (mg) per Strength (label claim) approx: | | | | | | | |
|---|---|---|---|---|---|---|---|---|
| | 25 mg | 30 mg | 35 mg | 45 mg | 55mg | 70mg | 85mg | 100 mg | % |
| Methylphenidate HCl, USP | 25 | 30 | 35 | 45 | 55 | 70 | 85 | 100 | 12.3 |
| Sugar spheres 14/18 mesh, USP/NF | 107.1 | 128.5 | 150.0 | 192.8 | 235.7 | 299.9 | 364.2 | 428.5 | 52.7 |
| Opadry Clear YS-1-7006 | 7.9 | 9.5 | 11.1 | 14.3 | 17.4 | 22.2 | 27.0 | 31.7 | 3.9 |
| Ammonio methacrylate copolymer dispersion, Type B, 30% dispersion (Eudragit RS30D Solids), NF | 21.3 | 25.6 | 29.9 | 38.4 | 47.0 | 59.8 | 72.6 | 85.4 | 10.5 |
| Triethyl Citrate, USP/NF | 3.3 | 3.9 | 4.6 | 5.9 | 7.2 | 9.1 | 11.1 | 13.0 | 1.6 |
| Glyceryl monostearate emulsion (Plasacryl T20), HS, solids | 5.5 | 6.6 | 7.7 | 9.9 | 12.1 | 15.4 | 18.7 | 22.0 | 2.7 |
| Silicon dioxide, (Syloid 244FP), NF | 1.0 | 1.2 | 1.4 | 1.8 | 2.2 | 2.8 | 3.5 | 4.1 | 0.5 |
| Eudragit FS30D, HS, solids | 32.1 | 38.5 | 45.0 | 57.8 | 70.7 | 89.9 | 109.2 | 128.5 | 15.8 |
| TOTAL (approx.) | 203 | 244 | 285 | 366 | 447 | 569 | 691 | 813 | 100 |

Figure 28

Composition of the dosage form (Formulation J 80:20) MPH IR distal:

| Ingredient | Quantity per capsule (mg) per Strength (label claim) approx: | | | | | | | | |
|---|---|---|---|---|---|---|---|---|---|
| | 25 mg | 30 mg | 35 mg | 45 mg | 55 mg | 70 mg | 85 mg | 100 mg | % |
| Methylphenidate HCl, USP | 25 | 30 | 35 | 45 | 55 | 70 | 85 | 100 | 18.4 |
| Sugar spheres 14/18 mesh, USP/NF | 60.8 | 72.9 | 84.9 | 109.5 | 133.7 | 169.9 | 206.5 | 243.1 | 44.7 |
| Opadry Clear YS-1-7006 | 8.0 | 9.6 | 11.2 | 14.5 | 17.6 | 22.4 | 27.3 | 32.2 | 5.9 |
| Ammonio methacrylate copolymer dispersion, Type B, 30% dispersion (Eudragit RS30D Solids), NF | 14.0 | 16.8 | 19.6 | 25.2 | 30.8 | 39.1 | 47.6 | 55.55 | 10.3 |
| Triethyl Citrate, USP/NF | 2.2 | 2.6 | 3.0 | 3.9 | 4.8 | 6.1 | 7.4 | 8.61 | 1.6 |
| Glyceryl monostearate emulsion (Plasacryl T20), HS, solids | 3.5 | 4.3 | 4.9 | 6.4 | 7.8 | 9.9 | 12.0 | 14.1 | 2.6 |
| Silicon dioxide, (Syloid 244FP), NF | 1.1 | 1.3 | 1.5 | 2.0 | 2.4 | 3.0 | 3.7 | 4.52 | 0.8 |
| Eudragit FS30D,HS, solids | 21.2 | 25.4 | 29.6 | 38.2 | 46.6 | 59.3 | 72.1 | 84.61 | 15.6 |
| TOTAL (approx.) | 136 | 163 | 190 | 245 | 299 | 380 | 462 | 543 | 100 |

Figure 30

| Parameter (units) | Formulation I | | | | Ritalin | | | |
|---|---|---|---|---|---|---|---|---|
| | N | Mean | SD | CV% | N | Mean | SD | CV% |
| $AUC_{0-t}$ (h*pg/mL) | 17 | 192132.91 | 88094.82 | 45.85 | 17 | 192501.02 | 65057.41 | 33.80 |
| $AUC_{0-inf}$ (h*pg/mL) | 16 | 205802.65 | 90414.45 | 43.93 | 16 | 198638.40 | 63654.28 | 32.05 |
| Residual area (%) | 16 | 4.97 | 8.29 | 167.00 | 16 | 0.59 | 0.33 | 56.51 |
| $C_{max}$ (pg/mL) | 17 | 13639.74 | 6208.80 | 45.52 | 17 | 19938.04 | 8005.27 | 40.15 |
| $T_{½el}$ (h) | 16 | 4.91 | 3.04 | 61.84 | 16 | 2.77 | 0.29 | 10.63 |
| $K_{el}$ (/h) | 16 | 0.1659 | 0.0487 | 29.3398 | 16 | 0.2527 | 0.0259 | 10.2445 |
| Correlation | 16 | -0.9820 | 0.0250 | -2.5414 | 16 | -0.9972 | 0.0044 | -0.4393 |
| $K_{el}$ Lower (h) | 16 | 16.3 | 4.74 | 29.1 | 16 | 12.8 | 0.688 | 5.36 |
| $K_{el}$ Upper (h) | 16 | 29.5 | 0.848 | 2.87 | 16 | 26.6 | 2.11 | 7.93 |
| $AUC_{0-8}$ (h*pg/mL) | 17 | 46517.87 | 18403.97 | 39.56 | 17 | 83864.20 | 31704.77 | 37.80 |
| $AUC_{0-12}$ (h*pg/mL) | 17 | 88171.26 | 39500.37 | 44.80 | 17 | 140672.35 | 51058.27 | 36.30 |
| $AUC_{0-14}$ (h*pg/mL) | 17 | 110274.27 | 50398.82 | 45.70 | 17 | 156881.18 | 55213.83 | 35.19 |
| $AUC_{0-24}$ (h*pg/mL) | 17 | 179368.01 | 84890.64 | 47.33 | 17 | 191140.40 | 64139.79 | 33.56 |

| Parameter (units) | Formulation I | | | | Ritalin | | | |
|---|---|---|---|---|---|---|---|---|
| | N | Median | Min | Max | N | Median | Min | Max |
| $T_{max}$ (h) | 17 | 11.3 | 1.23 | 26.6 | 17 | 8.75 | 1.28 | 11.2 |

Figure 31

| Parameter (units) | Formulation I | | | | Ritalin | | | |
|---|---|---|---|---|---|---|---|---|
| | N | Mean | SD | CV% | N | Mean | SD | CV% |
| $AUC_{0-4}$ (h*pg/mL) | 17 | 25062.71 | 12238.03 | 48.83 | 17 | 37250.87 | 14497.45 | 38.92 |
| $AUC_{4-8}$ (h*pg/mL) | 17 | 32707.69 | 10979.77 | 33.57 | 17 | 62400.16 | 25227.36 | 40.43 |
| $AUC_{8-12}$ (h*pg/mL) | 17 | 41667.74 | 22228.50 | 53.35 | 17 | 56742.88 | 20904.80 | 36.84 |
| $AUC_{12-t}$ (h*pg/mL) | 17 | 172948.40 | 87877.30 | 50.81 | 17 | 114340.69 | 40102.67 | 35.07 |
| $C_{max\ 0-4}$ (pg/mL) | 17 | 9168.86 | 4948.34 | 53.97 | 17 | 13570.62 | 6367.77 | 46.92 |
| $C_{max\ 4-8}$ (pg/mL) | 17 | 8011.14 | 3337.47 | 41.66 | 17 | 16497.30 | 6129.70 | 37.16 |
| $C_{max\ 8-14}$ (pg/mL) | 17 | 13161.06 | 6726.86 | 51.11 | 17 | 18553.56 | 8278.01 | 44.62 |

| Parameter (units) | Formulation I | | | | Ritalin | | | |
|---|---|---|---|---|---|---|---|---|
| | N | Median | Min | Max | N | Median | Min | Max |
| $T_{max\ 0-4}$ (h) | 17 | 1.98 | 1.05 | 3.88 | 17 | 2.03 | 0.567 | 2.97 |
| $T_{max\ 4-8}$ (h) | 17 | 8.12 | 4.22 | 8.47 | 17 | 5.97 | 4.93 | 8.30 |
| $T_{max\ 8-14}$ (h) | 17 | 11.2 | 7.68 | 14.2 | 17 | 9.82 | 8.58 | 11.2 |

Figure 32 a) Non-dose-normalized

|           | p-values  |        |          |
|-----------|-----------|--------|----------|
| Parameter | Treatment | Period | Sequence |
| $AUC_{0-t}$ | 0.4848 | 0.2822 | 0.2449 |
| $AUC_{0-inf}$ | 0.8721 | 0.6181 | 0.1623 |
| Cmax | <0.0001 | 0.8916 | 0.5146 | b) Dose-normalized

|           | p-values  |        |          |
|-----------|-----------|--------|----------|
| Parameter | Treatment | Period | Sequence |
| $AUC_{0-t}$ | 0.0019 | 0.2392 | 0.4719 |
| $AUC_{0-inf}$ | 0.0109 | 0.5346 | 0.6460 |
| Cmax | <0.0001 | 0.8367 | 0.8390 |

Figure 33 a) Non-dose-normalized

| Parameter | Treatment Comparisons | Ratio[1] | 90% Geometric C.I.[2] | | Intra-subject CV | Intra-subject CV |
|---|---|---|---|---|---|---|
| | | | Lower | Upper | | |
| $AUC_{0-t}$ | Reference(B) - Test(A) | 103.45% | 95.21% | 112.41% | 13.86% | 36.95% |
| $AUC_{0-inf}$ | Reference(B) - Test(A) | 99.25% | 91.54% | 107.61% | 13.04% | 34.87% |
| Cmax | Reference(B) - Test(A) | 149.13% | 134.56% | 165.27% | 17.19% | 40.96% |

[1] Calculated using least-squares means according to the formula: $e^{(DIFFERENCE)} \times 100$.
[2] 90% Geometric Confidence Interval using ln-transformed data.

b) Dose-normalized

| Parameter | Treatment Comparisons | Ratio[1] | 90% Geometric C.I.[2] | | Intra-subject CV | Intra-subject CV |
|---|---|---|---|---|---|---|
| | | | Lower | Upper | | |
| $AUC_{0-t}$ | Reference(B) - Test(A) | 119.27% | 109.86% | 129.49% | 13.70% | 31.97% |
| $AUC_{0-inf}$ | Reference(B) - Test(A) | 114.31% | 105.49% | 123.87% | 12.95% | 35.93% |
| Cmax | Reference(B) - Test(A) | 171.93% | 154.58% | 191.24% | 17.80% | 30.63% |

[1] Calculated using least-squares means according to the formula: $e^{(DIFFERENCE)} \times 100$.
[2] 90% Geometric Confidence Interval using ln-transformed data.

Figure 35

| Parameter (units) | Formulation I | | | | Ritalin | | | |
|---|---|---|---|---|---|---|---|---|
| | N | Mean | SD | CV% | N | Mean | SD | CV% |
| $AUC_{0-t}$ (h*pg/mL) | 17 | 2549.37 | 2104.78 | 82.56 | 17 | 1419.21 | 1071.14 | 75.47 |
| $AUC_{0-inf}$ (h*pg/mL) | 15 | 2878.44 | 2200.78 | 76.46 | 15 | 1538.40 | 1113.23 | 72.36 |
| Residual area (%) | 15 | 6.40 | 6.94 | 108.54 | 15 | 2.41 | 2.04 | 84.64 |
| $C_{max}$ (pg/mL) | 17 | 262.09 | 226.78 | 86.53 | 17 | 310.90 | 365.88 | 117.68 |
| $T_{½,el}$ (h) | 15 | 5.38 | 3.39 | 62.94 | 15 | 1.17 | 0.35 | 29.59 |
| $K_{el}$ (/h) | 15 | 0.1827 | 0.1226 | 67.1135 | 15 | 0.6376 | 0.1667 | 26.1485 |
| Correlation | 15 | -0.9628 | 0.0468 | -4.8573 | 15 | -0.9917 | 0.0107 | -1.0796 |
| $K_{el\ Lower}$ (h) | 15 | 14.1 | 2.78 | 19.7 | 15 | 10.9 | 0.661 | 6.06 |
| $K_{el\ Upper}$ (h) | 15 | 27.9 | 4.19 | 15.0 | 15 | 13.6 | 0.563 | 4.15 |
| $AUC_{0-8}$ (h*pg/mL) | 17 | 553.70 | 438.45 | 79.19 | 17 | 924.40 | 743.05 | 80.38 |
| $AUC_{0-12}$ (h*pg/mL) | 17 | 1206.84 | 918.47 | 76.11 | 17 | 1374.79 | 1062.13 | 77.26 |
| $AUC_{0-14}$ (h*pg/mL) | 17 | 1508.68 | 1150.19 | 76.24 | 17 | 1422.91 | 1072.03 | 75.34 |
| $AUC_{0-24}$ (h*pg/mL) | 17 | 2383.19 | 1995.86 | 83.75 | 17 | 1489.82 | 1086.24 | 72.91 |

| Parameter (units) | Formulation I | | | | Ritalin | | | |
|---|---|---|---|---|---|---|---|---|
| | N | Median | Min | Max | N | Median | Min | Max |
| $T_{max}$ (h) | 17 | 11.1 | 1.18 | 26.6 | 17 | 2.03 | 0.567 | 9.27 |

Figure 36

| Parameter (units) | Formulation I | | | | | Ritalin | | | |
|---|---|---|---|---|---|---|---|---|---|
| | N | Mean | SD | CV% | | N | Mean | SD | CV% |
| $AUC_{0-4}$ (h*pg/mL) | 17 | 256.46 | 256.87 | 100.16 | | 17 | 490.69 | 427.27 | 87.08 |
| $AUC_{4-8}$ (h*pg/mL) | 17 | 390.72 | 268.27 | 68.66 | | 17 | 525.69 | 376.63 | 71.65 |
| $AUC_{8-12}$ (h*pg/mL) | 17 | 653.15 | 551.80 | 84.48 | | 17 | 449.85 | 336.15 | 74.72 |
| $AUC_{12-t}$ (h*pg/mL) | 17 | 2363.62 | 2358.84 | 99.80 | | 16 | 296.04 | 189.20 | 63.91 |
| $C_{max\,0-4}$ (pg/mL) | 17 | 134.29 | 160.57 | 119.58 | | 17 | 273.44 | 378.83 | 138.54 |
| $C_{max\,4-8}$ (pg/mL) | 17 | 137.70 | 104.56 | 75.94 | | 17 | 185.32 | 125.03 | 67.47 |
| $C_{max\,8-14}$ (pg/mL) | 17 | 235.78 | 217.50 | 92.25 | | 17 | 216.94 | 205.01 | 94.50 |

| Parameter (units) | Formulation I | | | | | Ritalin | | | |
|---|---|---|---|---|---|---|---|---|---|
| | N | Median | Min | Max | | N | Median | Min | Max |
| $T_{max\,0-4}$ (h) | 17 | 1.18 | 0.600 | 3.88 | | 17 | 1.10 | 0.567 | 2.08 |
| $T_{max\,4-8}$ (h) | 17 | 8.05 | 3.88 | 8.45 | | 17 | 5.40 | 4.82 | 8.30 |
| $T_{max\,8-14}$ (h) | 17 | 11.1 | 7.68 | 13.6 | | 17 | 9.15 | 8.58 | 11.2 |

Figure 37 a) Non-dose-normalized

| | p-values | | |
|---|---|---|---|
| Parameter | Treatment | Period | Sequence |
| $AUC_{0-t}$ | 0.0033 | 0.3931 | 0.9702 |
| $AUC_{0-inf}$ | 0.0027 | 0.1571 | 0.8358 |
| Cmax | 0.2866 | 0.8103 | 0.6712 | b) Dose-normalized

| | p-values | | |
|---|---|---|---|
| Parameter | Treatment | Period | Sequence |
| $AUC_{0-t}$ | 0.0229 | 0.4034 | 0.8203 |
| $AUC_{0-inf}$ | 0.0150 | 0.1596 | 0.6614 |
| Cmax | 0.0605 | 0.8336 | 0.5028 |

Figure 38 a) Non-dose-normalized

|           |                        |        | 90% Geometric C.I.[2] | | Intra-subject | Intra-subject |
| Parameter | Treatment Comparisons  | Ratio[1] | Lower  | Upper   | CV            | CV            |
|-----------|------------------------|--------|--------|---------|---------------|---------------|
| $AUC_{0-t}$  | Reference(B) - Test(A) | 103.45% | 95.21% | 112.41% | 13.86%        | 36.95%        |
| $AUC_{0-inf}$ | Reference(B) - Test(A) | 99.25%  | 91.54% | 107.61% | 13.04%        | 34.87%        |
| Cmax      | Reference(B) - Test(A) | 149.13% | 134.56% | 165.27% | 17.19%       | 40.96%        |

[1] Calculated using least-squares means according to the formula: $e^{(DIFFERENCE)} \times 100$.
[2] 90% Geometric Confidence Interval using ln-transformed data.

b) Dose-normalized

|           |                        |        | 90% Geometric C.I.[2] | | Intra-subject | Intra-subject |
| Parameter | Treatment Comparisons  | Ratio[1] | Lower  | Upper   | CV            | CV            |
|-----------|------------------------|--------|--------|---------|---------------|---------------|
| $AUC_{0-t}$  | Reference(B) - Test(A) | 60.70%  | 47.25% | 77.98%  | 43.45%        | 80.02%        |
| $AUC_{0-inf}$ | Reference(B) - Test(A) | 57.31%  | 43.86% | 74.87%  | 43.06%        | 83.53%        |
| Cmax      | Reference(B) - Test(A) | 118.43% | 90.56% | 154.89% | 46.86%        | 84.99%        |

[1] Calculated using least-squares means according to the formula: $e^{(DIFFERENCE)} \times 100$.
[2] 90% Geometric Confidence Interval using ln-transformed data.

Figure 40

| Parameter (units) | Formulation I | | | | | Ritalin | | | | |
|---|---|---|---|---|---|---|---|---|---|---|
| | N | Mean | SD | CV% | | N | Mean | SD | CV% | |
| $AUC_{0-t}$ (h*pg/mL) | 17 | 194688.21 | 88781.49 | 45.60 | | 17 | 194002.70 | 65540.71 | 33.78 | |
| $AUC_{0-inf}$ (h*pg/mL) | 16 | 208855.26 | 92252.58 | 44.17 | | 17 | 195031.78 | 65615.22 | 33.64 | |
| Residual area (%) | 16 | 5.02 | 8.21 | 163.71 | | 17 | 0.60 | 0.32 | 54.14 | |
| $C_{max}$ (pg/mL) | 17 | 13846.56 | 6306.05 | 45.54 | | 17 | 20154.20 | 8124.07 | 40.31 | |
| $T_{½el}$ (h) | 16 | 4.97 | 3.00 | 60.38 | | 17 | 2.81 | 0.34 | 11.95 | |
| $K_{el}$ (/h) | 16 | 0.1639 | 0.0497 | 30.35 | | 17 | 0.2497 | 0.0284 | 11.38 | |
| Correlation | 16 | -0.9815 | 0.0251 | -2.56 | | 17 | -0.9971 | 0.0043 | -0.43 | |
| $K_{el\,Lower}$ (h) | 16 | 15.7 | 4.31 | 27.50 | | 17 | 12.9 | 0.707 | 5.48 | |
| $K_{el\,Upper}$ (h) | 16 | 29.5 | 0.848 | 2.87 | | 17 | 26.8 | 2.14 | 8.00 | |
| $AUC_{0-8}$ (h*pg/mL) | 17 | 47071.58 | 18636.19 | 39.59 | | 17 | 84788.60 | 32066.97 | 37.82 | |
| $AUC_{0-12}$ (h*pg/mL) | 17 | 89378.09 | 40002.25 | 44.76 | | 17 | 142047.14 | 51630.89 | 36.35 | |
| $AUC_{0-14}$ (h*pg/mL) | 17 | 111782.95 | 50962.82 | 45.59 | | 17 | 158304.08 | 55766.83 | 35.23 | |
| $AUC_{0-24}$ (h*pg/mL) | 17 | 181751.20 | 85596.61 | 47.10 | | 17 | 192641.71 | 64628.12 | 33.55 | |

| Parameter (units) | Formulation I | | | | | Ritalin | | | | |
|---|---|---|---|---|---|---|---|---|---|---|
| | N | Median | Min | Max | | N | Median | Min | Max | |
| $T_{max}$ (h) | 17 | 11.3 | 1.23 | 26.6 | | 17 | 8.75 | 1.28 | 11.2 | |

Figure 41

| Parameter (units) | Formulation I | | | | Ritalin | | | |
|---|---|---|---|---|---|---|---|---|
| | N | Mean | SD | CV% | N | Mean | SD | CV% |
| $AUC_{0-4}$ (h*pg/mL) | 17 | 24325.24 | 11688.18 | 48.05 | 17 | 36269.92 | 14479.84 | 39.92 |
| $AUC_{4-8}$ (h*pg/mL) | 17 | 22746.34 | 7952.96 | 34.96 | 17 | 48518.68 | 19503.85 | 40.20 |
| $AUC_{8-12}$ (h*pg/mL) | 17 | 42306.52 | 22535.51 | 53.27 | 17 | 57258.54 | 21096.66 | 36.84 |
| $AUC_{12-t}$ (h*pg/mL) | 17 | 105310.12 | 52158.33 | 49.53 | 17 | 51955.56 | 19811.19 | 38.13 |
| $C_{max\ 0-4}$ (pg/mL) | 17 | 9278.64 | 5065.53 | 54.59 | 17 | 13833.46 | 6602.69 | 47.73 |
| $C_{max\ 4-8}$ (pg/mL) | 17 | 8139.92 | 3390.50 | 41.65 | 17 | 16655.46 | 6170.36 | 37.05 |
| $C_{max\ 8-14}$ (pg/mL) | 17 | 13363.00 | 6830.20 | 51.11 | 17 | 18754.96 | 8421.91 | 44.90 |

| Parameter (units) | Formulation I | | | | Ritalin | | | |
|---|---|---|---|---|---|---|---|---|
| | N | Median | Min | Max | N | Median | Min | Max |
| $T_{max\ 0-4}$ (h) | 17 | 1.98 | 1.05 | 3.88 | 17 | 1.28 | 0.567 | 2.97 |
| $T_{max\ 4-8}$ (h) | 17 | 8.12 | 4.22 | 8.47 | 17 | 5.97 | 4.93 | 8.30 |
| $T_{max\ 8-14}$ (h) | 17 | 11.2 | 7.68 | 14.2 | 17 | 9.82 | 8.58 | 11.2 |

Figure 42 a) Non-dose-normalized p-values

| Parameter | Treatment | Period | Sequence |
|---|---|---|---|
| $AUC_{0-t}$ | 0.5713 | 0.3012 | 0.2506 |
| $AUC_{0-inf}$ | 0.7430 | 0.6495 | 0.1655 |
| Cmax | <0.0001 | 0.9274 | 0.5230 | b) Dose-normalized p-values

| Parameter | Treatment | Period | Sequence |
|---|---|---|---|
| $AUC_{0-t}$ | 0.0021 | 0.2532 | 0.4839 |
| $AUC_{0-inf}$ | 0.0130 | 0.5600 | 0.6567 |
| Cmax | <0.0001 | 0.8698 | 0.8527 |

Figure 43 a) Non-dose-normalized

| Parameter | Treatment Comparisons | Ratio[1] | 90% Geometric C.I.[2] | | Intra-subject CV | Intra-subject CV |
|---|---|---|---|---|---|---|
| | | | Lower | Upper | | |
| $AUC_{0-t}$ | Reference(B) - Test(A) | 102.72% | 94.71% | 111.40% | 13.53% | 36.83% |
| $AUC_{0-inf}$ | Reference(B) - Test(A) | 98.51% | 91.00% | 106.63% | 12.77% | 40.96% |
| Cmax | Reference(B) - Test(A) | 148.3% | 134.06% | 164.06% | 16.88% | 40.96% |

[1] Calculated using least-squares means according to the formula: $e^{(DIFFERENCE)} \times 100$.
[2] 90% Geometric Confidence Interval using ln-transformed data.

b) Dose-normalized

| Parameter | Treatment Comparisons | Ratio[1] | 90% Geometric C.I.[2] | | Intra-subject CV | Intra-subject CV |
|---|---|---|---|---|---|---|
| | | | Lower | Upper | | |
| $AUC_{0-t}$ | Reference(B) - Test(A) | 118.42% | 109.33% | 128.28% | 13.33% | 31.88% |
| $AUC_{0-inf}$ | Reference(B) - Test(A) | 113.45% | 104.92% | 122.69% | 12.61% | 35.91% |
| Cmax | Reference(B) - Test(A) | 170.98% | 154.01% | 189.82% | 17.48% | 30.61% |

[1] Calculated using least-squares means according to the formula: $e^{(DIFFERENCE)} \times 100$.
[2] 90% Geometric Confidence Interval using ln-transformed data.

Mean (± Standard Deviation) Difficulty Falling Sleep (Initial Insomnia) by Visit and vs. Placebo Mean (± Standard Deviation) Mood on Awakening (Sleep Quality) by Visit and vs. Placebo (Study 063-015)

Mean (± Standard Deviation) Appetite Level by Visit and vs. Placebo

Figure 47

| Adverse Event Category [n (%)] m[a] | 25 mg Formulation I | 35 mg Formulation I | 45 mg Formulation I | 55 mg Formulation I | 70 mg Formulation I | 85 mg Formulation I | Total Formulation I | Total Placebo |
|---|---|---|---|---|---|---|---|---|
| Open-label dose-optimization period[b] | 156 | 142 | 107 | 64 | 26 | 9 | 156 | |
| Any TEAE | 66 (42.3) 121 | 50 (35.2) 93 | 43 (40.2) 69 | 25 (39.1) 39 | 8 (30.8) 14 | 2 (22.2) 2 | 104 (66.7) 338 | |
| Any severe TEAE | 0 | 0 | 0 | 0 | 0 | 0 | 0 | |
| Any serious TEAE | 0 | 0 | 0 | 0 | 0 | 0 | 0 | |
| Any treatment-related AE | 54 (34.6) 97 | 40 (28.2) 65 | 38 (35.5) 55 | 19 (29.7) 27 | 7 (26.9) 9 | 2 (22.2) 2 | 95 (60.9) 255 | |
| Any TEAE leading to study discontinuation | 0 | 2 (1.4) 3 | 0 | 0 | 0 | 0 | 2 (1.3) 3 | |
| Any TEAE with outcome of death | 0 | 0 | 0 | 0 | 0 | 0 | 0 | |
| Double-blind treatment period[c] | 9 | 15 | 20 | 19 | 8 | 4 | 75 | 73 |
| Any TEAE | 3 (33.3) 3 | 2 (13.3) 2 | 5 (25.0) 8 | 3 (15.8) 3 | 3 (37.5) 3 | 2 (50.0) 2 | 18 (24.0) 21 | 7 (9.6) 9 |
| Any severe TEAE | 0 | 0 | 0 | 0 | 0 | 0 | 0 | 0 |
| Any serious TEAE | 0 | 0 | 0 | 0 | 0 | 0 | 0 | 0 |
| Any treatment-related AE | 1 (11.1) 1 | 1 (6.7) 1 | 4 (20.0) 6 | 2 (10.5) 2 | 3 (37.5) 3 | 1 (25.0) 1 | 12 (16.0) 14 | 2 (2.7) 2 |
| Any TEAE leading to study discontinuation | 0 | 0 | 0 | 0 | 0 | 0 | 0 | 0 |
| Any TEAE with outcome of death | 0 | 0 | 0 | 0 | 0 | 0 | 0 | 0 |

AE = adverse event; TEAE = treatment-emergent adverse event.

[a] n = Number of subjects; m = Number of events. For each category, subjects were included only once, even if they experienced multiple events in that category.

[b] Number of subjects in the Safety Population that received this treatment at least once during the open-label dose-optimization period.

[c] Number of subjects in the Safety Population that received this treatment during the double-blind period.

Note: TEAEs began after and were not present prior to treatment, or were present prior but worsened in severity following treatment. AE descriptors severe and serious were chosen in the eCRF. The AE descriptor "treatment-related" was chosen in the eCRF as relationship to study treatment: reasonable possibility.

Figure 48

| Adverse Event Category [n (%)] m[a] | Maximum Severity[b] | Treatment at Onset of Adverse Event | | | | | | | | | | | |
|---|---|---|---|---|---|---|---|---|---|---|---|---|---|
| | | 25 mg Formulation I | | 35 mg Formulation I | | 45 mg Formulation I | | 55 mg Formulation I | | 70 mg Formulation I | | 85 mg Formulation I | | Total Formulation I | |
| OL DO Period[c] | N | 156 | | 142 | | 107 | | 64 | | 26 | | 9 | | 156 | |
| Any TEAE | Mild | 47 (30.1) | 94 | 33 (23.2) | 68 | 27 (25.2) | 51 | 20 (31.3) | 32 | 6 (23.1) | 11 | 2 (22.2) | 2 | 86 (55.1) | 258 |
| | Moderate | 19 (12.2) | 27 | 17 (12.0) | 25 | 16 (15.0) | 18 | 5 (7.8) | 7 | 2 (7.7) | 3 | 0 | 0 | 43 (27.6) | 80 |
| | Severe | 0 | | 0 | | 0 | | 0 | | 0 | | 0 | | 0 | |
| | Total | 66 (42.3) | 121 | 50 (35.2) | 93 | 43 (40.2) | 69 | 25 (39.1) | 39 | 8 (30.8) | 14 | 2 (22.2) | 2 | 104 (66.7) | 338 |
| Metabolism and nutrition disorders | Mild | 21 (13.5) | 21 | 14 (9.9) | 14 | 9 (8.4) | 9 | 3 (4.7) | 3 | 0 | | 1 (11.1) | 1 | 47 (30.1) | 48 |
| | Moderate | 4 (2.6) | 4 | 3 (2.1) | 3 | 1 (0.9) | 1 | 1 (1.6) | 1 | 0 | | 0 | | 9 (5.8) | 9 |
| | Severe | 0 | | 0 | | 0 | | 0 | | 0 | | 0 | | 0 | |
| | Total | 25 (16.0) | 25 | 17 (12.0) | 17 | 10 (9.3) | 10 | 4 (6.3) | 4 | 0 | | 1 (11.1) | 1 | 55 (35.3) | 57 |
| Gastrointestinal disorders | Mild | 22 (14.1) | 28 | 12 (8.5) | 15 | 4 (3.7) | 5 | 6 (9.4) | 10 | 3 (11.5) | 3 | 0 | | 38 (24.4) | 61 |
| | Moderate | 6 (3.8) | 7 | 2 (1.4) | 3 | 3 (2.8) | 4 | 0 | | 0 | | 0 | | 10 (6.4) | 14 |
| | Severe | 0 | | 0 | | 0 | | 0 | | 0 | | 0 | | 0 | |
| | Total | 28 (17.9) | 35 | 14 (9.9) | 18 | 7 (6.5) | 9 | 6 (9.4) | 10 | 3 (11.5) | 3 | 0 | | 44 (28.2) | 75 |
| Psychiatric disorders | Mild | 14 (9.0) | 18 | 16 (11.3) | 17 | 5 (4.7) | 5 | 1 (1.6) | 1 | 1 (3.8) | 3 | 0 | | 35 (22.4) | 44 |
| | Moderate | 7 (4.5) | 8 | 4 (2.8) | 7 | 7 (6.5) | 7 | 1 (1.6) | 2 | 1 (3.8) | 1 | 0 | | 17 (10.9) | 25 |
| | Severe | 0 | | 0 | | 0 | | 0 | | 0 | | 0 | | 0 | |
| | Total | 21 (13.5) | 26 | 20 (14.1) | 24 | 12 (11.2) | 12 | 2 (3.1) | 3 | 2 (7.7) | 4 | 0 | | 49 (31.4) | 69 |
| Investigations | Mild | 6 (3.8) | 8 | 5 (3.5) | 7 | 13 (12.1) | 14 | 6 (9.4) | 7 | 3 (11.5) | 3 | 1 (11.1) | 1 | 30 (19.2) | 40 |
| | Moderate | 0 | | 1 (0.7) | 1 | 1 (0.9) | 1 | 0 | | 0 | | 0 | | 2 (1.3) | 2 |
| | Severe | 0 | | 0 | | 0 | | 0 | | 0 | | 0 | | 0 | |
| | Total | 6 (3.8) | 8 | 6 (4.2) | 8 | 14 (13.1) | 15 | 6 (9.4) | 7 | 3 (11.5) | 3 | 1 (11.1) | 1 | 32 (20.5) | 42 |
| Nervous system disorders | Mild | 9 (5.8) | 9 | 5 (3.5) | 5 | 6 (5.6) | 6 | 2 (3.1) | 2 | 0 | | 0 | | 20 (12.8) | 22 |
| | Moderate | 2 (1.3) | 2 | 3 (2.1) | 3 | 0 | | 1 (1.6) | 1 | 1 (3.8) | 1 | 0 | | 7 (4.5) | 7 |
| | Severe | 0 | | 0 | | 0 | | 0 | | 0 | | 0 | | 0 | |
| | Total | 11 (7.1) | 11 | 8 (5.6) | 8 | 6 (5.6) | 6 | 3 (4.7) | 3 | 1 (3.8) | 1 | 0 | | 26 (16.7) | 29 |

Figure 49

| Adverse Event Category [n (%) m][a] | Maximum Severity[b] | 25 mg Formulation I | 35 mg Formulation I | 45 mg Formulation I | Treatment at Onset of Adverse Event 55 mg Formulation I | 70 mg Formulation I | 85 mg Formulation I | Total Formulation I |
|---|---|---|---|---|---|---|---|---|
| OL DO Period[c] | N | 156 | 142 | 107 | 64 | 26 | 9 | 156 |
| Infections and infestations | Mild | 4 (2.6) 4 | 2 (1.4) 2 | 2 (1.9) 2 | 1 (1.6) 1 | 0 | 0 | 9 (5.8) 9 |
|  | Moderate | 1 (0.6) 1 | 4 (2.8) 5 | 3 (2.8) 3 | 1 (1.6) 1 | 1 (3.8) 1 | 0 | 10 (6.4) 11 |
|  | Severe | 0 | 0 | 0 | 0 | 0 | 0 | 0 |
|  | Total | 5 (3.2) 5 | 6 (4.2) 7 | 5 (4.7) 5 | 2 (3.1) 2 | 1 (3.8) 1 | 0 | 18 (11.5) 20 |
| Injury, poisoning and procedural complications | Mild | 3 (1.9) 3 | 2 (1.4) 2 | 1 (0.9) 1 | 3 (4.7) 4 | 0 | 0 | 9 (5.8) 10 |
|  | Moderate | 0 | 1 (0.7) 1 | 0 | 1 (1.6) 1 | 0 | 0 | 2 (1.3) 2 |
|  | Severe | 0 | 0 | 0 | 0 | 0 | 0 | 0 |
|  | Total | 3 (1.9) 3 | 3 (2.1) 3 | 1 (0.9) 1 | 4 (6.3) 5 | 0 | 0 | 11 (7.1) 12 |
| Cardiac disorders | Mild | 0 | 3 (2.1) 3 | 3 (2.8) 4 | 0 | 1 (3.8) 1 | 0 | 7 (4.5) 8 |
|  | Moderate | 0 | 0 | 0 | 0 | 0 | 0 | 0 |
|  | Severe | 0 | 0 | 0 | 0 | 0 | 0 | 0 |
|  | Total | 0 | 3 (2.1) 3 | 3 (2.8) 4 | 0 | 1 (3.8) 1 | 0 | 7 (4.5) 8 |
| General disorders and administration site conditions | Mild | 2 (1.3) 2 | 1 (0.7) 1 | 2 (1.9) 2 | 1 (1.6) 1 | 0 | 0 | 5 (3.2) 6 |
|  | Moderate | 3 (1.9) 3 | 0 | 2 (1.9) 2 | 0 | 0 | 0 | 5 (3.2) 5 |
|  | Severe | 0 | 0 | 0 | 0 | 0 | 0 | 0 |
|  | Total | 5 (3.2) 5 | 1 (0.7) 1 | 4 (3.7) 4 | 1 (1.6) 1 | 0 | 0 | 10 (6.4) 11 |
| Respiratory, thoracic and mediastinal disorders | Mild | 0 | 0 | 1 (0.9) 1 | 2 (3.1) 2 | 0 | 0 | 3 (1.9) 3 |
|  | Moderate | 1 (0.6) 1 | 1 (0.7) 1 | 0 | 0 | 0 | 0 | 2 (1.3) 2 |
|  | Severe | 0 | 0 | 0 | 0 | 0 | 0 | 0 |
|  | Total | 1 (0.6) 1 | 1 (0.7) 1 | 1 (0.9) 1 | 2 (3.1) 2 | 0 | 0 | 5 (3.2) 5 |
| Skin and subcutaneous tissue disorders | Mild | 0 | 1 (0.7) 1 | 1 (0.9) 1 | 1 (1.6) 1 | 0 | 0 | 3 (1.9) 3 |
|  | Moderate | 1 (0.6) 1 | 0 | 0 | 1 (1.6) 1 | 0 | 0 | 2 (1.3) 2 |
|  | Severe | 0 | 0 | 0 | 0 | 0 | 0 | 0 |
|  | Total | 1 (0.6) 1 | 1 (0.7) 1 | 1 (0.9) 1 | 2 (3.1) 2 | 0 | 0 | 5 (3.2) 5 |

Figure 50

| Adverse Event Category [n (%)] m]a | Maximum Severityb | 25 mg Formulation I | 35 mg Formulation I | 45 mg Formulation I | 55 mg Formulation I | 70 mg Formulation I | 85 mg Formulation I | Total Formulation I |
|---|---|---|---|---|---|---|---|---|
| OL DO Periodc | N | 156 | 142 | 107 | 64 | 26 | 9 | 156 |
| Ear and labyrinth disorders | Mild | 0 | 1 (0.7) 1 | 0 | 0 | 0 | 0 | 1 (0.6) 1 |
|  | Moderate | 0 | 0 | 0 | 0 | 0 | 0 | 0 |
|  | Severe | 0 | 0 | 0 | 0 | 0 | 0 | 0 |
|  | Total | 0 | 1 (0.7) 1 | 0 | 0 | 0 | 0 | 1 (0.6) 1 |
| Musculoskeletal and connective tissue disorders | Mild | 0 | 0 | 1 (0.9) 1 | 0 | 1 (3.8) 1 | 0 | 1 (0.6) 2 |
|  | Moderate | 0 | 0 | 0 | 0 | 0 | 0 | 0 |
|  | Severe | 0 | 0 | 0 | 0 | 0 | 0 | 0 |
|  | Total | 0 | 0 | 1 (0.9) 1 | 0 | 1 (3.8) 1 | 0 | 1 (0.6) 2 |
| Reproductive system and breast disorders | Mild | 1 (0.6) 1 | 0 | 0 | 0 | 0 | 0 | 1 (0.6) 1 |
|  | Moderate | 0 | 0 | 0 | 0 | 0 | 0 | 0 |
|  | Severe | 0 | 0 | 0 | 0 | 0 | 0 | 0 |
|  | Total | 1 (0.6) 1 | 0 | 0 | 0 | 0 | 0 | 1 (0.6) 1 |
| Immune system disorders | Mild | 0 | 0 | 0 | 0 | 0 | 0 | 0 |
|  | Moderate | 0 | 1 (0.7) 1 | 0 | 0 | 0 | 0 | 1 (0.6) 1 |
|  | Severe | 0 | 0 | 0 | 0 | 0 | 0 | 0 |
|  | Total | 0 | 1 (0.7) 1 | 0 | 0 | 0 | 0 | 1 (0.6) 1 |

AE = adverse event; DO = dose-optimization; OL = open-label; TEAE = treatment-emergent adverse event

[a] n = Number of subjects; m = Number of events. For each SOC, PT and Severity, subjects are included only once, even if they experienced multiple events in that SOC or PT.

[b] For each event, number of subjects were summarized in the row corresponding to the most severe event among the events of that type reported.

[c] Number of subjects in the SA that received this treatment at least once during the OL DO period.

Note: AEs were coded using MedDRA version 20.0. TEAEs began after and were not present prior to treatment, or were present prior but worsened in severity following treatment.

Figure 51

| Adverse Event Category [n (%) m][a] | Maximum Severity[b] | 25 mg Formulation I | 35 mg Formulation I | 45 mg Formulation I | Treatment at Onset of Adverse Event 55 mg Formulation I | 70 mg Formulation I | 85 mg Formulation I | Total Formulation I | Total Placebo |
|---|---|---|---|---|---|---|---|---|---|
| Double-blind Period | N | 9 | 15 | 20 | 19 | 8 | 4 | 75 | 73 |
| Any TEAE | Mild | 3 (33.3) 3 | 1 (6.7) 1 | 4 (20.0) 7 | 2 (10.5) 2 | 3 (37.5) 3 | 0 | 13 (17.3) 16 | 4 (5.5) 5 |
|  | Moderate | 0 | 1 (6.7) 1 | 1 (5.0) 1 | 1 (5.3) 1 | 0 | 2 (50.0) 2 | 5 (6.7) 5 | 3 (4.1) 4 |
|  | Severe | 0 | 0 | 0 | 0 | 0 | 0 | 0 | 0 |
|  | Total | 3 (33.3) 3 | 2 (13.3) 2 | 5 (25.0) 8 | 3 (15.8) 3 | 3 (37.5) 3 | 2 (50.0) 2 | 18 (24.0) 21 | 7 (9.6) 9 |
| Investigations | Mild | 0 | 0 | 2 (10.0) 2 | 1 (5.3) 1 | 2 (25.0) 2 | 0 | 5 (6.7) 5 | 1 (1.4) 1 |
|  | Moderate | 0 | 0 | 0 | 0 | 0 | 0 | 0 | 0 |
|  | Severe | 0 | 0 | 0 | 0 | 0 | 0 | 0 | 0 |
|  | Total | 0 | 0 | 2 (10.0) 2 | 1 (5.3) 1 | 2 (25.0) 2 | 0 | 5 (6.7) 5 | 1 (1.4) 1 |
| Cardiac disorders | Mild | 1 (11.1) 1 | 0 | 1 (5.0) 1 | 0 | 0 | 0 | 2 (2.7) 2 | 1 (1.4) 1 |
|  | Moderate | 0 | 0 | 0 | 0 | 0 | 0 | 0 | 1 (1.4) 1 |
|  | Severe | 0 | 0 | 0 | 0 | 0 | 0 | 0 | 0 |
|  | Total | 1 (11.1) 1 | 0 | 1 (5.0) 1 | 0 | 0 | 0 | 2 (2.7) 2 | 2 (2.7) 2 |
| Gastrointestinal disorders | Mild | 1 (11.1) 1 | 0 | 1 (5.0) 1 | 1 (5.3) 1 | 0 | 0 | 3 (4.0) 3 | 0 |
|  | Moderate | 0 | 0 | 1 (5.0) 1 | 0 | 0 | 0 | 1 (1.3) 1 | 1 (1.4) 1 |
|  | Severe | 0 | 0 | 0 | 0 | 0 | 0 | 0 | 0 |
|  | Total | 1 (11.1) 1 | 0 | 2 (10.0) 2 | 1 (5.3) 1 | 0 | 0 | 4 (5.3) 4 | 1 (1.4) 1 |
| Nervous system disorders | Mild | 0 | 0 | 0 | 0 | 1 (12.5) 1 | 0 | 1 (1.3) 1 | 1 (1.4) 1 |
|  | Moderate | 0 | 0 | 0 | 0 | 0 | 1 (25.0) 1 | 1 (1.3) 1 | 0 |
|  | Severe | 0 | 0 | 0 | 0 | 0 | 0 | 0 | 0 |
|  | Total | 0 | 0 | 0 | 0 | 1 (12.5) 1 | 1 (25.0) 1 | 2 (2.7) 2 | 1 (1.4) 1 |
| Ear and labyrinth disorders | Mild | 0 | 0 | 0 | 0 | 0 | 0 | 0 | 1 (1.4) 1 |
|  | Moderate | 0 | 0 | 0 | 0 | 0 | 0 | 0 | 0 |
|  | Severe | 0 | 0 | 0 | 0 | 0 | 0 | 0 | 0 |
|  | Total | 0 | 0 | 0 | 0 | 0 | 0 | 0 | 1 (1.4) 1 |
| Infections and infestations | Mild | 0 | 0 | 1 (5.0) 1 | 0 | 0 | 0 | 1 (1.3) 1 | 0 |
|  | Moderate | 0 | 0 | 0 | 0 | 0 | 1 (25.0) 1 | 1 (1.3) 1 | 2 (2.7) 2 |
|  | Severe | 0 | 0 | 0 | 0 | 0 | 0 | 0 | 0 |
|  | Total | 0 | 0 | 1 (5.0) 1 | 0 | 0 | 1 (25.0) 1 | 2 (2.7) 2 | 2 (2.7) 2 |
| Injury, poisoning and procedural complications | Mild | 0 | 0 | 1 (5.0) 1 | 0 | 0 | 0 | 1 (1.3) 1 | 0 |
|  | Moderate | 0 | 1 (6.7) 1 | 0 | 0 | 0 | 0 | 1 (1.3) 1 | 0 |
|  | Severe | 0 | 0 | 0 | 0 | 0 | 0 | 0 | 0 |
|  | Total | 0 | 1 (6.7) 1 | 1 (5.0) 1 | 0 | 0 | 0 | 2 (2.7) 2 | 0 |

Figure 52

| Adverse Event Category [n (%)] m[a] | Maximum Severity[c] | Treatment at Onset of Adverse Event | | | | | | | |
|---|---|---|---|---|---|---|---|---|---|
| | | 25 mg Formulation | 35 mg Formulation | 45 mg Formulation | 55 mg Formulation | 70 mg Formulation | 85 mg Formulation | Total Formulation | Total Placebo |
| Double-blind Period | N | 9 | 15 | 20 | 19 | 8 | 4 | 75 | 73 |
| Metabolism and nutrition disorders | Mild | 0 | 0 | 1 (5.0) 1 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 (5.0) 1 | 0 | 0 | 0 | 1 (1.3) 1 | 0 |
| Musculoskeletal and connective tissue disorders | Mild | 1 (11.1) 1 | 0 | 0 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 1 (11.1) 1 | 0 | 0 | 0 | 0 | 0 | 1 (1.3) 1 | 0 |
| Reproductive system and breast disorders | Mild | 0 | 1 (6.7) 1 | 0 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 1 (6.7) 1 | 0 | 0 | 0 | 0 | 1 (1.3) 1 | 0 |
| Respiratory, thoracic and mediastinal disorders | Mild | 0 | 0 | 0 | 0 | 0 | 0 | 0 | 1 (1.4) 1 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 0 | 0 | 0 | 0 | 0 | 1 (1.4) 1 |
| Psychiatric disorders | Mild | 0 | 0 | 0 | 0 | 0 | 0 | 0 | 0 |
| | Moderate | 0 | 0 | 0 | 1 (5.3) 1 | 0 | 0 | 1 (1.3) 1 | 0 |
| | Severe | 0 | 0 | 0 | 0 | 0 | 0 | 0 | 0 |
| | Total | 0 | 0 | 0 | 1 (5.3) 1 | 0 | 0 | 1 (1.3) 1 | 0 |

TEAE = treatment-emergent adverse event

[a] n = Number of subjects; m = Number of events. For each SOC, and severity, subjects were included only once, even if they experienced multiple events in that SOC or PT.

[b] For each event, number of subjects were summarized in the row corresponding to the most severe event among the events of that type reported.

[c] Number of subjects in the Safety Analysis population that received this treatment at least once during the Open-Label Dose-Optimization period.

Note: Adverse events were coded using MedDRA version 20.0. TEAEs began after and were not present prior to treatment, or were present prior but worsened in severity following treatment.

Figure 53

| Adverse Event Category [n (%) m][a] | Maximum Severity[b] | Treatment at Onset of Adverse Event | | | | | | |
|---|---|---|---|---|---|---|---|---|
| | | 25 mg Formulation I | 35 mg Formulation I | 45 mg Formulation I | 55 mg Formulation I | 70 mg Formulation I | 85 mg Formulation I | Total Formulation I |
| Open-label Dose-optimization | Period | 156 | 142 | 107 | 64 | 26 | 9 | 156 |
| Decreased appetite | Mild | 21 (13.5) 21 | 14 (9.9) 14 | 9 (8.4) 9 | 3 (4.7) 3 | 0 | 1 (11.1) 1 | 47 (30.1) 48 |
| | Moderate | 4 (2.6) 4 | 3 (2.1) 3 | 1 (0.9) 1 | 1 (1.6) 1 | 0 | 0 | 9 (5.8) 9 |
| | Severe | 0 | 0 | 0 | 0 | 0 | 0 | 0 |
| | Total | 25 (16.0) 25 | 17 (12.0) 17 | 10 (9.3) 10 | 4 (6.3) 4 | 0 | 1 (11.1) 1 | 55 (35.3) 57 |
| Abdominal pain upper | Mild | 12 (7.7) 12 | 7 (4.9) 7 | 3 (2.8) 3 | 4 (6.3) 4 | 3 (11.5) 3 | 0 | 23 (14.7) 29 |
| | Moderate | 3 (1.9) 3 | 0 | 0 | 0 | 0 | 0 | 3 (1.9) 3 |
| | Severe | 0 | 0 | 0 | 0 | 0 | 0 | 0 |
| | Total | 15 (9.6) 15 | 7 (4.9) 7 | 3 (2.8) 3 | 4 (6.3) 4 | 3 (11.5) 3 | 0 | 26 (16.7) 32 |
| Affect lability | Mild | 4 (2.6) 4 | 7 (4.9) 7 | 2 (1.9) 2 | 0 | 1 (3.8) 1 | 0 | 14 (9.0) 14 |
| | Moderate | 3 (1.9) 3 | 2 (1.4) 2 | 2 (1.9) 2 | 0 | 1 (3.8) 1 | 0 | 8 (5.1) 8 |
| | Severe | 0 | 0 | 0 | 0 | 0 | 0 | 0 |
| | Total | 7 (4.5) 7 | 9 (6.3) 9 | 4 (3.7) 4 | 0 | 2 (7.7) 2 | 0 | 22 (14.1) 22 |
| Weight decreased | Mild | 3 (1.9) 4 | 3 (2.1) 4 | 7 (6.5) 7 | 4 (6.3) 4 | 1 (3.8) 1 | 0 | 16 (10.3) 20 |
| | Moderate | 0 | 1 (0.7) 1 | 1 (0.9) 1 | 0 | 0 | 0 | 2 (1.3) 2 |
| | Severe | 0 | 0 | 0 | 0 | 0 | 0 | 0 |
| | Total | 3 (1.9) 4 | 4 (2.8) 5 | 8 (7.5) 8 | 4 (6.3) 4 | 1 (3.8) 1 | 0 | 18 (11.5) 22 |
| Headache | Mild | 5 (3.2) 5 | 4 (2.8) 4 | 2 (1.9) 2 | 1 (1.6) 1 | 0 | 0 | 11 (7.1) 12 |
| | Moderate | 2 (1.3) 2 | 3 (2.1) 3 | 0 | 1 (1.6) 1 | 1 (3.8) 1 | 0 | 7 (4.5) 7 |
| | Severe | 0 | 0 | 0 | 0 | 0 | 0 | 0 |
| | Total | 7 (4.5) 7 | 7 (4.9) 7 | 2 (1.9) 2 | 2 (3.1) 2 | 1 (3.8) 1 | 0 | 17 (10.9) 19 |
| Irritability | Mild | 7 (4.5) 7 | 5 (3.5) 5 | 1 (0.9) 1 | 1 (1.6) 1 | 0 | 0 | 14 (9.0) 14 |
| | Moderate | 0 | 0 | 1 (0.9) 1 | 1 (1.6) 1 | 0 | 0 | 2 (1.3) 2 |
| | Severe | 0 | 0 | 0 | 0 | 0 | 0 | 0 |
| | Total | 7 (4.5) 7 | 5 (3.5) 5 | 2 (1.9) 2 | 2 (3.1) 2 | 0 | 0 | 16 (10.3) 16 |
| Insomnia | Mild | 4 (2.6) 4 | 3 (2.1) 3 | 2 (1.9) 2 | 0 | 0 | 0 | 9 (5.8) 9 |
| | Moderate | 3 (1.9) 3 | 2 (1.4) 2 | 4 (3.7) 4 | 1 (1.6) 1 | 0 | 0 | 9 (5.8) 10 |
| | Severe | 0 | 0 | 0 | 0 | 0 | 0 | 0 |
| | Total | 7 (4.5) 7 | 5 (3.5) 5 | 6 (5.6) 6 | 1 (1.6) 1 | 0 | 0 | 16 (10.3) 19 |

[a] n = Number of subjects; m = Number of events. For each PT and severity, subjects were included only once, even if they experienced multiple events in that PT.
[b] For each event, number of subjects were summarized in the row corresponding to the most severe event among the events of that type reported.
Note. Adverse events were coded using MedDRA version 20.0. TEAEs began after and were not present prior to treatment, or were present but worsened in severity following treatment.

Figure 54

| Adverse Event Category [n (%) m][a] | Maximum Severity[b] | Treatment at Onset of Adverse Event | | | | | | | |
|---|---|---|---|---|---|---|---|---|---|
| | | 25 mg Formulation | 35 mg Formulation | 45 mg Formulation | 55 mg Formulation | 70 mg Formulation | 85 mg Formulation | Total Formulation | Total Placebo |
| Double-Blind Period[c] | | | | | | | | | |
| Heart rate increased | | 9 | 15 | 20 | 19 | 8 | 4 | 75 | 73 |
| | Mild | 0 | 0 | 1 ( 5.0) 1 | 1 ( 5.3) 1 | 1 (12.5) 1 | 0 | 3 ( 4.0) 3 | 1 ( 1.4) 1 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 ( 5.0) 1 | 1 ( 5.3) 1 | 1 (12.5) 1 | 0 | 3 ( 4.0) 3 | 1 ( 1.4) 1 |
| Sinus tachycardia | Mild | 0 | 0 | 1 ( 5.0) 1 | 0 | 0 | 0 | 1 ( 1.3) 1 | 1 ( 1.4) 1 |
| | Moderate | 0 | 0 | 0 | 0 | 0 | 0 | 0 | 1 ( 1.4) 1 |
| | Severe | 0 | 0 | 0 | 0 | 0 | 0 | 0 | 0 |
| | Total | 0 | 0 | 1 ( 5.0) 1 | 0 | 0 | 0 | 1 ( 1.3) 1 | 2 ( 2.7) 2 |
| Vomiting | Mild | 1 (11.1) 1 | 0 | 0 | 1 ( 5.3) 1 | 0 | 0 | 2 ( 2.7) 2 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 1 (11.1) 1 | 0 | 0 | 1 ( 5.3) 1 | 0 | 0 | 2 ( 2.7) 2 | 0 |
| Headache | Mild | 0 | 0 | 0 | 0 | 1 (12.5) 1 | 0 | 1 ( 1.3) 1 | 0 |
| | Moderate | 0 | 0 | 0 | 0 | 0 | 1 (25.0) 1 | 1 ( 1.3) 1 | 0 |
| | Severe | 0 | 0 | 0 | 0 | 0 | 0 | 0 | 0 |
| | Total | 0 | 0 | 0 | 0 | 1 (12.5) 1 | 1 (25.0) 1 | 2 ( 2.7) 2 | 0 |
| Upper respiratory tract infection | Mild | 0 | 0 | 1 ( 5.0) 1 | 0 | 0 | 0 | 1 ( 1.3) 1 | 0 |
| | Moderate | 0 | 0 | 0 | 0 | 0 | 1 (25.0) 1 | 1 ( 1.3) 1 | 0 |
| | Severe | 0 | 0 | 0 | 0 | 0 | 0 | 0 | 0 |
| | Total | 0 | 0 | 1 ( 5.0) 1 | 0 | 0 | 1 (25.0) 1 | 2 ( 2.7) 2 | 0 |

[a] n = Number of subjects; m = Number of events. For each PT and severity, subjects were included only once, even if they experienced multiple events in that PT.

[b] For each event, number of subjects was summarized in the row corresponding to the most severe event among the events of that type reported.

[c] Number of subjects in the Safety Analysis population that received this treatment at least once during the double-blind period.

Figure 55

| Adverse Event Category [n (%)] m[a] | Maximum Severity[c] | Treatment at Onset of Adverse Event | | | | | | |
|---|---|---|---|---|---|---|---|---|
| | | 25 mg Formulation I | 35 mg Formulation I | 45 mg Formulation I | 55 mg Formulation I | 70 mg Formulation I | 85 mg Formulation I | Total Formulation I |
| Open-label Dose-optimization Period[e] | | 156 | 142 | 107 | 64 | 26 | 9 | 156 |
| Any related AE | Mild | 38 (24.4) 77 | 30 (21.1) 52 | 26 (24.3) 42 | 17 (26.6) 23 | 5 (19.2) 7 | 2 (22.2) 2 | 78 (50.0) 203 |
| | Moderate | 16 (10.3) 20 | 10 (7.0) 13 | 12 (11.2) 13 | 2 (3.1) 4 | 2 (7.7) 2 | 0 | 34 (21.8) 52 |
| | Severe | 0 | 0 | 0 | 0 | 0 | 0 | 0 |
| | Total | 54 (34.6) 97 | 40 (28.2) 65 | 38 (35.5) 55 | 19 (29.7) 27 | 7 (26.9) 9 | 2 (22.2) 2 | 95 (60.9) 255 |
| Decreased appetite | Mild | 21 (13.5) 21 | 14 (9.9) 14 | 8 (7.5) 8 | 3 (4.7) 3 | 0 | 1 (11.1) 1 | 46 (29.5) 47 |
| | Moderate | 4 (2.6) 4 | 3 (2.1) 3 | 1 (0.9) 1 | 1 (1.6) 1 | 0 | 0 | 9 (5.8) 9 |
| | Severe | 0 | 0 | 0 | 0 | 0 | 0 | 0 |
| | Total | 25 (16.0) 25 | 17 (12.0) 17 | 9 (8.4) 9 | 4 (6.3) 4 | 0 | 1 (11.1) 1 | 55 (35.3) 56 |
| Abdominal pain upper | Mild | 11 (7.1) 11 | 7 (4.9) 7 | 3 (2.8) 3 | 4 (6.3) 4 | 1 (3.8) 1 | 0 | 20 (12.8) 26 |
| | Moderate | 3 (1.9) 3 | 0 | 0 | 0 | 0 | 0 | 3 (1.9) 3 |
| | Severe | 0 | 0 | 0 | 0 | 0 | 0 | 0 |
| | Total | 14 (9.0) 14 | 7 (4.9) 7 | 3 (2.8) 3 | 4 (6.3) 4 | 1 (3.8) 1 | 0 | 23 (14.7) 29 |
| Affect lability | Mild | 3 (1.9) 3 | 7 (4.9) 7 | 2 (1.9) 2 | 0 | 1 (3.8) 1 | 0 | 13 (8.3) 13 |
| | Moderate | 3 (1.9) 3 | 2 (1.4) 2 | 2 (1.9) 2 | 0 | 1 (3.8) 1 | 0 | 8 (5.1) 8 |
| | Severe | 0 | 0 | 0 | 0 | 0 | 0 | 0 |
| | Total | 6 (3.8) 6 | 9 (6.3) 9 | 4 (3.7) 4 | 0 | 2 (7.7) 2 | 0 | 21 (13.5) 21 |
| Weight decreased | Mild | 3 (1.9) 4 | 3 (2.1) 4 | 7 (6.5) 7 | 4 (6.3) 4 | 1 (3.8) 1 | 0 | 16 (10.3) 20 |
| | Moderate | 0 | 1 (0.7) 1 | 1 (0.9) 1 | 0 | 0 | 0 | 2 (1.3) 2 |
| | Severe | 0 | 0 | 0 | 0 | 0 | 0 | 0 |
| | Total | 3 (1.9) 4 | 4 (2.8) 5 | 8 (7.5) 8 | 4 (6.3) 4 | 1 (3.8) 1 | 0 | 18 (11.5) 22 |
| Insomnia | Mild | 4 (2.6) 4 | 3 (2.1) 3 | 2 (1.9) 2 | 0 | 0 | 0 | 9 (5.8) 9 |
| | Moderate | 3 (1.9) 3 | 2 (1.4) 2 | 4 (3.7) 4 | 1 (1.6) 1 | 0 | 0 | 9 (5.8) 10 |
| | Severe | 0 | 0 | 0 | 0 | 0 | 0 | 0 |
| | Total | 7 (4.5) 7 | 5 (3.5) 5 | 6 (5.6) 6 | 1 (1.6) 1 | 0 | 0 | 16 (10.3) 19 |
| Irritability | Mild | 7 (4.5) 7 | 4 (2.8) 4 | 1 (0.9) 1 | 1 (1.6) 1 | 0 | 0 | 13 (8.3) 13 |
| | Moderate | 0 | 0 | 1 (0.9) 1 | 1 (1.6) 1 | 0 | 0 | 2 (1.3) 2 |
| | Severe | 0 | 0 | 0 | 0 | 0 | 0 | 0 |
| | Total | 7 (4.5) 7 | 4 (2.8) 4 | 2 (1.9) 2 | 2 (3.1) 2 | 0 | 0 | 15 (9.6) 15 |
| Headache | Mild | 4 (2.6) 4 | 2 (1.4) 2 | 2 (1.9) 2 | 1 (1.6) 1 | 0 | 0 | 9 (5.8) 9 |
| | Moderate | 2 (1.3) 2 | 2 (1.4) 2 | 2 (1.9) 2 | 1 (1.6) 1 | 1 (3.8) 1 | 0 | 6 (3.8) 6 |
| | Severe | 0 | 0 | 0 | 0 | 0 | 0 | 0 |
| | Total | 6 (3.8) 6 | 4 (2.8) 4 | 2 (1.9) 2 | 2 (3.1) 2 | 1 (3.8) 1 | 0 | 15 (9.6) 15 |

Figure 56

| Adverse Event Category [n (%) m][a] | Maximum Severity[c] | Treatment at Onset of Adverse Event | | | | | | |
|---|---|---|---|---|---|---|---|---|
| | | 25 mg Formulation I | 35 mg Formulation I | 45 mg Formulation I | 55 mg Formulation I | 70 mg Formulation I | 85 mg Formulation I | Total Formulation I |
| Open-label Dose-optimization Period[b] | | 156 | 142 | 107 | 64 | 26 | 9 | 156 |
| Vomiting | Mild | 2 (1.3) 2 | 2 (1.4) 2 | 2 (1.9) 2 | 2 (3.1) 2 | 0 | 0 | 8 (5.1) 8 |
| | Moderate | 1 (0.6) 1 | 0 | 2 (1.9) 2 | 0 | 0 | 0 | 3 (1.9) 3 |
| | Severe | 0 | 0 | 0 | 0 | 0 | 0 | 0 |
| | Total | 3 (1.9) 3 | 2 (1.4) 2 | 4 (3.7) 4 | 2 (3.1) 2 | 0 | 0 | 11 (7.1) 11 |
| Nausea | Mild | 5 (3.2) 5 | 1 (0.7) 1 | 0 | 2 (3.1) 2 | 0 | 0 | 7 (4.5) 8 |
| | Moderate | 1 (0.6) 1 | 0 | 1 (0.9) 1 | 0 | 0 | 0 | 2 (1.3) 2 |
| | Severe | 0 | 0 | 0 | 0 | 0 | 0 | 0 |
| | Total | 6 (3.8) 6 | 1 (0.7) 1 | 1 (0.9) 1 | 2 (3.1) 2 | 0 | 0 | 9 (5.8) 10 |
| Heart rate increased | Mild | 0 | 1 (0.7) 1 | 5 (4.7) 6 | 1 (1.6) 2 | 1 (3.8) 1 | 0 | 8 (5.1) 10 |
| | Moderate | 0 | 0 | 0 | 0 | 0 | 0 | 0 |
| | Severe | 0 | 0 | 0 | 0 | 0 | 0 | 0 |
| | Total | 0 | 1 (0.7) 1 | 5 (4.7) 6 | 1 (1.6) 2 | 1 (3.8) 1 | 0 | 8 (5.1) 10 |

[a] n = Number of subjects; m = Number of events. For each SOC, PT and severity, subjects were included only once, even if they experienced multiple events in that SOC or PT.

[b] For each event, number of subjects were summarized in the row corresponding to the most severe event among the events of that type reported.

[c] Number of subjects in the Safety Analysis population that received this treatment at least once during the Open-Label Dose-Optimization period.

Note: Adverse events were coded using MedDRA version 20.0. TEAEs began after and were not present prior to treatment, or were present prior but worsened in severity following treatment.

The AE descriptor "treatment-related" was assigned in the eCRF as relationship to study treatment: reasonable possibility.

Figure 57

| Adverse Event Category [n (%)] m]ª | Maximum Severityᵇ | Treatment at Onset of Adverse Event | | | | | | | |
|---|---|---|---|---|---|---|---|---|---|
| | | 25 mg Formulation | 35 mg Formulation | 45 mg Formulation | 55 mg Formulation | 70 mg Formulation | 85 mg Formulation | Total Formulation | Total Placebo |
| Double-blind Periodᶜ | N | 9 | 15 | 20 | 19 | 8 | 4 | 75 | 73 |
| Any related AE | Mild | 1 (11.1) 1 | 1 (6.7) 1 | 3 (15.0) 5 | 2 (10.5) 2 | 3 (37.5) 3 | 0 | 10 (13.3) 12 | 2 (2.7) 2 |
| | Moderate | 0 | 0 | 1 (5.0) 1 | 0 | 0 | 1 (25.0) 1 | 2 (2.7) 2 | 0 |
| | Severe | 0 | 0 | 0 | 0 | 0 | 0 | 0 | 0 |
| | Total | 1 (11.1) 1 | 1 (6.7) 1 | 4 (20.0) 6 | 2 (10.5) 2 | 3 (37.5) 3 | 1 (25.0) 1 | 12 (16.0) 14 | 2 (2.7) 2 |
| Heart rate increased | Mild | 0 | 0 | 1 (5.0) 1 | 1 (5.3) 1 | 1 (12.5) 1 | 0 | 3 (4.0) 3 | 1 (1.4) 1 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 (5.0) 1 | 1 (5.3) 1 | 1 (12.5) 1 | 0 | 3 (4.0) 3 | 1 (1.4) 1 |
| Sinus tachycardia | Mild | 0 | 0 | 1 (5.0) 1 | 0 | 0 | 0 | 1 (1.3) 1 | 1 (1.4) 1 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 (5.0) 1 | 0 | 0 | 0 | 1 (1.3) 1 | 1 (1.4) 1 |
| Headache | Mild | 0 | 0 | 0 | 0 | 1 (12.5) 1 | 0 | 1 (1.3) 1 | 0 |
| | Moderate | 0 | 0 | 0 | 0 | 0 | 1 (25.0) 1 | 1 (1.3) 1 | 0 |
| | Severe | 0 | 0 | 0 | 0 | 0 | 0 | 0 | 0 |
| | Total | 0 | 0 | 0 | 0 | 1 (12.5) 1 | 1 (25.0) 1 | 2 (2.7) 2 | 0 |
| Blood pressure diastolic increased | Mild | 0 | 0 | 0 | 0 | 1 (12.5) 1 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 0 | 0 | 1 (12.5) 1 | 0 | 1 (1.3) 1 | 0 |
| Weight decreased | Mild | 0 | 0 | 1 (5.0) 1 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 (5.0) 1 | 0 | 0 | 0 | 1 (1.3) 1 | 0 |
| Tachycardia | Mild | 1 (11.1) 1 | 0 | 0 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 1 (11.1) 1 | 0 | 0 | 0 | 0 | 0 | 1 (1.3) 1 | 0 |
| Abdominal pain upper | Mild | 0 | 0 | 1 (5.0) 1 | 0 | 0 | 0 | 1 (1.3) 1 | 0 |
| | Moderate | 0 | 0 | 0 | 0 | 0 | 0 | 0 | 0 |
| | Severe | 0 | 0 | 0 | 0 | 0 | 0 | 0 | 0 |
| | Total | 0 | 0 | 1 (5.0) 1 | 0 | 0 | 0 | 1 (1.3) 1 | 0 |

Figure 58

| Adverse Event Category [n (%)] m[a] | Maximum Severity[c] | 25 mg Formulation | 35 mg Formulation | 45 mg Formulation | 55 mg Formulation | 70 mg Formulation | 85 mg Formulation | Total Formulation | Total Placebo |
|---|---|---|---|---|---|---|---|---|---|
| Double-blind Period[b] | N | 9 | 15 | 20 | 19 | 8 | 4 | 75 | 73 |
| Vomiting | Mild | 0 | 0 | 0 | 1 (5.3) 1 | 0 | 0 | 1 (1.3) 1 | 0 |
|  | Moderate | 0 | 0 | 0 | 0 | 0 | 0 | 0 | 0 |
|  | Severe | 0 | 0 | 0 | 0 | 0 | 0 | 0 | 0 |
|  | Total | 0 | 0 | 0 | 1 (5.3) 1 | 0 | 0 | 1 (1.3) 1 | 0 |
| Nausea | Mild | 0 | 0 | 0 | 0 | 0 | 0 | 0 | 0 |
|  | Moderate | 0 | 0 | 1 (5.0) 1 | 0 | 0 | 0 | 1 (1.3) 1 | 0 |
|  | Severe | 0 | 0 | 0 | 0 | 0 | 0 | 0 | 0 |
|  | Total | 0 | 0 | 1 (5.0) 1 | 0 | 0 | 0 | 1 (1.3) 1 | 0 |
| Decreased appetite | Mild | 0 | 0 | 1 (5.0) 1 | 0 | 0 | 0 | 1 (1.3) 1 | 0 |
|  | Moderate | 0 | 0 | 0 | 0 | 0 | 0 | 0 | 0 |
|  | Severe | 0 | 0 | 0 | 0 | 0 | 0 | 0 | 0 |
|  | Total | 0 | 0 | 1 (5.0) 1 | 0 | 0 | 0 | 1 (1.3) 1 | 0 |
| Dysmenorrhoea | Mild | 0 | 1 (6.7) 1 | 0 | 0 | 0 | 0 | 1 (1.3) 1 | 0 |
|  | Moderate | 0 | 0 | 0 | 0 | 0 | 0 | 0 | 0 |
|  | Severe | 0 | 0 | 0 | 0 | 0 | 0 | 0 | 0 |
|  | Total | 0 | 1 (6.7) 1 | 0 | 0 | 0 | 0 | 1 (1.3) 1 | 0 |

[a] n = Number of subjects; m = Number of events. For each SOC, PT and severity, subjects were included only once, even if they experienced multiple events in that SOC or PT.

[b] For each event, number of subjects are summarized in the row corresponding to the most severe event among the events of that type reported.

[c] Number of subjects in the Safety Analysis population that received this treatment at least once during the Double-blind period.

Note: Adverse events were coded using MedDRA version 20.0. TEAEs began after and were not present prior to treatment, or were present prior but worsened in severity following treatment.

Figure 59

| | Formulation I | Cotempla XR-ODT | Dyanavel XR | LDX | Quillivant XR | Aptensio XR | Evekeo | Quillichew ER | Jornay PM |
|---|---|---|---|---|---|---|---|---|---|
| N | 156 | 87 | 107 | 129 | 45 | 26 | 105 | 90 | 125 |
| Weeks of OL | 6 wk | 5 wk | 5 wk | 4 wk | 3 wk | 2-4 wks | 8 wk | 6 wk | 6 wk |
| Decreased appetite | 35.3% | 26.4% | 26.2% | 47.3% | 55.6% | 23.1% | 27.6% | 36.7% | 27% |
| Abdominal Pain Upper | 16.7% | 21.8% | 7.5% | 15.5% | 42.2% | 11.5% | 14.3% | 14.4% | 9% |
| Affect Lability* | 14.1% | 9.2% | 9.3% | 10.1% | 26.7% | 7.7% | 5.7% | 13.3% | 22% |
| Weight Decreased | 11.5% | NR | NR | NR | NR | NR | NR | NR | NR |
| Headache | 10.9% | 19.5% | 5.6% | 17.1% | 17.8% | 23.1% | 13.3% | 8.9% | 19% |
| Irritability | 10.3% | 6.9% | NR | 16.3% | NR | 19.2% | 14.3% | 13.3% | 6% |
| Insomnia | 10.3% | 12.6% | 13.1% | 27.1% | 17.8% | 30.8% | 6.7% | 11.1% | 41% |

Note: The studies presented in this table were dose-optimized and conducted in children.
* mood swings or emotional lability
NR = not reported; OL = open-label

Figure 62

| Planned Time (in hours) | 85 mg Formulation I<br>N=6 | 55 mg Formulation I<br>N=6 | 35 mg Formulation I<br>N=6 |
|---|---|---|---|
| Pre-dose | | | |
| n | 6 | 6 | 6 |
| m | 0 | 0 | 0 |
| Mean (SD) | 0.000 (0.0000) | 0.000 (0.0000) | 0.000 (0.0000) |
| %CV | | | |
| Median | 0.000 | 0.000 | 0.000 |
| Min, Max | 0.00, 0.00 | 0.00, 0.00 | 0.00, 0.00 |
| Geometric Mean (SD) | | | |
| %CV for Geometric Mean | | | |
| 1 hour post-dose | | | |
| n | 6 | 6 | 6 |
| m | 6 | 6 | 6 |
| Mean (SD) | 15.343 (5.2516) | 9.273 (3.2341) | 5.488 (2.3372) |
| %CV | 34.23 | 34.88 | 42.58 |
| Median | 13.425 | 8.415 | 6.495 |
| Min, Max | 9.05, 22.85 | 5.70, 14.22 | 1.70, 7.41 |
| Geometric Mean (SD) | 14.618 (1.4063) | 8.827 (1.4082) | 4.891 (1.7969) |
| %CV for Geometric Mean | 35.11 | 35.26 | 64.02 |
| 2 hours post-dose | | | |
| n | 6 | 6 | 6 |
| m | 6 | 6 | 6 |
| Mean (SD) | 20.665 (1.4356) | 11.063 (2.7943) | 6.608 (1.0144) |
| %CV | 6.95 | 25.26 | 15.35 |
| Median | 20.190 | 11.395 | 6.295 |
| Min, Max | 19.55, 23.29 | 7.77, 14.95 | 5.91, 8.57 |
| Geometric Mean (SD) | 20.625 (1.0696) | 10.764 (1.2956) | 6.550 (1.1520) |
| %CV for Geometric Mean | 6.74 | 26.33 | 14.22 |
| 3 hours post-dose | | | |
| n | 6 | 6 | 6 |
| m | 6 | 6 | 6 |
| Mean (SD) | 17.007 (2.5607) | 8.810 (2.2350) | 5.760 (1.2745) |
| %CV | 15.06 | 25.37 | 22.13 |
| Median | 16.400 | 9.990 | 5.680 |
| Min, Max | 13.77, 20.54 | 5.27, 10.53 | 3.99, 7.23 |
| Geometric Mean (SD) | 16.848 (1.1613) | 8.533 (1.3355) | 5.638 (1.2575) |
| %CV for Geometric Mean | 15.04 | 29.54 | 23.22 |
| 4 hours post-dose | | | |
| n | 6 | 6 | 6 |
| m | 6 | 6 | 6 |
| Mean (SD) | 15.558 (1.8090) | 7.340 (1.6456) | 5.728 (1.1913) |
| %CV | 11.63 | 22.42 | 20.80 |
| Median | 15.655 | 8.085 | 5.675 |
| Min, Max | 13.64, 17.57 | 4.58, 8.82 | 4.10, 7.46 |
| Geometric Mean (SD) | 15.470 (1.1241) | 7.161 (1.2892) | 5.624 (1.2360) |
| %CV for Geometric Mean | 11.74 | 25.82 | 21.43 |

Figure 63

| Planned Time (in hours) | 85 mg Formulation I N=6 | 55 mg Formulation I N=6 | 35 mg Formulation I N=6 |
|---|---|---|---|
| 5 hours post-dose | | | |
| n | 6 | 6 | 6 |
| m | 6 | 6 | 6 |
| Mean (SD) | 16.847 (4.0993) | 7.995 (2.1168) | 7.160 (1.8358) |
| %CV | 24.33 | 26.48 | 25.64 |
| Median | 17.170 | 8.435 | 7.470 |
| Min, Max | 12.03, 21.69 | 5.20, 10.45 | 3.88, 8.82 |
| Geometric Mean (SD) | 16.419 (1.2853) | 7.742 (1.3296) | 6.917 (1.3577) |
| %CV for Geometric Mean | 25.50 | 29.08 | 31.30 |
| 6 hours post-dose | | | |
| n | 6 | 6 | 6 |
| m | 6 | 6 | 6 |
| Mean (SD) | 19.652 (6.7420) | 10.855 (4.9956) | 8.038 (2.2680) |
| %CV | 34.31 | 46.02 | 28.21 |
| Median | 20.670 | 9.325 | 8.065 |
| Min, Max | 11.74, 29.46 | 7.01, 20.79 | 4.49, 11.20 |
| Geometric Mean (SD) | 18.649 (1.4346) | 10.149 (1.4556) | 7.741 (1.3665) |
| %CV for Geometric Mean | 37.30 | 38.90 | 32.00 |
| 7 hours post-dose | | | |
| n | 6 | 6 | 6 |
| m | 6 | 6 | 6 |
| Mean (SD) | 20.412 (7.8422) | 12.172 (3.2971) | 9.157 (1.9661) |
| %CV | 38.42 | 27.09 | 21.47 |
| Median | 20.115 | 11.015 | 9.080 |
| Min, Max | 10.76, 33.18 | 10.47, 18.87 | 6.03, 11.95 |
| Geometric Mean (SD) | 19.168 (1.4815) | 11.878 (1.2570) | 8.968 (1.2574) |
| %CV for Geometric Mean | 40.88 | 23.17 | 23.21 |
| 8 hours post-dose | | | |
| n | 6 | 6 | 6 |
| m | 6 | 6 | 6 |
| Mean (SD) | 23.480 (8.1471) | 12.857 (3.4601) | 9.847 (2.4503) |
| %CV | 34.70 | 26.91 | 24.88 |
| Median | 22.365 | 11.485 | 9.100 |
| Min, Max | 14.81, 37.12 | 10.75, 19.80 | 6.82, 14.00 |
| Geometric Mean (SD) | 22.383 (1.3989) | 12.545 (1.2587) | 9.606 (1.2734) |
| %CV for Geometric Mean | 34.53 | 23.32 | 24.53 |
| 9 hours post-dose | | | |
| n | 6 | 6 | 6 |
| m | 6 | 6 | 6 |
| Mean (SD) | 23.727 (7.9939) | 14.557 (4.0908) | 10.325 (2.6068) |
| %CV | 33.69 | 28.10 | 25.25 |
| Median | 23.800 | 13.675 | 9.855 |
| Min, Max | 15.69, 37.58 | 10.84, 22.54 | 7.89, 15.35 |
| Geometric Mean (SD) | 22.682 (1.3854) | 14.159 (1.2808) | 10.091 (1.2542) |
| %CV for Geometric Mean | 33.48 | 25.13 | 22.94 |

Figure 64

| Planned Time (in hours) | 85 mg Formulation I<br>N=6 | 55 mg Formulation I<br>N=6 | 35 mg Formulation I<br>N=6 |
|---|---|---|---|
| 10 hours post-dose | | | |
| n | 6 | 6 | 6 |
| m | 6 | 6 | 6 |
| Mean (SD) | 22.982 (9.4387) | 14.087 (3.3968) | 9.957 (2.4613) |
| %CV | 41.07 | 24.11 | 24.72 |
| Median | 21.910 | 13.240 | 9.280 |
| Min, Max | 13.46, 39.42 | 11.19, 20.81 | 7.52, 14.02 |
| Geometric Mean (SD) | 21.519 (1.4804) | 13.802 (1.2365) | 9.721 (1.2660) |
| %CV for Geometric Mean | 40.79 | 21.47 | 23.92 |
| 11 hours post-dose | | | |
| n | 6 | 6 | 6 |
| m | 6 | 6 | 6 |
| Mean (SD) | 22.372 (7.4024) | 14.473 (2.3930) | 9.210 (2.4234) |
| %CV | 33.09 | 16.53 | 26.31 |
| Median | 20.230 | 13.960 | 8.925 |
| Min, Max | 15.96, 35.58 | 11.88, 18.42 | 6.57, 13.56 |
| Geometric Mean (SD) | 21.478 (1.3557) | 14.316 (1.1736) | 8.969 (1.2815) |
| %CV for Geometric Mean | 31.15 | 16.11 | 25.19 |
| 12 hours post-dose | | | |
| n | 6 | 6 | 6 |
| m | 6 | 6 | 6 |
| Mean (SD) | 21.157 (5.9155) | 13.070 (2.7873) | 9.053 (2.3820) |
| %CV | 27.96 | 21.33 | 26.31 |
| Median | 21.040 | 13.215 | 9.115 |
| Min, Max | 13.43, 31.11 | 8.47, 16.51 | 5.81, 11.72 |
| Geometric Mean (SD) | 20.484 (1.3223) | 12.795 (1.2625) | 8.777 (1.3204) |
| %CV for Geometric Mean | 28.49 | 23.63 | 28.34 |
| 13 hours post-dose | | | |
| n | 6 | 6 | 6 |
| m | 6 | 6 | 6 |
| Mean (SD) | 22.398 (4.1739) | 12.813 (2.7911) | 8.433 (2.6996) |
| %CV | 18.63 | 21.78 | 32.01 |
| Median | 21.610 | 13.405 | 8.585 |
| Min, Max | 18.18, 28.82 | 7.49, 15.21 | 5.03, 12.23 |
| Geometric Mean (SD) | 22.086 (1.1998) | 12.496 (1.2979) | 8.057 (1.4015) |
| %CV for Geometric Mean | 18.37 | 26.52 | 34.74 |
| 14 hours post-dose | | | |
| n | 6 | 6 | 6 |
| m | 6 | 6 | 6 |
| Mean (SD) | 19.860 (3.6683) | 11.648 (3.1725) | 7.538 (2.5505) |
| %CV | 18.47 | 27.24 | 33.83 |
| Median | 18.560 | 12.720 | 7.420 |
| Min, Max | 15.71, 26.16 | 5.54, 13.96 | 4.87, 11.76 |
| Geometric Mean (SD) | 19.596 (1.1933) | 11.151 (1.4232) | 7.196 (1.3946) |
| %CV for Geometric Mean | 17.82 | 36.42 | 34.20 |

Figure 65

| Planned Time (in hours) | 85 mg Formulation I<br>N=6 | 55 mg Formulation I<br>N=6 | 35 mg Formulation I<br>N=6 |
|---|---|---|---|
| 15 hours post-dose | | | |
| n | 6 | 6 | 6 |
| m | 6 | 6 | 6 |
| Mean (SD) | 17.513 (3.2047) | 10.148 (2.7971) | 7.122 (3.1190) |
| %CV | 18.30 | 27.56 | 43.80 |
| Median | 17.540 | 10.765 | 6.800 |
| Min, Max | 13.82, 23.05 | 4.87, 12.98 | 4.15, 12.39 |
| Geometric Mean (SD) | 17.281 (1.1939) | 9.715 (1.4206) | 6.594 (1.5331) |
| %CV for Geometric Mean | 17.86 | 36.22 | 44.76 |
| 16 hours post-dose | | | |
| n | 6 | 6 | 6 |
| m | 6 | 6 | 6 |
| Mean (SD) | 14.812 (2.7898) | 9.130 (2.7838) | 6.062 (2.6837) |
| %CV | 18.83 | 30.49 | 44.27 |
| Median | 15.045 | 9.610 | 5.815 |
| Min, Max | 11.08, 18.96 | 4.00, 12.26 | 3.50, 10.74 |
| Geometric Mean (SD) | 14.590 (1.2109) | 8.647 (1.4837) | 5.614 (1.5290) |
| %CV for Geometric Mean | 19.31 | 41.04 | 44.45 |
| 20 hours post-dose | | | |
| n | 6 | 6 | 6 |
| m | 6 | 6 | 6 |
| Mean (SD) | 8.905 (2.9322) | 4.842 (1.8707) | 3.325 (2.1901) |
| %CV | 32.93 | 38.64 | 65.87 |
| Median | 8.610 | 5.460 | 2.730 |
| Min, Max | 5.38, 14.08 | 1.34, 6.16 | 1.66, 7.50 |
| Geometric Mean (SD) | 8.531 (1.3757) | 4.340 (1.8084) | 2.873 (1.7566) |
| %CV for Geometric Mean | 32.72 | 64.84 | 61.12 |
| 24 hours post-dose | | | |
| n | 6 | 6 | 6 |
| m | 6 | 6 | 6 |
| Mean (SD) | 6.135 (2.8838) | 2.988 (1.1527) | 1.910 (1.2565) |
| %CV | 47.00 | 38.57 | 65.79 |
| Median | 5.770 | 3.400 | 1.365 |
| Min, Max | 2.88, 10.92 | 0.65, 3.64 | 0.81, 4.18 |
| Geometric Mean (SD) | 5.593 (1.6085) | 2.614 (1.9795) | 1.634 (1.8077) |
| %CV for Geometric Mean | 50.35 | 77.08 | 64.79 |
| 27 hours post-dose | | | |
| n | 6 | 6 | 6 |
| m | 6 | 6 | 6 |
| Mean (SD) | 5.260 (3.1582) | 2.088 (0.8855) | 1.233 (0.9413) |
| %CV | 60.04 | 42.40 | 76.32 |
| Median | 5.350 | 2.315 | 0.900 |
| Min, Max | 1.62, 8.44 | 0.40, 2.87 | 0.43, 2.90 |
| Geometric Mean (SD) | 4.350 (2.0370) | 1.784 (2.1047) | 0.984 (2.0647) |
| %CV for Geometric Mean | 81.18 | 86.01 | 83.16 |

Figure 66

| Planned Time (in hours) | 85 mg Formulation I N=6 | 55 mg Formulation I N=6 | 35 mg Formulation I N=6 |
|---|---|---|---|
| 30 hours post-dose | | | |
| n | 5 | 6 | 6 |
| m | 5 | 5 | 6 |
| Mean (SD) | 3.320 (2.7709) | 1.075 (0.8074) | 0.762 (0.6781) |
| %CV | 83.46 | 75.11 | 89.02 |
| Median | 1.670 | 0.955 | 0.460 |
| Min, Max | 1.12, 6.73 | 0.00, 2.51 | 0.26, 1.96 |
| Geometric Mean (SD) | 2.436 (2.4233) | 1.186 (1.5257) | 0.562 (2.3006) |
| %CV for Geometric Mean | 109.04 | 44.21 | 100.10 |
| 33 hours post-dose | | | |
| n | 6 | 6 | 6 |
| m | 6 | 5 | 4 |
| Mean (SD) | 2.585 (2.0850) | 0.650 (0.5439) | 0.357 (0.4730) |
| %CV | 80.66 | 83.67 | 132.61 |
| Median | 2.350 | 0.515 | 0.150 |
| Min, Max | 0.42, 5.17 | 0.00, 1.63 | 0.00, 1.16 |
| Geometric Mean (SD) | 1.744 (2.8772) | 0.688 (1.6940) | 0.283 (5.0138) |
| %CV for Geometric Mean | 143.37 | 56.59 | 352.88 |
| 36 hours post-dose | | | |
| n | 6 | 6 | 6 |
| m | 6 | 5 | 2 |
| Mean (SD) | 1.872 (1.5988) | 0.353 (0.3039) | 0.215 (0.3510) |
| %CV | 85.42 | 86.01 | 163.25 |
| Median | 1.725 | 0.280 | 0.000 |
| Min, Max | 0.21, 4.18 | 0.00, 0.91 | 0.00, 0.82 |
| Geometric Mean (SD) | 1.180 (3.2362) | 0.371 (1.7160) | 0.621 (1.4822) |
| %CV for Geometric Mean | 172.38 | 58.19 | 40.93 |

CV = coefficient of variation; GM = geometric mean; max = maximum; min = minimum; SD = standard deviation.

Figure 69

| Parameter | 85 mg Formulation I<br>N=6 | 55 mg Formulation I<br>N=6 | 35 mg Formulation I<br>N=6 |
|---|---|---|---|
| AUC 0-t (h*ng/mL) | | | |
| n | 6 | 6 | 6 |
| Mean (std) | 427.955 (59.1070) | 233.750 (48.3445) | 160.582 (47.5454) |
| CV% Mean | 13.81 | 20.68 | 29.61 |
| Geometric Mean (std) | 424.417 (1.1534) | 228.811 (1.2676) | 155.597 (1.3038) |
| CV% Geometric Mean | 14.35 | 24.05 | 27.00 |
| Median | 441.710 | 249.765 | 143.625 |
| Min, Max | 340.89, 497.58 | 146.26, 284.92 | 126.17, 249.36 |
| | | | |
| Regression Results | Slope = 1.13; Intercept = 7.90 | | |
| 90% CI for Slope (Dose Proportionality) | [0.88, 1.38] Exploratory Analysis | | |
| Planned Critical Region | [0.75, 1.25] | | |
| AUC 0-inf (h*ng/mL) | | | |
| n | 6 | 6 | 6 |
| Mean (std) | 453.887 (71.6307) | 236.570 (48.5924) | 162.910 (49.4924) |
| CV% Mean | 15.78 | 20.54 | 30.38 |
| Geometric Mean (std) | 448.759 (1.1839) | 231.624 (1.2662) | 157.603 (1.3122) |
| CV% Geometric Mean | 17.00 | 23.94 | 27.68 |
| Median | 492.385 | 254.535 | 145.020 |
| Min, Max | 344.50, 509.48 | 148.20, 286.50 | 126.26, 255.28 |
| | | | |
| Regression Results | Slope = 1.18; Intercept = 7.73 | | |
| 90% CI for Slope (Dose Proportionality) | [0.91, 1.44] Exploratory Analysis | | |
| Planned Critical Region | [0.75, 1.25] | | |
| AUC 0-4 (h*ng/mL) | | | |
| n | 6 | 6 | 6 |
| Mean (std) | 60.418 (4.0002) | 32.658 (7.7385) | 20.715 (3.0292) |
| CV% Mean | 6.62 | 23.70 | 14.62 |
| Geometric Mean (std) | 60.307 (1.0688) | 31.903 (1.2676) | 20.548 (1.1460) |
| CV% Geometric Mean | 6.66 | 24.05 | 13.70 |
| Median | 60.480 | 31.605 | 19.730 |
| Min, Max | 54.79, 65.66 | 23.27, 43.88 | 18.01, 26.47 |
| AUC 0-8 (h*ng/mL) | | | |
| n | 6 | 6 | 6 |
| Mean (std) | 136.887 (21.2333) | 73.713 (14.0892) | 52.847 (7.8795) |
| CV% Mean | 15.51 | 19.11 | 14.91 |
| Geometric Mean (std) | 135.550 (1.1649) | 72.576 (1.2144) | 52.323 (1.1706) |
| CV% Geometric Mean | 15.35 | 19.61 | 15.85 |
| Median | 133.715 | 75.485 | 53.775 |
| Min, Max | 113.65, 169.02 | 57.12, 93.02 | 39.93, 61.91 |

Figure 70

| Parameter | 85 mg Formulation I N=6 | 55 mg Formulation I N=6 | 35 mg Formulation I N=6 |
|---|---|---|---|
| AUC 0-14 (h*ng/mL) | | | |
| n | 6 | 6 | 6 |
| Mean (std) | 270.898 (53.1627) | 154.917 (27.7277) | 108.608 (18.5074) |
| CV% Mean | 19.62 | 17.90 | 17.04 |
| Geometric Mean (std) | 267.048 (1.1974) | 152.932 (1.1909) | 107.399 (1.1747) |
| CV% Geometric Mean | 18.16 | 17.60 | 16.20 |
| Median | 250.120 | 156.155 | 106.110 |
| Min, Max | 231.62, 369.88 | 121.49, 202.10 | 89.63, 142.29 |
| AUC 0-24 (h*ng/mL) | | | |
| n | 6 | 6 | 6 |
| Mean (std) | 381.775 (52.5930) | 217.797 (42.4264) | 150.767 (39.5603) |
| CV% Mean | 13.78 | 19.48 | 26.24 |
| Geometric Mean (std) | 378.915 (1.1419) | 213.907 (1.2401) | 147.010 (1.2693) |
| CV% Geometric Mean | 13.33 | 21.77 | 24.19 |
| Median | 377.195 | 228.050 | 139.515 |
| Min, Max | 325.49, 473.73 | 144.72, 268.19 | 121.46, 224.14 |
| Regression Results | Slope = 1.07; Intercept = 8.07 | | |
| 90% CI for Slope (Dose Proportionality) | [0.84, 1.29] Exploratory Analysis | | |
| Planned Critical Region | [0.75, 1.25] | | |
| AUC 4-8 (h*ng/mL) | | | |
| n | 6 | 6 | 6 |
| Mean (std) | 76.470 (22.1562) | 41.055 (11.3912) | 32.133 (7.6228) |
| CV% Mean | 28.97 | 27.75 | 23.72 |
| Geometric Mean (std) | 73.806 (1.3409) | 39.970 (1.2742) | 31.296 (1.2975) |
| CV% Geometric Mean | 29.97 | 24.59 | 26.49 |
| Median | 77.265 | 37.525 | 31.670 |
| Min, Max | 51.06, 110.65 | 32.42, 63.33 | 19.63, 42.75 |
| AUC 8-14 (h*ng/mL) | | | |
| n | 6 | 6 | 6 |
| Mean (std) | 134.007 (35.9302) | 81.205 (15.0489) | 55.762 (13.8513) |
| CV% Mean | 26.81 | 18.53 | 24.84 |
| Geometric Mean (std) | 130.513 (1.2768) | 80.145 (1.1903) | 54.460 (1.2630) |
| CV% Geometric Mean | 24.81 | 17.55 | 23.67 |
| Median | 125.860 | 77.960 | 51.100 |
| Min, Max | 100.55, 200.86 | 64.37, 109.08 | 40.61, 80.39 |
| AUC 14-24 (h*ng/mL) | | | |
| n | 6 | 6 | 6 |
| Mean (std) | 110.877 (27.6957) | 62.880 (20.2889) | 42.158 (21.6225) |
| CV% Mean | 24.98 | 32.27 | 51.29 |
| Geometric Mean (std) | 108.218 (1.2691) | 58.644 (1.5853) | 38.315 (1.5921) |
| CV% Geometric Mean | 24.18 | 48.64 | 49.14 |
| Median | 106.980 | 67.405 | 37.785 |
| Min, Max | 76.60, 161.31 | 23.23, 80.91 | 23.07, 81.85 |

Figure 71

| Parameter | 85 mg Formulation I N=6 | 55 mg Formulation I N=6 | 35 mg Formulation I N=6 |
|---|---|---|---|
| AUC 14-t (h*ng/mL) | | | |
| n | 6 | 6 | 6 |
| Mean (std) | 157.058 (50.6218) | 78.833 (27.3645) | 51.973 (29.7361) |
| CV% Mean | 32.23 | 34.71 | 57.21 |
| Geometric Mean (std) | 150.181 (1.3934) | 72.171 (1.6981) | 46.296 (1.6617) |
| CV% Geometric Mean | 34.11 | 56.89 | 54.24 |
| Median | 151.390 | 86.145 | 41.975 |
| Min, Max | 92.00, 233.40 | 24.77, 98.46 | 25.91, 107.07 |
| Cmax (ng/mL) | | | |
| n | 6 | 6 | 6 |
| Mean (std) | 27.445 (6.1937) | 16.122 (3.2348) | 11.315 (2.1299) |
| CV% Mean | 22.57 | 20.07 | 18.82 |
| Geometric Mean (std) | 26.940 (1.2268) | 15.892 (1.1956) | 11.166 (1.1893) |
| CV% Geometric Mean | 20.66 | 18.01 | 17.47 |
| Median | 26.060 | 15.080 | 10.710 |
| Min, Max | 21.22, 39.42 | 13.89, 22.54 | 9.33, 15.35 |
| Regression Results | Slope = 0.99; Intercept = 5.76 | | |
| 90% CI for Slope (Dose Proportionality) | [0.78, 1.20] Exploratory Analysis | | |
| Planned Critical Region | [0.75, 1.25] | | |
| Cmax 0-4 (ng/mL) | | | |
| n | 6 | 6 | 6 |
| Mean (std) | 21.235 (1.5399) | 11.198 (2.6332) | 7.055 (0.9393) |
| CV% Mean | 7.25 | 23.51 | 13.31 |
| Geometric Mean (std) | 21.189 (1.0746) | 10.938 (1.2703) | 7.004 (1.1399) |
| CV% Geometric Mean | 7.20 | 24.27 | 13.15 |
| Median | 20.910 | 11.395 | 7.050 |
| Min, Max | 19.55, 23.29 | 7.93, 14.95 | 6.02, 8.57 |
| Cmax 4-8 (ng/mL) | | | |
| n | 6 | 6 | 6 |
| Mean (std) | 23.782 (7.9088) | 13.035 (3.8503) | 10.038 (2.4285) |
| CV% Mean | 33.26 | 29.54 | 24.19 |
| Geometric Mean (std) | 22.755 (1.3815) | 12.663 (1.2825) | 9.798 (1.2733) |
| CV% Geometric Mean | 33.18 | 25.27 | 24.52 |
| Median | 22.420 | 11.510 | 9.665 |
| Min, Max | 14.81, 37.12 | 10.75, 20.79 | 6.82, 14.00 |
| Cmax 8-14 (ng/mL) | | | |
| n | 6 | 6 | 6 |
| Mean (std) | 27.045 (6.7304) | 15.933 (3.3476) | 11.127 (2.2831) |
| CV% Mean | 24.89 | 21.01 | 20.52 |
| Geometric Mean (std) | 26.407 (1.2661) | 15.685 (1.2053) | 10.952 (1.2093) |
| CV% Geometric Mean | 23.92 | 18.84 | 19.18 |
| Median | 26.060 | 14.675 | 10.655 |
| Min, Max | 18.82, 39.42 | 13.82, 22.54 | 9.16, 15.35 |

Figure 72

| Parameter | 85 mg Formulation I N=6 | 55 mg Formulation I N=6 | 35 mg Formulation I N=6 |
|---|---|---|---|
| Residual Area | | | |
| n | 6 | 6 | 6 |
| Mean (std) | 5.263 (5.9459) | 1.208 (1.0395) | 1.268 (0.8586) |
| CV% Mean | 112.97 | 86.03 | 67.69 |
| Geometric Mean (std) | 2.347 (4.9386) | 0.936 (2.1188) | 0.811 (3.8968) |
| CV% Geometric Mean | 343.74 | 87.02 | 231.52 |
| Median | 3.050 | 0.890 | 1.260 |
| Min, Max | 0.22, 15.44 | 0.46, 3.19 | 0.06, 2.32 |
| Tmax (h) | | | |
| n | 6 | 6 | 6 |
| Mean (std) | 9.152 (4.0156) | 9.663 (4.2802) | 8.990 (1.4031) |
| CV% Mean | 43.88 | 44.29 | 15.61 |
| Geometric Mean (std) | 7.906 (2.0082) | 8.285 (2.0548) | 8.897 (1.1719) |
| CV% Geometric Mean | 79.12 | 82.44 | 15.96 |
| Median | 9.970 | 9.985 | 9.000 |
| Min, Max | 2.00, 14.00 | 2.00, 14.02 | 7.02, 10.98 |
| Tmax 0-4 (h) | | | |
| n | 6 | 6 | 6 |
| Mean (std) | 1.667 (0.5164) | 1.667 (0.5164) | 1.833 (1.1690) |
| CV% Mean | 30.98 | 30.98 | 63.77 |
| Geometric Mean (std) | 1.587 (1.4304) | 1.587 (1.4304) | 1.587 (1.7611) |
| CV% Geometric Mean | 36.97 | 36.97 | 61.44 |
| Median | 2.000 | 2.000 | 1.500 |
| Min, Max | 1.00, 2.00 | 1.00, 2.00 | 1.00, 4.00 |
| Tmax 4-8 (h) | | | |
| n | 6 | 6 | 6 |
| Mean (std) | 7.500 (1.2247) | 7.500 (0.8367) | 7.667 (0.5164) |
| CV% Mean | 16.33 | 11.16 | 6.74 |
| Geometric Mean (std) | 7.397 (1.2115) | 7.458 (1.1266) | 7.652 (1.0714) |
| CV% Geometric Mean | 19.37 | 11.96 | 6.90 |
| Median | 8.000 | 8.000 | 8.000 |
| Min, Max | 5.00, 8.00 | 6.00, 8.00 | 7.00, 8.00 |
| Tmax 8-14 (h) | | | |
| n | 6 | 6 | 6 |
| Mean (std) | 11.000 (2.1909) | 11.167 (2.0412) | 9.167 (1.1690) |
| CV% Mean | 19.92 | 18.28 | 12.75 |
| Geometric Mean (std) | 10.817 (1.2238) | 11.013 (1.2003) | 9.106 (1.1333) |
| CV% Geometric Mean | 20.40 | 18.41 | 12.56 |
| Median | 10.500 | 11.000 | 9.000 |
| Min, Max | 8.00, 14.00 | 9.00, 14.00 | 8.00, 11.00 |

Figure 73

| Parameter | 85 mg Formulation I N=6 | 55 mg Formulation I N=6 | 35 mg Formulation I N=6 |
|---|---|---|---|
| Half-Life Lambda z (h) | | | |
| n | 6 | 6 | 6 |
| Mean (std) | 7.035 (3.8560) | 4.110 (1.1565) | 3.953 (1.2911) |
| CV% Mean | 54.81 | 28.14 | 32.66 |
| Geometric Mean (std) | 6.184 (1.7559) | 3.996 (1.2839) | 3.758 (1.4327) |
| CV% Geometric Mean | 61.07 | 25.39 | 37.15 |
| Median | 5.590 | 3.585 | 4.215 |
| Min, Max | 2.80, 12.67 | 3.35, 6.29 | 2.24, 5.41 |
| Lambda z (/h) | | | |
| n | 6 | 6 | 6 |
| Mean (std) | 0.127 (0.0728) | 0.177 (0.0398) | 0.195 (0.0734) |
| CV% Mean | 57.51 | 22.55 | 37.65 |
| Geometric Mean (std) | 0.110 (1.8274) | 0.172 (1.2894) | 0.185 (1.4258) |
| CV% Geometric Mean | 66.21 | 25.83 | 36.62 |
| Median | 0.125 | 0.190 | 0.165 |
| Min, Max | 0.05, 0.25 | 0.11, 0.21 | 0.13, 0.31 |

$AUC_{0-t}$ = area under the curve from time 0 to the last quantifiable concentration; $AUC_{0-inf}$ = area under the curve from time 0 to infinity; CI = confidence interval; CV = coefficient of variation; max = maximum; min = minimum; SD = standard deviation.

Note: Any subject with a pre-dose concentration > $0.05*C_{max}$ for this analyte was excluded from this summary table.

Figure 74

OPEN LABEL (DOSE TITRATION) PHASE

| Adverse Event | Body System | N patient | # events | % of 12 year olds |
|---|---|---|---|---|
| Abdominal pain upper | Gastrointestinal disorders | 2 | 2 | 6.90% |
| Affect lability | Psychiatric disorders | 3 | 3 | 10.34% |
| Allergic sinusitis | Respiratory, thoracic and mediastinal disorders | 1 | 1 | 3.45% |
| Anxiety | Psychiatric disorders | 1 | 1 | 3.45% |
| Blood pressure systolic increased | Investigations | 1 | 1 | 3.45% |
| Decreased appetite | Metabolism and nutrition disorders | 11 | 11 | 37.93% |
| Diarrhoea | Gastrointestinal disorders | 4 | 4 | 13.79% |
| Dizziness | Nervous system disorders | 1 | 1 | 3.45% |
| Dry mouth | Gastrointestinal disorders | 1 | 1 | 3.45% |
| Dysmenorrhoea | Reproductive system and breast disorders | 1 | 1 | 3.45% |
| Dyspepsia | Gastrointestinal disorders | 1 | 1 | 3.45% |
| Facial spasm | Nervous system disorders | 1 | 1 | 3.45% |
| Fatigue | General disorders and administration site conditions | 1 | 1 | 3.45% |
| Gastroenteritis | Infections and infestations | 1 | 1 | 3.45% |
| Gastroenteritis viral | Infections and infestations | 1 | 1 | 3.45% |
| Hand fracture | Injury, poisoning and procedural complications | 1 | 1 | 3.45% |
| Headache | Nervous system disorders | 3 | 4 | 10.34% |
| Heart rate increased | Investigations | 3 | 4 | 10.34% |
| Insomnia | Psychiatric disorders | 3 | 3 | 10.34% |
| Irritability | Psychiatric disorders | 2 | 2 | 6.90% |
| Nausea | Gastrointestinal disorders | 2 | 2 | 6.90% |
| Pyrexia | General disorders and administration site conditions | 1 | 1 | 3.45% |
| Upper respiratory tract infection | Infections and infestations | 2 | 2 | 6.90% |
| Vomiting | Gastrointestinal disorders | 2 | 2 | 6.90% |
| Weight decreased | Investigations | 4 | 5 | 13.79% |

Figure 75

DOUBLE-BLIND PHASE

| Adverse Event | Body System | N patient | # events | % of 12 year olds |
|---|---|---|---|---|
| ACTIVE PRC-063 | | | | |
| Tachycardia | Cardiac disorders | 1 | 1 | 3.45% |
| Blood pressure diastolic increased | Investigations | 1 | 1 | 3.45% |
| PLACEBO | | | | |
| No events | | | | |

METHODS AND COMPOSITIONS PARTICULARLY FOR TREATMENT OF ATTENTION DEFICIT DISORDER

BACKGROUND OF THE INVENTION

Field of the Invention

The present invention relates to methods and compositions, particularly for treatment of attention deficit disorder.

Description of the Prior Art

Sustained release dosage forms are important in the search for improved therapy, both through improved patient compliance and decreased incidences of adverse drug reactions.

It is the intent of sustained release formulations to provide a longer period of pharmacologic action after administration than is ordinarily obtained after administration of immediate release dosage forms. Sustained release compositions may be used to delay absorption of a medicament until it has reached certain portions of the alimentary tract, and maintain a desired concentration of the medicament in the blood stream for a longer duration than would occur if conventional rapid release dosage forms are administered. Such longer periods of response provide for many therapeutic benefits that are not achieved with corresponding short acting, immediate release preparations. Thus, therapy may be continued without interrupting the sleep of the patient, which is of special importance, for example, when treating a patient for moderate to severe pain (e.g., a post-surgery patient, a cancer patient, etc.), or for those patients who experience migraine headaches on awakening, as well as for the debilitated patient for whom sleep is essential. A further general advantage of longer acting drug preparations is improved patient compliance resulting from the avoidance of missed doses through patient forgetfulness.

Unless conventional rapid acting drug therapy is carefully administered at frequent intervals to maintain effective steady state blood levels of the drug, peaks and valleys in the blood level of the active drug occur due to rapid absorption, systemic excretion of the compound and through metabolic inactivation, thereby producing special problems in maintenance therapy of the patient.

In view of this, it is considered a goal of many skilled in the art that a controlled release dosage form will ideally provide therapeutic concentration of the drug in blood that is maintained throughout the dosing interval with a reduction in the peak/trough concentration ratio. Central to the development process are the many variables that influence the in vivo release and subsequent absorption of the active ingredients from the gastrointestinal tract.

It is known in the pharmaceutical art to prepare compositions which provide for sustained release of pharmacologically active substances contained in the compositions after oral administration to humans and animals. Sustained release formulations known in the art include specially coated pellets, coated tablets and capsules, and ion exchange resins, wherein the slow release of the active medicament is brought about through selective breakdown of the coating of the preparation or through compounding with a special matrix to affect the release of a drug. Some sustained release formulations provide for related sequential release of a single dose of an active compound at predetermined periods after administration.

Thus, sustained release dosage forms are important in the search for improved therapy, both through improved patient compliance and decreased incidences of adverse drug reactions.

While controlled and/or sustained release compositions have constituted a definite advance in the art, improvements in these compositions have been sought, particularly for preparations available for conditions such as Attention Deficit Hyperactivity Disorder (ADHD), diabetes etc.

Attention Deficit Disorders are the most common psychiatric disorders in children (Campbell et al. 1992) with reported rates ranging from 4% to 9% (Aman et al. 1983).

Attention Deficit Disorder (ADD) is characterized by inattention and impulsivity and may be present with hyperactivity (ADHD) (Shaywitz et al. 1984). Other characteristics may include aggressiveness, stealing, lying, truancy, setting fires, running away, explosiveness, cognitive and learning problems as well as poor social skills (Campbell et al. 1992). It is four to five times more frequent in boys than girls (Campbell et al. 1992).

Stimulant medication, such as amphetamines, have been shown to be the most effective agents in the treatment of children with disorders of activity modulation and attention regulation and result in significant improvement in 70 to 80 percent of affected children (Shaywitz et al. 1984). Positive effects of stimulants have been documented in a variety of areas including behavioral, social, perceptual performance, motor activity, impulse control, attention regulation and cognitive performance (Barkley 1977, Kavale 1983, Offenbacher et al. 1983, Rosenthal et al 1978).

Long thought of as a childhood disorder, ADHD is now known to persist into adolescence and adulthood (Practice Parameter for the Use of Stimulant Medications in the treatment of Children, Adolescents, and Adults. J. AM. ACAD. CHILD ADOLESC. PSYCHIATRY, 41:2 SUPPLEMENT, February 2002)

Methylphenidate [dl-threo-methyl-2-phenyl-2-(2-piperidyl)acetate] is the psycho-stimulant used most frequently in the treatment of hyperactivity and attention deficit disorder. It appears to have a higher incidence of positive effects and a lower incidence of adverse effects than other psychostimulants. The efficacy of methylphenidate ("MPH") in improving attention and behavioral symptoms has been supported by many studies.

Immediate release methylphenidate preparations, because of their short half-life, require frequent administration at short intervals to ensure adequate treatment throughout a child's school day, adolescent's school day (high school, college, university) and adult working day. The rapid onset and offset of immediate release methylphenidate preparations means that a medicated person with attention deficit disorder will be maximally affected only for relatively brief periods during the day. Due to its short half-life, it has been known to administer MPH given twice per day, usually once after breakfast and once during the day, an event that some children and some school personnel apparently avoid, resulting in poor compliance with prescribed regimens (Brown et al., 1985; Firestone 1982).

Compliance is a major problem for children, adolescents and adults. Poor compliance in taking medication may explain, in part, the variable and conflicting results reported in many studies of the effect of medication on improving the behavior of hyperactive children, adolescents and adults. These limitations of immediate release methylphenidate led to interest in products with longer effective periods of action.

Thus, much of the prior art has focused on development of formulations for treatment of ADHD with a focus on administration to children and improving patient compliance in the patient population. This has led to commercialization of a number of sustained release formulations of methylphenidate—e.g., Ritalin SR™, Concerta™ and Biphentin™.

Duration of efficacy with long-acting methylphenidate formulations was maintained from one hour to 12 hours post-dosing for osmotically controlled-release oral delivery systems (four trials), 1.5 hours to 7.5 hours for methylphenidate extended release in one trial, one hour to 12 hours post-dosing for methylphenidate spheroidal oral drug absorption systems (two trials) and 30 minutes to 12 hours post-dosing for dexmethylphenidate extended release (five trials). Most long-acting stimulants conferred benefits on ADHD symptoms in patients across the age spectrum for up to 12 hours after a single morning dose as measured by the permanent product measure of performance mathematics test (PERMP). Formulations may differ in time to peak effect and maintenance of effect as well as magnitude of effect at different time points during the day (Brams M, Moon E, Pucci M, Lopez F A. Duration of effect of oral long-acting stimulant medications for ADHD throughout the day. Curr Med Res Opin. 2010 August; 26(8):1809-25. doi: 10.1185/03007995.2010.488553).

Despite the advances in the art, there is still room for improvement.

First, some or all of the commercially available sustained release formulations of methylphenidate do not have, in combination, a rapid onset of action and a duration of action that exceeds 12 hours. The provision of a sustained release formulation having this combination of features would be highly desirable for adolescents or adults whose daily activities require them to have a rapid onset of therapeutic effect and duration of action that lasts at least 14 hours to get them through the day and into the evening without the need of another dose of the medication.

Second, some or all of the commercially available sustained release formulations of methylphenidate are susceptible to premature release of the active ingredient in a gastric environment that contains alcohol (e.g., ethanol). This can be a significant problem if the subject taking the formulation is an alcohol abuser.

This, it would be highly desirable to have a pharmaceutical composition that obviates or mitigates one or both of these problems in the prior art.

SUMMARY OF THE INVENTION

It is an object of the present invention to obviate or mitigate at least one of the above-mentioned disadvantages of the prior art.

It is another object of the present invention to provide a novel coated bead.

It is another object of the present invention to provide a novel solid oral pharmaceutical composition.

Accordingly, in one of its aspects, the present invention provides a coated bead comprising:

(a) a granule;

(b) a first layer coated over the granule, the first layer comprising a first amount of an active pharmaceutical ingredient comprising a central nervous system stimulant;

(c) a second layer coated over the first layer, the second layer being present in an amount sufficient to substantially delay release of the active pharmaceutical ingredient in the first layer until after the coated bead reaches a distal intestine portion of a subject to whom the coated bead is administered; and (d) a third layer coated over the second layer, the third layer comprising a second amount of the active pharmaceutical ingredient, the third layer being configured to permit substantially immediate release of the active pharmaceutical ingredient comprised therein.

In another of its aspects, the present invention provides an oral solid pharmaceutical composition comprising a first plurality of coated beads and a second plurality of coated beads, wherein:

each coated bead in the first plurality of coated beads comprising: a first granule and a first layer coated over the first granule, the first layer comprising an active pharmaceutical ingredient comprising a central nervous system stimulant, the first plurality of coated beads being configured to provide substantially immediate release of the active pharmaceutical ingredient; and each coated bead in the second plurality of coated beads comprising: a second granule; a first layer coated over the second granule, the first layer comprising an active pharmaceutical ingredient comprising a central nervous system stimulant; and a second layer coated over the first layer, the second layer being present in an amount sufficient to substantially delay release of the active pharmaceutical ingredient in the first layer until after the coated bead reaches a distal intestine portion of a subject to whom the coated bead is administered, the coated bead being substantially free of an outer layer configured to provide substantially immediate release of the active pharmaceutical ingredient.

In yet another of its aspects, the present invention provides an oral solid pharmaceutical composition comprising a first plurality of coated beads, a second plurality of coated beads and a third plurality of coated bead, wherein:

each coated bead in the first plurality of coated beads comprising: a first granule and a first layer coated over the first granule, the first layer comprising an active pharmaceutical ingredient comprising a central nervous system stimulant, the first plurality of coated beads being configured to provide substantially immediate release of the active pharmaceutical ingredient;

each coated bead in the second plurality of coated beads comprising: a second granule; a first layer coated over the second granule, the first layer comprising an active pharmaceutical ingredient comprising a central nervous system stimulant; and a second layer coated over the first layer, the second layer being present in an amount sufficient to substantially delay release of the active pharmaceutical ingredient in the first layer; and each coated bead in the third plurality of coated beads comprising: a third granule; a first layer coated over the third granule, the first layer comprising an active pharmaceutical ingredient comprising a central nervous system stimulant, a second layer coated over the first layer, the second layer being present in an amount sufficient to substantially delay release of the active pharmaceutical ingredient in the first layer until after the coated bead reaches a distal intestine portion of a subject to whom the coated bead is administered.

In yet another of its aspects, the present invention provides a coated bead comprising:

(a) a granule;

(b) an inner layer coated over the granule, the inner layer comprising an active pharmaceutical ingredient comprising a central nervous system stimulant; and (c) an outer delayed release layer coated over inner layer which is substantially free of a salt of alginic acid;

wherein release of the active pharmaceutical ingredient is not more than 20% when measured under in vitro conditions with stirring at 100 rpm at pH 1.2 for 2 hours in 900 mL of a medium comprising up to about 35% v/v ethanol.

In yet another of its aspects, the present invention provides a coated bead comprising:
(a) a granule;
(b) an inner layer coated over the granule, the inner layer comprising an active pharmaceutical ingredient comprising a central nervous system stimulant; and
(c) an outer delayed release layer coated over the inner layer, the outer delayed release coating comprising an anionic copolymer based on methyl acrylate, methyl methacrylate and methacrylic acid with the proviso that the outer delayed release layer is substantially free of a salt of alginic acid, the outer delayed release layer being present at an average thickness in the range of from about 5 μm to about 50 μm.

In yet another of its aspects, the present invention provides a coated bead comprising:
(a) a granule comprising a first amount of an active pharmaceutical ingredient comprising a central nervous system stimulant (e.g., the granule can comprise a granule substrate in admixture with the active pharmaceutical ingredient or the active pharmaceutical ingredient could be coated over the granule substrate); and
(b) a first layer coated over the granule, the first layer being present in an amount sufficient to substantially delay release of the active pharmaceutical ingredient in the first layer until after the coated bead reaches a distal intestine portion of a subject to whom the coated bead is administered; and
(c) a second layer coated over the first layer, the second layer comprising a second amount of the active pharmaceutical ingredient, the second layer being configured to permit substantially immediate release of the active pharmaceutical ingredient comprised therein.

Throughout this specification, the term "coated over" (or the functional equivalent thereof) is used to describe a first layer of material disposed exteriorly with respect to a second layer of material. It should be clearly understood that, in such a case, the first layer of material may be directly coated over (i.e., in contacting relation with) the second layer of material or indirectly coated over (i.e., in non-contacting relation with) the second layer of material. An example of "indirectly coated over" would be when the first layer of material and the second layer of material have disposed between them one or more intermediate layers of material. The point is the term "coated over" (or the functional equivalent thereof), when used on its own encompasses both "directly coated over" and "indirectly coated over" described above.

The present inventors have developed a novel coated bead and a novel pharmaceutical composition which are believed to obviate or mitigate one or both of the above-mentioned disadvantages described above with reference to some or all of the commercially available sustained release formulations of methylphenidate. The present coated bead and pharmaceutical composition are believed to be highly advantageous in that they have a rapid onset of action (e.g., approximately 1 hour after administration) and a long duration of action (e.g., approximately 16 hours or more) after reaching steady state in the subject. While not wishing to be bound by any particular theory or mode of action, it is believed that the long duration of action results in a blood plasma concentration of the active ingredient at 24 hours after administration which allows for a rapid onset of action when another dose of the active ingredient is taken—i.e., there appears to be a baseline blood plasma concentration of the active ingredient when it is time to take a subsequent dose to allow for a rapid onset of action of that subsequent dose.

The present coated bead and pharmaceutical composition are believed to address a limitation of some or all current commercially available long-acting methylphenidate formulations which are not reported to provide and maintain duration of action beyond 12 hours. The present coated bead and pharmaceutical composition are also believed to address the limitation with long-acting lisdexamfetamine dimesylate that is reported to last up to 14 hours but does not have a rapid onset of action. These two characteristics (rapid onset of action and long duration of action) of the present coated bead and pharmaceutical composition are believed to address a significant limitation for adolescents or adults whose daily activities require them to have a rapid onset of therapeutic effect and duration of action that lasts at least 14 hours to get them through the day and well into the evening without the need of another dose of the medication.

In one preferred embodiment, the present coated bead and pharmaceutical composition are characterized by having a resistance to release of the active ingredient in an aqueous composition comprising up to about 35% by volume of an alcohol (e.g., ethanol)—i.e., release of the active pharmaceutical ingredient is not more than 20% when measured under in vitro conditions with stirring at 100 rpm at pH 1.2 for 2 hours in 900 mL of a medium comprising up to about 35% v/v ethanol. This resistance to alcohol-related release of the active pharmaceutical ingredient can be achieved without the need to use a coating layer comprising one or more salts of alginic acid thereby simplifying manufacturing costs and the like.

The present disclosure also provides a method of treating Attention Deficit Hyperactivity Disorder (ADHD) in a pediatric subject in need thereof, the method comprising administering to the pediatric subject an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof, after administration to the subject; or (a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the oral solid pharmaceutical composition provides the following in vitro methylphenidate dissolution profile:

| Time (hours) | Methylphenidate (% dissolved) |
| --- | --- |
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

In some embodiments, the pediatric subject is from 6 to 11 years of age.

In some embodiments, the pediatric subject is from 12 to 17 years of age.

In some embodiments, the oral solid pharmaceutical composition is in the form of a capsule comprising the plurality of coated beads.

In some embodiments, the inner controlled release coating is selected from the group consisting of an ethylcellulose polymer, a cellulose ether, polyethylene oxide, a polyvinyl alcohol derivate, a methacrylic acid copolymer, polyethylene glycol, polyglycolic acid, polylactic acid, polycaprolactone, poly(n-hydroxybutyrate), a polyamino acids a poly (amide-enamine), a polyesters, ethylene-vinyl acetate (EVA), polyvinyl pyrrolidone (PVP), poly (acrylic acid) (PAA), poly (methacrylic acid) (PMAA), and mixtures of any two or more thereof.

In some embodiments, the inner controlled release coating comprises ammonio Methacrylate Copolymer, Type B USP/NF.

In some embodiments, the inner controlled release coating is present in an amount of 3% to 16% by weight of each coated bead.

In some embodiments, the inner controlled release coating is present in an amount of 10.0% to 10.7% by weight of each coated bead.

In some embodiments, the outer delayed release coating comprises poly(methyl acrylate-co-methyl methacrylate-co-methacrylic acid) 7:3:1.

In some embodiments, the outer delayed release coating is present in an amount of from 3% to 20% by weight of each coated bead.

In some embodiments, the outer delayed release coating is present in an amount of from 15.0% to 16.0% by weight of each coated bead.

In some embodiments, the first amount of methylphenidate or pharmaceutically acceptable salt thereof and the second amount of methylphenidate or pharmaceutically acceptable salt thereof, together, provide a total amount (100%) of methylphenidate or pharmaceutically acceptable salt thereof in each coated bead, and wherein the first amount of methylphenidate or pharmaceutically acceptable salt thereof comprises from 70% to 99% by weight of the total amount of the methylphenidate or pharmaceutically acceptable salt thereof in each coated bead.

In some embodiments, the first amount of methylphenidate or pharmaceutically acceptable salt thereof comprises from 78% to 82% by weight of the total amount of methylphenidate or pharmaceutically acceptable salt thereof.

In some embodiments, the first amount of methylphenidate or pharmaceutically acceptable salt thereof comprises 80% by weight of the total amount of the methylphenidate or pharmaceutically acceptable salt thereof and the second amount of methylphenidate or pharmaceutically acceptable salt thereof comprises 20% by weight of the total amount of the methylphenidate or pharmaceutically acceptable salt thereof.

In some embodiments, the inner controlled release coating is present in an amount of 3% to 16% by weight of each coated bead, and the outer delayed release coating is present in an amount of from 3% to 20% by weight of each coated bead.

In some embodiments, the inner controlled release coating is present in an amount of 10.0% to 10.7% by weight of each coated bead, and the outer delayed release coating is present in an amount of from 15.0% to 16.0% by weight of each coated bead.

In some embodiments, the granule is selected from the group consisting of: a sugar sphere, a microcrystalline cellulose granule, a silica granule, a starch granule, a lactose granule, a calcium carbonate granule, and a mannitol-polyvinylpyrrolidone granule.

In some embodiments, the oral solid pharmaceutical composition comprises 25 mg, 30 mg, 35 mg, 45 mg, 55 mg, 70 mg, 85 mg, or 100 mg of methylphenidate hydrochloride.

In some embodiments, the oral solid pharmaceutical composition comprises 85 mg of methylphenidate hydrochloride.

The present disclosure also provides a method of treating Attention Deficit Hyperactivity Disorder (ADHD) in a pediatric subject from 6 to 11 years of age in need thereof, the method comprising administering to a pediatric subject from 6 to 11 years of age an oral solid pharmaceutical composition comprising a plurality of coated beads, wherein each coated bead comprises elements (a), (b), (c), and (d), or elements (a'), (b'), and (c'), as follows:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof, after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the oral solid pharmaceutical composition, when comprising 35, 55, or 85 mg of methylphenidate hydrochloride, and when administered to pediatric subjects from 6 to 11 years of age in a fasted state, provides a methylphenidate $AUC_{0-4}$, a methylphenidate $AUC_{8-14}$, and a methylphenidate $AUC_{14-24}$ in the ranges as specified below:

| Oral Methylphenidate HCl dosage (mg) | Methylphenidate AUC$_{0-4}$ | Methylphenidate AUC$_{8-14}$ | Methylphenidate AUC$_{14-24}$ |
|---|---|---|---|
| 35 | from 18010 pg · hr/mL to 26470 pg · hr/mL | from 40610 pg · hr/mL to 80390 pg · hr/mL | from 23070 pg · hr/mL to 81850 pg · hr/mL |
| 55 | from 23270 pg · hr/mL to 43880 pg · hr/mL | from 64370 pg · hr/mL to 109080 pg · hr/mL | from 23230 pg · hr/mL to 80910 pg · hr/mL |
| 85 | from 54790 pg · hr/mL to 65660 pg · hr/mL | from 100550 pg · hr/mL to 200860 pg · hr/mL | from 76600 pg · hr/mL to 161310 pg · hr/mL |

In some embodiments, the oral solid pharmaceutical composition comprising 35, 55, or 85 mg of methylphenidate hydrochloride provides, when administered to pediatric subjects from 6 to 11 years of age in a fasted state, an average methylphenidate AUC$_{0-4}$, an average methylphenidate AUC$_{8-14}$, and an average methylphenidate AUC$_{14-24}$ as specified below:

| Oral Methylphenidate HCl dosage (mg) | Average methylphenidate AUC$_{0-4}$ (±1 standard deviation) | Average methylphenidate AUC$_{8-14}$ (±1 standard deviation) | Average methylphenidate AUC$_{14-24}$ (±1 standard deviation) |
|---|---|---|---|
| 35 | 20715 ± 3029.2 pg · hr/mL | 55762 ± 13851.3 pg · hr/mL | 42158 ± 21622.5 pg · hr/mL |
| 55 | 32658 ± 7738.5 pg · hr/mL | 81205 ± 15048.9 pg · hr/mL | 62880 ± 20288.9 pg · hr/mL |
| 85 | 60418 ± 4000.2 pg · hr/mL | 134007 ± 35930.2 pg · hr/mL | 110877 ± 27695.7 pg · hr/mL |

In some embodiments, the oral solid pharmaceutical composition comprising 35, 55, or 85 mg of methylphenidate hydrochloride provides, when administered to pediatric subjects from 6 to 11 years of age in a fasted state, a methylphenidate AUC$_{0-8}$, a methylphenidate AUC$_{4-8}$, a methylphenidate AUC$_{0-14}$, and a methylphenidate AUC$_{0-24}$ in the ranges specified below:

| Oral Methylphenidate HCl dosage (mg) | Methylphenidate AUC$_{0-8}$ | Methylphenidate AUC$_{4-8}$ | Methylphenidate AUC$_{0-14}$ | Methylphenidate AUC$_{0-24}$ |
|---|---|---|---|---|
| 35 | from 39930 pg · hr/mL to 61910 pg · hr/mL | from 19630 pg · hr/mL to 42750 pg · hr/mL | from 89630 pg · hr/mL to 142290 pg · hr/mL | from 121460 pg · hr/mL to 224140 pg · hr/mL |
| 55 | from 57120 pg · hr/mL to 93020 pg · hr/mL | from 32420 pg · hr/mL to 63330 pg · hr/mL | from 121490 pg · hr/mL to 202100 pg · hr/mL | from 144720 pg · hr/mL to 268190 pg · hr/mL |
| 85 | from 113650 pg · hr/mL to 169020 pg · hr/mL | from 51060 pg · hr/mL to 110650 pg · hr/mL | from 231620 pg · hr/mL to 369880 pg · hr/mL | from 325490 pg · hr/mL to 473730 pg · hr/mL |

In some embodiments, the oral solid pharmaceutical composition comprising 35, 55, or 85 mg of methylphenidate hydrochloride provides, when administered to pediatric subjects from 6 to 11 years of age in a fasted state, an average methylphenidate AUC$_{0-8}$, an average methylphenidate AUC$_{4-8}$, an average methylphenidate AUC$_{0-14}$, and an average methylphenidate AUC$_{0-24}$ as specified below:

| Oral Methylphenidate HCl dosage (mg) | Average methylphenidate AUC$_{0-8}$ (±1 standard deviation) | Average methylphenidate AUC$_{4-8}$ (±1 standard deviation) | Average methylphenidate AUC$_{0-14}$ (±1 standard deviation) | Average methylphenidate AUC$_{0-24}$ (±1 standard deviation) |
|---|---|---|---|---|
| 35 | 52847 ± 7879.5 pg · hr/mL | 32133 ± 7622.8 pg · hr/mL | 108608 ± 18507.4 pg · hr/mL | 150767 ± 39560.3 pg · hr/mL |
| 55 | 73713 ± 14089.2 pg · hr/mL | 41055 ± 11391.2 pg · hr/mL | 154917 ± 27727.7 pg · hr/mL | 217797 ± 42426.4 pg · hr/mL |
| 85 | 136887 ± 21233.3 pg · hr/mL | 76470 ± 22156.2 pg · hr/mL | 270898 ± 53162.7 pg · hr/mL | 381775 ± 52593.0 pg · hr/mL |

In some embodiments, the oral solid pharmaceutical composition comprising 35, 55, or 85 mg of methylphenidate hydrochloride provides, when administered to pediatric subjects from 6 to 11 years of age in a fasted state, a methylphenidate $Cmax_{0-4}$, a methylphenidate $Cmax_{4-8}$, and a methylphenidate $Cmax_{8-14}$ in the ranges specified below:

| Oral methylphenidate HCl dosage (mg) | Methylphenidate $Cmax_{0-4}$ | Methylphenidate $Cmax_{4-8}$ | Methylphenidate $Cmax_{8-14}$ |
|---|---|---|---|
| 35 | from 6020 pg/mL to 8570 pg/mL | from 6820 pg/mL to 14000 pg/mL | from 9160 pg/mL to 15350 pg/mL |
| 55 | from 7930 pg/mL to 14950 pg/mL | from 10750 pg/mL to 20790 pg/mL | from 13820 pg/mL to 22540 pg/mL |
| 85 | from 19550 pg/mL to 23290 pg/mL | from 14810 pg/mL to 37120 pg/mL | from 18820 pg/mL to 39420 pg/mL |

In some embodiments, the oral solid pharmaceutical composition comprising 35, 55, or 85 mg of methylphenidate hydrochloride provides, when administered to pediatric subjects from 6 to 11 years of age in a fasted state, an average methylphenidate $Cmax_{0-4}$, an average methylphenidate $Cmax_{4-8}$, and an average methylphenidate $Cmax_{8-14}$ as specified below:

| Oral methylphenidate HCl dosage (mg) | Average methylphenidate $Cmax_{0-4}$ (±1 standard deviation) | Average methylphenidate $Cmax_{4-8}$ (±1 standard deviation) | Average methylphenidate $Cmax_{8-14}$ (±1 standard deviation) |
|---|---|---|---|
| 35 | 7055 ± 939.3 pg/mL | 10038 ± 2428.5 pg/mL | 11127 ± 2283.1 pg/mL |
| 55 | 11198 ± 2633.2 pg/mL | 13035 ± 3850.3 pg/mL | 15933 ± 3347.6 pg/mL |
| 85 | 21235 ± 1539.9 pg/mL | 23782 ± 7908.8 pg/mL | 27045 ± 6730.4 pg/mL |

In some embodiments, the oral solid pharmaceutical composition comprising 35, 55, or 85 mg of methylphenidate hydrochloride provides, when administered to pediatric subjects from 6 to 11 years of age in a fasted state, a methylphenidate $Tmax_{0-4}$, a methylphenidate $Tmax_{4-8}$, and a methylphenidate $Tmax_{8-14}$ in the ranges specified below:

| Oral methylphenidate HCl dosage (mg) | Methylphenidate $Tmax_{0-4}$ | Methylphenidate $Tmax_{8-14}$ |
|---|---|---|
| 35 | from 1.0 hours to 4.0 hours | from 8.0 hours to 11.0 hours |
| 55 | from 1.0 hours to 2.0 hours | from 9.0 hours to 14.0 hours |
| 85 | from 1.0 hours to 2.0 hours | from 8.0 hours to 14.0 hours |

In some embodiments, the oral solid pharmaceutical composition comprising 35, 55, or 85 mg of methylphenidate hydrochloride provides, when administered to pediatric subjects from 6 to 11 years of age in a fasted state, an average methylphenidate $Tmax_{0-4}$, an average methylphenidate $Tmax_{4-8}$, and an average methylphenidate $Tmax_{8-14}$ as specified below:

| Oral dosage methylphenidate HCl (mg) | Average methylphenidate $Tmax_{0-4}$ (±1 standard deviation) | Average methylphenidate $Tmax_{8-14}$ (±1 standard deviation) |
|---|---|---|
| 35 | 1.833 ± 1.1690 hours | 9.167 ± 1.1690 hours |
| 55 | 1.667 ± 0.5164 hours | 11.167 ± 2.0412 hours |
| 85 | 1.667 ± 0.5164 hours | 11.0 ± 2.1909 hours |

In some embodiments, the oral solid pharmaceutical composition is in the form of a capsule comprising the plurality of coated beads.

In some embodiments, the inner controlled release coating is selected from the group consisting of an ethylcellulose polymer, a cellulose ether, polyethylene oxide, a polyvinyl alcohol derivate, a methacrylic acid copolymer, polyethylene glycol, polyglycolic acid, polylactic acid, polycaprolactone, poly(n-hydroxybutyrate), a polyamino acids, a poly(amide-enamine), a polyesters, ethylene-vinyl acetate (EVA), polyvinyl pyrrolidone (PVP), poly (acrylic acid) (PAA), poly (methacrylic acid) (PMAA), and combinations thereof.

In some embodiments, the inner controlled release coating is present in an amount of 3% to 16% by weight of each coated bead.

In some embodiments, the inner controlled release coating is present in an amount of 10.0% to 10.7% by weight of each coated bead.

In some embodiments, the outer delayed release coating comprises poly(methyl acrylate-co-methyl methacrylate-co-methacrylic acid) 7:3:1.

In some embodiments, the outer delayed release coating is present in an amount of from 3% to 20% by weight of each coated bead.

In some embodiments, the outer delayed release coating is present in an amount of from 15.0% to 16.0% by weight of each coated bead.

In some embodiments, the first amount of methylphenidate or pharmaceutically acceptable salt thereof and the second amount of methylphenidate or pharmaceutically acceptable salt thereof, together, provide a total amount (100%) of methylphenidate or pharmaceutically acceptable salt thereof in each coated bead, and wherein the first amount of methylphenidate or pharmaceutically acceptable salt thereof comprises from 70% to 99% by weight of the total amount of the methylphenidate or pharmaceutically acceptable salt thereof in each coated bead.

In some embodiments, the first amount of methylphenidate or pharmaceutically acceptable salt thereof comprises from 78% to 82% by weight of the total amount of methylphenidate or pharmaceutically acceptable salt thereof.

In some embodiments, the first amount of methylphenidate or pharmaceutically acceptable salt thereof comprises 80% by weight of the total amount of the methylphenidate or pharmaceutically acceptable salt thereof and the second amount of methylphenidate or pharmaceutically acceptable salt thereof comprises 20% by weight of the total amount of the methylphenidate or pharmaceutically acceptable salt thereof.

In some embodiments, the inner controlled release coating is present in an amount of 3% to 16% by weight of each coated bead, and the outer delayed release coating is present in an amount of from 3% to 20% by weight of each coated bead.

In some embodiments, the inner controlled release coating is present in an amount of 10.0% to 10.7% by weight of each coated bead, and the outer delayed release coating is present in an amount of from 15.0% to 16.0% by weight of each coated bead.

In some embodiments, the granule is selected from the group consisting of: a sugar sphere, a microcrystalline cellulose granule, a silica granule, a starch granule, a lactose granule, a calcium carbonate granule, and a mannitol-polyvinylpyrrolidone granule.

In some embodiments, the oral solid pharmaceutical composition provides the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

The present disclosure also provides a method of treating Attention Deficit Hyperactivity Disorder (ADHD) in a pediatric subject from 6 to 12 years of age in need thereof, the method comprising administering to a pediatric subject from 6 to 12 years of age an oral solid pharmaceutical composition comprising a plurality of coated beads, wherein each coated bead comprises (a), (b), (c), and (d) or (a'), (b'), and (c'), as follows:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof, after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of appetite suppression in a population of pediatric subjects from 6 to 12 years of age in the fasted state being treated with the composition is 36% or less.

In some embodiments, the incidence of severe appetite suppression in a population of pediatric subjects from 6 to 12 years of age in the fasted state being treated is 1% or less.

In some embodiments, the incidence of moderate appetite suppression in a population of pediatric subjects from 6 to 12 years of age in the fasted state being treated is 6% or less.

The present disclosure also provides a method of treating Attention Deficit Hyperactivity Disorder (ADHD) in a pediatric subject from 6 to 12 years of age in need thereof, the method comprising administering to the pediatric subject from 6 to 12 years of age an oral solid pharmaceutical composition comprising a plurality of coated beads, wherein each coated bead comprises elements (a), (b), (c), and (d) or elements (a'), (b'), and (c'), as follows:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof, after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the incidence of insomnia in a population of pediatric subjects from 6 to 12 years of age in the fasted state being treated with the composition is 11% or less.

In some embodiments, the incidence of severe insomnia in a population of pediatric subjects from 6 to 12 years of age in the fasted stated being treated with the composition is 1% or less.

In some embodiments, the incidence of moderate insomnia in a population of pediatric subjects from 6 to 12 years of age in the fasted state being treated with the composition is 6% or less.

The present disclosure also provides a method of treating Attention Deficit Hyperactivity Disorder (ADHD) in a pediatric subject from 6 to 12 years of age in need thereof, the method comprising administering to the subject an oral solid pharmaceutical composition comprising a plurality of coated beads, wherein each coated bead comprises elements (a), (b), (c), and (d) or elements (a'), (b'), and (c'), as follows:
- (a) a granule;
- (b) a first layer coated over the granule, the first layer comprising a first amount of methylphenidate or a pharmaceutically acceptable salt thereof;
- (c) an inner controlled release coating coated over the first layer and an outer delayed release coating coated over the inner controlled release coating; and
- (d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; or
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the incidence of initial insomnia in a population of pediatric subjects from 6 to 12 years of age in the fasted state being treated with the composition is 2% or less.

The present disclosure also provides a method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein each coated bead comprises elements (a), (b), (c), and (d) or elements (a'), (b'), and (c'), as follows:
- (a) a granule;
- (b) a first layer coated over the granule, the first layer comprising a first amount of methylphenidate or a pharmaceutically acceptable salt thereof;
- (c) an inner controlled release coating coated over the first layer and an outer delayed release coating coated over the inner controlled release coating; and
- (d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; or
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the oral solid pharmaceutical composition, when administered to a pediatric subject from 12 to 17 years of age in a fasted state, provides:
a methylphenidate $AUC_{0-8}$ from 21830.6 pg·hr/mL to 96316.2 pg·hr/mL;
a methylphenidate $AUC_{0-14}$ from 40576.9 pg·hr/mL to 234533.4 pg·hr/mL; and
a methylphenidate $AUC_{0-24}$ from 86897.7 pg·hr/mL to 415037.5 pg·hr/mL when the oral solid pharmaceutical composition comprises from 25 mg to 85 mg of methylphenidate hydrochloride.

In some embodiments, the oral solid pharmaceutical composition provides:
an average methylphenidate $AUC_{0-4}$ of 47071.6 pg·hr/mL;
an average methylphenidate $AUC_{0-14}$ of 111783.0 pg·hr/mL;
and an average methylphenidate $AUC_{0-24}$ of 181751.2 pg·hr/mL
when the oral solid pharmaceutical composition comprises from 25 mg to 85 mg of methylphenidate.

In some embodiments, the oral solid pharmaceutical composition provides a methylphenidate $AUC_{0-12}$ ranging from 36823.7 pg·hr/mL to 186389.9 pg·hr/mL, when the oral solid pharmaceutical composition comprises from 25 mg to 85 mg of methylphenidate hydrochloride.

In some embodiments, the oral solid pharmaceutical composition provides an average methylphenidate $AUC_{0-12}$ of 89378.1 pg·hr/mL, when the oral solid pharmaceutical composition comprises from 25 mg to 85 mg of methylphenidate hydrochloride.

In some embodiments, the oral solid pharmaceutical composition provides the following in vitro methylphenidate dissolution profile:

| Time (hours) | Methylphenidate (% dissolved) |
| --- | --- |
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

The present disclosure also provides a method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of appetite suppression in a population of pediatric subjects from 12 to 17 years of age in the fasted state being treated with the composition is 21% or less.

The present disclosure also provides a method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein the coated beads comprise elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of insomnia in a population of pediatric subjects from 6 to 12 years of age in the fasted state being treated with the composition is 7% or less.

The present disclosure also provides a method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein the coated beads comprise elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of initial insomnia in a population of pediatric subjects from 6 to 12 years of age in the fasted state being treated with the composition is 6% or less.

The present disclosure also provides a method of treating Attention Deficit Hyperactivity Disorder (ADHD) in a pediatric subject in need thereof, the method comprising administering to the pediatric subject, an oral pharmaceutical composition comprising from 25 to 100 mg methylphenidate hydrochloride, wherein the oral solid pharmaceutical composition, when administered to a pediatric subject from 6 to 11 years of age in a fasted state, provides an average methylphenidate $AUC_{0-4}$ (pg·hr/mL) that is from 80 to 125% of the value resulting from the formula:

$$\text{Average } AUC_{0-4}=1714.4*(\text{dose of methylphenidate hydrochloride in mg})-12188.$$

In some embodiments, the oral pharmaceutical composition further provides an average methylphenidate $AUC_{8-14}$ (pg·hr/mL) that is from 80 to 125% of the value resulting from the formula:

$$\text{Average } AUC_{8-14}=1580.3*(\text{dose of methylphenidate hydrochloride in mg})-1860.$$

In some embodiments, the oral pharmaceutical composition further provides an average methylphenidate $AUC_{14-24}$ (pg·hr/mL) that is from 80 to 125% of the value resulting from the formula:

Average $AUC_{14-24}$=1392.2*(dose of methylphenidate hydrochloride in mg)−9239.1.

In some embodiments, the oral pharmaceutical composition further provides an average methylphenidate $AUC_{0-\infty}$ (pg·hr/mL) that is from 80 to 125% of the value resulting from the formula:

Average $AUC_{0-\infty}$=5932*(dose of methylphenidate hydrochloride in mg)−51.578.

BRIEF DESCRIPTION OF THE DRAWINGS

Embodiments of the present invention will be described with reference to the accompanying drawings, wherein like reference numerals denote like parts, and in which:

FIG. 1 is a graph showing the in vitro dissolution of d-methylphenidate over time for Formulation A (7% Eudragit), Formulation B (10% Eudragit), and biphentin.

FIG. 2 is a graph showing the in vitro dissolution of d-methylphenidate over time for Formulation C (16% Eudragit), Formulation D (20% Eudragit), Formulation E, and biphentin.

FIG. 3 is a graph showing the in vitro dissolution of d-methylphenidate over time for Formulation F, Formulation G, Formulation H (fasted conditions), Formulation H (fed conditions), and Ritalin.

FIG. 4 is a graph showing the in vitro dissolution of d-methylphenidate over time for Formulation I.

FIG. 5 is a graph showing the in vivo dissolution of d-methylphenidate over time for Formulation I (fasted conditions), Formulation I (fed conditions), Ritalin (fasted conditions), and Ritalin (fed conditions).

FIG. 6 is a graph showing the plasma concentration of d-methylphenidate in adult ADHD subjects over time for Formulation I after it is sprinkled on applesauce, yogurt, or ice cream.

FIG. 7 is a graph showing the plasma concentration of d-methylphenidate in adult ADHD subjects over time for Formulation I and IR MPH after 5 days of dosing.

FIG. 8 is a graph showing the plasma concentration of d-methylphenidate over time of Formulation I (fasted conditions), Formulation J (fasted conditions), Formulation I (fed conditions), and Formulation J (fed conditions). Formulation J has a similar pharmacokinetic profile and properties as Formulation I.

FIG. 11 is a table showing the composition of four formulations: Formulation A (7% Eudragit), Formulation B (10% Eudragit), Formulation C (16% Eudragit), and Formulation D (20% Eudragit).

FIGS. 12-14 present a table showing the compositions of Formulation E (ECCRIR bead (70%)+DRCRIR bead (30%)), Formulation F (DRCRIR bead (80%)+immediate release (IR) bead (20%)), Formulation G (ECCRIR bead (30%)+DRCRIR bead (55%)+IR bead (15%)), Formulation H (ECCRIR bead (35%)+DRCRIR bead (55%)+IR bead (10%)), Formulation I (MPH IR distal bead), and Formulation J (MPH IR distal bead).

FIG. 15 is a table showing the dissolution results/profiles for Formulations A-J.

FIG. 16 is a table showing $AUC_{0-t}$, $AUC_{0-inf}$ and Cmax comparisons between Formulation I (fed and fasted) versus IR-MPH (Ritalin 20 mg×3 fed and fasted).

FIG. 17 is a table showing non-dose-normalized pharmacokinetic results for Formulation I and for Ritalin.

FIG. 18 is a table showing non-dose normalized $AUC_{0-t}$, $AUC_{0-inf}$ and Cmax for Formulation I after it is sprinkled on applesauce, yogurt, or ice cream.

FIG. 19A is a table showing non-dose normalized $AUC_{0-24}$, Cmax, and Cmin for Formulation I versus IR-MPH.

FIG. 19B is a table showing the 90% geometric confidence intervals for $AUC_{0-t}$, $AUC_{0-inf}$ and Cmax for Formulation I versus Formulation J.

FIG. 20 is a table showing the percentage of methylphenidate HCl dissolved at various times.

FIG. 21 is a table showing the processing parameters for production of methylphenidate immediate release beads.

FIG. 22 is a table showing the processing parameters for production of methylphenidate controlled release beads.

FIG. 23 is a table showing the processing parameters for production of methylphenidate distal (DRCRIR) beads.

FIG. 24 is a table showing the processing parameters for production of methylphenidate IR distal (MPH IR distal) beads.

FIG. 25 is a table showing the processing parameters for production of methylphenidate IR (MPH IR distal) beads coated with sodium alginate.

FIG. 26 is a table showing the dissolution parameters of Example 10.

FIG. 27 is a table showing the composition of the dosage form of Formulation I (80:20) MPH IR distal bead in varying dosage strengths.

FIG. 28 is a table showing the composition of the dosage form of Formulation J (80:20) MPH IR distal bead in varying dosage strengths.

FIG. 30 is a table showing a summary of pharmacokinetic parameters for d-methylphenidate of Formulation I and immediate-release methylphenidate (Ritalin).

FIG. 31 is a table showing a summary of partial pharmacokinetic parameters for d-methylphenidate of Formulation I and immediate-release methylphenidate (Ritalin).

FIG. 32 is table showing p-values for $AUC_{0-t}$, $AUC_{0-inf}$ and Cmax measured using ANOVA performed on the ln-transformed non-dose normalized and dose-normalized data for d-methylphenidate.

FIG. 33 is a table showing least-squares means ratios, the 90% geometric confidence intervals, intra- and inter-subject CVs for non-dose normalized and dose-normalized data for d-methylphenidate.

FIG. 35 is a table showing a summary of pharmacokinetic parameters for l-methylphenidate of Formulation I and immediate-release methylphenidate (Ritalin).

FIG. 36 is a table showing a summary of partial pharmacokinetic parameters for l-methylphenidate of Formulation I and immediate-release methylphenidate (Ritalin).

FIG. 37 is table showing p-values for $AUC_{0-t}$, $AUC_{0-inf}$ and Cmax measured using ANOVA performed on the ln-transformed non-dose normalized and dose-normalized data for l-methylphenidate.

FIG. 38 is a table showing least-squares means ratios, the 90% geometric confidence intervals, intra- and inter-subject CVs for non-dose normalized and dose-normalized data for l-methylphenidate.

FIG. 40 is a table showing a summary of pharmacokinetic parameters for combined methylphenidate of Formulation I and immediate-release methylphenidate (Ritalin).

FIG. 41 is a table showing a summary of partial pharmacokinetic parameters for combined methylphenidate of Formulation I and immediate-release methylphenidate (Ritalin).

FIG. 42 is table showing p-values for $AUC_{0-t}$, $AUC_{0-inf}$, and Cmax measured using ANOVA performed on the ln-transformed non-dose normalized and dose-normalized data for combined methylphenidate.

FIG. 43 is a table showing least-squares means ratios, the 90% geometric confidence intervals, intra- and inter-subject CVs for non-dose normalized and dose-normalized data for combined methylphenidate.

FIG. 47 is a table showing an overall summary of treatment-emergent adverse events (TEAEs) for Formulation I in an open-label dose-optimization period and for Formulation I and placebo in a double-blind treatment period in pediatric subjects 6 to 12 years of age diagnosed with ADHD.

FIGS. 48-50 is a table showing TEAEs by system organ class and maximum severity for Formulation I in an open-label dose-optimization period in pediatric subjects 6 to 12 years of age diagnosed with ADHD.

FIGS. 51-52 is a table showing TEAEs by system organ class and maximum severity for Formulation I in a double-blind treatment period in pediatric subjects 6 to 12 years of age diagnosed with ADHD.

FIG. 53 is a table showing the most common (≥10% of subjects overall) TEAEs by preferred term and maximum severity for Formulation I in an open-label dose-optimization period in pediatric subjects 6 to 12 years of age diagnosed with ADHD.

FIG. 54 is a table showing the most common (≥2% of subjects overall) TEAEs by preferred term and maximum severity for Formulation I in double-blind treatment period in pediatric subjects 6 to 12 years of age diagnosed with ADHD.

FIGS. 55-56 is a table showing the most common (≥5% of subjects overall) TEAEs by preferred term and maximum severity in descending frequency for Formulation I in an open-label dose-optimization period in pediatric subjects 6 to 12 years of age diagnosed with ADHD.

FIGS. 57-58 is a table showing treatment-related adverse events by preferred term and maximum severity in descending frequency for Formulation I in double-blind treatment period in pediatric subjects 6 to 12 years of age diagnosed with ADHD.

FIG. 59 is table providing a comparison of TEAEs from open-label, dose-optimization periods in similarly designed laboratory classroom studies with long-acting stimulants including Formulation I.

FIGS. 62-66 is a table showing plasma concentrations for d,l-methylphenidate by dose group for Formulation I.

FIGS. 69-73 are a table showing pharmacokinetic parameters for d,l-methylphenidate of Formulation I.

FIG. 74 is a table showing TEAEs by system organ class for Formulation I in an open-label dose-optimization period in pediatric subjects 12 years of age diagnosed with ADHD.

FIG. 75 is a table showing TEAEs by system organ class for Formulation I in a double-blind treatment period in pediatric subjects 12 years of age diagnosed with ADHD.

DETAILED DESCRIPTION OF THE PREFERRED EMBODIMENTS

Figure 9:
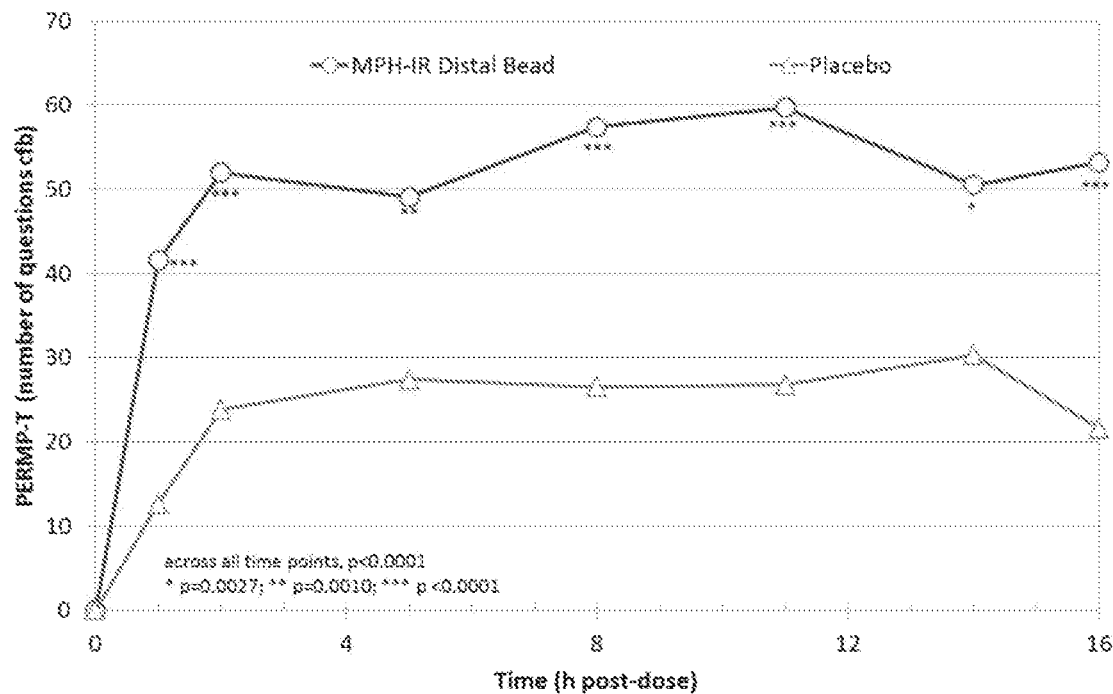
FIG. 9 is a graph showing mean change from pre-dose PERMP-Total Scores over time for adult ADHD subjects receiving MPH IR distal bead and a placebo.

Methods and compositions for the treatment of attention deficit disorder are described in U.S. Pat. No. 9,974,752, which is incorporated herein by reference in its entirety.

The coated bead and solid oral pharmaceutical compositions of the present invention include a central nervous system stimulant which can be generally defined as a chemical entity that affects the dopamine or norepinephrine neural pathways. Preferred pharmaceutically active ingredients include, but are not limited to amphetamine, dextroamphetamine, the active isomers of amphetamines and amphetamine salts including salts of dextroamphetamine, methylphenidate and its active salts, or combinations thereof, all of which can be used as racemic mixtures or pure isomers such as d-threo methylphenidate, or a prodrug or pharmaceutical salt, or mixed pharmaceutical salts of any thereof alone or in combination. The disclosed coated bead and solid oral pharmaceutical compositions can also include a prodrug, including but not limited to amino acid conjugated active ingredients such as 1-lysine-d-amphetamine.

Conditions or disorders that can be treated using the present coated bead or solid oral pharmaceutical compositions include, but are not limited to attention deficit disorder (ADD), attention deficit hyperactivity disorder (ADHD), excessive daytime sleepiness, major depressive disorder, bipolar depression, negative symptoms in schizophrenia, chronic fatigue, fatigue associated with chemotherapy or binge eating disorder. Attention deficit disorders are characterized by hyperactive, impulsive or inattentive symptoms that cause impairment in social, academic, or occupational functioning, and are often present in two or more settings, school (or work) and at home, for example. For the Inattentive Type, at least 6 (5 for adults≥18 years of age) of the following symptoms have persisted for at least 6 months: lack of attention to details/careless mistakes; lack of sustained attention; poor listener; failure to follow through on tasks; poor organization; avoids tasks requiring sustained mental effort; loses things; easily distracted; and forgetful. For the Hyperactive-Impulsive Type, at least 6 (5 for adults≥18 years of age) of the following symptoms have persisted for at least 6 months: fidgeting/squirming; leaving seat; inappropriate running/climbing; difficulty with quiet activities; "on the go;" excessive talking; blurting answers; can't wait turn, and intrusive. The combined type includes both inattentive and hyperactive-impulsive behaviors.

In some embodiments, the subject in need of treatment is a pediatric subject. A pediatric subject is from 0 to 17 years of age, i.e. less than 18 years of age. In some embodiments, the pediatric subject can be from 6 to 17 years of age. In other embodiments, the pediatric subject can be from 6 to 8, 6 to 9, 6 to 10, 6 to 11, 6 to 12, 6 to 13, 6 to 14, 6 to 15, or 6 to 16 years of age. In particular embodiments, the pediatric subject can be 6 to 11 or 6 to 12 years of age. In other embodiments, the pediatric subject can be from 12 to 17 years of age. In some embodiments, the pediatric subject is 6, 7, 8, 9, 10, 11, 12, 13, 14, 15, 16, or 17 years of age.

In some studies described herein, the population of pediatric subjects are from 6 to 11 years of age. In other studies, the population of pediatric subjects is from 6 to 12 years of age. In some studies, the population of pediatric subjects are from 12 to 17 years of age. The ages of pediatric subjects in a given study population will be apparent from the study.

It is understood that the term treatment as used herein is not limited to the cure or elimination of any condition or disorder nor is that term limited to the achievement of certain milestones or improvement criteria in a particular subject, but includes the administration of an agent for the purpose of achieving positive effects in terms of cognitive or behavioral function, reduction of symptoms or side effects. All such activities are considered to be treatment whether or not any improvement is immediately observable or measurable.

In a highly preferred embodiment, the present invention relates to a controlled release oral formulation of methylphenidate (or a pharmaceutically acceptable salt thereof) that provides a rapid onset of therapeutic effect and a gradual drop in plasma concentration after a prolonged period of therapeutic effect (e.g., 16 hours). This oral formulation comprises a plurality of substrates, preferably in the form of coated beads. Preferably, the coated bead comprises: (i) an initial portion of an effective dose of methylphenidate (or a pharmaceutically acceptable salt thereof) in immediate release form coated over a granule; (ii) a controlled release (e.g., hydrophobic) material, preferably in the form of an acrylic polymer, coated over (i); (iii) a delayed (or distal) release (e.g., colonic delivery) coating over (ii) in an amount sufficient to substantially delay the release of the drug from the substrate until after coated bead passes through the stomach and reaches the distal part of the gastrointestinal tract; and, optionally, (iv) a remaining portion of the effective dose of methylphenidate (or a pharmaceutically acceptable salt thereof) in immediate release form coated over (iii).

Preferably, the delayed release coating is derived from an aqueous dispersion of an anionic copolymer based on methyl acrylate, methyl methacrylate and methacrylic acid, a plasticizer and a glidant. The contents of the encapsulated product may be sprinkled on soft foods before administration.

The substrate (e.g., granules) can be chosen from spheres, also referred as pellets, also referred as beads, made of microcrystalline cellulose, mannitol-PVP, silica, starch, lactose, calcium carbonate or combination thereof. The preferred substrate to be used is sugar spheres 14/18 mesh to 18/20 mesh.

It can be preferred to use sugar spheres 14/18 mesh to 18/20 mesh amount of about 20% to about 70% by weight, of about 25% to about 65% by weight, of about 40% to about 64% by weight, of about 41% to about 63% by weight, of about 42% to about 62% by weight, of about 43% to about 61% by weight, based on the weight of the pharmaceutical composition. An amount of about 44.0% to about 53.5% by weight based on the weight of the pharmaceutical composition can be preferred of the nonpareil substrate, particularly of sugar spheres 14/18 mesh to 18/20 mesh.

The controlled release polymer can include ethylcellulose polymers, cellulose ethers (e.g., hydroxypropyl methylcellulose, hydroxypropylcellulose, methylcellulose, hydroxyethylcellulose, etc.), polyethylene oxide, polyvinyl alcohol derivates, methacrylic acid copolymers (e.g., poly(ethylene glycol) diacrylate, poly(ethylene glycol) triacrylate, poly (ethylene glycol) dimethacrylate, poly(ethylene glycol) trimethacrylate, polymulti (meth)acrylates], polyethylene glycol, polyglycolic acid, polylactic acid, poly caprolactone, poly(n-hydroxybutyrate), polyamino acids, poly(amide-enamines), poly(esters) (see Chem. Rev. 1999, 99, 3181-3198. *Polymeric Systems for Controlled Drug Release* (Uhrich et al.)), ethylene-vinyl acetate (EVA), polyvinyl pyrrolidone (PVP), poly acrylic acid (PAA), poly methacrylic acid (PMAA) or combinations thereof in amounts that would deliver the active pharmaceutical ingredient at the desired release rate. Preferably, the controlled release polymer is derived from a mixture copolymer of ethyl acrylate, methyl methacrylate and methacrylic acid ester with quaternary ammonium groups (Ammonio Methacrylate Copolymer, Type B USP/NF).

It can be preferred to use ammonio methacrylate copolymer, Type B USP/NF as a controlled release material. Such a material is commercially available from Evonik under the trade name Eudragit® RS30D.

It thus can be preferred to use a controlled release polymer amount of about 3% to about 16% by weight, of about 4% to about 15% by weight, of about 5% to about 14% by weight, of about 5.1% to about 13.5% by weight, such as of about 8.0% by weight, of about 8.1% by weight, of about 8.2% by weight, of about 8.3% by weight, of about 8.4% by weight, of about 8.5% by weight, of about 8.6% by weight, of about 8.7% by weight, of about 8.8% by weight, of about 8.9% by weight, of about 9.0% by weight, of about 9.1% by weight, of about 9.2% by weight, of about 9.3% by weight, of about 9.4% by weight, of about 9.5% by weight, of about 9.6% by weight, of about 9.7% by weight, of about 9.8% by weight, of about 9.9% by weight, of about 10.0%, of about 10.1% by weight, of about 10.2% by weight, of about 10.3% by weight, of about 10.4% by weight, of about 10.5% by weight, of about 10.6% by weight or of about 10.7% by weight, based on the weight of the pharmaceutical composition and the coated bead.

An amount of about 10.0% to about 10.7% by weight based on the weight of the pharmaceutical composition can be preferred, particularly if ammonio methacrylate copolymer, Type B USP/NF is used as controlled release modifier. The aforementioned amounts refer to the amount of all controlled release (e.g., hydrophobic) materials in the pharmaceutical composition or coated bead.

The delayed (or distal) release (e.g., colonic delivery) coating material can include guar gum, pectin, hydroxypropyl methylcellulose phthalate, cellulose acetate phthalate, cellulose acetate trimelliate, biodegradable polysaccharides (amylose, arabinogalactan, chitosan, chondroitin sulfate, cyclodextrin, dextran, guar gum, pectin, xanthan gum, xylan), poly(methacrylic acid-co-methyl methacrylate) 1:2, poly(methacrylic acid-co-methyl methacrylate) 1:1, polyvinyl acetate phthalate, covalent linkage of the drug with carrier (azo conjugates, cyclodextrin conjugates, glycoside conjugates, glucuronate conjugates, dextran conjugates, polypeptide conjugates, polymeric drugs), acidic comonomers, methacryloyloxy azobenzene and 2-hydroxyethyl methacrylate (HEMA), dextran hydrogels, and combinations thereof in amounts that would control the delivery of the product to the distal part of the GI tract. The preferred system to be used is the anionic copolymer based on methyl acrylate, methyl methacrylate and methacrylic acid (IUPAC name: Poly(methyl acrylate-co-methyl methacrylate-co-methacrylic acid) 7:3:1).

It can be preferred to use poly(methyl acrylate-co-methyl methacrylate-co-methacrylic acid) 7:3:1 as the delayed (or distal) release (e.g., colonic delivery) material. Such a material is commercially available from Evonik under the trade name Eudragit® FS30D.

It thus can be preferred to use a distal release modifier amount of about 3% to about 20% by weight, of about 8% to about 18% by weight, of about 10% to about 17% by weight, of about 10.1% to about 16.5 by weight, such as of about 15.0% by weight, of about 15.1% by weight, of about 15.2% by weight, of about 15.3% by weight, of about 15.4% by weight, of about 15.5% by weight, of about 15.6% by weight, of about 15.7% by weight, of about 15.8% by weight, of about 15.9% by weight, of about 16.0% by weight, of about 16.1% by weight, of about 16.2% by weight, of about 16.3% by weight, or of about 16.4% by weight based on the weight of the pharmaceutical composition.

An amount of about 15.0% to about 16.0% by weight based on the weight of the pharmaceutical composition can be preferred, particularly if poly(methyl acrylate-co-methyl methacrylate-co-methacrylic acid) 7:3:1 is used as distal release modifier. The aforementioned amounts refer to the amount of all delayed (or distal) release (e.g., colonic delivery) materials (i.e., including mixtures) in the pharmaceutical composition and the coated bead.

Plasticizers can optionally be used. Examples of useful plasticizers include citrates (triethyl citrate, acetyl triethyl citrate, tributyl citrate and acetyl tributyl citrate, acetyl tributyl citrate), triacetin, dibutyl sebacate, sebacate and azelate esters (di-2-ethylhexyl sebacate, di-2-ethylhexyl azelate, diisodecyl sebacate), ester of glycol and polyhydric alcohol [propylene glycol, glycerol (glycerin), polyethylene glycol, glyceryl triacetate], glyceryl monostearate (GMS), polysorbate 80, phthalates (di-octyl phthalate, diisodecyl phthalate, diisononyl phthalate), dibutyl phthalate, diethyl phthalate, adipates, phosphate esters, Polymerics, trimelliates (tris-2-ethylhexyltrimelliate), glutarates, castor oil, acetylated monoglycerides, fractionated coconut oil and mixtures of any two or more thereof. The preferred plasticizers to be used are triethyl citrate, glyceryl monostearate in combination with polyoxyethylene (20) sorbitan monooleate (Polysorbate 80™).

It can be preferred to use triethyl citrate and glyceryl monostearate emulsion as plasticizer system.

It thus can be preferred to use a plasticizer system amount of about 0.1% to about 10% by weight, of about 0.5% to about 9% by weight, of about 1% to about 7% by weight, of about 2% to about 6% by weight, of about 2.5% to about 5.5% by weight, of about 3.5% to about 4.5% by weight such as of about 3.6% by weight, of about 3.7% by weight, of about 3.8% by weight, of about 3.9% by weight, of about 4.0% by weight, of about 4.1% by weight, of about 4.2% by weight, of about 4.3% by weight, of about 4.4% by weight, or of about 4.5% by weight based on the weight of the pharmaceutical composition.

An amount of about 4.0% to about 4.5% by weight based on the weight of the pharmaceutical composition can be preferred, particularly if triethyl citrate and glyceryl monostearate emulsion is used as plasticizer system. The aforementioned amounts refer to the amount of all plasticizers (i.e., including mixtures) in the composition.

Glidants can include talc, fumed silica, lecithin. The preferred glidants to be used are talc and fumed silica.

Binders can include hydroxypropyl cellulose (HPMC), hydroxypropyl cellulose (HPC), polyvinyl pyrollidone, carbopol, and combinations thereof. It can be preferred to use HMPC as a binder.

It thus can be preferred to use a binder amount of about 1% to about 10% by weight, of about 2% to about 9% by weight, of about 3% to about 7% by weight, of about 3% to about 6% by weight, such as of about 3.0% by weight, of about 3.1% by weight, of about 3.2% by weight, of about 3.3% by weight, of about 3.4% by weight, of about 3.5% by weight, of about 3.6% by weight, of about 3.7% by weight, of about 3.8% by weight, of about 3.9% by weight, of about 4.0% by weight, of about 4.1% by weight, of about 4.2% by weight, of about 4.3% by weight, of about 4.4% by weight, of about 4.5% by weight, of about 4.6% by weight, of about 4.7% by weight, of about 4.8% by weight, of about 4.9% by weight, of about 5.0% by weight, of about 5.1% by weight, of about 5.2% by weight, of about 5.3% by weight, of about 5.4% by weight, of about 5.5% by weight, of about 5.6% by weight, of about 5.7% by weight, of about 5.8% by weight, of about 5.9% by weight or of about 6.0% by weight, based on the weight of the pharmaceutical composition.

An amount of about 3.8% to about 6.0% by weight based on the weight of the pharmaceutical composition can be preferred, particularly if HPMC is used as binder. The aforementioned amounts refer to the amount of all binders (i.e., including mixtures) in the composition.

It is preferred to use an outer layer of immediate release methylphenidate HCl amount of about 1% to about 30% by weight, of about 5% to about 28% by weight, of about 15% to about 27% by weight, of about 18% to about 25% by weight, such as of about 19.0% to about 25.0% by weight, of about 19.1% by weight, of about 19.2% by weight, of about 19.3% by weight, of about 19.4% by weight, of about 19.5% by weight, of about 19.6% by weight, of about 19.7% by weight, of about 19.8% by weight, of about 19.9% by weight, of about 20.0% by weight, of about 20.1% by weight, of about 20.2% by weight, of about 20.3% by weight, of about 20.4% by weight, of about 20.5% by weight, of about 20.6% by weight, of about 20.7% by weight, of about 20.8% by weight, of about 20.9% by weight, of about 21.0% by weight, of about 21.1% by weight, of about 21.2% by weight, of about 21.3% by weight, of about 21.4% by weight, of about 21.5% by weight, of about 21.6% by weight, of about 21.7% by weight, of about 21.8% by weight, of about 21.9% by weight or of about 22.0% by weight, based on the weight of the pharmaceutical composition. An amount of about 18.0% to about 22.0% by weight based on the weight of the pharmaceutical composition can be preferred. The aforementioned amounts refer to the amount of methylphenidate hydrochloride or its respective amount of the base or any of its salts in the outer immediate release layer composition.

It is also preferred to use an inner core layer of immediate release methylphenidate HCl amount of about 1% to about 99% by weight, of about 5% to about 95% by weight, of about 60% to about 90% by weight, of about 70% to about 85% by weight, such as of about 73.0% to about 83.0% by weight, of about 79.0% by weight, of about 79.1% by weight, of about 79.2% by weight, of about 79.3% by weight, of about 79.4% by weight, of about 79.5% by weight, of about 79.6% by weight, of about 79.7% by weight, of about 79.8% by weight, of about 79.9% by weight, of about 80.0% by weight, of about 80.1% by weight, of about 80.2% by weight, of about 80.3% by weight, of about 80.4% by weight, of about 80.5% by weight, of about 80.6% by weight, of about 80.7% by weight, of about 80.8% by weight, of about 80.9% by weight, of about 81.0% by weight, of about 81.1% by weight, of about 81.2% by weight, of about 81.3% by weight, of about 81.4% by weight, of about 81.5% by weight, of about 81.6% by weight, of about 81.7% by weight, of about 81.8% by weight, of about 81.9% by weight or of about 82.0% by weight, based on the weight of the pharmaceutical composition. An amount of about 78.0% to about 82.0% by weight based on the weight of the pharmaceutical composition can be preferred. The aforementioned amounts refer to the amount of methylphenidate hydrochloride or its respective amount of the base or any of its salts in the inner core immediate release layer composition.

As described above, several solid dose controlled-release formulations of methylphenidate are commercially available in the market. However, the therapeutic effect of some or all of those formulations is not expected to last for more than 12 hours after adminstration.

An advantage of the present invention is believed to be that the formulation will have a therapeutic effect of at least 14 hours of duration, or at least 16 hours. To achieve this, the delivery of methylphenidate in the distal part of the GI tract was investigated to prolong the duration of action of the drug. The present inventors are unaware of an actual reported example of the delivery of methylphenidate in the distal part of the GI tract. Also, no relevant in vivo data was found reporting the release of methylphenidate or its pharmaceutically acceptable salts in the distal part of the GI tract.

Methylphenidate hydrochloride is freely soluble in water and methanol, soluble in alcohol, slightly soluble in chloroform and acetone; melts between 224-226° C.; and has a pKa of approximately 8.8. Methylphenidate is relatively stable in acidic solutions but it is degraded extensively in basic solutions. The degradation occurs via the hydrolysis of the methyl ester to the free acid, α-phenyl 1-2-piperidineacetic acid. Therefore, the degradation amount increases up to 100% as the pH increases to 8.9. See Chemical Stability of Pharmaceuticals a Handbook for Pharmacists 1986, 587-590 (Kenneth A. Connors, Gordon L. Amidon and Valentino J. Stella) and Analytical Profiles of Drug Substances. 1981, 473-497 (Gandharva R. Padmanabhan) for additional information.

As a result, it was not known whether methylphenidate could be absorbed systemtically in sufficient amount to have therapeutic effect at distal locations within the GI tract where the pH is known to be above pH 6.0. Thus, the present inventors performed in vitro and in vivo studies to determine the amount released and the extent of absorption of several methylphenidate controlled release formulations. FIGS. 11-14 show some of the different formulations explored; FIG. 15 shows their correspondent in vitro dissolution data and FIGS. 1-4 shows their respective in vivo results.

The preferred oral dosage form of the present invention is a capsule containing multilayer release (MLR) beads which have multiple layers to achieve the desired release rate profile of methylphenidate hydrochloride. Some of those layers have immediate release and controlled release components. It is made up of a controlled release bead which is coated to delay dissolution until it has reached the distal part of the GI tract. The distal coated controlled release bead has an immediate release topcoat to provide an initial rate of absorption needed to have the desired therapeutic effect. In a highly preferred embodiment, the immediate release component represents 20% of the total dose per bead and the controlled release component represents 80% of the total dose per bead. This formulation is designed to produce rapid rise to therapeutic plasma levels after oral administration, due to the rapid dissolution and absorption of the outer immediate release layer, followed by a period of minimum absorption and then controlled release of the immediate release core. Plasma levels would then gradually decrease according to the elimination kinetics of methylphenidate.

In a preferred embodiment, the pharmaceutical dosage forms comprise methylphenidate or a pharmaceutical acceptable salt or derivate thereof as the sole pharmaceutically active agent.

The pharmaceutical composition of methylphenidate HCl, Controlled Release Capsules (e.g., Formulation I and J 80:20 described below) MPH IR distal beads may comprise about 1 to 150 mg such as about 15 mg, 25 mg, 30 mg, 35 mg, 45 mg, 55 mg, 70 mg, 85 mg, 100 mg, and 120 mg.

The present coated beads are preferably formulated as a plurality of single multilayer coated beads for use as oral solid pharmaceutical compositions, preferably in the form of a capsule. The capsule material is preferably a hard gelatin capsule or a hard HPMC capsule. Other capsule materials may also be used and the selection thereof is within the purview of a person of ordinary skill in the art.

In other embodiments of the present invention, it may be preferred to provide an outer layer on the coated bead, wherein the outer layer comprises one or more salts of alginic acid. The salts of alginic acid may be selected from sodium alginate, potassium alginate, magnesium alginate, lithium alginate or ammonium alginate or mixtures thereof. Preferably, the salts of alginic acid may have a viscosity of 30 to 720, preferably 40 to 450, preferably 40 to 400 or preferably 50 to 300 centipoise (cp) of a 1% aqueous solution (weight/weight). The provision of such an outer layer can improve the coated bead resistance to alcohol (e.g., ethanol) in concentrations of greater than 35% (volume/volume)—e.g., 40% (volume/volume)—since such the presence of alcohol (e.g., ethanol) in the gastric fluid usually leads to an increase to the release rates in the stomach. Due to distribution effect, the effect of ingested ethanol in the intestine is not of the same importance as in the stomach. A preferred embodiment of the invention relates to the use of coating layers described above in the coated bead to confer resistance to alcohol (e.g., ethanol) in concentrations of up to about 35% (volume/volume) in the gastric fluid without the need to use a coating comprising one or more salts of alginic acid. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

It is well-known that methylphenidate can cause significant side effects including, but not limited to, insomnia and appetite suppression. See Wilens, T., et al., *Child Adolesc Psychiatr Clin N. Am.* 9(3):573-603 (2000).

In some embodiments, the oral solid pharmaceutical composition comprising 35 mg of methylphenidate hydrochloride provides in pediatric subjects from 6 to 11 years of age in a fasted state a methylphenidate $AUC_{0-4}$ of from 18010 pg·hr/mL to 26470 pg·hr/mL. In some embodiments, the oral solid pharmaceutical composition comprising 35 mg of methylphenidate hydrochloride provides in pediatric subjects from 6 to 11 years of age in a fasted state a methylphenidate $AUC_{8-14}$ of from 40610 pg·hr/mL to 80390 pg·hr/mL. In some embodiments, the oral solid pharmaceutical composition comprising 35 mg of methylphenidate hydrochloride provides in pediatric subjects from 6 to 11 years of age in a fasted state a methylphenidate $AUC_{14-24}$ of from 23070 pg·hr/mL to 81850 pg·hr/mL.

In some embodiments, the oral solid pharmaceutical composition comprising 55 mg of methylphenidate hydrochloride provides in pediatric subjects from 6 to 11 years of age in a fasted state a methylphenidate $AUC_{0-4}$ of from 23270 pg·hr/mL to 43880 pg·hr/mL. In some embodiments, the oral solid pharmaceutical composition comprising 55 mg of methylphenidate hydrochloride provides in pediatric subjects from 6 to 11 years of age in a fasted state a methylphenidate $AUC_{8-14}$ of from 64370 pg·hr/mL to 109080 pg·hr/mL. In some embodiments, the oral solid pharmaceutical composition comprising 55 mg of methylphenidate hydrochloride provides in pediatric subjects from 6 to 11 years of age in a fasted state a methylphenidate $AUC_{14-24}$ of from 23230 pg·hr/mL to 80910 pg·hr/mL.

In some embodiments, the oral solid pharmaceutical composition comprising 85 mg of methylphenidate hydrochloride provides in pediatric subjects from 6 to 11 years of age in a fasted state a methylphenidate $AUC_{0-4}$ of from 54790 pg·hr/mL to 65660 pg·hr/mL. In some embodiments, the oral solid pharmaceutical composition comprising 85 mg of methylphenidate hydrochloride provides in pediatric subjects from 6 to 11 years of age in a fasted state a methylphenidate $AUC_{8-14}$ of from 100550 pg·hr/mL to 200860 pg·hr/mL. In some embodiments, the oral solid pharmaceutical composition comprising 85 mg of methylphenidate hydrochloride provides in pediatric subjects from 6 to 11 years of age in a fasted state a methylphenidate $AUC_{14-24}$ of from 76600 pg·hr/mL to 161310 pg·hr/mL.

In some embodiments, the oral solid pharmaceutical composition comprising 35 mg of methylphenidate hydrochloride provides in pediatric subjects from 6 to 11 years of age in a fasted state a methylphenidate $AUC_{0-8}$ of from 39930 pg·hr/mL to 61910 pg·hr/mL. In some embodiments, the oral solid pharmaceutical composition comprising 35 mg of methylphenidate hydrochloride provides in pediatric subjects from 6 to 11 years of age in a fasted state a methylphenidate $AUC_{4-8}$ of from 19630 pg·hr/mL to 42750 pg·hr/mL. In some embodiments, the oral solid pharmaceutical composition comprising 35 mg of methylphenidate hydrochloride provides in pediatric subjects from 6 to 11 years of age in a fasted state a methylphenidate $AUC_0.14$ of from 89630 pg·hr/mL to 142290 pg·hr/mL. In some embodiments, the oral solid pharmaceutical composition comprising 35 mg of methylphenidate hydrochloride provides in pediatric subjects from 6 to 11 years of age in a fasted state a methylphenidate $AUC_{0-24}$ of from 121460 pg·hr/mL to 224140 pg·hr/mL.

In some embodiments, the oral solid pharmaceutical composition comprising 55 mg of methylphenidate hydrochloride provides in pediatric subjects from 6 to 11 years of age in a fasted state a methylphenidate $AUC_{0-8}$ of from 57120 pg·hr/mL to 93020 pg·hr/mL. In some embodiments, the oral solid pharmaceutical composition comprising 55 mg of methylphenidate hydrochloride provides in pediatric subjects from 6 to 11 years of age in a fasted state a methylphenidate $AUC_{4-8}$ of from 32420 pg·hr/mL to 63330 pg·hr/mL. In some embodiments, the oral solid pharmaceutical composition comprising 55 mg of methylphenidate hydrochloride provides in pediatric subjects from 6 to 11 years of age in a fasted state a methylphenidate $AUC_{0-14}$ of from 121490 pg·hr/mL to 202100 pg·hr/mL. In some embodiments, the oral solid pharmaceutical composition comprising 55 mg of methylphenidate hydrochloride provides in pediatric subjects from 6 to 11 years of age in a fasted state a methylphenidate $AUC_{0-24}$ of from 144720 pg·hr/mL to 268190 pg·hr/mL.

In some embodiments, the oral solid pharmaceutical composition comprising 85 mg of methylphenidate hydrochloride provides in pediatric subjects from 6 to 11 years of age in a fasted state a methylphenidate $AUC_{0-8}$ of from 113650 pg·hr/mL to 169020 pg·hr/mL. In some embodiments, the oral solid pharmaceutical composition comprising 85 mg of methylphenidate hydrochloride provides in pediatric subjects from 6 to 11 years of age in a fasted state a methylphenidate $AUC_{4-8}$ of from 51060 pg·hr/mL to 110650 pg·hr/mL. In some embodiments, the oral solid pharmaceutical composition comprising 85 mg of methylphenidate hydrochloride provides in pediatric subjects from 6 to 11 years of age in a fasted state a methylphenidate $AUC_0.14$ of from 231620 pg·hr/mL to 369880 pg·hr/mL. In some embodiments, the oral solid pharmaceutical composition comprising 85 mg of methylphenidate hydrochloride provides in pediatric subjects from 6 to 11 years of age in a fasted state a methylphenidate $AUC_{0-24}$ of from 325490 pg·hr/mL to 473730 pg·hr/mL.

In some embodiments, the oral solid pharmaceutical composition comprising 35 mg of methylphenidate hydrochloride provides in pediatric subjects from 6 to 11 years of age in a fasted state a methylphenidate $Cmax_{0-4}$ of from 6020 pg/mL to 8570 pg/mL. In some embodiments, the oral solid pharmaceutical composition comprising 35 mg of methylphenidate hydrochloride provides in pediatric subjects from 6 to 11 years of age in a fasted state a methylphenidate $Cmax_{4-8}$ of from 6820 pg/mL to 14000 pg/mL. In some embodiments, the oral solid pharmaceutical composition comprising 35 mg of methylphenidate hydrochloride provides in pediatric subjects from 6 to 11 years of age in a fasted state a methylphenidate $Cmax_{8-14}$ of from 9160 pg/mL to 15350 pg/mL.

In some embodiments, the oral solid pharmaceutical composition comprising 55 mg of methylphenidate hydrochloride provides in pediatric subjects from 6 to 11 years of age in a fasted state a methylphenidate $Cmax_{0-4}$ of from 7930 pg/mL to 14950 pg/mL. In some embodiments, the oral solid pharmaceutical composition comprising 55 mg of methylphenidate hydrochloride provides in pediatric subjects from 6 to 11 years of age in a fasted state a methylphenidate $Cmax_{4-8}$ of from 10750 pg/mL to 20790 pg/mL. In some embodiments, the oral solid pharmaceutical composition comprising 55 mg of methylphenidate hydrochloride provides in pediatric subjects from 6 to 11 years of age in a fasted state a methylphenidate $Cmax_{8-14}$ of from 13820 pg/mL to 22540 pg/mL.

In some embodiments, the oral solid pharmaceutical composition comprising 85 mg of methylphenidate hydrochloride provides in pediatric subjects from 6 to 11 years of age in a fasted state a methylphenidate $Cmax_{0-4}$ of from 19550 pg/mL to 23290 pg/mL. In some embodiments, the oral solid pharmaceutical composition comprising 85 mg of methylphenidate hydrochloride provides in pediatric subjects from 6 to 11 years of age in a fasted state a methylphenidate $Cmax_{4-8}$ of from 14810 pg/mL to 37120 pg/mL. In some embodiments, the oral solid pharmaceutical composition comprising 85 mg of methylphenidate hydrochloride provides in pediatric subjects from 6 to 11 years of age in a fasted state a methylphenidate $Cmax_{8-14}$ of from 18820 pg/mL to 39420 pg/mL.

In some embodiments, the oral solid pharmaceutical composition comprising 35 mg of methylphenidate hydrochloride provides in pediatric subjects from 6 to 11 years of age in a fasted state a methylphenidate $Tmax_{0-4}$ of from 1.0 hours to 4.0 hours. In some embodiments, the oral solid pharmaceutical composition comprising 35 mg of methylphenidate hydrochloride provides in pediatric subjects from 6 to 11 years of age in a fasted state a methylphenidate $Tmax_{8-14}$ of from 8.0 hours to 11.0 hours.

In some embodiments, the oral solid pharmaceutical composition comprising 55 mg of methylphenidate hydrochloride provides in pediatric subjects from 6 to 11 years of age in a fasted state a methylphenidate $Tmax_{0-4}$ of from 1.0 hours to 2.0 hours. In some embodiments, the oral solid pharmaceutical composition comprising 55 mg of methylphenidate hydrochloride provides in pediatric subjects from 6 to 11 years of age in a fasted state a methylphenidate $Tmax_{8-14}$ of from 9.0 hours to 14.0 hours.

In some embodiments, the oral solid pharmaceutical composition comprising 85 mg of methylphenidate hydrochloride provides in pediatric subjects from 6 to 11 years of age in a fasted state a methylphenidate $Tmax_{0-4}$ of from 1.0 hours to 2.0 hours. In some embodiments, the oral solid pharmaceutical composition comprising 85 mg of methylphenidate hydrochloride provides in pediatric subjects from 6 to 11 years of age in a fasted state a methylphenidate $Tmax_{8-14}$ of from 8.0 hours to 14.0 hours.

In some embodiments, the incidence of appetite suppression in a population of pediatric subjects from 6 to 12 years of age in the fasted state being treated with the composition is 36% or less. In some embodiments, the incidence of appetite suppression in a population of pediatric subjects from 6 to 12 years of age in the fasted state being treated with the composition is 36% or less, 25% or less, 20% or less, 12% or less, 10% or less, 8% or less, 6% or less, 4% or less, or 2% or less.

As used herein, the term "severe appetite suppression" refers to appetite suppression of an intensity that was incapacitating such that the subject was unable to work or complete usual activity. The intensity of appetite suppression was based on investigator observation of the pediatric subject.

As used herein, the term "moderate appetite suppression" refers to appetite suppression of an intensity that it interfered with daily activity, but where the subject was still able to function. The intensity of appetite suppression was based on investigator observation of the pediatric subject.

In some embodiments, the incidence of severe appetite suppression in a population of pediatric subjects from 6 to 12 years of age in the fasted state being treated with the composition is 1% or less.

In some embodiments, the incidence of moderate appetite suppression in a population of pediatric subjects from 6 to 12 years of age in the fasted state being treated with the composition is 2% or less.

In some embodiments, the incidence of insomnia in a population of pediatric subjects from 6 to 12 years of age in the fasted state being treated with the composition is 11% or less. In some embodiments, the incidence of appetite suppression in a population of pediatric subjects from 6 to 12 years of age in the fasted state being treated with the composition is 11% or less, 10% or less, 8% or less, 6% or less, 4% or less, or 2% or less.

As used herein, the term "severe insomnia" refers to insomnia of an intensity that was incapacitating such that the subject was unable to work or complete usual activity. The intensity of insomnia was based on investigator observation of the pediatric subject.

As used herein, the term "moderate insomnia" refers to insomnia of an intensity that it interfered with daily activity, but where the subject was still able to function. The intensity of insomnia was based on investigator observation of the pediatric subject.

In some embodiments, the incidence of severe insomnia in a population of pediatric subjects from 6 to 12 years of age in the fasted state being treated with the composition is 1% or less.

In some embodiments, the incidence of moderate insomnia in a population of pediatric subjects from 6 to 12 years of age in the fasted state being treated with the composition is 6% or less.

As used herein, the term "initial insomnia" refers to difficulty in falling asleep at the beginning of the night. Initial insomnia was based on investigator observation of the pediatric subject.

In some embodiments, the incidence of initial insomnia in a population of pediatric subjects from 6 to 12 years of age in the fasted state being treated with the composition is 2% or less.

In some embodiments, the incidence of appetite suppression in a population of pediatric subjects from 12 to 17 years of age in the fasted state being treated with the composition is 9% or less, and in certain embodiments, 8% or less, 6% or less, 4% or less, 2% or less, or 1% or less.

In some embodiments, the incidence of insomnia in a population of pediatric subjects from 12 to 17 years of age in the fasted state being treated with the composition is 11% or less, and in certain embodiments, 10% or less, 8% or less, 6% or less, 4% or less, 2% or less, or 1% or less.

In some embodiments, the incidence of initial insomnia in a population of pediatric subjects from 12 to 17 years of age in the fasted state being treated with the composition is 7% or less, and in certain embodiments, 6% or less, 4% or less, 2% or less, or 1% or less.

In some embodiments, the present disclosure provides a method of treating Attention Deficit Hyperactivity Disorder (ADHD) in a pediatric subject from 6 to 11 years of age in need thereof, the method comprising administering to the pediatric subject, an oral pharmaceutical composition comprising from about 25 to about 100 mg methylphenidate hydrochloride, wherein the oral solid pharmaceutical composition, when administered to a pediatric subject from 6 to 11 years of age in a fasted state, provides an average methylphenidate $AUC_{0-4}$ (pg·hr/mL) that is from 80 to 125% of the value resulting from the formula: average $AUC_{0-4}$=804.42*(dose of methylphenidate hydrochloride in mg)−8994.4.

In some embodiments, the present disclosure provides a method of treating Attention Deficit Hyperactivity Disorder (ADHD) in a pediatric subject from 6 to 11 years of age in need thereof, the method comprising administering to the pediatric subject, an oral pharmaceutical composition comprising from about 25 to about 100 mg methylphenidate hydrochloride, wherein the oral solid pharmaceutical composition, when administered to a pediatric subject from 6 to 11 years of age in a fasted state, provides an average methylphenidate $AUC_{8-14}$ (pg·hr/mL) that is from 80 to 125% of the value resulting from the formula: average $AUC_{8-14}$−1580.3*(dose of methylphenidate hydrochloride in mg)−1860.

In some embodiments, the present disclosure provides a method of treating Attention Deficit Hyperactivity Disorder (ADHD) in a pediatric subject from 6 to 11 years of age in need thereof, the method comprising administering to the pediatric subject, an oral pharmaceutical composition comprising from about 25 to about 100 mg methylphenidate hydrochloride, wherein the oral solid pharmaceutical composition, when administered to a pediatric subject from 6 to 11 years of age in a fasted state, provides an average methylphenidate $AUC_{14\text{-}24}$ (pg·hr/mL) that is from 80 to 125% of the value resulting from the formula: average $AUC_{14\text{-}24}=1392.2*$(dose of methylphenidate hydrochloride in mg)−9239.1.

In addition to the various embodiments described above, the present disclosure includes the following specific embodiments number E1 through E70. This list of embodiments is presented as an exemplary list and the application is not limited to these embodiments.

E1. A method of treating Attention Deficit Hyperactivity Disorder (ADHD) in a pediatric subject in need thereof, the method comprising administering to the pediatric subject an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the oral solid pharmaceutical composition provides the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

E2. The method of E1, wherein the pediatric subject is from 6 to 12 years of age.

E3. The method of E1, wherein the pediatric subject is from 12 to 17 years of age.

E4. The method of E1, wherein the oral solid pharmaceutical composition is in the form of a capsule comprising the plurality of coated beads.

E5. The method of E1, wherein the inner controlled release coating is selected from the group consisting of an ethylcellulose polymer, a cellulose ether, polyethylene oxide, a polyvinyl alcohol derivate, a methacrylic acid copolymer, polyethylene glycol, polyglycolic acid, polylactic acid, polycaprolactone, poly(n-hydroxybutyrate), a polyamino acids, a poly(amide-enamine), a polyesters, ethylene-vinyl acetate (EVA), polyvinyl pyrrolidone (PVP), poly (acrylic acid) (PAA), poly (methacrylic acid) (PMAA), and mixtures of any two or more thereof.

E6. The method of E1, wherein the inner controlled release coating comprises ammonio Methacrylate Copolymer, Type B USP/NF.

E7. The method of E1, wherein the inner controlled release coating is present in an amount of 3% to 16% by weight of each coated bead.

E8. The method of E7, wherein the inner controlled release coating is present in an amount of 10.0% to 10.7% by weight of each coated bead.

E9. The method of E1, wherein the outer delayed release coating comprises poly(methyl acrylate-co-methyl methacrylate-co-methacrylic acid) 7:3:1.

E10. The method of E1, wherein the outer delayed release coating is present in an amount of from 3% to 20% by weight of each coated bead.

E11. The method of E8, wherein the outer delayed release coating is present in an amount of from 15.0% to 16.0% by weight of each coated bead.

E12. The method of E1, wherein the first amount of methylphenidate or pharmaceutically acceptable salt thereof and the second amount of methylphenidate or pharmaceutically acceptable salt thereof, together, provide a total amount of methylphenidate or pharmaceutically acceptable salt thereof in each coated bead, and wherein the first amount of methylphenidate or pharmaceutically acceptable salt thereof comprises from 70% to 99% by weight of the total amount of the methylphenidate or pharmaceutically acceptable salt thereof in each coated bead.

E13. The method of E12, wherein the first amount of methylphenidate or pharmaceutically acceptable salt thereof comprises from 78% to 82% by weight of the total amount of methylphenidate or pharmaceutically acceptable salt thereof.

E14. The method of E13, wherein the first amount of methylphenidate or pharmaceutically acceptable salt thereof comprises 80% by weight of the total amount of the methylphenidate or pharmaceutically acceptable salt thereof and the second amount of methylphenidate or pharmaceutically acceptable salt thereof comprises 20% by weight of the total amount of the methylphenidate or pharmaceutically acceptable salt thereof.

E15. The method of E1, wherein the inner controlled release coating is present in an amount of 3% to 16% by weight of each coated bead, and the outer delayed release coating is present in an amount of from 3% to 20% by weight of each coated bead.

E16. The method of E1, wherein the inner controlled release coating is present in an amount of 10.0% to 10.7% by weight of each coated bead, and the outer delayed release coating is present in an amount of from 15.0% to 16.0% by weight of each coated bead.

E17. The method of E1, wherein the granule is selected from the group consisting of: a sugar sphere, a microcrystalline cellulose granule, a silica granule, a starch granule, a lactose granule, a calcium carbonate granule, and a mannitol-polyvinylpyrrolidone granule.

E18. The method of E1, wherein the oral solid pharmaceutical composition comprises 25 mg, 30 mg, 35 mg, 45 mg, 55 mg, 70 mg, 85 mg, or 100 mg of methylphenidate hydrochloride.

E19. The method of E1, wherein the oral solid pharmaceutical composition comprises 85 mg of methylphenidate hydrochloride.

E20. The method of E1, wherein each coated bead comprises:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject.

E21. The method of E1, wherein each coated bead comprises:

(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject.

E22. A method of treating Attention Deficit Hyperactivity Disorder (ADHD) in a pediatric subject from 6 to 11 years of age in need thereof, the method comprising administering to a pediatric subject from 6 to 11 years of age an oral solid pharmaceutical composition comprising a plurality of coated beads, wherein each coated bead comprises elements (a), (b), (c), and (d) or elements (a'), (b'), and (c'), as follows:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or (a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the oral solid pharmaceutical composition, when administered to pediatric subjects from 6 to 11 years of age in a fasted state, provides a methylphenidate $AUC_{0-4}$, a methylphenidate $AUC_{8-14}$, and a methylphenidate $AUC_{14-24}$ for 35, 55, and 85 mg methylphenidate hydrochloride dosages in the ranges as specified below:

| Oral Methylphenidate HCl dosage (mg) | Methylphenidate $AUC_{0-4}$ | Methylphenidate $AUC_{8-14}$ | Methylphenidate $AUC_{14-24}$ |
|---|---|---|---|
| 35 | from 18010 pg · hr/mL to 26470 pg · hr/mL | from 40610 pg · hr/mL to 80390 pg · hr/mL | from 23070 pg · hr/mL to 81850 pg · hr/mL |
| 55 | from 23270 pg · hr/mL to 43880 pg · hr/mL | from 64370 pg · hr/mL to 109080 pg · hr/mL | from 23230 pg · hr/mL to 80910 pg · hr/mL |
| 85 | from 54790 pg · hr/mL to 65660 pg · hr/mL | from 100550 pg · hr/mL to 200860 pg · hr/mL | from 76600 pg · hr/mL to 161310 pg · hr/mL |

E23. The method of E22, wherein the oral solid pharmaceutical composition, when administered to pediatric subjects from 6 to 11 years of age in a fasted state, provides an average methylphenidate $AUC_{0-4}$, an average methylphenidate $AUC_{8-14}$, and an average methylphenidate $AUC_{14-24}$ for the 35, 55, and 85 mg dosages as specified below:

| Oral Methylphenidate HCl dosage (mg) | Average methylphenidate $AUC_{0-4}$ (±1 standard deviation) | Average methylphenidate $AUC_{8-14}$ (±1 standard deviation) | Average methylphenidate $AUC_{14-24}$ (±1 standard deviation) |
|---|---|---|---|
| 35 | 20715 ± 3029.2 pg · hr/mL | 55762 ± 13851.3 pg · hr/mL | 42158 ± 21622.5 pg · hr/mL |
| 55 | 32658 ± 7738.5 pg · hr/mL | 81205 ± 15048.9 pg · hr/mL | 62880 ± 20288.9 pg · hr/mL |
| 85 | 60418 ± 4000.2 pg · hr/mL | 134007 ± 35930.2 pg · hr/mL | 110877 ± 27695.7 pg · hr/mL |

E24. The method of E22, wherein the oral solid pharmaceutical composition, when administered to pediatric subjects from 6 to 11 years of age in a fasted state, provides a methylphenidate $AUC_{0-8}$, a methylphenidate $AUC_{4-8}$, a methylphenidate $AUC_{0-14}$, and a methylphenidate $AUC_{0-24}$ for the 35, 55, and 85 mg dosages in the ranges specified below:

| Oral Methylphenidate HCl dosage (mg) | Methylphenidate $AUC_{0-8}$ | Methylphenidate $AUC_{4-8}$ | Methylphenidate $AUC_{0-14}$ | Methylphenidate $AUC_{0-24}$ |
|---|---|---|---|---|
| 35 | from 39930 pg · hr/mL to 61910 pg · hr/mL | from 19630 pg · hr/mL to 42750 pg · hr/mL | from 89630 pg · hr/mL to 142290 pg · hr/mL | from 121460 pg · hr/mL to 224140 pg · hr/mL |
| 55 | from 57120 pg · hr/mL to 93020 pg · hr/mL | from 32420 pg · hr/mL to 63330 pg · hr/mL | from 121490 pg · hr/mL to 202100 pg · hr/mL | from 144720 pg · hr/mL to 268190 pg · hr/mL |
| 85 | from 113650 pg · hr/mL to 169020 pg · hr/mL | from 51060 pg · hr/mL to 110650 pg · hr/mL | from 231620 pg · hr/mL to 369880 pg · hr/mL | from 325490 pg · hr/mL to 473730 pg · hr/mL |

E25. The method of E22, wherein the oral solid pharmaceutical composition, when administered to pediatric subjects from 6 to 11 years of age in a fasted state, provides the average methylphenidate $AUC_{0-8}$, average methylphenidate $AUC_{4-8}$, average methylphenidate $AUC_{0-14}$, and average methylphenidate $AUC_{0-24}$ for the 35, 55, and 85 mg dosages as specified in the table below:

| Oral Methylphenidate HCl dosage (mg) | Average methylphenidate $AUC_{0-8}$ (±1 standard deviation) | Average methylphenidate $AUC_{4-8}$ (±1 standard deviation) | Average methylphenidate $AUC_{0-14}$ (±1 standard deviation) | Average methylphenidate $AUC_{0-24}$ (±1 standard deviation) |
|---|---|---|---|---|
| 35 | 52847 ± 7879.5 pg · hr/mL | 32133 ± 7622.8 pg · hr/mL | 108608 ± 18507.4 pg · hr/mL | 150767 ± 39560.3 pg · hr/mL |
| 55 | 73713 ± 14089.2 pg · hr/mL | 41055 ± 11391.2 pg · hr/mL | 154917 ± 27727.7 pg · hr/mL | 217797 ± 42426.4 pg · hr/mL |
| 85 | 136887 ± 21233.3 pg · hr/mL | 76470 ± 22156.2 pg · hr/mL | 270898 ± 53162.7 pg · hr/mL | 381775 ± 52593.0 pg · hr/mL |

E26. The method of E22, wherein the oral solid pharmaceutical composition, when administered to pediatric subjects from 6 to 11 years of age in a fasted state, provides a methylphenidate $Cmax_{0-4}$, a methylphenidate $Cmax_{4-8}$, and a methylphenidate $Cmax_{8-14}$ for the for the 35, 55, and 85 mg dosages in the ranges as specified below:

| Oral Methylphenidate HCl dosage (mg) | Methylphenidate $Cmax_{0-4}$ | Methylphenidate $Cmax_{4-8}$ | Methylphenidate $Cmax_{8-14}$ |
|---|---|---|---|
| 35 | from 6020 pg/mL to 8570 pg/mL | from 6820 pg/mL to 14000 pg/mL | from 9160 pg/mL to 15350 pg/mL |
| 55 | from 7930 pg/mL to 14950 pg/mL | from 10750 pg/mL to 20790 pg/mL | from 13820 pg/mL to 22540 pg/mL |
| 85 | from 19550 pg/mL to 23290 pg/mL | from 14810 pg/mL to 37120 pg/mL | from 18820 pg/mL to 39420 pg/mL |

E27. The method of E22, wherein the oral solid pharmaceutical composition, when administered to pediatric subjects from 6 to 11 years of age in a fasted state, provides an average methylphenidate $Cmax_{0-4}$, an average methylphenidate $Cmax_{4-8}$, and an average methylphenidate $Cmax_{8-14}$ for the 35, 55, and 85 mg dosages as specified below:

| Oral Methylphenidate HCl dosage (mg) | Average methylphenidate $Cmax_{0-4}$ (±1 standard deviation) | Average methylphenidate $Cmax_{4-8}$ (±1 standard deviation) | Average methylphenidate $Cmax_{8-14}$ (±1 standard deviation) |
|---|---|---|---|
| 35 | 7055 ± 939.3 pg/mL | 10038 ± 2428.5 pg/mL | 11127 ± 2283.1 pg/mL |
| 55 | 11198 ± 2633.2 pg/mL | 13035 ± 3850.3 pg/mL | 15933 ± 3347.6 pg/mL |
| 85 | 21235 ± 1539.9 pg/mL | 23782 ± 7908.8 pg/mL | 27045 ± 6730.4 pg/mL |

E28. The method of E22, wherein the oral solid pharmaceutical composition, when administered to pediatric subjects from 6 to 11 years of age in a fasted state, provides a methylphenidate $Tmax_{0-4}$, a methylphenidate $Tmax_{4-8}$, and a methylphenidate $Tmax_{8-14}$ for the 35, 55, and 85 mg dosages in the ranges as specified below:

| Oral Methylphenidate HCl dosage (mg) | Methylphenidate $Tmax_{0-4}$ | Methylphenidate $Tmax_{8-14}$ |
|---|---|---|
| 35 | from 1.0 hours to 4.0 hours | from 8.0 hours to 11.0 hours |
| 55 | from 1.0 hours to 2.0 hours | from 9.0 hours to 14.0 hours |
| 85 | from 1.0 hours to 2.0 hours | from 8.0 hours to 14.0 hours |

E29. The method of E22, wherein the oral solid pharmaceutical composition provides, when administered to pediatric subjects from 6 to 11 years of age in a fasted state, an average methylphenidate $Tmax_{0-4}$, an average methylphenidate $Tmax_{4-8}$, and an average methylphenidate $Tmax_{8-14}$ for the 35, 55, and 85 mg dosages as specified below:

| Oral dosage Methylphenidate HCl (mg) | Average methylphenidate $Tmax_{0-4}$ (±1 standard deviation) | Average methylphenidate $Tmax_{8-14}$ (±1 standard deviation) |
|---|---|---|
| 35 | 1.833 ± 1.1690 hours | 9.167 ± 1.1690 hours |
| 55 | 1.667 ± 0.5164 hours | 11.167 ± 2.0412 hours |
| 85 | 1.667 ± 0.5164 hours | 11.0 ± 2.1909 hours |

E30. The method of E22, wherein the oral solid pharmaceutical composition is in the form of a capsule comprising the plurality of coated beads.

E31. The method of E22, wherein the inner controlled release coating is selected from the group consisting of an ethylcellulose polymer, a cellulose ether, polyethylene oxide, a polyvinyl alcohol derivate, a methacrylic acid copolymer, polyethylene glycol, polyglycolic acid, polylactic acid, polycaprolactone, poly(n-hydroxybutyrate), a polyamino acids a poly(amide-enamine), a polyesters, ethylene-vinyl acetate (EVA), polyvinyl pyrrolidone (PVP), poly (acrylic acid) (PAA), poly (methacrylic acid) (PMAA), and combinations thereof.

E32. The method of E22, wherein the inner controlled release coating is present in an amount of 3% to 16% by weight of each coated bead.

E33. The method of E32, wherein the inner controlled release coating is present in an amount of 10.0% to 10.7% by weight of each coated bead.

E34. The method of E22, wherein the outer delayed release coating comprises poly(methyl acrylate-co-methyl methacrylate-co-methacrylic acid) 7:3:1.

E35. The method of E22, wherein the outer delayed release coating is present in an amount of from 3% to 20% by weight of each coated bead.

E36. The method of E35, wherein the outer delayed release coating is present in an amount of from 15.0% to 16.0% by weight of each coated bead.

E37. The method of E22, wherein the first amount of methylphenidate or pharmaceutically acceptable salt thereof and the second amount of methylphenidate or pharmaceutically acceptable salt thereof, together, provide a total amount of methylphenidate or pharmaceutically acceptable salt thereof in each coated bead, and wherein the first amount of methylphenidate or pharmaceutically acceptable salt thereof comprises from 70% to 99% by weight of the total amount of the methylphenidate or pharmaceutically acceptable salt thereof in each coated bead.

E38. The method of E22, wherein the first amount of methylphenidate or pharmaceutically acceptable salt thereof comprises from 78% to 82% by weight of the total amount of methylphenidate or pharmaceutically acceptable salt thereof.

E39. The method of E38, wherein the first amount of methylphenidate or pharmaceutically acceptable salt thereof comprises 80% by weight of the total amount of the methylphenidate or pharmaceutically acceptable salt thereof and the second amount of methylphenidate or pharmaceutically acceptable salt thereof comprises 20% by weight of the total amount of the methylphenidate or pharmaceutically acceptable salt thereof.

E40. The method of E22, wherein the inner controlled release coating is present in an amount of 3% to 16% by weight of each coated bead, and the outer delayed release coating is present in an amount of from 3% to 20% by weight of each coated bead.

E41. The method of E22, wherein the inner controlled release coating is present in an amount of 10.0% to 10.7% by weight of each coated bead, and the outer delayed release coating is present in an amount of from 15.0% to 16.0% by weight of each coated bead.

E42. The method of E22, wherein the granule is selected from the group consisting of: a sugar sphere, a microcrystalline cellulose granule, a silica granule, a starch granule, a lactose granule, a calcium carbonate granule, and a mannitol-polyvinylpyrrolidone granule.

E43. The method of E22, wherein the oral solid pharmaceutical composition provides the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

E44. The method of E22, wherein each coated bead comprises:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject.

E45. The method of E22, wherein each coated bead comprises:
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject.

E46. A method of treating Attention Deficit Hyperactivity Disorder (ADHD) in a pediatric subject from 6 to 12 years of age in need thereof, the method comprising administering to a pediatric subject from 6 to 12 years of age an oral solid pharmaceutical composition comprising a plurality of coated beads, wherein each coated bead comprises elements (a), (b), (c), and (d) or elements (a'), (b'), and (c'), as follows:
- (a) a granule;
- (b) a first layer coated over the granule, the first layer comprising a first amount of methylphenidate or a pharmaceutically acceptable salt thereof;
- (c) an inner controlled release coating coated over the first layer and an outer delayed release coating coated over the inner controlled release coating; and
- (d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the incidence of appetite suppression in a population of pediatric subjects from 6 to 12 years of age in the fasted state being treated with the composition is 36% or less.

E47. The method of E46, wherein the incidence of severe appetite suppression in a population of pediatric subjects from 6 to 12 years of age in the fasted state being treated with the composition is 1% or less.

E48. The method of E46, wherein the incidence of moderate appetite suppression in a population of pediatric subjects from 6 to 12 years of age in the fasted state being treated with the composition is 6% or less.

E49. A method of treating Attention Deficit Hyperactivity Disorder (ADHD) in a pediatric subject from 6 to 12 years of age in need thereof, the method comprising administering to the subject an oral solid pharmaceutical composition comprising a plurality of coated beads, wherein each coated bead comprises elements (a), (b), (c), and (d) or elements (a'), (b'), and (c'), as follows:
- (a) a granule;
- (b) a first layer coated over the granule, the first layer comprising a first amount of methylphenidate or a pharmaceutically acceptable salt thereof;
- (c) an inner controlled release coating coated over the first layer and an outer delayed release coating coated over the inner controlled release coating; and
- (d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;

wherein the incidence of insomnia in a population of pediatric subjects from 6 to 12 years of age in the fasted state being treated with the composition is 11% or less.

E50. The method of E49, wherein the incidence of severe insomnia in a population of pediatric subjects from 6 to 12 years of age in the fasted state being treated with the composition is 1% or less.

E51. The method of E49, wherein the incidence of moderate insomnia in a population of pediatric subjects from 6 to 12 years of age in the fasted state being treated with the composition is 6% or less.

E52. A method of treating Attention Deficit Hyperactivity Disorder (ADHD) in a pediatric subject from 6 to 12 years of age in need thereof, the method comprising administering to the subject an oral solid pharmaceutical composition comprising a plurality of coated beads, wherein each coated bead comprises (a), (b), (c), and (d) or (a'), (b'), and (c'), as follows:
- (a) a granule;
- (b) a first layer coated over the granule, the first layer comprising a first amount of methylphenidate or a pharmaceutically acceptable salt thereof;
- (c) an inner controlled release coating coated over the first layer and an outer delayed release coating coated over the inner controlled release coating; and
- (d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
- (a') a core comprising a first amount of methylphenidate or a pharmaceutically acceptable salt thereof;
- (b') an inner controlled release coating coated over the core and an outer delayed release coating coated over the inner controlled release coating; and
- (c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; wherein the incidence of initial insomnia in a population of pediatric subjects from 6 to 12 years of age in the fasted state being treated with the composition is 2% or less.

E53. A method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject; wherein the oral solid pharmaceutical composition, when administered to a pediatric subject from 12 to 17 years of age in a fasted state, provides:
a methylphenidate $AUC_{0-8}$ ranging from 21830.6 pg·hr/mL to 96316.2 pg·hr/mL;
a methylphenidate $AUC_{0-14}$ ranging from 40576.9 pg·hr/mL to 234533.4 pg·hr/mL; and
a methylphenidate $AUC_{0-24}$ ranging from 86897.7 pg·hr/mL to 415037.5 pg·hr/mL when the administered oral solid pharmaceutical composition comprises from 25 mg to 85 mg of methylphenidate hydrochloride.

E54. The method of E53, wherein the oral solid pharmaceutical composition provides:
an average methylphenidate $AUC_{0-8}$ of 47071.6 pg·hr/mL;
an average methylphenidate $AUC_{0-14}$ of 111783.0 pg·hr/mL;
and an average methylphenidate $AUC_{0-24}$ of 181751.2 pg·hr/mL when the administered oral solid pharmaceutical composition comprises from 25 mg to 85 mg of methylphenidate hydrochloride.

E55. The method of E53, wherein the oral solid pharmaceutical composition provides a methylphenidate $AUC_{0-12}$ ranging from 36823.7 pg·hr/mL to 186389.9 pg·hr/mL, when the oral solid pharmaceutical composition comprises from 25 mg to 85 mg of methylphenidate hydrochloride.

E56. The method of E53, wherein the oral solid pharmaceutical composition provides an average methylphenidate $AUC_{0-12}$ of 89378.1 pg·hr/mL, when the oral solid pharmaceutical composition comprises from 25 mg to 85 mg of methylphenidate hydrochloride.

E57. The method of E53, wherein the oral solid pharmaceutical composition provides the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

E58. A method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of appetite suppression in a population of pediatric subjects from 12 to 17 years of age in the fasted state being treated with the composition is 21% or less.

E59. A method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein the coated beads comprise elements
(a), (b), (c), and (d) or elements (a'), (b'), and (c'), as follows:

(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of insomnia in a population of pediatric subjects from 12 to 17 years of age in the fasted state being treated with the composition is 7% or less.

E60. A method of treating Attention Deficit Hyperactivity Disorder (ADHD) in a pediatric subject from 12 to 17 years of age in need thereof, the method comprising administering to a pediatric subject from 12 to 17 years of age an oral solid pharmaceutical composition comprising a plurality of coated beads, wherein the coated beads comprise elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the incidence of initial insomnia in a population of pediatric subjects from 12 to 17 years of age in the fasted state being treated with the composition is 6% or less.

E61. A method of treating Attention Deficit Hyperactivity Disorder (ADHD) in a pediatric subject from 6 to 11 years of age in need thereof, the method comprising administering to the pediatric subject from 6 to 11 years of age, an oral pharmaceutical composition comprising from 25 to 100 mg methylphenidate hydrochloride, wherein the oral solid pharmaceutical composition, when administered to a pediatric subject from 6 to 11 years of age in a fasted state, provides an average methylphenidate $AUC_{0-4}$ (pg·hr/mL) that is from 80 to 125% of the value resulting from the formula:

Average $AUC_{0-4}$=804.42*(dose of methylphenidate hydrochloride in mg)−8994.4.

E62. The method of E61, wherein the oral pharmaceutical composition further provides an average methylphenidate $AUC_{8-14}$ (pg·hr/mL) that is from 80 to 125% of the value resulting from the formula:

Average $AUC_{8-14}$=1580.3*(dose of methylphenidate hydrochloride in mg)−1860.

E63. The method of E61, wherein the oral pharmaceutical composition further provides an average methylphenidate $AUC_{14-24}$ (pg·hr/mL) that is from 80 to 125% of the value resulting from the formula:

Average $AUC_{14-24}$=1392.2*(dose of methylphenidate hydrochloride in mg)−9239.1.

E64. The method of E61, wherein the oral pharmaceutical composition further provides an average methylphenidate $AUC_{0-\infty}$ (pg·hr/mL) that is from 80 to 125% of the value resulting from the formula:

Average $AUC_{0-\infty}$=5932*(dose of methylphenidate hydrochloride in mg)−51578.

E65. A method of treating Attention Deficit Hyperactivity Disorder (ADHD) in a pediatric subject in need thereof, the method comprising administering to the pediatric subject once daily in the morning upon awakening an oral solid pharmaceutical composition comprising a plurality of coated beads, wherein each coated bead comprises elements (a), (b), (c), and (d) or elements (a'), (b'), and (c'), as follows:
(a) a granule;
(b) a first layer coated over the granule, the first layer comprising a first amount of methylphenidate or a pharmaceutically acceptable salt thereof;
(c) an inner controlled release coating coated over the first layer and an outer delayed release coating coated over the inner controlled release coating; and
(d) an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject, or
(a') a core comprising a first amount of methylphenidate or a pharmaceutically acceptable salt thereof;
(b') an inner controlled release coating coated over the core and an outer delayed release coating coated over the inner controlled release coating; and
(c') an immediate release layer comprising a second amount of methylphenidate or a pharmaceutically acceptable salt thereof, coated over the outer delayed release coating, the immediate release layer providing immediate release of the second amount of methylphenidate or pharmaceutically acceptable salt thereof after administration to the subject;
wherein the oral solid pharmaceutical composition provides the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle method, 100 rpm, at 37° C.; (i) starting with 900 mL simulated gastric fluid for 2 hours, (ii) followed by 900 mL phosphate buffer pH 6.0 for 4 hours, and (iii) for the 7th hour onwards, 900 mL of phosphate buffer pH 7.4; USP <711> Acceptance Table 2.

E66. The method of E65, wherein the the pharmaceutical composition is efficacious for at least 16 hours.

E67. A method of treating ADHD in a pediatric subject aged at least 6 years old to 17 years of age, the method comprising administering to the pediatric subject in need thereof an oral solid pharmaceutical composition comprising 25 mg of methylphenidate hydrochloride once daily with or without food in the morning and optionally titrating to 35 mg, 45 mg, 55 mg, 70 mg, or 85 mg methylphenidate hydrochloride using an oral solid pharmaceutical composition comprising 35 mg, 45 mg, 55 mg, 70 mg, or 85 mg methylphenidate hydrochloride, in intervals of no less than five days.

Embodiments of the present invention will be illustrated with references to the following examples which should not be used to limit or otherwise construe the invention.

In the examples the following abbreviations are used:
IR beads—these are beads coated with the methylphenidate hydrochloride (MPH) and having no controlled or delayed release coating;
CRIR beads—these are IR beads which have been coated with a controlled release coating;
ECCRIR—these are CRIR beads which have been coated with an enteric coating (similar to commercially available Biphentin® product);
DRIR beads—these are IR beads which have been coated with a delayed or distal release coating;
DRCRIR beads—these are CRIR beads which have been coated with a delayed (enteric coating [ECCRIR]) or distal release coating; and
MPH IR distal beads—these are DRCRIR beads which have been coated with an immediate release layer of MPH.

Various of these beads were coated with sodium alginate which can confer resistance to 40% alcohol.

The general method of manufacture of Formulation I or Formulation J is described below followed by the various studies and findings.

The MPH IR distal beads were manufactured in four different stages involving separate coating process at each stage—immediate-release coating (drug layering [IR]), controlled-release coating [CR], distal release coating [DR] and top immediate release coating [CRDRIR]. All four stages are carried out in a fluid bed dryer with Wurster column. More detailed information of the process parameters used at each stage of the manufacturing process is found in FIGS. 21-24, respectively.

In some cases, a layer of sodium alginate-talc is also applied as a fifth stage on top of the top immediate release coating to improve dose dumping of methylphenidate HCl in hydro-ethanolic solutions compared with coated bead formulations that do not have a layer comprising one or more salts of alginic acid without affecting the immediate release performance of the top immediate release coating. More detailed information of the process parameters used at this stage of the manufacturing process is found in FIG. 25.

The following is a description of the manufacturing process.

Example 1—IR Beads

The following protocol was used to produce the IR beads.
Add Opadry clear YS-1-7006 to water and mix, then add methylphenidate hydrochloride and stir until a clear solution is obtained.
Charge fluid bed dryer (FBD) equipped with Wurster column with sugar spheres 14-18 or 18-20 mesh.
Coat the beads at an inlet temperature of 65°±10° C. and product temperature of 37.5°±3.5° C. by spraying the solution of methylphenidate hydrochloride.
After completion of the spraying process, allow the beads to dry at 41°±4° C. for approximately 3 minutes.
Cool the beads to 30°±1° C. product temperature and weigh.

Example 2—CRIR Beads

The following protocol was used to produce the methylphenidate CR beads.
Prepare a coating dispersion by mixing Plasacryl T20, filtered (250 micrometer screen) Eudragit RS 30 D and Triethyl Citrate in a container for at least 60 minutes.
Charge fluid bed dryer (FBD) equipped with Wurster column with IR beads.
Coat the IR beads at product temperature of 25°±5° C. by spraying the coating dispersion.
After completion of the coating dispersion, spray rinse water at a product temperature of 25°±5° C.

Example 3—DRCRIR Beads, Uncured

Charge fluid bed dryer (FBD) equipped with Wurster column with CRIR beads.
Prepare a coating dispersion by mixing Plasacryl T20, filtered (250 micrometer screen) Eudragit FS 30 D and water in a container for at least 60 minutes.
Coat the CRIR beads with Eudragit FS30D dispersion.
Note: In case the manufacturing process is interrupted, Syloid 244FP, quantity based on 0.43% of the theoretical yield of CRDR beads, is added to the beads and blended.

Example 4—DRCRIR Beads, Cured

The following protocol was used to produce the methylphenidate DRCRIR beads.
Charge fluid bed dryer (FBD) equipped with Wurster column with CRIR beads.
Prepare a coating dispersion by mixing Plasacryl T20, filtered (250 micrometer screen) Eudragit FS 30D and water in a container for at least 60 minutes.
Coat the CRIR beads with Eudragit FS30D dispersion at product temperature of 25°±3° C. by spraying the coating dispersion.
After completion of the coating dispersion, spray rinse water at a product temperature of 25°±3° C.
Suck into the FBD, Syloid 244FP, quantity based on 0.43% of the theoretical yield of DRCRIRbeads and blend.
Cure the beads at a product temperature of 40°±2° C. for 60 minutes.
Cool the beads to product temperature of 25°±3° C.

Screen the beads on 0.85 mm screen and remove fines if any.

Note: In case the manufacturing process is interrupted, Syloid 244FP, quantity based on 0.43% of the theoretical yield of DRCRIRbeads, is added to the beads and blended.

Example 5—MPH IR Distal Beads

The following protocol was used to produce the MPH IR distal beads.

Add Opadry clear YS-1-7006 to water and mix, then add methylphenidate hydrochloride and stir until a clear solution is obtained.

Charge fluid bed dryer (FBD) equipped with Wurster column with DRCRIR beads.

Coat the beads at an inlet temperature of 56°±15° C. and product temperature of 37.5°±3.5° C. by spraying the solution of methylphenidate hydrochloride.

After completion of the solution, spray rinse water at a product temperature of 37.5°±3.5° C.

Allow the beads to dry at product temperature of 41°±4° C. for 5 minutes.

Cool the beads to 30°±1° C. product temperature and weigh.

Screen the beads and collect the beads passing through 1.8 mm screen and retained on 0.85 mm screen.

Example 6—MPH IR Distal Beads Coated with Sodium Alginate Beads

The following protocol was used to produce the MPH IR distal beads coated with sodium alginate beads.

Add talc to water and mix; stir using a homogenizer until a uniform dispersion is obtained.

Add sodium alginate to water and mix, stir until a uniform dispersion is obtained.

Add the talc dispersion on the sodium alginate and mix until a uniform dispersion is obtained.

Charge fluid bed dryer (FBD) equipped with Wurster column with MPH IR distal beads.

Coat the beads at an inlet temperature of 70°±15° C. and product temperature of 50°±5° C. by spraying the solution of sodium alginate.

Allow the beads to dry at product temperature of 41°±4° C. for 5 minutes.

Cool the beads to 30°±1° C. product temperature and weigh.

Screen the beads and collect the beads passing through 1.8 mm screen and retained on 0.85 mm screen.

Example 7—MPH IR Distal Beads (with or without Sodium Alginate) with Silicon Dioxide The following protocol was used to produce these beads.

Charge V blender with approximately half the total quantity of MPH IR Distal Beads (with or without sodium alginate).

Screen Syloid FP 244 through 20 mesh screen and add to the V blender.

Load remaining quantity of MPH IR Distal Beads (with or without sodium alginate) into the V blender.

Blend for 3 minutes.

Discharge the blend into plastic drums lined with polyethylene bags.

Example 8—Encapsulation of MPH IR Distal Beads (with or without Sodium Alginate) with Silicon Dioxide The following equipment is used during the capsule filling process of the MPH IR Distal Beads (with or without sodium alginate) with silicon dioxide in either hard gelatin capsules (used in these Examples) or hard hypromellose (HPMC) capsules (an alternative to hard gelatin capsules):

Bosch GKF 1400 Encapsulator & Checkweigher
Metal Detector
Empty Capsule Conveying Bin

Example 9—Testing (pK Studies and Preliminary Studies on Alcohol Resistance)

The following methodology was used.

The dissolution of various formulations was performed using USP paddle method at 100 rpm in 900 mL at 37° C. of simulated gastric fluid (without enzyme) for 2 hours, 900 mL phosphate buffer pH 6.0 for 4 hours and 7th hour onwards, 900 mL of phosphate buffer pH 7.4. The samples were withdrawn at the respective time points and analysed on HPLC using UV detector. The in vitro release data is indicated as percentage dissolved based on the label content of the active tested.

The results of a bioavailability study of this formulation indicate a biphasic release profile (FIG. 5).

It can be concluded from the in vitro dissolution data and its correspondent in vivo plasma concentration that methylphenidate can be absorbed in the distal part of the GI tract. It can also be concluded that the amount and extent of methylphenidate being absorbed depends on the excipients used in the formulation.

FIG. 1 shows that 7 to 10% of the controlled release polymer might be sufficient to provide a therapeutic effect that lasts for more than 14 hours but without the desired rapid on set of action and distinctive biphasic or triphasic pattern shown in FIG. 3 or 4. However, the next study showed that increasing the amount of the controlled release polymer up to 20% as shown in FIG. 2 prolonged the extent of release of methylphenidate. Nonetheless, the higher the amount of controlled release polymer, the less the total amount of methylphenidate is absorbed. This could be due to the degradation of methylphenidate at higher pH environments, thus less amount of methylphenidate is available at distal part of the GI tract to be absorbed in systemic circulation.

Therefore, the amount of controlled release polymer needs to be adjusted accordingly to achieve the desired distinctive in vivo plasma concentration pattern. In the case of the preferred embodiments of the present invention, the longer duration of action and distinctive pattern might be achieved between 7% to 20% weight gain of the controlled release polymer, more specifically about 16% weight gain of the controlled polymer. The 16% would provide the desired total amount and extent of methylphenidate in plasma concentration over time in a distinctive pattern that differentiates this formulation from any other long acting solid dose methylphenidate formulation available in the market. Moreover, it achieves duration of action of no less than 14 hours.

Formulation I also has the property that does not undergo food effect as shown in FIG. 5 and FIG. 16. It can also be sprinkled on apple sauce, yogurt or ice cream for up to 10 minutes without affecting its bioavailability performance as shown in FIG. 6 and FIG. 18. Compared to three equivalent doses of immediate-release methylphenidate administered separately at 4 hourly intervals, Formulation I has greater residual levels of methylphenidate at hour 24 post-administration and different partial AUCs during the dosing interval, particularly in the 12-16 hour period where the pAUC is significantly larger than immediate-release methylphenidate (FIG. 17). In addition, the second peak of methylphenidate occurs more than 2 hours after the third peak of immediate-release methylphenidate (FIG. 5 and FIG. 17). As a result of the significant residual methylphenidate plasma levels at hour 24 post-administration (FIG. 5), the pharmacokinetic profile changes after multiple days of dosing resulting in an overall increase in plasma levels (FIG. 7 and FIG. 19A) and higher peak concentrations. Formulation J has a similar pharmacokinetic profile and properties as Formulation I (FIG. 8 and FIG. 19B).

The in vitro dissolution specifications of the drug at various time points for formulations in accordance with Formulations A-J are shown in FIG. 15. Based on these results and the correlation between in vivo and in vitro data, the present inventors developed the target dissolution specification shown in FIG. 20 for preferred embodiments of the present coated bead.

Based on the studies excipients were identified and adjusted to obtain a finished product that is stable with a product shelf life of at least 24 months and provides no less than 14 hours of therapeutic effect. Stability testing of the above formulation showed that the total related substances at 6 months 40° C./75% RH are within 2.0% and no individual unknown is higher than 0.2%.

In vitro dissolution testing at 40% ethanol in SFG dissolution media was performed. As will be illustrated in Example 10, Formulation I and Formulation J were found to be resistant up to about 35% v/v and up to about 32% v/v, respectively, ethanol in SGF. Therefore, different trials were performed with immediate release excipients to be applied to the outer immediate release layer methylphenidate hydrochloride to increase the ethanol resistance to 40% ethanol v/v. Some of the excipients that were investigated individually or in combination are: sodium alginate, Kollicoat™ IR, hypromellose, Lycoat™, pectin, lactose, methylcellulose, ethylcellulose and talc. An outer layer of these excipients was applied on top of the desired methylphenidate DRCRIRformulation or Formulation I/Formulation J and a test to determine in vitro alcohol resistance (see Example 10 for details of the test) was performed to determine the impact of the excipients in the formulation.

The experiment with sodium alginate in combination with talc showed that above 40% weight gain of sodium alginate the dissolution rate in 40% v/v ethanol would impart alcohol resistance to Formulation I under the prescribed test conditions. At weight gains between 55 to 75% the dissolution rate in the first two hours of the product would meet the criteria at 40% v/v ethanol and released about 20% of the IR component. Therefore, an improved methylphenidate formulation (Formulation I or Formulation J) was developed. This formulation would have an outermost layer of about 55-75% weight gain of sodium alginate. This layer is applied on top of the external IR layer to provide a 40% v/v ethanol resistant formulation without affecting the original release rate of the formulation.

Example 10—Testing (Further Studies on Alcohol Resistance)

Generally dose dumping is observed as a result of a compromise of the release-rate controlling mechanism in a pharmaceutical product. Some products can be expected to exhibit a more rapid drug dissolution and release rate in the presence of ethanol. Therefore, when a modified-release product is consumed with alcohol, the modified-release mechanism could be adversely affected, which could lead to dose dumping.

The following study was performed to evaluate the alcohol induced dose dumping in IRDR Methylphenidate HCl capsules. The effect of varying concentrations of ethanol on the drug release was evaluated at 0% (no ethanol added), 5%, 20% and 40% ethanol which are considered to be representative of consumption of beer (5% ethanol), mixed drinks (20% ethanol), and neat liquor (40% ethanol). The dissolution evaluation was also carried out in 35% ethanol to understand the effect of ethanol concentrations from 20% to 40% and at what level the alcohol induced dose dumping becomes significant.

The dissolution profiles showed that even though in the presence of 40% ethanol, the rate of dissolution rapidly increased as compared to that observed in control, the release was never considered to be dose dumping of methylphenidate HCl. Furthermore, in the presence of 35% ethanol the rate of release increased but the average percentage release amount was determined to be similar when the f2, similarity factor, was calculated against the control sample. The calculated value was 50. An f2 value of 50-100 suggests similar dissolution profiles.

The experiments were carried out on 12 units as following: The ethanolic dissolution media used were 5%, 20%, 35% and 40% USP anhydrous ethanol in 0.1 N HCl (v/v). The experiments were performed in 900 mL of respective media using USP apparatus 1 (baskets) at 100 rpm and 37° C. The control (0% ethanol) was also run using 900 mL of 0.1 N HCl. The 0.1 N HCl was selected to approximate the conditions in the stomach.

The samples were collected every 15 minutes up to 2 hours to understand the release profile starting as early as 15 minutes. Since the dissolution experiments were run for 2 hours, and the vessels were covered at all times, the media evaporation had no impact on the results. The samples were analyzed on HPLC as per specified IRDR Methylphenidate HCl capsule dissolution method and the percent released methylphenidate HCl at each time point was calculated. The dissolution parameters are reported in FIG. 26.

Resistance to ethanol means that the release of the pharmaceutical active ingredient is in the presence of ethanol not more than 20% to be measured under in-vitro conditions at pH 1.2 for 2 hours in 900 mL medium according to USP with the addition of 5, 10, 20 or 40% (v/v) ethanol at 100 rpm using USP. Dose Dumping is defined as unintended, rapid drug release in a short period of time of a significant amount of the drug contained in a modified release dosage form. Dose dumping shall mean that the release of the pharmaceutical active ingredient is faster but does not release more than 25%, no more than 20% to be measured under in-vitro conditions at pH 1.2 for 60 minutes in medium according to USP with the addition of 5, 10, 20 or 40% (v/v) ethanol.

In this study, the focus was on coating application as a function of theoretical weight gain of coating applied to the nonpareil beads. Since it is also common to quantify film coating amount as mass/surface area, film coating amount (mg/cm$^2$) was determined using a calculation for surface area, assuming the bead is a perfect sphere:

$$SA=4(\pi r^2)$$

wherein SA is the surface area and r is the radius of the bead.

Conventional round nonpareil beads with diameters ranging from 0.85 to 1.4 mm with an average of 1.125 mm were used in this ethanol resistance study. The surface area of beads of this average diameter was calculated as follows:

$$SA = 4(\pi(0.5625^2))$$

$$SA = 3.98 \text{ mm}^2$$

Conventional round nonpareil beads with diameters ranging from 0.85 to 1.4 mm with an average of 1.125 mm were used in this ethanol resistance study.

Since a certain layer thickness is desired in a film coating with Eudragit FS30D to impart alcohol resistant properties up to 30%, up to 32%, up to 35% without the capsules possessing dose dumping characteristics of the active pharmaceutical ingredient within the first 60 minutes; the amount of coating material is related to the surface area of the substrate per cm$^2$ of surface area. Thus, the inventors divided the surface area of a substrate A (mm$^2$) by its weight gain w (mg), to obtain the desired coating quantity in % (w/w), i.e. as shown in the following equation:

$$\text{Coating weight (\%)} = [A(\text{mm}^2)/w(\text{mg})]*1 \text{ (mg/cm}^2\text{)}$$

The total amount of the delayed (or distal) release (e.g., colonic delivery) material may be in the range of from about 5% to about 35% by weight, preferably from about 10% to 30% by weight, most preferably from about 15 to about 25% by weight, in relation to the weight of the core.

The absolute amount of the delayed (or distal) release (e.g., colonic delivery) material described above (prior to the examples) may, in the case of pellets or granules with a diameter size in the range of from about 840 to 1410 µm, be present at an average thickness in the range in from about 5 µm to about 50 µm, preferably from about 10 µm to about 50 µm, more preferably from about 33 µm to about 47 µm, most preferably about 40 µm.

It can be preferred to use poly(methyl acrylate-co-methyl methacrylate-co-methacrylic acid) 7:3:1 as the delayed (or distal) release (e.g., colonic delivery) material. Such a material is commercially available from Evonik under the trade name Eudragit® FS30D.

The presence of ethanol in concentrations of 5, 10, 20 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical active ingredient in the stomach in the first place. Furthermore it may be desired that protection against the influence of ethanol shall at least not influence the comparably fast release rates at pH 6.8 in media without ethanol.

International Patent Publication WO 2012/0224998 describes a gastric resistant pharmaceutical or nutraceutical composition, comprising a core, comprising a pharmaceutical or nutraceutical active ingredient and a gastric resistant coating layer onto the core, wherein the release of the pharmaceutical active ingredient is not more than 15% under in-vitro conditions at pH 1.2 for 2 hours in a buffered medium according to LISP with and without the addition of 40% (v/v) ethanol, wherein the gastric resistant coating layer comprises 10 to 100% by weight of one or more salts of alginic acid with a viscosity of 30 to 720 cP of a 1% aqueous solution. The one layer system as described is stated to solve the problem of protection against the influence of ethanol. However, there is no reference of ethanol protection provided by coating layer containing Eudragit™ FS30D at any ethanol concentration by itself or when the coatings which include the ammonium alginate, coatings which employ other alginate salts, like sodium or potassium alginate, are deposited in the most outer layer of the bead.

The data demonstrated that the in-vitro rate of dissolution of methylphenidate HCl did not increase in the presence of 5% and 20% ethanol within two hours as compared to that in control; and the in-vitro rate of dissolution of methylphenidate HCl did not increase in the presence of 5%, 20%, 35% and 40% ethanol within 30 minutes as compared to that in control. Nevertheless, in the presence of 35% and 40% ethanol, more rapid increase was observed in the dissolution release rate after 30 minutes. Even though a faster release was observed, the release of the active pharmaceutical ingredients was still in a controlled release manner. Dose dumping of methylphenidate hydrochloride did not occur at any time of the release in presence of different concentration of ethanol up to 40%.

The results of this study are believed to be a reasonable basis for the present inventors to predict similar resistance to alcohol (e.g., ethanol) would be observed clinically and for active ingredients other than methylphenidate HCl.

Example 11—A Randomized, Double-Blind Study of the Time Course of Response of MPH-IR Distal Bead (Formulation I) in Adults with ADHD in a Simulated Adult Workplace Environment (AWE)

Objectives

The purpose of this randomized, double-blind, crossover, placebo-controlled, optimized-dose study was to assess the clinical efficacy, time of onset and time course of efficacy over 16 hours of MPH-IR Distal Bead compared to placebo in adults diagnosed with ADHD in an AWE setting.

Methodology

This study (063-008) was a randomized, double-blind, placebo-controlled cross-over study in adult, male and female ADHD subjects conducted to assess clinical efficacy, the time of onset and time course of efficacy of MPH-IR Distal Bead measured by the Permanent Product Measure of Performance (PERMP) (an objective, skill-adjusted math test that measures attention in ADHD) score. Subjects were titrated to an optimal dose in an open-label phase of between 2 and 7 weeks, familiarized with study procedures in a practice AWE session and then randomized to one of two sequences (ACTIVE to PLACEBO or PLACEBO to ACTIVE) and received one treatment for one week, followed by an AWE session, then crossed over to the other treatment for one week, followed by a second AWE session.

Number of Subjects

Planned: 60 subjects. Randomised: 59 subjects. Completed: 46 subjects.

Test Treatment, Dose, and Mode of Administration

Active or matching placebo MPH-IR Distal Bead (methylphenidate hydrochloride controlled-release—Formulation I in FIG. 11-14) 25, 35, 45, 55, 70, 85 or 100 mg oral capsules were administered once-daily in the morning.

Duration of Treatment

Subjects received open label medication during a 2 to 9 week dose titration, followed by a double-blind crossover of one week of placebo treatment and one week of active treatment.

Criteria for Evaluation

The primary outcome measure was the mean between-treatment PERMP Total score across the AWE sessions. Secondary outcome measures included the onset and time course of efficacy of MPH-IR Distal Bead compared to placebo as measured by the PERMP Total Score (PERMP-T), PERMP Attempted Score (PERMP-A) and PERMP Correct Score (PERMP-C) at pre-dose and 1.0, 2.0, 5.0, 8.0, 11.0, 14.0 and 16.0 hours post-dose and the onset and time course of efficacy of MPH-IR Distal Bead compared to placebo as measured by the SKAMP (a subjective measure of behaviour), using the combined score (SKAMP-C), the SKAMP-Deportment (SKAMP-D) subscale and SKAMP Attention (SKAMP-A) subscale at pre-dose and 0.5, 1.0, 2.0, 4.0, 5.0, 7.0, 8.0, 11.0, 13.0, 14.0 and 16.0 hours post-dose.

Efficacy & Safety Results

The study met the primary endpoint in that subjects treated with MPH-IR Distal Bead had improved attention compared to subjects receiving placebo, as measured by the mean change from pre-dose PERMP-Total Scores (FIG. 9).

Subjects receiving MPH-IR Distal Bead showed improvement in attention with an onset of action within 1.0 hour of receiving active medication compared to placebo with duration of effect continuing for up to and including 16.0 hours post-dose, based on change from pre-dose LS mean difference from placebo PERMP-Total Scores (FIG. 9).

Figure 10:
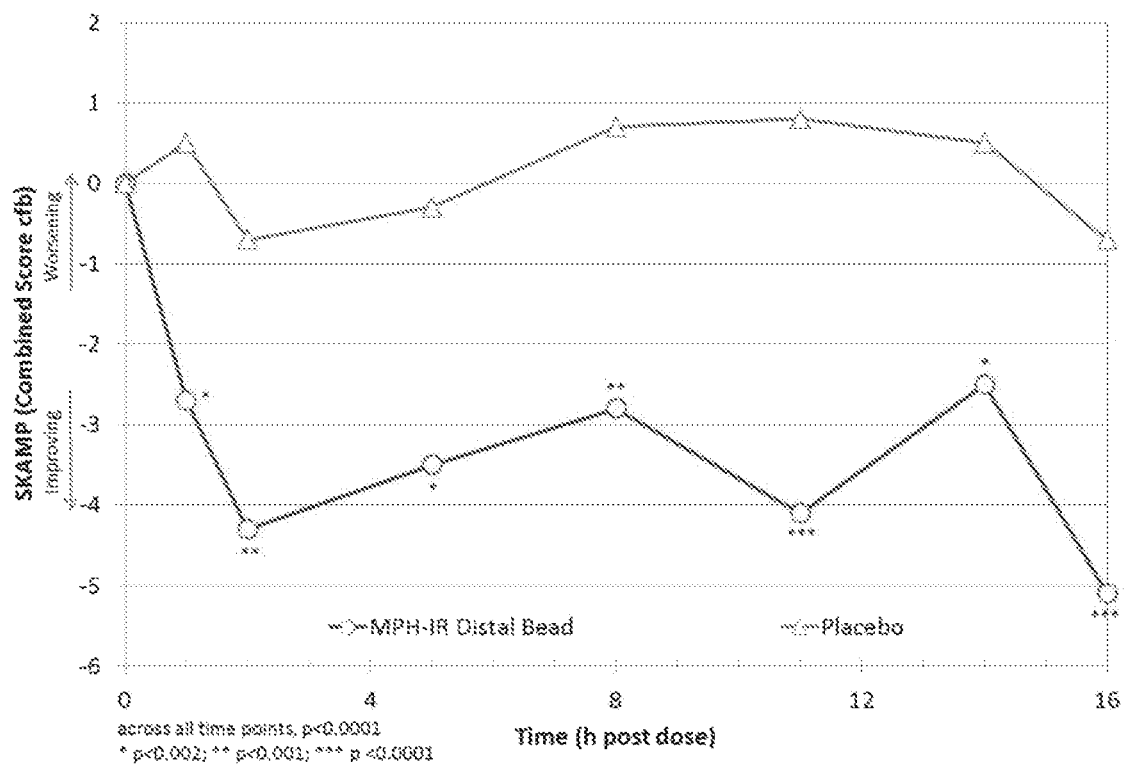
FIG. 10 is a graph showing mean change from pre-dose SKAMP-C Scores over time for adult ADHD subjects receiving MPH IR distal bead and a placebo.

Subjects receiving MPH-IR Distal Bead showed improvement in behaviour with an onset of action within 1.0 hour of receiving active medication compared to placebo with duration of effect continuing for up to and including 16.0 hours post-dose based on change from pre-dose LS mean difference from placebo SKAMP-C Scores (FIG. 10).

MPH-IR Distal Bead was relatively safe and well-tolerated medication.

Overall Conclusions

MPH-IR Distal Bead was safe and effective in the treatment of adults with ADHD, demonstrating efficacy from one hour to 16 hours post administration on both objective and subjective measures. Subjects demonstrated significant improvement in the primary endpoint—an objective measure of attention (the PERMP)—the secondary endpoint—a subjective measure of behaviour (the SKAMP)—during the double-blind phase of the study when treated with MPH-IR Distal Bead compared to when treated with placebo.

In addition, the study medication was well-tolerated, with no serious adverse events. Patients reported satisfaction with ability to fall asleep, appetite for lunch, appetite for dinner or overall adverse effects and no significant differences compared to placebo in sleep quality.

The onset and duration of action at one hour and 16 hours post-administration respectively, is the result of the pharmacokinetic profile of MPH-IR Distal Bead. The residual methylphenidate plasma concentration at hour 24 post-administration leads to an increase in the first peak of methylphenidate following multiple days of dosing, resulting in an onset of action with one hour. In addition, the second peak of methylphenidate is also increased following multiple days of dosing, providing sufficient plasma levels of methylphenidate late in the day that results in a prolonged duration of action extending to 16 hours post-administration. The pharmacokinetic profile of this formulation provides a combination of rapid onset and a prolonged duration of action in a single daily administration.

Example 12—Preferred Formulations

Based on the exemplary work described above, Formulations I and J were identified as the most preferred for the present coated bead. FIGS. 27 and 28 provide complete formulation specifications for oral solid pharmaceutical composition based on Formulations I and J, respectively for the following dosage strengths of methylphenidate HCl: 25 mg, 30, mg, 35 mg, 45 mg, 55 mg, 70 mg, 85 mg and 100 mg.

Example 13—A Randomized, Single-Dose, Open-Label, 2-Period, 2-Way Crossover Comparative Bioavailability Study Comparing Controlled-Release Methylphenidate Capsules with Immediate-Release Methylphenidate Tablets in Pediatric Subjects 12 to 17 Years of Age Diagnosed with ADHD Objectives The purpose of this study was to evaluate the rate and extent of absorption of Formulation I administered orally once a day versus the reference immediate-release Ritalin tablet administered orally three-times a day (TID).

Methodology

This was a single center, randomized, single-dose, open-label, 2-period, 2-way crossover comparative bioavailability study to compare the rate and extent of absorption of a Formulation I capsule administered as a single dose versus methylphenidate immediate-release Ritalin tablet (Reference) administered TID, under fasting conditions.
  A total of 18 to 24 pediatric male or female subjects 12 to 17 years of age diagnosed with ADHD were to be included in this study. Prior to study commencement, subjects were randomly assigned to a treatment in accordance with the randomization scheme generated. Subjects were confined to the clinical study site from at least 1 hour prior to first drug administration until after the 14.0-hour post-dose blood draw, in each period. Subjects were asked to return to the clinical site for a return visit. The treatment phases were separated by a washout period of 7 days.

Number of Subjects

Planned: 18-24 subjects. Randomized: 17 subjects. Completed: 17 subjects.

Test Treatment, Dose, and Mode of Administration

Breakfast was provided 2 hours post-dose in Period 1 and provided 1 hour post-dose in Period 2 to improve the well-being of the subjects. Treatment A consisted of Formulation I capsules (25 mg, 35 mg, 45 mg, 55 mg, 70 mg, or 85 mg) administered orally once a day under fasting conditions. Treatment B consisted of methylphendiate hydrochloride immediate-release Ritalin tablets (5 mg, 10 mg, 5 mg+10 mg, 20 mg, or 5 mg+20 mg) administered orally three times a day under fasting conditions. In Period 1, 8 of the subjects received Treatment A and 9 of the subjects received Treatment B. In Period 2, 9 of the subjects received Treatment A and 8 of the subject received Treatment A.

Criteria for Evaluation

The actual clock time for dosing and the actual clock time for each collection time were recorded using electronic data capture. For all sampling times, the actual sampling times were calculated as the difference between the actual clock time of dosing and the sample collection time, rounded to the closest minute. The difference between the scheduled and the actual sampling time was considered acceptable if it was less than 30 seconds. When the difference exceeded this time limit, the actual sampling times (rounded off to 3 decimal digits) were used to calculate pharmacokinetic parameters, except for pre-dose samples, which were always reported as zero (0.000), regardless of time deviations.

Scheduled sampling times are presented in concentration tables and graphs in the pharmacokinetic section of the report.

Pharmacokinetic analysis were performed using Pharsight® Knowledgebase Server™ and WinNonlin® versions 5.3 and 6.4, which are validated for bioequivalence/bioavailability studies by inVentiv. Inferential statistical analyses as well as tables and listings were created using SAS® (release 9.2 or higher version) and figures were created using R (release 3.0.1 or higher version).

The number of observations (N), mean, standard deviation (SD), coefficient of variation CV (%), range (min. and max.), median and geometric mean were calculated for plasma concentrations of d-methylphenidate and l-methylphenidate for each sampling time and treatment. These descriptive statistics were also presented for $AUC_{0-t}$, $AUC_{0-inf}$, $AUC_{0-4}$, $AUC_{4-8}$, $AUC_{8-12}$, $AUC_{12-t}$, $AUC_{0-8}$, $AUC_{0-12}$, $AUC_{0-14}$, $AUC_{0-24}$, Cmax, $Cmax_{0-4}$, $Cmax_{4-8}$, $Cmax_{8-14}$, Residual area, Tmax, $Tmax_{0-4}$, $Tmax_{4-8}$, $Tmax_{8-14}$, $T_{1/2\,el}$, $K_{el}$, $K_{el\,Lower}$, and $K_{el\,upper}$.

For d-methylphenidate, l-methylphenidate, and combined methylphenidate, analysis of variance was performed on the ln-transformed data of $AUC_{0-t}$, $AUC_{0-inf}$, and Cmax. ANOVA was also carried out on the untransformed $T_{max}$, $K_{el}$, and $T_{1/2el}$. All ANOVAs were performed with the SAS (version 9.2 for Windows) General Linear Models Procedure (GLM). Analyses on $AUC_{0-t}$, $AUC_{0-inf}$ and Cmax were performed on dose-normalized data, as well as non-dose-normalized data.

The model included sequence, subject within sequence, period and treatment as factors. The sequence effect was tested using subjects within sequence effect as the error term. The treatment and period effects were tested against the residual mean square error. All sums of squares (Types I, II, III, and IV) were reported. Probability (p) values were derived from Type III sums of squares. For all analyses, effects were considered statistically significant if the probability associated with 'F' was less than 0.05.

Based on pairwise comparisons of the ln-transformed $AUC_{0-t}$, $AUC_{0-inf}$ and Cmax data, the ratios of the least-squares means (B/A), calculated according to the formula "$e^{(DIFFERENCE)} \times 100$", as well as the 90% geometric confidence intervals were determined. Finally, the inter- and intra-subject CVs were also determined.

Blood samples for pharmacokinetic analysis were collected at pre-dose and 0.500, 1.00, 2.00, 3.00, 4.00, 5.00, 6.00, 8.00, 9.00, 10.0, 11.0, 12.0, 13.0, 14.0, 24.0, 27.0, and 30.0 hours post-dose in each period.

Efficacy & Safety Results

Figure 29:
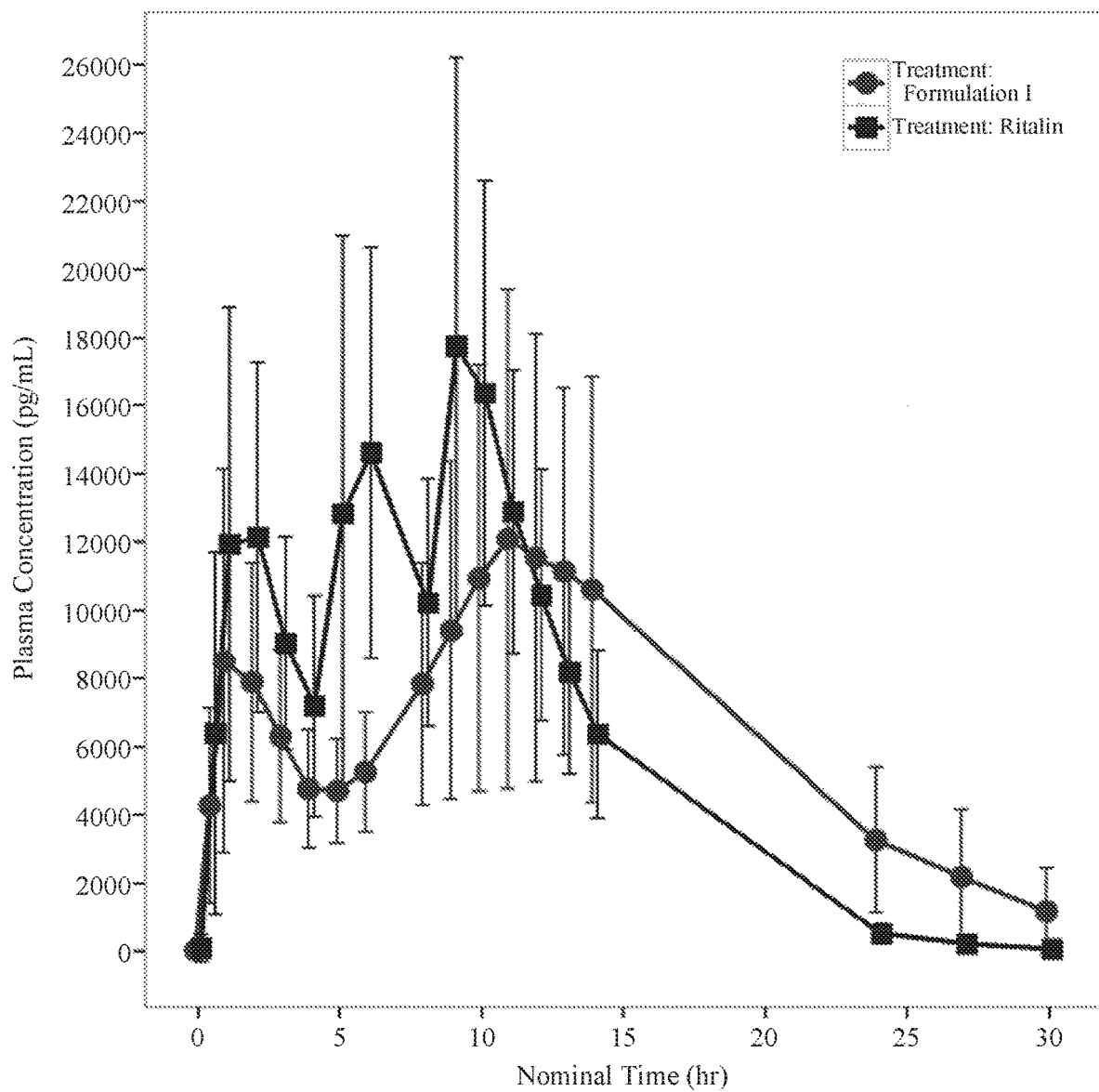
FIG. 29 is a graph showing the mean concentration-time profile for d-methylphenidate of Formulation I (Treatment: Formulation I) and immediate-release methylphenidate (Treatment: Ritalin).

The mean plot for untransformed data for d-methylphenidate plasma concentrations over the sampling period for each treatment method (Treatment A using Formulation I (labeled as Treatment: Formulation I)) and Treatment B (labeled as Treatment: Ritalin) are presented in FIG. 29. And, the mean pharmacokinetic parameter values for d-methylphenidate for each treatment method are summarized in FIG. 30 and FIG. 31.

The p-values for treatment, period, and sequence effects are summarized in FIG. 32 for $AUC_{0-t}$, $AUC_{0-inf}$, and Cmax for d-methylphenidate. For the dose-normalized data, ANOVA detected a statistically significant (p-values<0.050) difference between treatments for all parameters.

The least-squares means ratios (B/A), the 90% geometric confidence intervals, intra- and inter-subject coefficients of variation (CVs) were also determined for non-dose normalized and dose-normalized data. FIG. 33 shows ratios at the 90% geometric confidence interval (C.I.) for $AUC_{0-t}$, $AUC_{0-inf}$, and Cmax for d-methylphenidate. The mean Residual area was lower than 20% for all treatments indicating that the duration of sampling was sufficient for d-methylphenidate. This is equivalent to a mean $AUC_{0-t}$ to $AUC_{0-inf}$ ratio above 80%.

Figure 34:
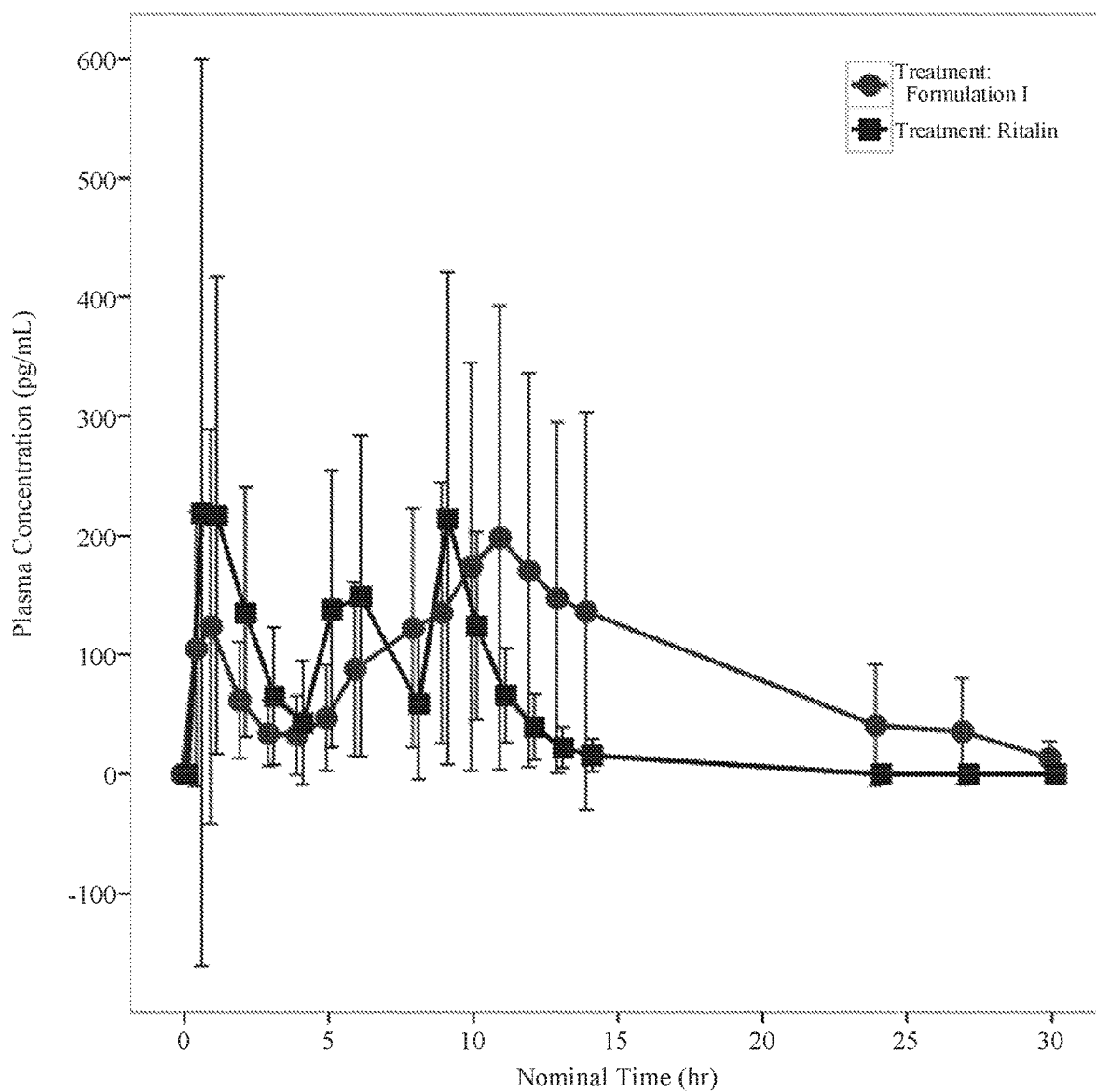
FIG. 34 is a graph showing the mean concentration-time profile for l-methylphenidate of Formulation I (Treatment: Formulation I) and immediate-release methylphenidate (Treatment: Ritalin).

The mean plot for untransformed data for l-methylphenidate plasma concentrations over the sampling period for each treatment method (Treatment A (labeled as Treatment: Formulation I)) and Treatment B (labeled as Treatment: Ritalin) are presented in FIG. 34. And, the mean pharmacokinetic parameter values for l-methylphenidate for each treatment method are summarized in FIG. 35 and FIG. 36.

The p-values for treatment, period, and sequence effects are summarized in FIG. 37 for $AUC_{0-t}$, $AUC_{0-inf}$, and Cmax for l-methylphenidate. For the non-dose-normalized and dose-normalized data, ANOVA detected a statistically significant (p-values<0.050) difference between treatments for $AUC_{0-t}$ and $AUC_{0-inf}$, but not for Cmax.

The least-squares means ratios (B/A), the 90% geometric confidence intervals, intra- and inter-subject CVs were also determined for non-dose normalized and dose-normalized data. FIG. 38 shows ratios at the 90% geometric C.I. for $AUC_{0-t}$, $AUC_{0-inf}$, and Cmax for l-methylphenidate. The mean Residual area was lower than 20% for all treatments indicating that the duration of sampling was sufficient for l-methylphenidate. This is equivalent to a mean $AUC_{0-t}$ to $AUC_{0-inf}$ ratio above 80%.

Figure 39:
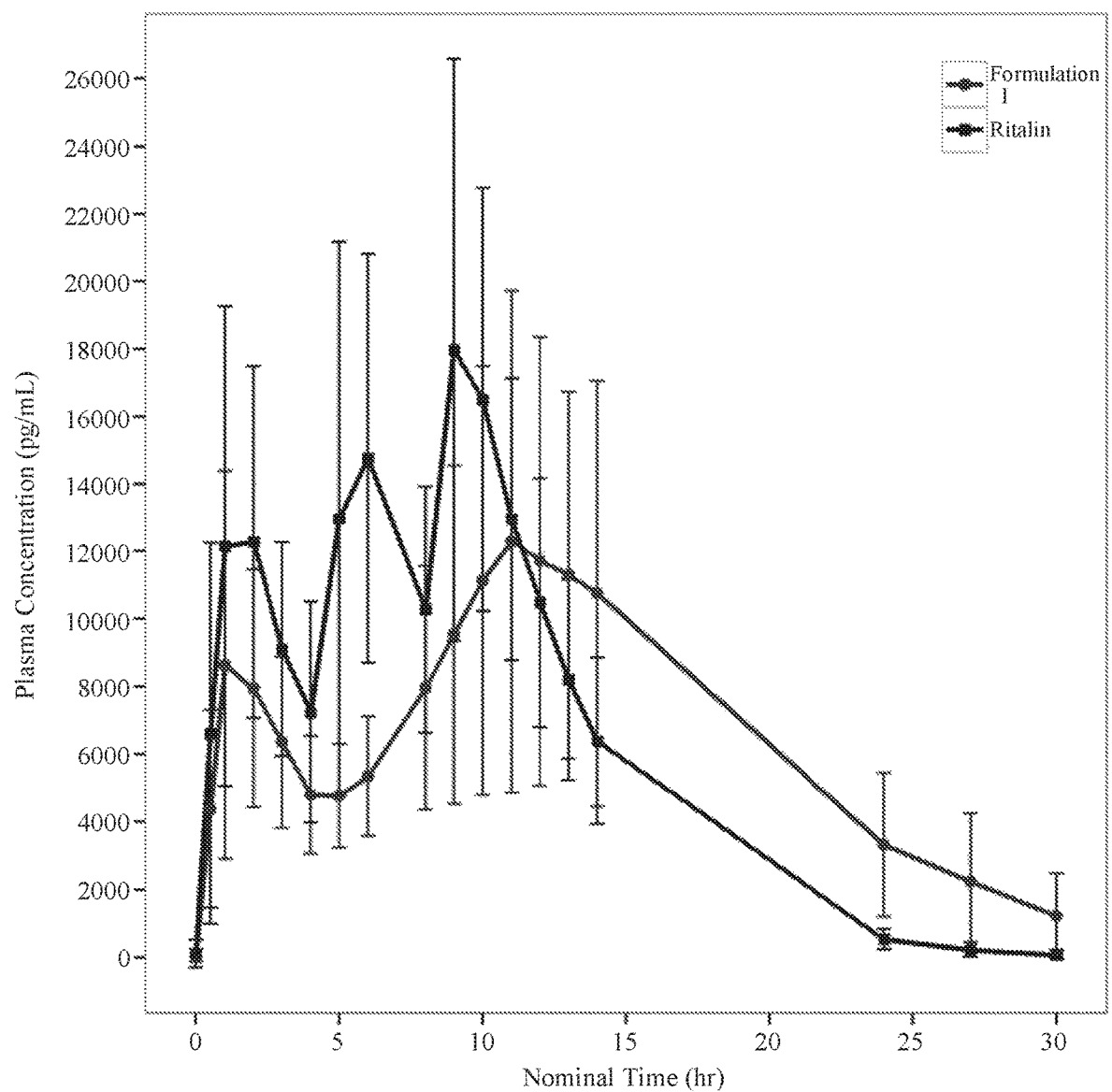
FIG. 39 is a graph showing the mean concentration-time profile for combined methylphenidate of Formulation I and immediate-release methylphenidate (Ritalin).

The mean plot for untransformed data for combined methylphenidate (d-methylphenidate and l-methylphenidate) plasma concentrations over the sampling period for each treatment method (Treatment A (labeled as Formulation I)) and Treatment B (labeled as Ritalin) are presented in FIG. 39. And, the mean pharmacokinetic parameter values for combined methylphenidate for each treatment method are summarized in FIG. 40 and FIG. 41.

The p-values for treatment, period, and sequence effects are summarized in FIG. 42 for $AUC_{0-t}$, $AUC_{0-inf}$ and Cmax for combined methylphenidate. For the dose-normalized data, ANOVA detected a statistically significant (p-values<0.05) difference between treatments for $AUC_{0-t}$, $AUC_{0-inf}$, and Cmax.

The least-squares means ratios (B/A), the 90% geometric confidence intervals, intra- and inter-subject CVs were also determined for non-dose normalized and dose-normalized data. FIG. 43 shows ratios at the 90% geometric C.I. for $AUC_{0-t}$, $AUC_{0-inf}$ and Cmax for l-methylphenidate. The mean Residual area was lower than 20% for all treatments indicating that the duration of sampling was sufficient for l-methylphenidate. This is equivalent to a mean $AUC_{0-t}$ to $AUC_{0-inf}$ ratio above 80%.

Pharmacokinetic & Statistical Conclusions

For both d-methylphenidate and combined methylphenidate, a statistically significant difference between treatments was detected using ANOVA for the ln-transformed Cmax, but not for $AUC_{0-t}$ and $AUC_{0-inf}$. For l-methylphenidate, a statistically significant difference between treatments was detected using ANOVA for the ln-transformed $AUC_{0-t}$ and $AUC_{0-inf}$, but not for Cmax.

The mean Residual area was less than 20% for all treatments indicating that a sampling over a period of 30 hours was sufficient. This is equivalent to a mean $AUC_{0-t}$ to $AUC_{0-inf}$ ratio above 80%. For dose-normalized and non-dose-normalized data, the intra-subject CVs for AUCs and Cmax were around 13% and 17% for d-methylphenidate and around 43% and 47% for l-methylphenidate. For combined methylphenidate, the intra-subject CVs for AUCs and Cmax were respectively around 13% and 17% for both non-dose normalized and dose-normalized data.

Based on the point estimate for d-methylphenidate and combined methylphenidate, the extent of absorption was comparable between the Formulation I capsule administered as a single dose and the immediate-release Ritalin tablet administered three times; however, the rate of absorption was lower for the Formulation I capsule.

For the 1-methylphenidate, the extent of absorption was higher for the Formulation I capsule compared to the immediate-release Ritalin tablet; however, the rate of absorption was slightly lower for the Formulation I tablet.

Adverse Events

Serious AEs (SAES) included any events that were fatal, life-threatening, resulted in persistent or significant disability/incapacity, required in-patient or prolonged hospitalization, resulted in congenital anomalies/birth defects, or considered important medical events that jeopardized the subject and required medical or surgical intervention to prevent 1 of the previously listed outcomes.

A treatment-emergent adverse event (TEAE) is an AE that began on or after the first study drug administration or an AE that began before the first study drug administration and worsened in severity after study drug administration or may have been prolonged due to administration of the study drug.

In the case of a TEAE with an onset time during the washout period or just prior to the next study drug administration, it was attributed to the study drug taken during the previous treatment period.

Summary & Analysis of Adverse Events

Overall, a total of 6 TEAEs were reported by 4 of the 17 subjects who received at least 1 dose of the study medication (safety population). The breakdown by treatment group is as follows: 3 TEAEs reported by 11.8% (n=2) of the 17 subjects who received Treatment A (Formulation I capsule), and 3 TEAEs reported by 11.8% (n=2) of the 17 subjects who received Treatment B (immediate-release Ritalin tablet). None of these TEAEs were serious, severe, and no trend was observed. No TEAEs led to study participation termination.

The fact that most TEAEs resolved spontaneously within approximately 24 hours, and that none of the TEAEs reported were severe, or serious indicate that methylphenidate controlled-release capsule formulations administered as a single dose and immediate-release tablets administered 3 times a day were well tolerated under fasting conditions.

The most commonly reported TEAEs were "Hyperhidrosis" and "Nausea" each reported by 11.8% (n=2) of subjects who constituted the safety population. According to the product monograph these TEAEs are commonly experienced with the administration of methylphenidate.

The total number of TEAEs reported and the total number of subjects reporting TEAEs was similar between both treatment groups. There were no relevant differences between each treatment group when comparing the number of subjects for each Standard of Care (SOC). Both treatment groups were well tolerated, and no safety concerns were expected.

The severity of each AE event was graded according to the following categories: mild, moderate, or severe. Of the 6 TEAEs reported, 5 were graded as mild and 1 as moderate. The moderate TEAE was stomach ache reported by 1 subject overall following Treatment A (Formulation I capsule). There were no notable differences between both treatment groups in regards to the severity of the TEAEs.

Discussion & Overall Conclusions

The objective of this study was to compare the rate and extent of absorption of Formulation I capsules, administered to pediatric subjects from 12 to 17 years of age in a fasted state as a single dose, versus immediate-release tablets administered three times a day (tid).

Seventeen (17) pediatric subjects 12 to 17 years of age with ADHD were randomized and dosed in this study; all of these subjects completed all study periods. In accordance with the protocol, all subjects completing at least 1 period and for whom the PK profile was adequately characterized were used for PK and statistical analyses (N=17). All (17) subjects received at least 1 dose of the study medication and comprised the safety population.

The design of the study was adequate to determine the pharmacokinetic parameters of the Formulation I capsules and the immediate-release tablets. The washout period of 7 days was sufficient to allow the complete elimination of the drug before subsequent administration and to avoid any carry-over effects.

The mean Residual area was less than 20% for all treatments indicating that a sampling over a period of 30 hours was sufficient. This is equivalent to a mean $AUC_{0-t}$ to $AUC_{0-inf}$ ratio above 80%.

For the non-dose-normalized data, the ratios of least-squares means of the Treatment B (immediate-release Ritalin tablet) to Treatment A (Formulation I capsule) when administered under fasting conditions for ln-transformed $AUC_{0-t}$, $AUC_{0-inf}$ and Cmax were 103.45%, 99.25%, and 149.13% respectively for d-methylphenidate, 60.70%, 57.31%, and 118.43% for 1-methylphenidate and 102.72%, 98.51%, and 148.30% for combined methylphenidate. The intra subject CVs for $AUC_{0-t}$, $AUC_{0-inf}$ and Cmax were respectively 13.86%, 13.04%, and 17.19% for d-methylphenidate, 43.45%, 43.06%, and 46.86% for 1-methylphenidate and 13.53%, 12.77% and 16.88% for combined methylphenidate.

A total of 6 TEAEs were reported by 4 of the 17 subjects who received at least 1 dose of the study medication (safety population). The breakdown by treatment group is as follows: 3 TEAEs reported by 11.8% (n=2) of the 17 subjects who received Treatment A (Formulation I capsule), and 3 TEAEs reported by 11.8% (n=2) of the 17 subjects who received Treatment B (immediate-release Ritalin tablet).

The most commonly reported TEAEs were "Hyperhidrosis" and "Nausea" each reported by 11.8% (n=2) of subjects who constituted the safety population. According to the product monograph, these TEAEs are commonly experienced with the administration of methylphenidate.

Of the 6 TEAEs reported, 5 were graded as mild and 1 as moderate.

The relationship of all 6 TEAEs reported was judged as "no reasonable possibility."

No deaths, serious events, or other significant AEs were reported during this study. Upon conclusion of the clinical portion of the study, the results from the subjects who completed study exit procedures, including laboratory tests, vital signs measurements, and ECGs confirmed the absence of significant changes in the subjects' state of health.

Based on the point estimate for d-methylphenidate and combined methylphenidate, the extent of absorption was comparable between the Formulation I capsule administered as a single dose and the immediate-release Ritalin tablet administered three times; however, the rate of absorption was lower for the Formulation I capsule.

For the 1-methylphenidate, the extent of absorption was higher for the Formulation I capsule compared to the immediate-release tablet; however, the rate of absorption was slightly lower for the Formulation I capsule.

All formulations were well tolerated, with no major side effects, and no relevant differences in safety profiles were observed between the preparations, particularly with respect to the number and pattern of AEs.

Example 14—A Randomized, Double-Blind, Parallel Group, Placebo-Controlled, Dose Optimized, Phase 3 Study to Evaluate the Safety and Efficacy of Controlled-Release Methylphenidate for Pediatric Subjects 6 to 12 Years of Age Diagnosed with ADHD Objectives The primary objectives of this study were to 1) assess the efficacy of Formulation I compared to placebo, as measured by the SKAMP-C score during the full day laboratory classroom, and 2) to assess the safety of Formulation I.

Methodology

This was a randomized, double-blind, parallel group, placebo-controlled, dose optimized, phase 3 study to evaluate the safety and efficacy of Formulation I (25, 35, 45, 55, 70, or 85 mg/day) versus placebo for the treatment of ADHD in male and female pediatric subjects (≥6 years of age and ≤12 years of age) who were diagnosed with ADHD.

After giving written informed consent/assent, subjects were screened to ascertain their eligibility for the study according to the inclusion and exclusion criteria. The study had the following periods:
(1) Screening Period: up to 28 days;
(2) 3-day Washout Period: for washout and collection of baseline diary information. Some medications may have required a washout period>3 days or required a dose taper depending on the product labeling recommendations;
(3) Open-label, Dose-optimization Period: up to a 6-week open-label, dose-optimization period during which subjects were titrated from a starting dose of 25 mg up to his/her optimal dose (25, 35, 45, 55, 70, or 85 mg/day);
(4) Double-blind Treatment Period: 1-week double-blind period which included 1 full day of evaluations in a laboratory classroom;
(5) Safety Follow-up Period: 1-week safety follow-up after the last dose of study medication.

Number of Subjects

The study enrolled 156 subjects into the dose-optimization period, and of these, 148 subjects entered the double-blind period and were randomized in a 1:1 ratio to receive active treatment of Formulation I or placebo. Overall, 147 subjects completed to the full day laboratory classroom visit.

The median age of subjects was 9 years, 65.4% were males, and 55.8% were white. At the completion of the dose-optimization period, there was no observable trend between subject age and optimized Formulation I dose level. The highest number of subjects were optimized to the 45 mg dose level (40 subjects) and the 55 mg dose level (38 subjects).

Test Treatment, Dose, and Mode of Administration

Formulation I was supplied as 25, 35, 45, 55, 70 and 85 mg capsules packed in bottles of 10 capsules.

During the open-label period, Formulation I capsules (25, 35, 45, 55, 70 or 85 mg) were administered orally, once daily in the morning to pediatric subjects from 6 to 12 years of age in a fasted state.

Starting from Day 1 (day after the baseline visit), study medication was administered once daily in the morning at home by the parent/guardian. Study medication on the half day practice laboratory classroom was administered by the clinic staff after all pre-dose assessments were completed.

During the double-blind period, Formulation I (25, 35, 45, 55, 70 or 85 mg) or placebo capsules were administered once daily in the morning to pediatric subjects from 6 to 12 years of age in a fasted state.

Starting from the day after randomization, double-blind study medication was administered once daily in the morning at home by the parent/guardian. Study medication on the full day laboratory classroom was administered by the clinic staff after all pre-dose assessments were completed.

If a subject was unable to swallow the capsule (i.e., due to capsule size), the capsule may have been opened and the entire contents sprinkled onto a tablespoon of applesauce, ice cream, or yogurt. The entire mixture was to be consumed immediately. Subjects were to consume the capsule contents in its entirety without chewing. The dose of a single capsule was not to be divided.

Selection and Timing of Dose for each Subject

Study medication was administered once daily, in the morning.

During the dose-optimization period of this study, all subjects received open-label Formulation I. All subjects were initiated at the lowest available dose of Formulation I (25 mg/day) and were adjusted to the next dose level at weekly intervals, until their optimal dose was reached. Optimal dose was defined as the dose that produced a reduction in ADHD-RS-5 score≥30%, a CGI-I score of 1 or 2, and had tolerable side effects. Tolerability was determined by the investigator, based on review of AEs and clinical judgment. Once reached, the optimal dose was maintained for the remainder of the open-label, dose-optimization period, and during the double-blind period.

Subjects who met the definition of optimal dose, but may have benefited from additional dose increases may have had their dose further optimized. However, if a higher dose was not tolerated, subjects could step down 1 dose level.

Subjects who reached their optimal dose but were having tolerability issues may have had 1 downward dose adjustment at the discretion of the investigator.

Once a subject reached his/her optimal dose, they were eligible to attend a half day practice laboratory classroom.

Subjects who did not reach an optimal dose by Visit 8 (Day 42) or subjects who needed a dose adjustment on the day of the half day practice laboratory classroom visit were discontinued from the study.

Intensity of Adverse Events

The intensity of an adverse event was recorded based on investigator observations. The intensity of a particular adverse event to be recorded was the worst intensity experienced by the subject during the course of the event. Worsening of pre-treatment events, after initiation of Formulation I, were recorded as a new adverse event (for example, if a subject experienced mild intermittent dyspepsia prior to dosing of Formulation I, but the dyspepsia became severe and more frequent after the first dose of Formulation I occurred, a new adverse event of severe dyspepsia was recorded. The medical assessment of intensity was determined using the following definitions:

Mild: The adverse event was easily tolerated and did not interfere with usual activity.

Moderate: The adverse event interfered with daily activity, but the subject was still able to function.

Severe: The adverse event was incapacitating and the subject was unable to work or complete usual activity.

Randomization and Blinding

At the half day practice laboratory classroom visit, eligible subjects were randomized (1:1 ratio) to receive either Formulation I or placebo for the double-blind treatment period.

Randomization was applied centrally across all sites and was stratified by individual dose level so that approximately half the subjects within each dose level received Formulation I and half received placebo.

Study medication was packaged in bottles containing 10 capsules. The treatment assignment was not identified on the bottles, and the study medication capsules (Formulation I and placebo) were indistinguishable. Neither the subject nor the study staff were unblinded to treatment assignment.

Adverse Events

Open-Label, Dose-Optimization Period

A total of 104/156 subjects (66.7%) experienced at least one treatment-emergent adverse event (TEAE): 66 subjects (42.3%) in the 25 mg group, 50 subjects (35.2%) in the 35 mg group, 43 subjects (40.2%) in the 45 mg group, 25 subjects (39.1%) in the 55 mg group, 8 subjects (30.8%) in the 70 mg group, and 2 subjects (22.2%) in the 85 mg group. There was no evidence of increasing incidence of TEAEs with increasing dose level.

A total of 95 subjects (60.9%) experienced at least one treatment-related AE: 54 subjects (34.6%) in the 25 mg group, 40 subjects (28.2%) in the 35 mg group, 38 subjects (35.5%) in the 45 mg group, 19 subjects (29.7%) in the 55 mg group, 7 subjects (26.9%) in the 70 mg group, and 2 subjects (22.2%) in the 85 mg group. There was no evidence of increasing incidence of treatment-related AEs with increasing dose level.

Two subjects (1.3%) experienced an AE that led to study termination during week 2.

In the open-label dose-optimization period, there were no SAEs and no severe intensity AEs (FIG. 47).

During the course of the study, pediatric subjects and their parents were asked to record the claimed dosage form's effects on sleep and appetite on a daily basis. Each day during the study, study subjects were asked to evaluate: (a) difficulty falling asleep (initial insomnia) on a scale of 0 to 2 (0=easily; 1=after some time; 2=with difficulty); (b) mood on awakening (sleep quality) on a scale of 0 to 2 (0=rested; 1=somewhat rested; 2=tired); and (c) hunger on a 100 point scale (0=I'm not hungry; 100=I've never been hungrier).

Figure 44:
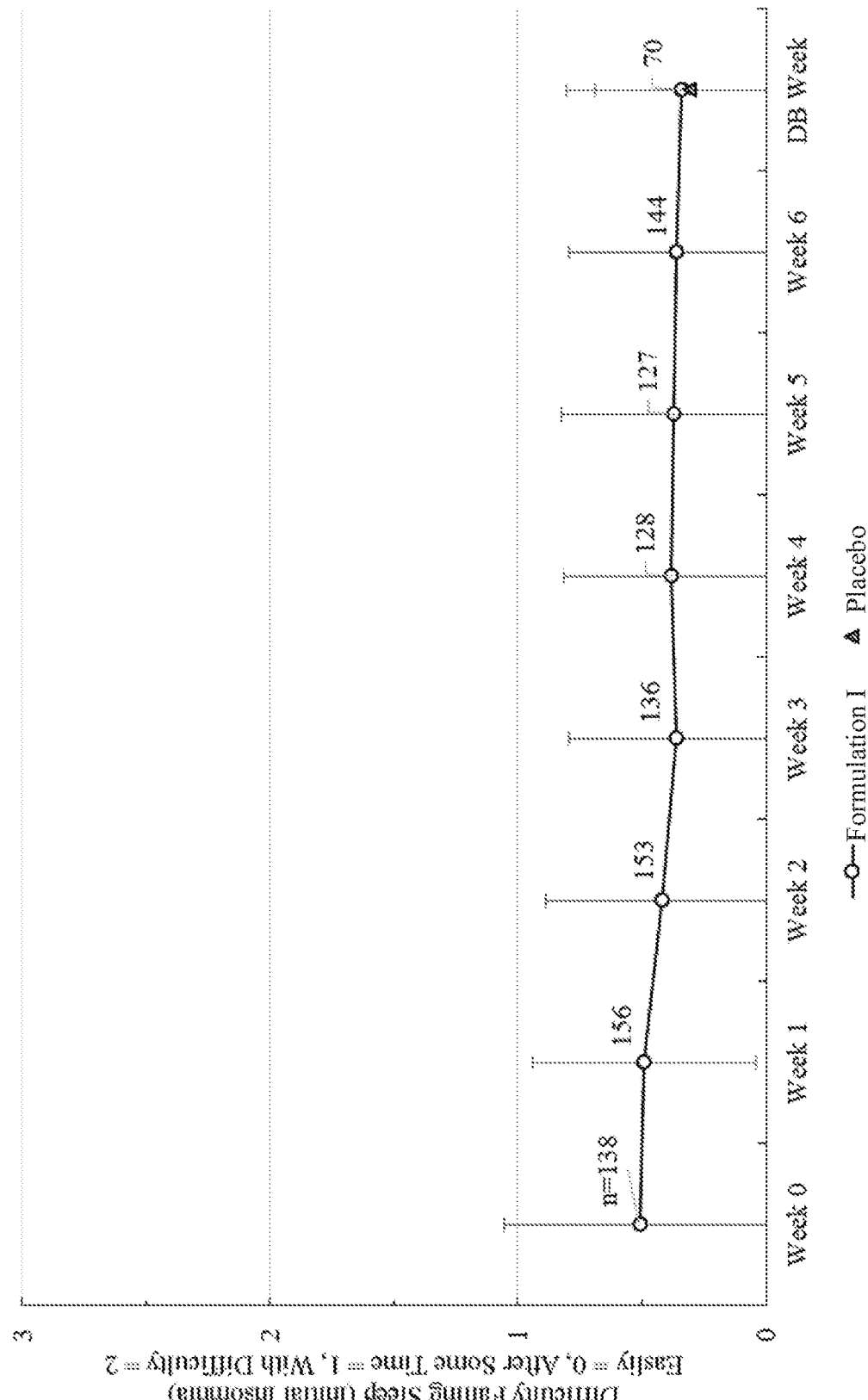
FIG. 44 is a graph showing the difficulty of falling asleep (initial insomnia) measured over 8 weeks in a dose-optimized study in 147 pediatric subjects 6 to 12 years of age diagnosed with ADHD. Results are shown for administration of Formulation I through study week 6. In study week 7, in a double-blind fashion, half of the study subjects received their optimal dose and the other half received a placebo. Data was reported by study participant's parents and collected with a daily electronic diary.

As shown in FIG. 44, subjects did not have any more difficulty falling asleep while on the dosage form of Formulation I than while on the placebo. And, surprisingly only 1.9% of study subjects reported initial insomnia at any point during the study.

Figure 45:
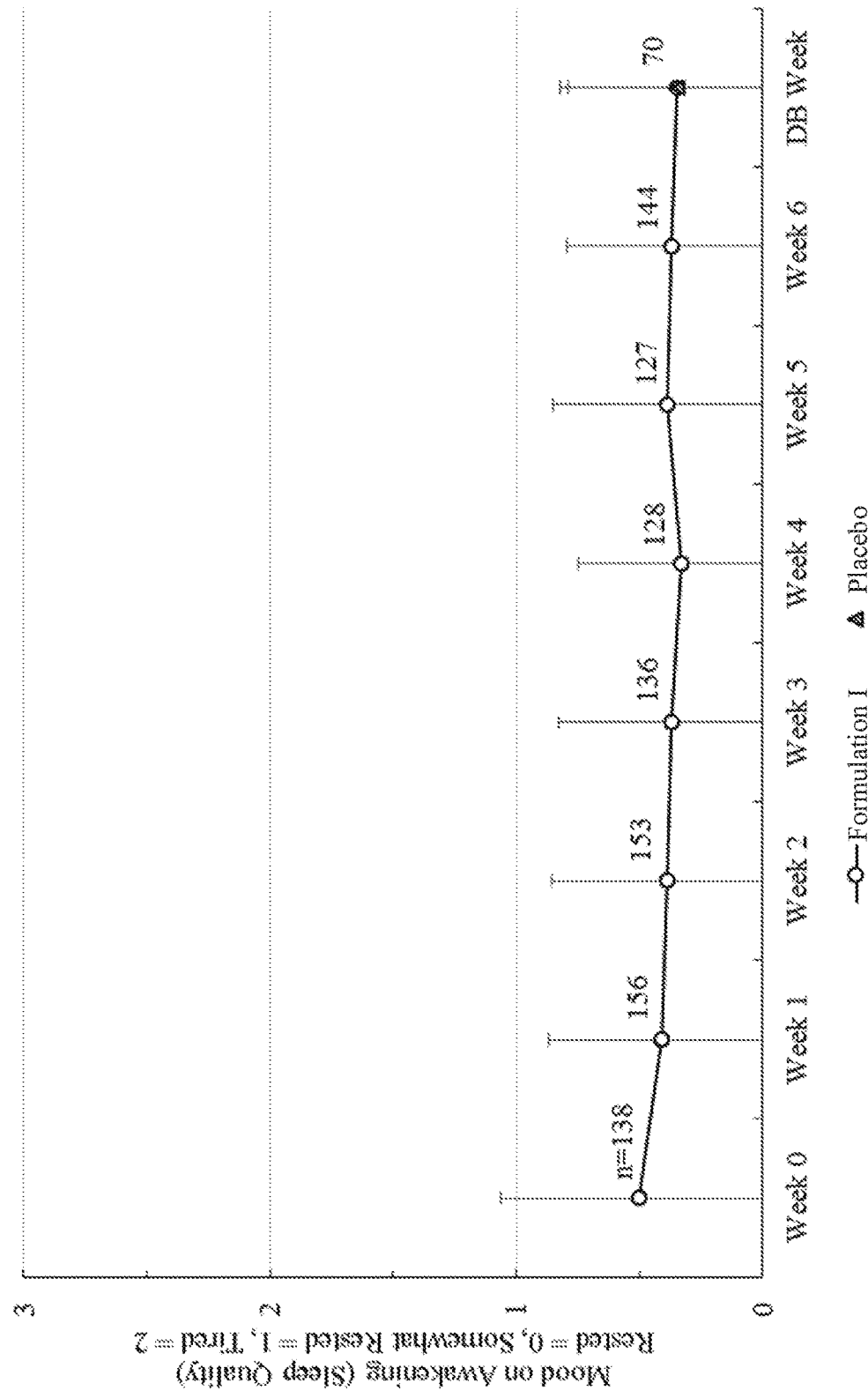
FIG. 45 is a graph showing the mood on awakening (sleep quality) measured over 8 weeks in a dose-optimized study in 147 pediatric subjects 6 to 12 years of age diagnosed with ADHD. Results are shown for administration of Formulation I through study week 6. In study week 7, in a double-blind fashion, half of the study subjects received their optimal dose and the other half received a placebo.

As shown in FIG. 45, sleep quality was also surprisingly unaffected by the dosage form of Formulation I compared to the placebo. Nearly all of the study subjects reported that they felt "rested" or "nearly rested" after a night's sleep.

Figure 46:
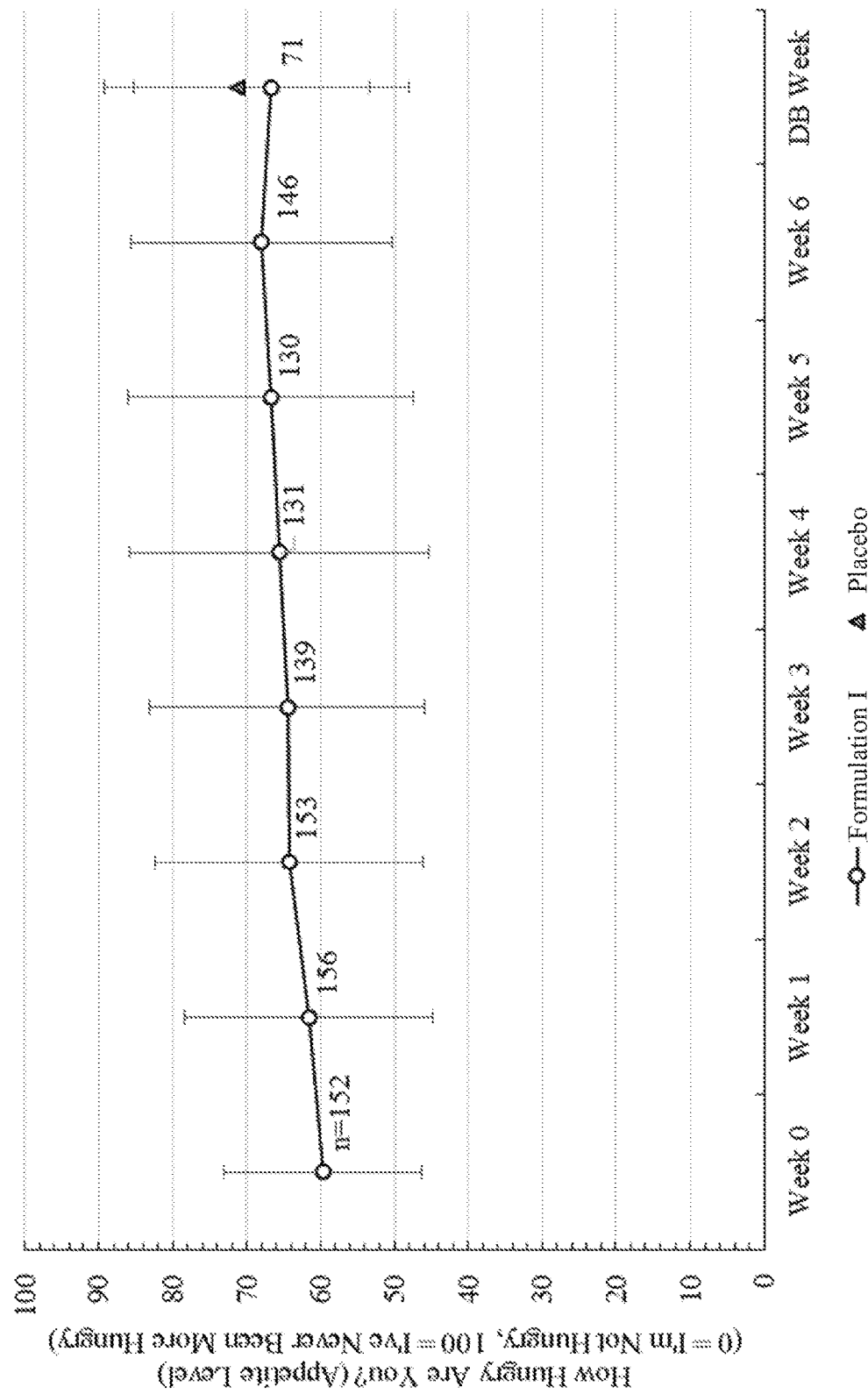
FIG. 46 is a graph showing the appetite level measured over 8 weeks in a dose-optimized study in 147 pediatric subjects 6 to 12 years of age diagnosed with ADHD. Results are shown for administration of Formulation I through study week 6. In study week 7, in a double-blind fashion, half of the study subjects received their optimal dose and the other half received a placebo.

And, the pediatric subjects enrolled in the study were, on average, equally hungry regardless of whether they received the dosage form of Formulation I or the placebo. As shown in FIG. 46, nearly all respondents reported hunger levels averaging about 60 to about 70 (visual analog scale), regardless of whether they were given the dosage form of Formulation I or the placebo. Given the pK profile of Formulation I and methylphenidate's known effects on appetite, this result was surprising.

Double-Blind Treatment Period

There was a higher incidence of TEAEs in the total Formulation I group (18 subjects [24.0%]) than in the placebo group (7 subjects [9.6%]).

TEAEs were experienced by 3 subjects (33.3%) in the 25 mg group, 2 subjects (13.3%) in the 35 mg group, 5 subjects (25.0%) in the 45 mg group, 3 subjects (15.8%) in the 55 mg group, 3 subjects (37.5%) in the 70 mg group, 2 subjects (50.0%) in the 85 mg group, and 7 subjects (9.6%) in the placebo group.

There was a higher incidence of treatment-related AEs in the total Formulation I group (12 subjects [16.0%]) than in the placebo group (2 subjects [2.7%]).

Treatment-related AEs were experienced by 1 subject (11.1%) in the 25 mg group, 1 subject (6.7%) in the 35 mg group, 4 subjects (20.0%) in the 45 mg group, 2 subjects (10.5%) in the 55 mg group, 3 subjects (37.5%) in the 70 mg group, 1 subject (25.0%) in the 85 mg group, and 2 subjects (2.7%) in the placebo group.

In the double-blind treatment period, there were no TEAEs leading to study termination, no SAEs, and no severe intensity AEs (FIG. 47).

Treatment-Emergent Adverse Events by System Organ Class

Open-Label, Dose-Optimization Period

During the open-label dose-optimization period, TEAEs experienced most commonly occurred in the metabolism and nutrition disorders SOC (55 subjects; 35.3%), psychiatric disorders SOC (49 subjects; 31.4%), gastrointestinal disorders SOC (44 subjects; 28.2%), and investigations SOC (32 subjects; 20.5%) (FIGS. 48-50).

Double-Blind Treatment Period

During the double-blind treatment period, TEAEs experienced more commonly in the Formulation I group than in the placebo group occurred in the investigations SOC (6.7% versus 1.4%), the gastrointestinal disorders SOC (5.3% versus 1.4%) and the nervous systems SOC (2.7% versus 1.4%) (FIGS. 51-52).

Treatment-Emergent Adverse Events by Preferred Term

Open-Label, Dose Optimization Period

Of the 156 subjects in the open-label dose optimization period, the most common TEAEs (≥10% of subjects overall) by PT were: decreased appetite (55 subjects; 35.3%), abdominal pain upper (26 subjects; 16.7%), affect lability (22 subjects; 14.1%), weight decreased (18 subjects; 11.5%), headache (17 subjects; 10.9%), irritability (16 subjects; 10.3%), and insomnia (16 subjects; 10.3%) (FIG. 53).

Double-Blind Treatment Period

As shown in FIG. 54, in the Formulation I and placebo groups, the most common TEAEs were heart rate increased (3 subjects; 4.0% in the Formulation I group versus 1 subject; 1.4% in the placebo group), vomiting (2 subjects; 2.7% in the Formulation I group versus 0 subjects in the placebo group), headache (2 subjects; 2.7% in the Formulation I group versus 0 subjects in the placebo group), and upper respiratory tract infection (2 subjects; 2.7% in the Formulation I group versus 0 subjects in the placebo group).

All of the AEs occurred more frequently in the Formulation I group than the placebo group with the exception of sinus tachycardia which occurred with a similar incidence rate in both groups (1 subject; 1.3% in the Formulation I group versus 2 subjects; 2.7% in the placebo group) (FIG. 54).

Treatment-Emergent Adverse Events by Preferred Term for Pediatric Subjects 12 Years of Age Of the 156 subjects in the open-label dose optimization period, there were 29 subjects aged 12 years in the study. In the 29 subjects aged 12 years, the most common TEAEs (≥10% of subjects overall) by PT were: decreased appetite (11 subjects; 37.93%), diarrhea (4 subjects; 13.79%), weight decreased (4 subjects; 13.79%), affect lability (3 subjects; 10.34%), headache (3 subjects; 10.34%), heart rate increased (3 subjects; 10.34%), and insomnia (3 subjects; 10.34%) (FIG. 74).

Double-Blind Treatment Period

As shown in FIG. 75, in the Formulation I and placebo groups, the most common TEAEs were tachycardia (1 subject; 3.45% in the Formulation I group versus 0 subjects in the placebo group) and blood pressure diastolic increased (1 subjects; 3.45% in the Formulation I group versus 0 subjects in the placebo group).

Treatment-Emergent Adverse Events by Severity

Open-Label, Dose Optimization Period

During the open-label, dose-optimization period, TEAEs experienced were of mild intensity in 86 subjects (55.1%) or moderate intensity in 43 subjects (27.6%). There were no subjects with TEAEs of severe intensity (FIGS. 55-56). The most common TEAEs of moderate intensity were:

Decreased appetite in 9 subjects (5.8%); 4 subjects (2.6%) in the 25 mg group, 3 subjects (2.1%) in the 35 mg group, 1 subject (0.9%) in the 45 mg group, and 1 subject (1.6%) in the 55 mg group.

Insomnia in 9 subjects (5.8%): 3 subjects (1.9%) in the 25 mg group, 2 subjects (1.4%) in the 35 mg group, 4 subjects (3.7%) in the 45 mg group, and 1 subject (1.6%) in the 55 mg group.

Affect lability in 8 subjects (5.1%): 3 subjects (1.9%) in the 25 mg group, 2 subjects (1.4%) in the 35 mg group, 2 subjects (1.9%) in the 45 mg group and 1 subject (3.8%) in the 70 mg group Headache in 7 subjects (4.5%): 2 subjects (1.3%) in the 25 mg group, 3 subjects (2.1%) in the 35 mg group, 1 subject (1.6%) in the 55 mg group and 1 subject (3.8%) in the 70 mg group.

Double-Blind Treatment Period

During the double-bind period, TEAEs were of mild intensity in 13 subjects (17.3%) of the Formulation I group and in 4 subjects (5.5%) of the placebo group. Treatment-emergent AEs were of moderate intensity in 5 subjects (6.7%) of the Formulation I group and in 3 subjects (4.1%) of the placebo group. There were no subjects with TEAEs of severe intensity.

All moderate intensity TEAEs occurred in one subject only: 1 subject (placebo) with sinus tachycardia and bronchitis, 1 subject (45 mg) with nausea, 1 subject (placebo) with toothache, 1 subject (85 mg) with headache, 1 subject (85 mg) with upper respiratory tract infection, 1 subject (placebo) with impetigo, 1 subject (35 mg) with arthropod bite and 1 subject (55 mg) with irritability.

Treatment-Emergent Adverse Events Leading to Discontinuation

Open-Label, Dose-Optimization Period

During the open-label, dose-optimization period, there were 2 subjects with TEAEs leading to study discontinuation.

Double-Blind Period

During the double-blind period, there were no subjects with TEAEs leading to discontinuation.

Treatment-Related Adverse Events

Open-Label, Dose-Optimization Period

Of the 156 subjects in the open-label dose optimization period, there were 95 subjects (60.9%) with AEs considered related to study medication.

The most common treatment-related AEs overall were: decreased appetite in 55 subjects (35.3%), abdominal pain upper in 23 subjects (14.7%), affect lability in 21 subjects (13.5%), weight decreased in 18 subjects (11.5%), and insomnia in 16 subjects (10.3%) (FIGS. 32A-B). There was no evidence of increasing incidence of treatment-related AEs with increasing dose level.

Double-Blind Treatment Period

As shown in FIGS. 33A-B, the most common treatment-related AEs were heart rate increased in 3 subjects (4.0%) in the Formulation I group versus 1 subject (1.4%) in the placebo group, headache in 2 subjects (2.7%) in the Formulation I group versus 0 subjects in the placebo group, and sinus tachycardia in 1 subject (1.3%) in the Formulation I group versus 1 subject (1.4%) in the placebo group. The remaining treatment-related AEs occurred in 1 subject only.

Overall, there were more subjects who experienced AEs considered related to study medication in the Formulation I group (12 subjects; 16.0%) than in the placebo group (2 subjects; 2.7%) (FIGS. 57-58).

Summary & Analysis of Adverse Events

Open-Label Dose-Optimization Period

Treatment-emergent AEs were experienced by 104 of the 156 subjects (66.7%). The most common TEAEs were: decreased appetite (55 subjects; 35.3%); abdominal pain upper (26 subjects; 16.7%); affect lability (22 subjects; 14.1%); weight decreased (18 subjects; 11.5%); headache (17 subjects; 10.9%); irritability (16 subjects; 10.3%); and insomnia (16 subjects; 10.3%). There was no evidence of increasing incidence of TEAEs with increasing dose level.

TEAEs were of mild or moderate intensity. There were no severe intensity AEs.

Two subjects each experienced an AE that led to study termination during week 2.

Treatment-related AEs were experienced by 95 of the 156 subjects (60.9%). The most common treatment-related AEs overall were: decreased appetite (55 subjects [35.3%]); abdominal pain upper (23 subjects [14.7%]); affect lability (21 subjects [13.5%]); weight decreased (18 subjects [11.5%]); and insomnia (16 subjects [10.3%]). There was no evidence of increasing incidence of treatment-related AEs with increasing dose level.

Double-Blind Treatment Period

The most common TEAEs were heart rate increased (3 subjects; 4.0% in the Formulation I group versus 1 subject; 1.4% in the placebo group), vomiting (2 subjects; 2.7% in the Formulation I group versus 0 subjects in the placebo group), headache (2 subjects; 2.7% in the Formulation I group versus 0 subjects in the placebo group), and upper respiratory tract infection (2 subjects; 2.7% in the Formulation I group versus 0 subjects in the placebo group). There was a higher incidence of TEAEs in the total Formulation I group (18 subjects [24.0%]) than in the placebo group (7 subjects [9.6%]).

TEAEs were of mild or moderate intensity. There were no severe intensity AEs and no subjects who discontinued due to an AE.

The most common treatment-related AEs were heart rate increased in 3 subjects (4.0%) in the Formulation I group versus 1 subject (1.4%) in the placebo group, headache in 2 subjects (2.7%) in the Formulation I group versus 0 subjects in the placebo group, and sinus tachycardia in 1 subject (1.3%) in the Formulation I group versus 1 subject (1.4%) in the placebo group. There was a higher incidence of treatment-related AEs in the total Formulation I group (12 subjects [16.0%]) than in the placebo group (2 subjects [2.7%]).

Discussion & Overall Conclusions

Over a 13-hour period in a simulated classroom setting, pediatric subjects 6 to 12 years of age in a fasted state with ADHD receiving Formulation I demonstrated superior attention and improved behavior compared to those receiving placebo.

Clinically and statistically significant differences in favor of Formulation I were observed from 1 hour post-dose, the earliest post-dose time point measured, and up to 13 hours post-dose, the latest time point measured. Formulation I was well tolerated and no SAEs or severe intensity AEs were reported. The incidence of TEAEs was similar for all optimized doses of Formulation I.

At the completion of the open-label, dose optimization period, with the subjects receiving up to 6 weeks of active treatment, the mean ADHD-RS-5 total scores improved from baseline to the half day laboratory classroom in all dose groups, and the CGI-S mean scores shifted from severe at baseline in 100% of subjects to non-severe at the half day laboratory classroom in 91.9% of subjects in the Formulation I group and in 91.9% of subjects in the placebo group. This demonstrates that subjects completing the dose-optimization period had their ADHD symptoms well-controlled, and provides a basis for comparison of subjects who, during the double-blind period, were no longer receiving treatment when they were randomized to placebo.

Subjects demonstrated significant improvement in the primary endpoint—a subjective measure of behavior (the SKAMP) when treated with Formulation I versus when treated with placebo. The primary efficacy endpoint was the mean SKAMP-C score assessed during the full day laboratory classroom. The Formulation I treatment arm had statistically significant improvements compared to placebo over the entire 13-hour classroom session (p<0.0001), with an LS mean difference between Formulation I and placebo of −8.6 (95% CI: [−10.6, −6.6]). Improvements in ADHD behavior observed at optimal dose were comparable to those observed with other stimulant-based treatments for ADHD in similarly designed classroom studies of pediatric subjects 6 to 12 years of age.

The key secondary efficacy endpoint was the onset and duration of efficacy as assessed by the SKAMP-C scores at each time point during the full day laboratory classroom. This study demonstrated that Formulation I had an onset of action within 1-hour post-dose and a duration of action of at least 13 hours post-dose. Comparisons between the Formulation I group and the placebo group SKAMP-C scores were statistically significant at all time points (p<0.0001).

The onset and duration of Formulation I was similar or superior to that of other extended-release stimulant treatments for ADHD. In classroom studies of extended-release stimulant treatments of ADHD in pediatric subjects 6 to 12 years of age with similar designs to this study, onset of action, in some studies was within 1.0 hours post-dose or less and in others, onset of action was at 1.5 to 2.0 hours post-dose, while duration of action has been found to be from 8 hours, and 10 hours post-dose to 12 hours post-dose.

In this study, prior to receiving Formulation I or placebo during the laboratory classroom day, a treatment difference (SE) of 3.1 (1.48) (95% CI: 0.2, 6.1; p=0.0367) was observed in placebo's favor. Similar differences at the pre-dose time point have been observed with other long-acting stimulant preparations.

By the second treatment time point (between 0.75 and 1.5 hours post-dose) in all of the aforementioned classroom studies, the performance of subjects receiving placebo has deteriorated, while the performance of subjects receiving active medication has improved to levels greater than or equivalent to the pre-dose of the placebo group. Although these data suggest a possible morning "rebound" effect for subjects medicated with long-acting stimulants, no study has been designed to examine this and any conclusions should be made with caution. This effect is not limited to stimulant treatment for ADHD.

The results of the primary and key secondary outcome measures were supported by additional secondary outcome measures of the study during both the open-label titration and double-blind periods, which showed significant improvements in clinical impressions and measures of ADHD symptoms by the subject. The secondary endpoints supported the efficacy of Formulation I over placebo at the full day laboratory classroom:

- The average mean SKAMP-A and SKAMP-D subscores demonstrated statistically significant improvements in the Formulation I group compared with the placebo group (p<0.0001).
- The mean PERMP-T scores assessed during the full day laboratory classroom were significantly improved in the Formulation I group compared with the placebo group at all time points post-dose (p<0.0001).
- The average mean PERMP-A and PERMP-C scores were statistically improved in the Formulation I group compared with the placebo group (p<0.0001).
- For the full analysis population, during the open-label dose-optimization period, the ADHD-RS-5 total score decreased from a mean±SD value of 42.8±7.19 at baseline following washout to a mean±SD value of 15.3±7.64 at the half-day practice laboratory classroom. Change from baseline values were similar at each optimized dose (mean±SD change from baseline varied from −26.0±12.71 for those optimized to 85 mg Formulation I to −29.2±9.95 for those optimized to 25 mg Formulation I), indicating that dose optimization was achieved during the open-label titration period. When ADHD-RS-5 total scores from the open-label dose-optimization period were analyzed by randomized treatment, there were negligible LS mean differences of −0.1 (95% CI: −2.39, 2.10) at baseline, and 0.1 (95% CI: −2.10, 2.36) at the half day laboratory classroom, indicating that subjects entering the double-blind period were equally dose-optimized.
- During the double-blind, full day laboratory classroom, the mean total ADHD-RS-5 scores showed a greater decrease from baseline in the Formulation I dose group (LS mean±SE decrease of −25.1±1.37) than in the placebo group (LS mean±SE decrease of −12.8±1.36). At the full day laboratory classroom, the clinician-rated ADHD-RS-5 symptoms showed significantly greater improvement for subjects receiving Formulation I than for those receiving placebo (LS mean treatment difference [SE]: 12.2 [1.88] (95% CI −15.92, −8.51, p<0.0001).
- The Clinical Global Impressions: Severity (CGI-S) demonstrated that there were more subjects in the Formulation I group who shifted from severe disease at baseline to non-severe disease at the full day laboratory classroom (60 subjects; 81.1%) than subjects who shifted in the placebo group (28 subjects; 38.4%).
- During the full day laboratory classroom, a much larger majority (85.1%) of subjects on Formulation I were rated as "much improved" or "very much improved" on the Clinical Global Impressions: Intensity (CGI-I) versus subjects on placebo (42.5%), demonstrating greater clinical improvement as assessed by clinicians.

As shown in FIG. 59, examination of studies of similar design with other long-acting stimulants for the treatment of ADHD (i.e., simulated classroom studies with open-label dose optimization periods followed by a placebo-controlled, double-blind period) shows that the frequencies of TEAEs which occurred during the open-label, dose titration period are much greater than those reported during the double-blind treatment period of the same study (Evekeo (Childress, A., et al., *J. Child Adolesc. Psychopharmacol.* 25:404-414 (2015)); Aptensio (Wigal, S., et al., *J. Child Adolesc. Psychopharmacol.* 24(10):562-569 (2014)); Quillivant XR (Wigal, S., et al., *J. Child Adolesc. Psychopharmacol.* 23:3-10 (2013)); Vyvanse (Wigal, S., et al., *Child and Adolescent Psychiatry and Mental Health* 3:17 (2009)); Cotempla XR-ODT (Childress, A., et al., *J. Child Adolesc. Psychopharmacol.* 27:66-74 (2017)); Quillichew ER (Wigal, S., et al., *J. Child Adolesc. Psychopharmacol.* 27(8):690-699 (2017)); Dyanavel XR (Childress, A., et al., *J. Child Adolesc. Psychopharmacol.* 28(5):306-313 (2018)); and Jornay PM™ (Prescribing Information, Reference ID: 4304173, Food and Drug Administration (Revised August 2018))). Evekeo, Vyvanse, and Dyanaval XR are amphetamine-based products. Aptensio, Quillivant XR, Cotempla XR-ODT, Quillichew ER, and Jornay PM are methylphenidate-based products.

In this study, out of the 156 subjects enrolled into the open-label, dose-optimization period, 104 subjects (66.7%) experienced at least one TEAE. The most common TEAEs (experienced by ≥10% of subjects overall) were: decreased appetite (35.3%), abdominal pain upper (16.7%), affect lability (14.1%), weight decreased (11.5%), headache (10.9%), irritability (10.3%), and insomnia (10.3%).

Of the most commonly reported AEs, the frequencies of decreased appetite, abdominal pain upper, affect lability, and irritability in subjects receiving Formulation I were bracketed in similar studies of other oral, long-acting MPH and amphetamine products (FIG. 59). All studies presented in FIG. 59 were dose-optimized and conducted in pediatric subjects 6 to 12 years of age. However, there are limitations to these comparisons due to differences in type of stimulant, study conduct, recording of events, subject numbers, and duration of exposure. Surprisingly, the frequencies of headache and insomnia in patients receiving Formulation I were lower than in similar studies of other oral MPH ER products.

In this study, the assessment of relatedness of AEs was performed by the investigators. The majority of AEs during the open-label period were considered treatment-related and were experienced by 95 subjects (60.9%). The most common treatment-related AE was decreased appetite which occurred in 35.3% of subjects. Also frequently experienced treatment-related AEs were abdominal pain upper (14.7%), affect lability (13.5%), weight decreased (11.5%) and insomnia (10.3%). There was no observable trend between the incidence or type of TEAE experienced and Formulation I dose level at onset.

There were two subjects who were discontinued due to treatment-related AEs, both discontinuations occurred during week 2 while subjects were taking 35 mg Formulation I. One subject experienced moderate intensity affect lability and dermatilliominia (both events were recovered/resolved at follow-up), and 1 subject experienced mild intensity ECG PR prolongation (which was ongoing at follow-up).

Over the duration of the open-label, dose-optimization period, there were no clinically meaningful mean changes in weight, but slight mean increases from baseline were observed in mean blood pressure systolic, mean blood pressure diastolic, and mean pulse rate. Overall, TEAEs of heart rate increase was experienced by 9 subjects (5.8%), blood pressure systolic increased was experienced by 4 subjects (2.6%), blood pressure diastolic increased was experienced by 3 subjects (1.9%), and blood pressure systolic decreased was experienced by 1 subject (0.6%).

The starting dose for all subjects in this study was 25 mg Formulation I and no subjects withdrew due to AEs during the first week of treatment, although 1 subject was withdrawn due to medication non-compliance. This indicates that 25 mg is an appropriate starting dose in pediatric subjects 6 to 12 years of age. In addition, 17 subjects were dose-optimized at 25 mg, thus supporting 25 mg/day Formulation I as the lowest effective dose in pediatric subjects 6 to 12 years of age.

During the double-blind treatment period, there were more subjects experiencing TEAEs in the Formulation I group (18 subjects; 24.0%) than the placebo group (7 subjects; 9.6%). The majority of these events were considered by the investigators to be treatment-related (12 subjects; 16.0% in the Formulation I group versus 2 subjects; 2.7% in the placebo group). The most common treatment-related AEs were heart rate increased in 3 subjects (4.0%) in the Formulation I group versus 1 subject (1.4%) in the placebo group, headache in 2 subjects (2.7%) in the Formulation I group versus 0 subjects in the placebo group, and sinus tachycardia in 1 subject (1.3%) in the Formulation I group versus 1 subject (1.4%) in the placebo group.

During this study, there were no severe intensity TEAEs, no SAEs, and no deaths.

Conclusions

This study successfully demonstrated significant improvements in attention and ADHD symptoms in pediatric subjects 6 to 12 years of age (inclusive) in a fasted state who received optimized oral doses of Formulation I (ranging from 25 to 85 mg daily) compared to placebo. This study demonstrated that Formulation I was a well-tolerated, safe, and effective treatment of ADHD with rates of AEs similar to those observed with other ER stimulant treatments. The onset of action of 1 hour and a duration of effect up to and including 13 hours post-dose provides an unmet clinical need in the treatment of pediatric subjects 6 to 12 years of age with ADHD.

Formulation I ER capsules are designed to provide a rapid onset of efficacy (within 1 hour postdose) and duration of action up to and including 13 hours post-dose, by optimizing the balance between the magnitude of a rapidly-attained initial post-dose peak MPH plasma concentration and a subsequent, delayed release of MPH resulting in a second peak later in the day. The AE profile observed with Formulation I is similar to currently-approved stimulants.

Example 15—a Randomized, Single-Dose, Open-Label, Parallel Group Pharmacokinetic Study Conducted in Pediatric Subjects 6 to 11 Years of Age Diagnosed with ADHD Objectives The objective of this study was to determine the rate and extent of absorption of methylphenidate from a single dose of Formulation I under fasting conditions in pediatric subjects 6 to 11 years of age with ADHD.

Methodology

This was an open-label, randomized, parallel group, single-dose pharmacokinetic (PK) study conducted in pediatric subjects 6 to 11 years of age who were diagnosed with ADHD. Subjects who met the eligibility criteria (inclusion/exclusion) following the Screening Visit, discontinued their current methylphenidate or amphetamine medication for a minimum of 7 days prior to dosing with Formulation I. Subjects arrived at the clinic (Visit 2) in a fasted condition on the morning of dosing, and remained as an inpatient with parental accompaniment until approximately 36 hours post-dose. Dosing with study medication occurred at approximately 7 am in the morning of Visit 2. Standardized meals and snacks were provided throughout the inpatient stay. Pharmacokinetic and safety assessments were conducted. Subjects were followed-up with a telephone call approximately 7 days after study completion.

There was no control group for this study. Subjects were randomized to receive a single dose of 35 mg, 55 mg, or 85 mg of Formulation I. There was no blinding, with the exception of the bioanalysis staff who were blinded to treatment.

Number of Subjects

Planned: 18 subjects. Randomised: 18 subjects. Completed: 18 subjects.

Test Treatment, Dose, and Mode of Administration

Formulation I was supplied as 35 mg, 55 mg, and 85 mg capsules.

Formulation I capsules were packed in bottles and each bottle was identified by the strength (i.e., 35 mg, 55 mg, or 85 mg).

The medication was stored in a locked, environmentally-controlled medication room with restricted access at a controlled room temperature of 15° C. to 30° C. (59° F. to 86° F.).

Individual subject doses were dispensed according to the dose assigned to the subject per the randomization code. No specific preparation was required at the site for dispensing from the bottles. The study staff were to instruct the subjects that study medication was not to be shared with anyone.

If subjects were unable to swallow the capsule (i.e., due to capsule size), the capsule may have been opened and the entire contents sprinkled onto a tablespoon of applesauce, ice cream, or yogurt. The capsule contents were not to be sprinkled in a liquid. The entire mixture was to be consumed immediately or within 10 minutes. Subjects were to consume the entire contents in its entirety without chewing. The dose of a single capsule was not to be divided. Ingestion was to be followed by rinsing the mouth with water to ensure that the entire contents were swallowed. All subjects in this study were able to ingest an intact capsule, therefore there were no subjects who opened the capsule and sprinkled the contents.

Pharmacokinetic Results and Tabulations of Individual Patient Data

Figure 60:
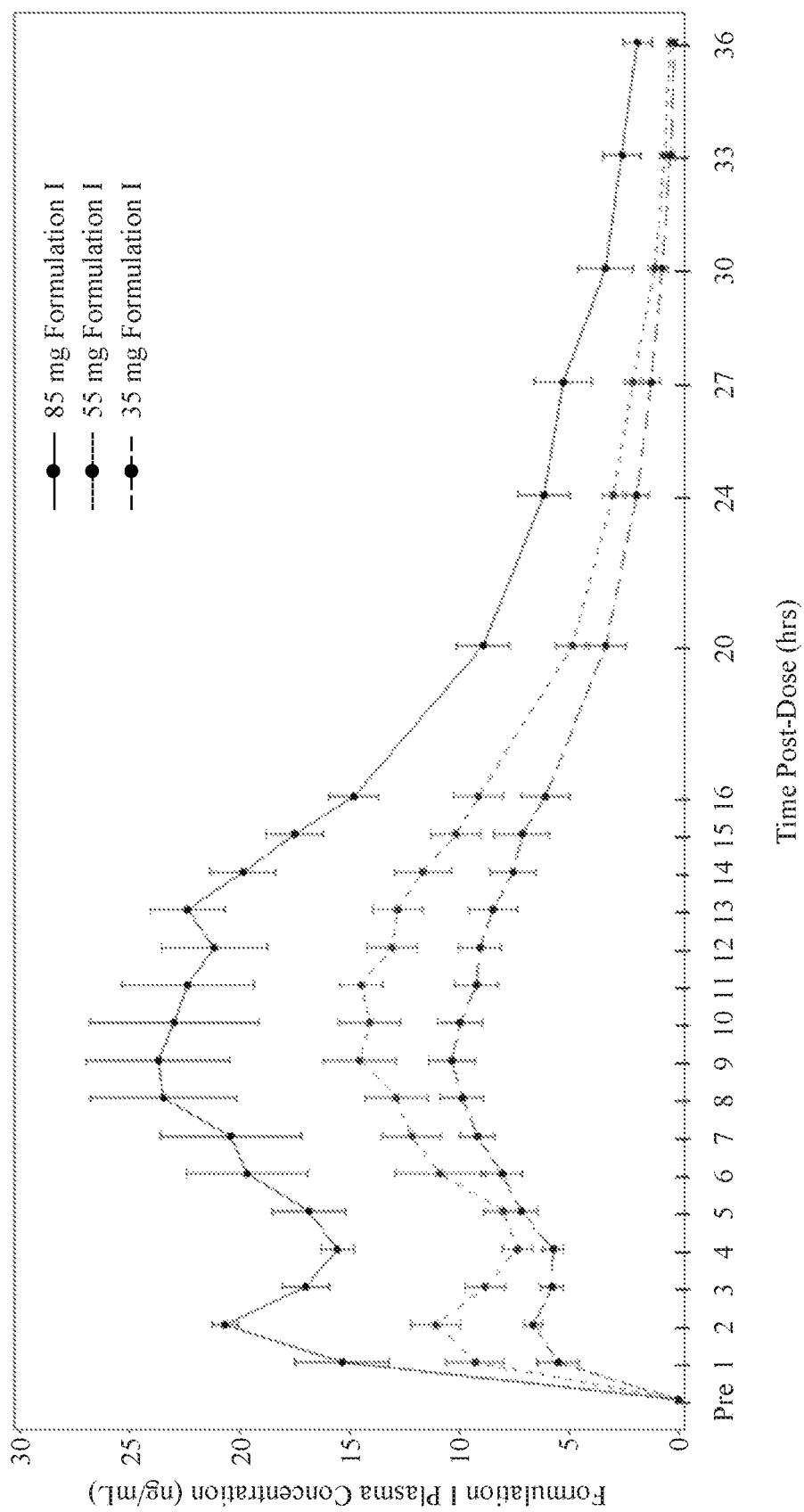
FIG. 60 is a graph showing mean d,l-methylphenidate plasma concentrations by dose level versus time on a linear scale for Formulation I.
Figure 61:
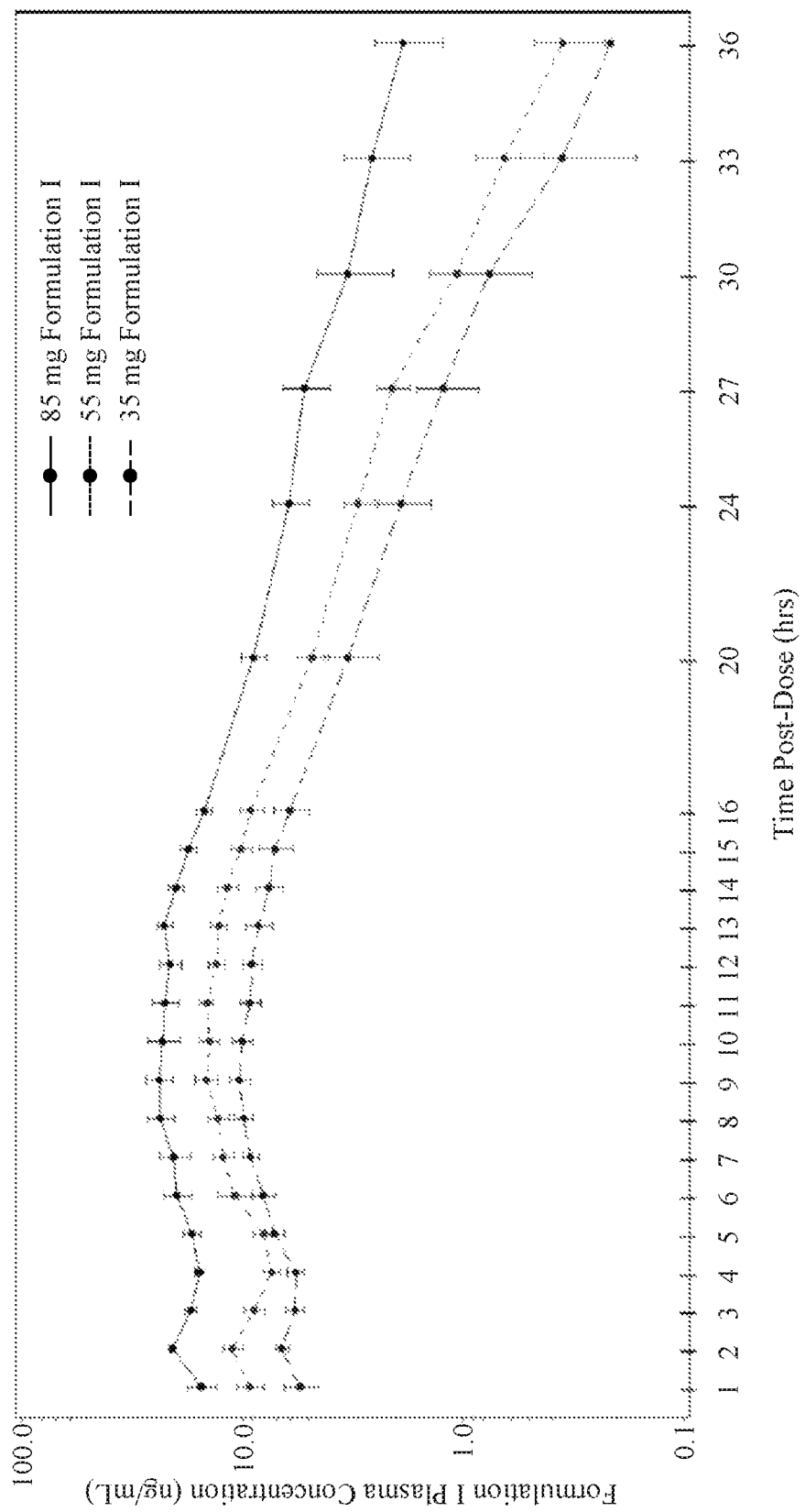
FIG. 61 is a graph showing mean d,l-methylphenidate plasma concentrations by dose level versus time on a logarithmic scale for Formulation I.

FIG. 60 presents mean d, l-methylphenidate plasma concentrations by dose level versus time on a linear scale and FIG. 61 presents mean d, l-methylphenidate plasma concentrations by dose level versus time on a semi-logarithmic scale.

The mean concentration time profiles showed that concentrations increased with increasing dose. In addition, multiple peaks were observed with the primary smaller peaks generally appearing between 0 to 4 hours post dose and the higher secondary peaks generally appearing between 8 to 14 hours post dose. The concentrations gradually declined following the 14 hour time point with the elimination phase occurring from 20 hours post-dose onward.

FIGS. 62-66 presents plasma concentrations for d, l-methylphenidate by dose group.

Figure 67:
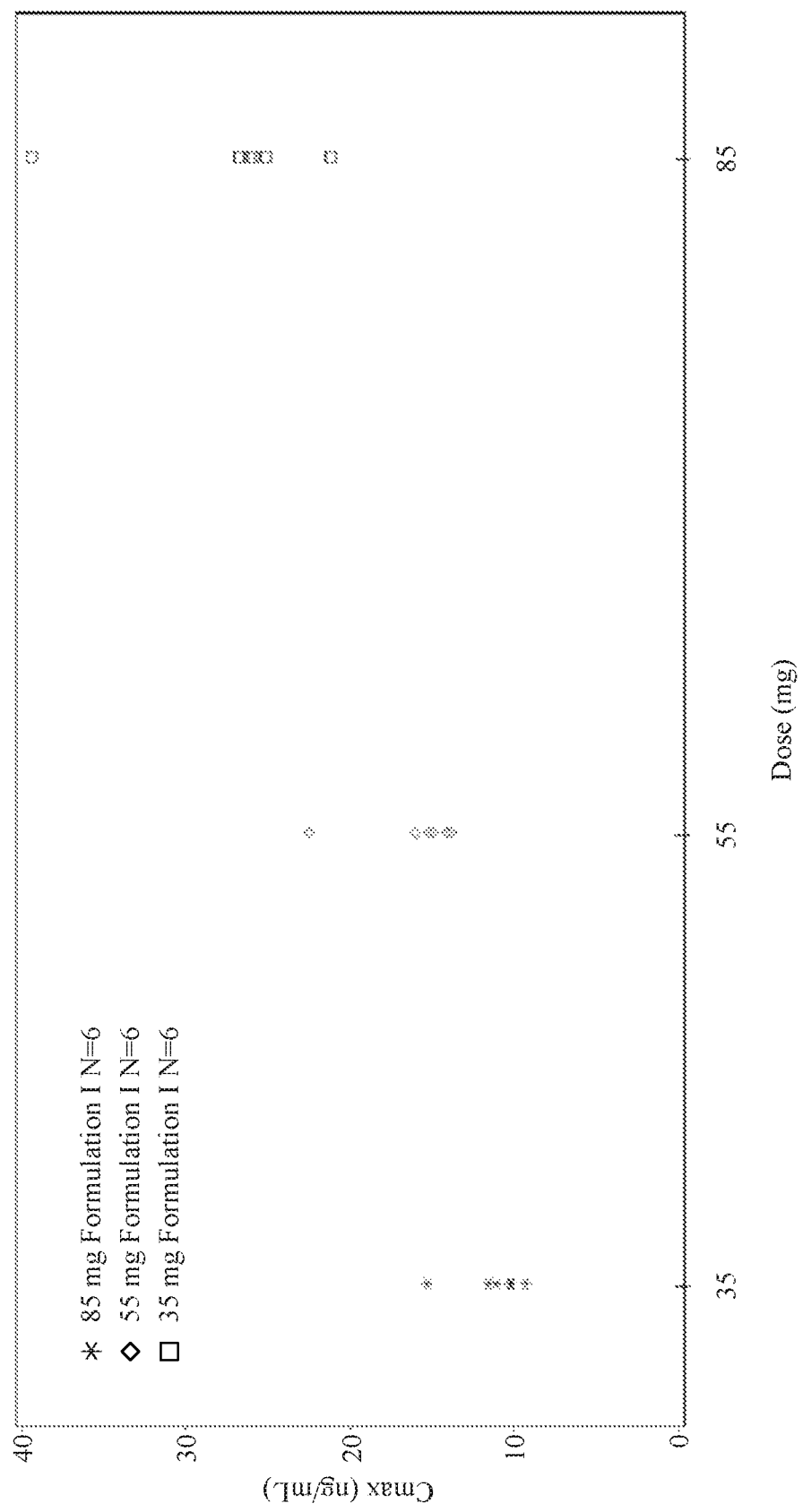
FIG. 67 is a graph showing Cmax versus dose on a linear scale for Formulation I.
Figure 68:
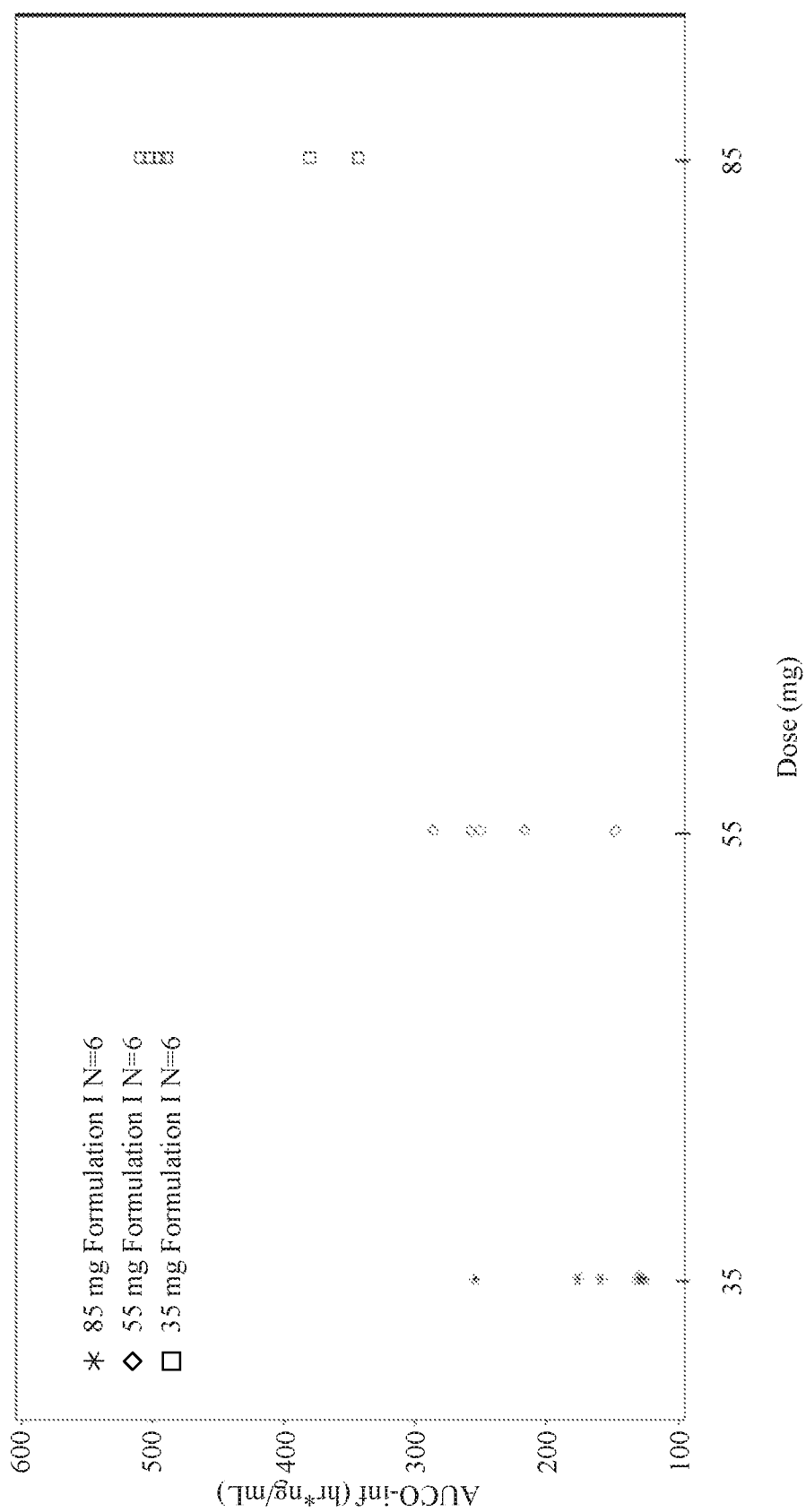
FIG. 68 is a graph showing $AUC_{0-inf}$ versus dose on a linear scale for Formulation I.

FIG. 67 presents Cmax versus dose on a linear scale and FIG. 68 presents $AUC_{0\text{-}inf}$ versus dose on a linear scale.

The peak concentrations were generally observed between 2 to 14 hours across all dose groups. The median time to peak concentration Tmax did not change with dose and ranged from 9.00 to 9.97 hours across the three dose groups. The majority of individual $T_{max}$ values were observed between 8 and 14 hours. Four subjects had Tmax prior to 8 hours comprising two subjects (7.02 and 7.97 hours) in the 35 mg dose group, one subject (2 hours) in the 55 mg dose group, and one subject (2 hours) in the 85 mg dose group.

The median Tmax was also determined for intervals of 0-4, 4-8 and 8-14 hours. For all 3 dose groups, the median Tmax ranged from 1.5 to 2 hours for $Tmax_{0\text{-}4}$, at 8 hours for $Tmax_{4\text{-}8}$, and ranged from 12.75 to 19.92 hours for $Tmax_{8\text{-}14}$. For each partial Tmax, the median estimates were similar across all dose groups.

In an exploratory analysis, the peak concentration Cmax increased with increasing dose and this increase was considered dose proportional as the 90% confidence interval (CI) for slope was contained within the planned critical region.

The Cmax was also determined for intervals of 0-4, 4-8, and 8-14 hours. The highest estimates were observed at later intervals with estimates $Cmax_{8\text{-}14}$ being greater than those of $Cmax_{4\text{-}8}$, which in turn were greater than $Cmax_{0\text{-}4}$. All Cmax related parameters increased with increasing dose.

In an exploratory analysis, the $AUC_{0\text{-}t}$ and $AUC_{0\text{-}inf}$ also increased with increasing dose. The lower bound CI was within the planned critical region, however the upper bound CI (1.4) slightly exceeded the upper bound of the planned critical region (1.3).

The partial AUCs from pre-dose or time 0 hours onward such as $AUC_{0\text{-}4}$, $AUC_{0\text{-}8}$, $AUC_{0\text{-}14}$ and $AUC_{0\text{-}24}$ increased with increasing dose. For all doses, the partial estimates up to the 24 hour time point were closer to those obtained up to the last time point, as the $AUC_{0\text{-}24}$ were generally slightly lower than $AUC_{0\text{-}t}$.

The partial AUCs for post dose intervals such as $AUC_{4\text{-}8}$, $AUC_{8\text{-}14}$, $AUC_{14\text{-}24}$ and $AUC_{14\text{-}t}$ also increased with increasing dose. The estimates for $AUC_{8\text{-}14}$ and $AUC_{14\text{-}t}$ were comparable and both were higher than $AUC_{14\text{-}24}$, which in turn was higher than $AUC_{4\text{-}8}$.

The geometric mean half-life estimates ranged from 3.758 to 6.184 hours across all dose groups. The estimates for the 35 mg (3.758 hours) and 55 mg (3.996 hours) doses were similar and that of 85 mg (6.184 hours) was slightly higher. The estimates for the 85 mg dose were associated with higher variability in terms of CV % (54.81) than those observed with the 35 mg (32.66) and 55 mg (28.14) dose levels.

Pharmacokinetic parameters for d, l-methylphenidate are presented in FIGS. 69-73.

Discussion & Overall Conclusions

The objective of this study was to determine the rate and extent of absorption of methylphenidate from a single dose of Formulation I under fasting conditions in pediatric subjects 6 to 11 years of age with ADHD. This study was conducted in 18 subjects; randomized in a 1:1:1 ratio to receive Formulation I at a dose level of 35 mg, 55 mg or 85 mg (6 subjects in each dose group). All subjects were administered a single dose of Formulation I and all subjects completed the study.

Overall, the mean age of subjects was 9.2 years, 66.7% were male, and 50% were white. However, there were slight differences in demographics between the 85 mg dose group and the 55 mg and 35 mg dose groups. The 85 mg dose group had a lower mean age (8.0 years of age versus 9.7 and 10.0 years of age, respectively), a higher percentage of black/African American subjects (66.7% versus 33.3% and 16.7%, respectively) and a lower mean weight (31.98 kg versus 35.73 and 35.93 kg, respectively) than the other two groups.

Following administration of a single, oral dose of 35 mg, 55 mg and 85 mg Formulation I, there were multiple concentration peaks observed. The initial peaks were observed between 0-4 hours. The secondary peaks were more prominent and were mostly observed between 8-14 hours. In all but 4 subjects, the later peaks between 8-14 hours represented the maximum concentrations across all dose levels. This was further supported by the median Tmax estimates which ranged from 9.00 to 9.97 hours across all dose levels and were not impacted by dose. These Tmax results are similar to those observed in adults and pediatric subjects 12 to 17 years of age.

The Cmax of Formulation I increased as the dose increased, ranging from 11.315±2.1299 ng/mL (35 mg) to 27.445±6.1937 ng/mL (85 mg). In previously-conducted PK studies, Cmax was measured as 13.640±6.2088 ng/mL (mean dose 62.9 mg Formulation I) in pediatric subjects 12 to 17 years of age and ranged from 11.656±3.5930 ng/mL (70 mg Formulation I) to 17.101±5.9437 ng/mL (100 mg Formulation I) in adults. Of the 4 time segments studied in this protocol (0 to 4 h, 4 to 8 h, 8 to 14 h and 14 h to t), the $Cmax_{8-14}$ was the largest for all three doses. This has also been previously observed in both adults and pediatric subjects 12 to 17 years of age. The overall exposures ($AUC_{0-t}$, $AUC_{0-inf}$) also increased with increasing dose.

The Mixed Effect Power model was used to conduct an exploratory dose proportionality analysis. Peak (Cmax) and overall exposures ($AUC_{0-t}$ and $AUC_{0-inf}$) increased with increasing dose from 35 mg to 85 mg. In this exploratory analysis, Cmax was entirely within the planned critical region; however, the lower bound CI for $AUC_{0-t}$ and $AUC_{0-inf}$ was within the critical region but the upper bound (1.4) was slightly out of the planned critical region (1.3) The partial Cmax and AUCs for the different time intervals also increased with increasing dose.

The mean half-life ranged from 3.758 to 6.184 hours over the dose range evaluated and was comparable across doses when taking into account the variability.

The plasma concentration-time profile of d, 1-methylphenidate in pediatric subjects 6 to 11 years of age was similar to the PK profile observed in previous studies with Formulation I in adults and pediatric subjects 12 to 17 years of age. These profiles show an initial peak concentration within the first 2 hours following administration due to the IR component, followed by a trough and a gradual ascending curve with a second, higher peak concentration between 9 and 12 hours post-dose.

The majority of AEs observed in this study were mild in severity. There were no SAEs or AEs leading to discontinuation. The adverse event profile was similar to those that have been observed for other methylphenidate formulations.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A method of treating Attention Deficit Hyperactivity Disorder (ADHD) in a pediatric subject from 6 to 11 years of age, the method comprising administering to the pediatric subject from 6 to 11 years of age in need thereof, an oral pharmaceutical composition comprising from 25 to 100 mg methylphenidate hydrochloride, wherein
the oral solid pharmaceutical composition, when administered to a pediatric subject from 6 to 11 years of age in a fasted state, provides an average methylphenidate $AUC_{0-4}$ (pg·hr/mL) that is from 80 to 125% of the value resulting from the formula:

Average $AUC_{0-4}$=804.42*(dose of methylphenidate hydrochloride in mg)−b 8994.4 further wherein the oral solid pharmaceutical composition provides efficacious treatment of ADHD for 16 hours after a single oral administration.

2. The method of claim 1, wherein the oral pharmaceutical composition further provides an average methylphenidate $AUC_{8-14}$ (pg·hr/mL) that is from 80 to 125% of the value resulting from the formula:

Average $AUC_{8-14}$=1580.3*(dose of methylphenidate hydrochloride in mg)−1860.

3. The method of claim 1, wherein the oral pharmaceutical composition further provides an average methylphenidate $AUC_{14-24}$ (pg·hr/mL) that is from 80 to 125% of the value resulting from the formula:

Average $AUC_{14-24}$=1392.2*(dose of methylphenidate hydrochloride in mg)−9239.1.

4. The method of claim 1, wherein the oral pharmaceutical composition further provides an average methylphenidate $AUC_{0-\infty}$ (pg·hr/mL) that is from 80 to 125% of the value resulting from the formula:

Average $AUC_{0-\infty}$=5932*(dose of methylphenidate hydrochloride in mg)−51578.

* * * * *